US007442772B2

(12) United States Patent
Goddard et al.

(10) Patent No.: US 7,442,772 B2
(45) Date of Patent: Oct. 28, 2008

(54) ANTIBODIES TO PRO361 POLYPEPTIDE

(75) Inventors: Audrey Goddard, San Francisco, CA (US); Paul J. Godowski, Burlingame, CA (US); J. Christopher Grimaldi, San Francisco, CA (US); Austin L. Gurney, Belmont, CA (US); Daniel Tumas, Orinda, CA (US); William I. Wood, Hillsborough, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 10/735,014

(22) Filed: Dec. 12, 2003

(65) Prior Publication Data

US 2004/0220385 A1    Nov. 4, 2004

Related U.S. Application Data

(63) Continuation of application No. 09/944,852, filed on Aug. 31, 2001, now abandoned, which is a continuation of application No. 09/866,028, filed on May 25, 2001, now Pat. No. 6,642,360, which is a continuation of application No. PCT/US99/28301, filed on Dec. 1, 1999, which is a continuation-in-part of application No. 09/254,311, filed as application No. PCT/US98/25108 on Dec. 1, 1998, now abandoned.

(60) Provisional application No. 60/075,945, filed on Feb. 25, 1998.

(51) Int. Cl.
*C07K 16/00* (2006.01)

(52) U.S. Cl. .............. 530/387.1; 530/387.9; 530/388.1; 530/388.15

(58) Field of Classification Search ................ 435/69.1, 435/320.1, 325, 455; 530/350, 387.1, 388.1, 530/388.15, 389.1
See application file for complete search history.

(56) References Cited

OTHER PUBLICATIONS

Kahan, Cur. Opin. Immunol. 4: 553-560, 1992.*
Piccotti et al., Transplantation 67: 1453-1460, 1999.*
Campo et al., Biological Trace Element Res. 79: 15-22, 2001.*
Basic and Clinical Immunlogy edited by Stites, Terr, and Parslow (pp. 30-31, 208-209, 247 and 280).*
Manual of Clinical Laboratory Immunology Edited by Rose, Hamiliton, and Detrick (pp. 1164-1166).*
Basic and Clinical Immunlogy edited by Stites, Terr, and Parslow (pp. 30-31, 208-209, 247 and 280), 1995.*
Manual of Clinical Laboratory Immunology Edited by Rose, Hamiliton, and Detrick (pp. 1164-1166), 1997.*
Ashkenazi, A.J., et al, GenBank Accession No. P_ADB96522, Nov. 15, 2001.
Ashkenazi, A.J., et al, GenBank Accession No. P_ADA39496, Nov. 15, 2001.
Ashkenazi, A.J., et al, GenBank Accession No. P_ADA06803, Nov. 16, 2001.
Ashkenazi, A.J., et al, GenBank Accession No. P_ACD39623, Nov. 16, 2001.
Ashkenazi, A.J., et al, GenBank Accession No. P_ADA22637, Nov. 19, 2001.
Ashkenazi, A.J., et al, GenBank Accession No. P_ACH65633, Nov. 15, 2001.
Ashkenazi, A.J., et al, GenBank Accession No. P_ADA93076, Nov. 14, 2001.
Ashkenazi, A.J., et al, GenBank Accession No. P_ADA38955, Nov. 14, 2001.
Ashkenazi, A.J., et al, GenBank Accession No. P_ADA94730, Nov. 15, 2001.
Ashkenazi, A.J., et al, GenBank Accession No. P_ADA28150, Nov. 14, 2001.
Ashkenazi, A.J., et al, GenBank Accession No. P_ADA18042, Nov. 14, 2001.
Ashkenazi, A.J., et al, GenBank Accession No. P_ADA10498, Nov. 19, 2001.
Ashkenazi, A.J., et al, GenBank Accession No. P_ADA21711, Nov. 15, 2001.
Ashkenazi, A.J., et al, GenBank Accession No. P_ADA38025, Nov. 15, 2001.
Ashkenazi, A.J., et al, GenBank Accession No. P_ACD82072, Nov. 20, 2001.
Ashkenazi, A.J., et al, GenBank Accession No. P_ACA88565, Nov. 16, 2001.
Ashkenazi, A.J., et al, GenBank Accession No. P_ACA68116, Nov. 20, 2001.
Baker, K.P., et al, GenBank Accession No. P_ACA04368, Aug. 30, 2001.
Baker, K.P., et al, GenBank Accession No. P_ABX34148, Aug. 31, 2001.
Wood, W.I., et al, GenBank Accession No. P_AAX80059, Dec. 1, 1998.
Ashkenazi, A.J., et al, GenBank Accession No. P_AAC58593, Mar. 2, 2000.
Baker, K.P., et al, GenBank Accession No. P_AAA49567, Dec. 1, 1999.
Ashkenazi, A.J., et al, GenBank Accession No. P_AAF44268, Mar. 30, 2000.
Baker, K.P., et al, GenBank Accession No. P_ABX75504, Aug. 31, 2001.

(Continued)

*Primary Examiner*—Robert Landsman
*Assistant Examiner*—Gyan Chandra
(74) *Attorney, Agent, or Firm*—Elizabeth M. Barnes; Mark T. Kresnak; Brinks Hofer Gilson & Lione

(57) ABSTRACT

The present invention is directed to secreted and transmembrane polypeptides and to nucleic acid molecules encoding those polypeptides. Also provided herein are vectors and host cells comprising those nucleic acid sequences, chimeric polypeptide molecules comprising the polypeptides of the present invention fused to heterologous polypeptide sequences, antibodies which bind to the polypeptides of the present invention and to methods for producing the polypeptides of the present invention.

4 Claims, 34 Drawing Sheets

OTHER PUBLICATIONS

Ashkenazi, A.J., et al, GenBank Accession No. P_ABX78062, Nov. 15, 2001.
Ashkenazi, A.J., et al, GenBank Accession No. P_ABX80474, Nov. 14, 2001.
Ashkenazi, A.J., et al, GenBank Accession No. P_ACA69380, Nov. 14, 2001.
Ashkenazi, A.J., et al, GenBank Accession No. P_ABX90451, Nov. 14, 2001.
Ashkenazi, A.J., et al, GenBank Accession No. P_ABX64297, Nov. 20, 2001.
Baker, K.P., et al, GenBank Accession No. P_ABX89495, Aug. 31, 2001.
Ashkenazi, A.J., et al, GenBank Accession No. P_ACA64519, Nov. 19, 2001.
Baker, K.P., et al, GenBank Accession No. P_ABX96832, Aug. 31, 2001.
Baker, K.P., et al, GenBank Accession No. P_ABX78486, Aug. 30, 2001.
Baker, K.P., et al, GenBank Accession No. P_ABX77120, Aug. 30, 2001.
Ashkenazi, A.J., et al, GenBank Accession No. P_ABX80978, Nov. 15, 2001.
Ashkenazi, A.J., et al, GenBank Accession No. P_ACD44487, Nov. 14, 2001.
Baker, K.P., et al, GenBank Accession No. P_ABX75951, Aug. 30, 2001.
Baker, K.P., et al, GenBank Accession No. P_ABX89662, Aug. 31, 2001.
Ashkenazi, A.J., et al, GenBank Accession No. P_ABX17261, Nov. 19, 2001.
Ashkenazi, A.J., et al, GenBank Accession No. P_ABX79658, Nov. 19, 2001.
Ashkenazi, A.J., et al, GenBank Accession No. P_ACA93679, Nov. 14, 2001.
Ashkenazi, A.J., et al, GenBank Accession No. P_ABX81361, Nov. 14, 2001.
Ashkenazi, A.J., et al, GenBank Accession No. P_ACA93177, Nov. 20, 2001.
Clark, H.F., et al, GenBank Accession No. AY358563, Aug. 1, 2003.
Wood, W.I., et al, GenBank Accession No. BD140585, Feb. 26, 2002.
Baker, K.P., et al, GenBank Accession No. AX403627, Dec. 7, 2000.
Valenzuela, D., et al, GenBank Accession No. P_AAC59840, Mar. 17, 2000.
Ota, T., et al, GenBank Accession No. P_AAH18096, Jul. 28, 2000.
Ota, T., et al, GenBank Accession No. AX883044, Feb. 7, 2001.
Ota, T., et al, GenBank Accession No. BD160088, Jul. 9, 2002.
Isogai, T., et al, GenBank Accession No. AK023622, Aug. 23, 2000.
Clark, H.F., et al, GenBank Accession No. NM_018050, 2003.
Strausberg, R.L., et al, GenBank Accession No. BC032998, Jul. 21, 2002.
Jacobs, D., et al, GenBank Accession No. P_AAA16637, Mar. 17, 2000.
Jacobs, K., et al., GenBank Accession No. BD227259, Jul. 23, 2002.
Ota, T., et al, GenBank Accession No. P_AAH13971, Jul. 28, 2000.
Ota, T., et al, GenBank Accession No. AX876122, Feb. 7, 2001.
Ota, T., et al, GenBank Accession No. BD155963, Jul. 9, 2002.
Isogai, T., et al, GenBank Accession No. AK001160, Feb. 16, 2000.
Ashkenazi, A.J., et al, GenBank Accession No. P_ADC83381, Nov. 15, 2001.
Ashkenazi, A.J., et al, GenBank Accession No. P_ADD07134, Nov. 14, 2001.
Ashkenazi, A.J., et al, GenBank Accession No. P_ADD08885, Nov. 16, 2001.
Ashkenazi, A.J., et al, GenBank Accession No. P_ADC82705, Nov. 15, 2001.
Ashkenazi, A.J., et al, GenBank Accession No. P_ADD07814, Nov. 19, 2001.
Ashkenazi, A.J., et al, GenBank Accession No. P_ADC82172, Nov. 14, 2001.
Ashkenazi, A.J., et al, GenBank Accession No. P_ADD08347, Nov. 14, 2001.
Ashkenazi, A.J., et al, GenBank Accession No. P_ADC14815, Aug. 28, 2001.
Baker, K.P., et al, GenBank Accession No. P_ADC25718, Aug. 31, 2001.
Ashkenazi, A.J., et al, GenBank Accession No. P_ADC11693, Nov. 14, 2001.
Ashkenazi, A.J., et al, GenBank Accession No. P_ADC56648, Nov. 15, 2001.
Ashkenazi, A.J., et al, GenBank Accession No. P_ADC12226, Nov. 15, 2001.
Ashkenazi, A.J., et al, GenBank Accession No. P_ADC55359, Nov. 16, 2001.
Baker, K.P., et al, GenBank Accession No. P_ADC25597, Aug. 30, 2001.
Baker, K.P., et al, GenBank Accession No. P_ADC25839, Aug. 30, 2001.
Ashkenazi, A.J., et al, GenBank Accession No. P_ADC57995, Nov. 14, 2001.
Ashkenazi, A.J., et al, GenBank Accession No. P_ADB96523, Nov. 15, 2001.
Ashkenazi, A.J., et al, GenBank Accession No. P_ADA39497, Nov. 15, 2001.
Ashkenazi, A.J., et al, GenBank Accession No. P_ADA06804, Nov. 16, 2001.
Ashkenazi, A.J., et al, GenBank Accession No. P_ABO22621, Nov. 16, 2001.
Ashkenazi, A.J., et al, GenBank Accession No. P_ADA22638, Nov. 19, 2001.
Ashkenazi, A.J., et al, GenBank Accession No. P_ABO53251, Nov. 15, 2001.
Ashkenazi, A.J., et al, GenBank Accession No. P_ADA93077, Nov. 14, 2001.
Ashkenazi, A.J., et al, GenBank Accession No. P_ADA38956, Nov. 14, 2001.
Ashkenazi, A.J., et al, GenBank Accession No. P_ADA94731, Nov. 15, 2001.
Ashkenazi, A.J., et al, GenBank Accession No. P_ADA28151, Nov. 14, 2001.
Ashkenazi, A.J., et al, GenBank Accession No. P_ADA18043, Nov. 14, 2001.
Ashkenazi, A.J., et al, GenBank Accession No. P_ADA10499, Nov. 19, 2001.
Ashkenazi, A.J., et al, GenBank Accession No. P_ADA21712, Nov. 15, 2001.
Ashkenazi, A.J., et al, GenBank Accession No. P_ADA38026, Nov. 15, 2001.
Ashkenazi, A.J., et al, GenBank Accession No. P_ABO34165, Nov. 20, 2001.
Ashkenazi, A.J., et al, GenBank Accession No. P_ABU88651, Nov. 16, 2001.
Ashkenazi, A.J., et al, GenBank Accession No. P_ABU81712, Nov. 20, 2001.
Baker, K.P., et al, GenBank Accession No. P_ABU67135, Aug. 30, 2001.
Baker, K.P., et al, GenBank Accession No. P_ABU11316, Aug. 31, 2001.
Ashkenazi, A.J., et al, GenBank Accession No. P_ABU10960, Nov. 19, 2001.
Ashkenazi, A.J., et al, GenBank Accession No. P_ABU92254, Nov. 20, 2001.
Ashkenazi, A.J., et al, GenBank Accession No. P_ABU59488, Nov. 14, 2001.
Ashkenazi, A.J., et al, GenBank Accession No. P_ABU92423, Nov. 14, 2001.
Ashkenazi, A.J., et al, GenBank Accession No. P_ABU59045, Nov. 19, 2001.
Baker, K.P., et al, GenBank Accession No. P_ABU60355, Aug. 31, 2001.
Baker, K.P., et al, GenBank Accession No. P_ABU56315, Aug. 30, 2001.
Ashkenazi, A.J., et al, GenBank Accession No. P_ABO26036, Nov. 14, 2001.

Ashkenazi, A.J., et al, GenBank Accession No. P__ABU59339, Nov. 15, 2001.
Baker, K.P., et al, GenBank Accession No. P__ABU57250, Aug. 30, 2001.
Baker, K.P., et al, GenBank Accession No. P__ABU58364, Aug. 30, 2001.
Baker, K.P., et al, GenBank Accession No. P__ABU64930, Aug. 31, 2001.
Ashkenazi, A.J., et al, GenBank Accession No. P__ABU72590, Nov. 19, 2001.
Baker, K.P., et al, GenBank Accession No. P__ABU60244, Aug. 31, 2001.
Ashkenazi, A.J., et al, GenBank Accession No. P__ABU14005, Nov. 20, 2001.
Ashkenazi, A.J., et al, GenBank Accession No. P__ABU60623, Nov. 14, 2001.
Ashkenazi, A.J., et al, GenBank Accession No. P__ABU82704, Nov. 14, 2001.
Ashkenazi, A.J., et al, GenBank Accession No. P__ABU59192, Nov. 14, 2001.
Ashkenazi, A.J., et al, GenBank Accession No. P__ABU58114, Nov. 15, 2001.
Baker, K.P., et al, GenBank Accession No. P__ABU55934, Aug. 31, 2001.
Ashkenazi, A.J., et al, GenBank Accession No. P__AAB65299, Mar. 30, 2000.
Ota, T., et al, GenBank Accession No. P__AAB95464, Jul. 28, 2000.
Valenzuela, D., et al, GenBank Accession No. P__AAB34739, Mar. 17, 2000.
Baker, K.P., et al, GenBank Accession No. P__AAB01325, Dec. 1, 1999.
Ashkenazi, A.J., et al, GenBank Accession No. P__AAB33428, Mar. 2, 2000.
Wood, W.I., et al, GenBank Accession No. P__AAY17834, Dec. 1, 1998.
Ota, T., et al, GenBank Accession No. CAE91819, Feb. 7, 2001.
Isogai, T., et al, GenBank Accession No. BAB14621, Aug. 23, 2000.
Clark, H.F., et al, GenBank Accession No. AAQ88926, Aug. 1, 2003.
Clark, H.F., et al, GenBank Accession No. NP__060520, 2003.
Strausberg, R., GenBank Accession No. AAH32998, Jun. 21, 2002.
Ota, T., et al, GenBank Accession No. P__AAB92667, Jul. 28, 2000.
Ota, T., et al, GenBank Accession No. CAE89131, Feb. 7, 2001.
Isogai, T., et al, GenBank Accession No. BAA91526, Feb. 16, 2000.
Tang, Y.T. et al GenBank Accession No. P__AAM25899, Dec. 22, 2000.
Coico, R (Ed.), AM et al. Proliferative Assays For T Cell Function. Current Protocols in Immunology, 1991 vol. 1; 3.12.1-3.12.14.
Steinman, RM. The Dendritic Cell Advantage: New Focus For Immune-Based Therapies. Drug News Perspect Dec. 2000; 13(10); 581-586.
Gubler, U et al. Coexpression of Two Distinct Genes is Required to Generate Secreted Bioactive Cytotoxic Lymphocyte Maturation Factor. Proc. Natl. Acad. Sci. USA, May 1991; vol. 88; 4143-4147.
Peterson, AC et al. Immunization With Melan-A Peptide-Pulsed Peripheral Blood Mononuclear Cells Plus Recombinant Human Interleukin-12 Induces Clinical Activity and T-Cell Responses in Advanced Melanoma. Journal of Clinical Oncology, Jun. 2003; vol. 21(12); 2342-2348.
Thurner, B, et al. Vaccination With Mage-3A1 Peptide-pulsed Mature, Monocyte-derived Dendritic Cells Expands Specific Cytotoxic T Cells and Induces Regression of Some Metastases in Advanced Stage IV Melanoma. J. Exp. Med. Dec. 1999; vol. 190(11); 1669-1678.

* cited by examiner

FIGURE 1

```
GGACTAATCTGTGGGAGCAGTTTATTCCAGTATCACCCAGGGTGCAGCCACACCAGGACTGT
GTTGAAGGGTGTTTTTTTTCTTTTAAATGTAATACCTCCTCATCTTTTCTTCTTACACAGTG
TCTGAGAACATTTACATTATAGATAAGTAGTACATGGTGGATAACTTCTACTTTTAGGAGGA
CTACTCTCTTCTGACAGTCCTAGACTGGTCTTCTACACTAAGACACCATGAAGGAGTATGTG
CTCCTATTATTCCTGGCTTTGTGCTCTGCCAAACCCTTCTTTAGCCCTTCACACATCGCACT
GAAGAATATGATGCTGAAGGATATGGAAGACACAGATGATGATGATGATGATGATGATGATG
ATGATGATGAGGACAACTCTCTTTTCCAACAAGAGAGCCAAGAAGCCATTTTTTCCA
TTTGATCTGTTTCCAATGTGTCCATTTGGATGTCAGTGCTATTCACGAGTTGTACATTGCTC
AGATTTAGGTTTGACCTCAGTCCCAACCAACATTCCATTTGATACTCGAATGCTTGATCTTC
AAAACAATAAAATTAAGGAAATCAAAGAAATGATTTTAAAGGACTCACTTCACTTTATGGT
CTGATCCTGAACAACAACAAGCTAACGAAGATTCACCCAAAAGCCTTTCTAACCACAAAGAA
GTTGCGAAGGCTGTATCTGTCCCACAATCAACTAAGTGAAATACCACTTAATCTTCCCAAAT
CATTAGCAGAACTCAGAATTCATGAAAATAAAGTTAAGAAAATACAAAAGGACACATTCAAA
GGAATGAATGCTTTACACGTTTTGGAAATGAGTGCAAACCCTCTTGATAATAATGGGATAGA
GCCAGGGGCATTTGAAGGGGTGACGGTGTTCCATATCAGAATTGCAGAAGCAAAACTGACCT
CAGTTCCTAAAGGCTTACCACCAACTTTATTGGAGCTTCACTTAGATTATAATAAAATTTCA
ACAGTGGAACTTGAGGATTTTAAACGATACAAGAACTACAAAGGCTGGGCCTAGGAAACAA
CAAAATCACAGATATCGAAAATGGGAGTCTTGCTAACATACCACGTGTGAGAGAAATACATT
TGGAAAACAATAAACTAAAAAAAATCCCTTCAGGATTACCAGAGTTGAAATACCTCCAGATA
ATCTTCCTTCATTCTAATTCAATTGCAAGAGTGGGAGTAAATGACTTCTGTCCAACAGTGCC
AAAGATGAAGAAATCTTTATACAGTGCAATAAGTTTATTCAACAACCCGGTGAAATACTGGG
AAATGCAACCTGCAACATTTCGTTGTGTTTTGAGCAGAATGAGTGTTCAGCTTGGGAACTTT
GGAATGTAATAATTAGTAATTGGTAATGTCCATTTAATATAAGATTCAAAAATCCCTACATT
TGGAATACTTGAACTCTATTAATAATGGTAGTATTATATATACAAGCAAATATCTATTCTCA
AGTGGTAAGTCCACTGACTTATTTTATGACAAGAAATTTCAACGGAATTTTGCCAAACTATT
GATACATAAGGGGTTGAGAGAAACAAGCATCTATTGCAGTTTCCTTTTTGCGTACAAATGAT
CTTACATAAATCTCATGCTTGACCATTCCTTTCTTCATAACAAAAAGTAAGATATTCGGTA
TTTAACACTTTGTTATCAAGCACATTTTAAAAGAACTGTACTGTAAATGGAATGCTTGACT
TAGCAAAATTTGTGCTCTTTCATTTGCTGTTAGAAAAACAGAATTAACAAAGACAGTAATGT
GAAGAGTGCATTACACTATTCTTATTCTTTAGTAACTTGGGTAGTACTGTAATATTTTTAAT
CATCTTAAAGTATGATTTGATATAATCTTATTGAAATTACCTTATCATGTCTTAGAGCCCGT
CTTTATGTTTAAAACTAATTTCTTAAAATAAAGCCTTCAGTAAATGTTCATTACCAACTTGA
TAAATGCTACTCATAAGAGCTGGTTTGGGGCTATAGCATATGCTTTTTTTTTTTAATTATT
ACCTGATTTAAAAATCTCTGTAAAAACGTGTAGTGTTTCATAAAATCTGTAACTCGCATTTT
AATGATCCGCTATTATAAGCTTTTAATAGCATGAAAATTGTTAGGCTATATAACATTGCCAC
TTCAACTCTAAGGAATATTTTGAGATATCCCTTGGAAGACCTTGCTTGGAAGAGCCTGGA
CACTAACAATTCTACACCAAATTGTCTCTTCAAATACGTATGGACTGGATAACTCTGAGAA
CACATCTAGTATAACTGAATAAGCAGAGCATCAAATTAAACAGACAGAAACCGAAAGCTCTA
TATAAATGCTCAGAGTTCTTTATGTATTTCTTATTGGCATTCAACATATGTAAAATCAGAAA
ACAGGGAAATTTTCATTAAAAATATTGGTTTGAAAT
```

FIGURE 2

</usr/seqdb2/sst/DNA/Dnaseqs.min/ss.DNA34392
<subunit 1 of 1, 379 aa, 1 stop
<MW: 43302, pI: 7.30, NX(S/T): 1

MKEYVLLLFLALCSAKPFFSPSHIALKNMMLKDMEDTDDDDDDDDDDDDEDNSLFPTREPR
SHFFPFDLFPMCPFGCQCYSRVVHCSDLGLTSVPTNIPFDTRMLDLQNNKIKEIKENDFKGL
TSLYGLILNNNKLTKIHPKAFLTTKKLRRLYLSHNQLSEIPLNLPKSLAELRIHENKVKKIQ
KDTFKGMNALHVLEMSANPLDNNGIEPGAFEGVTVFHIRIAEAKLTSVPKGLPPTLLELHLD
YNKISTVELEDFKRYKELQRLGLGNNKITDIENGSLANIPRVREIHLENNKLKKIPSGLPEL
KYLQIIFLHSNSIARVGVNDFCPTVPKMKKSLYSAISLFNNPVKYWEMQPATFRCVLSRMSV
QLGNFGM

Signal sequence.
amino acids 1-15

N-glycosylation site.
amino acids 281-285

N-myristoylation sites.
amino acids 129-135, 210-216, 214-220, 237-243, 270-276, 282-288

Leucine zipper pattern.
amino acids 154-176

FIGURE 3

```
CGGACGCGTGGGCGGACGCGTGGGCCCGCSGCACCGCCCCGGCCCGGCCCTCCGCCCTCCGCACTCGCGCCTCC
CTCCCTCCGCCCGCTCCCGCGCCCTCCTCCCTCCCTCCTCCCCAGCTGTCCCGTTCGCGTCATGCCGAGCCTCCC
GGCCCCGCCGGCCCCGCTGCTGCTCCTCGGGCTGCTGCTGCTCGGCTCCCGGCCGGCCCGCGGCGCCGGCCCAGA
GCCCCCGTGCTGCCCATCCGTTCTGAGAAGGAGCCGCTGCCCGTTCGGGGAGCGGCAGGCTGCACCTTCGGCGG
GAAGGTCTATGCCTTGGACGAGACGTGGCACCCGGACCTAGGGCAGCCATTCGGGGTGATGCGCTGCGTGCTGTG
CGCCTGCGAGGCGCCTCAGTGGGGTCGCCGTACCAGGGGCCCTGGCAGGGTCAGCTGCAAGAACATCAAACCAGA
GTGCCCAACCCCGGCCTGTGGGCAGCCGCGCCAGCTGCCGGGACACTGCTGCCAGACCTGCCCCAGGAGCGCAG
CAGTTCGGAGCGGCAGCCGAGCGGCCTGTCCTTCGAGTATCCGCGGGACCCGGAGCATCGCAGTTATAGCGACCG
CGGGGAGCCAGGCGCTGAGGAGCGGGCCCGTGGTGACGGCCACACGGACTTCGTGGCGCTGCTGACAGGGCCGAG
GTCGCAGGCGGTGGCACGAGCCCGAGTCTCGCTGCTGCGCTCTAGCCTCCGCTTCTCTATCTCCTACAGGCGGCT
GGACCGCCCTACCAGGATCCGCTTCTCAGACTCCAATGGCAGTGTCCTGTTTGAGCACCCTGCAGCCCCCACCCA
AGATGGCCTGGTCTGTGGGGTGTGGCGGGCAGTGCCTCGGTTGTCTCTGCGGCTCCTTAGGGCAGAACAGCTGCA
TGTGGCACTTGTGACACTCACTCACCCTTCAGGGGAGGTCTGGGGGCCTCTCATCCGGCACCGGGCCCTGGCTGC
AGAGACCTTCAGTGCCATCCTGACTCTAGAAGGCCCCCCACAGCAGGGCGTAGGGGGCATCACCCTGCTCACTCT
CAGTGACACAGAGGACTCCTTGCATTTTTGCTGCTCTTCCGAGGGCTGCTGGAACCCAGGAGTGGGGACTAAC
CCAGGTTCCCTTGAGGCTCCAGATTCTACACCAGGGGCAGCTACTGCGAGAACTTCAGGCCAATGTCTCAGCCCA
GGAACCAGGCTTTGCTGAGGTGCTGCCCAACCTGACAGTCCAGGAGATGGACTGGCTGGTGCTGGGGGAGCTGCA
GATGGCCCTGGAGTGGGCAGGCAGGCCAGGGCTGCGCATCAGTGGACACATTGCTGCCAGGAAGAGCTGCGACGT
CCTGCAAAGTGTCCTTTGTGGGGCTGATGCCCTGATCCCAGTCCAGACGGGTGCTGCCGGCTCAGCCAGCCTCAC
GCTGCTAGGAAATGGCTCCCTGATCTATCAGGTGCAAGTGGTAGGGACAAGCAGTGAGGTGGTGGCCATGACACT
GGAGACCAAGCCTCAGCGGAGGGATCAGCGCACTGTCCTGTGCCACATGGCTGGACTCCAGCCAGGAGGACACAC
GGCCGTGGGTATCTGCCCTGGGCTGGGTGCCCGAGGGGCTCATATGCTGCTGCAGAATGAGCTCTTCCTGAACGT
GGGCACCAAGGACTTCCCAGACGGAGAGCTTCGGGGGCACGTGGCTGCCCTGCCCTACTGTGGGCATAGCGCCCG
CCATGACACGCTGCCCGTGCCCCTAGCAGGAGCCCTGGTGCTACCCCTGTGAAGAGCCAAGCAGCAGGGCACGC
CTGGCTTTCCTTGGATACCCACTGTCACCTGCACTATGAAGTGCTGCTGGCTGGGCTTGGTGGCTCAGAACAAGG
CACTGTCACTGCCCACCTCCTTGGGCCTCCTGGAACGCCAGGGCCTCGGCGGCTGCTGAAGGGATTCTATGGCTC
AGAGGCCCAGGGTGTGGTGAAGGACCTGGAGCCGGAACTGCTGCGGCACCTGGCAAAAGGCATGGCCTCCCTGAT
GATCACCACCAAGGGTAGCCCCAGAGGGGAGCTCCGAGGGCAGGTGCACATAGCCAACCAATGTGAGGTTGGCGG
ACTGCGCCTGGAGGCGGCCGGGGCCGAGGGGGTGCGGGCGCTGGGGGCTCCGGATACAGCCTCTGCTGCGCCGCC
TGTGGTGCCTGGTCTCCCGGCCCTAGCGCCCGCCAAACCTGGTGGTCCTGGGCGGCCCCGAGACCCCAACACATG
CTTCTTCGAGGGGCAGCAGCGCCCCCACGGGGCTCGCTGGGCGCCCAACTACGACCCGCTCTGCTCACTCTGCAC
CTGCCAGAGACGAACGGTGATCTGTGACCCGGTGGTGTGCCCACCGCCCAGCTGCCCACACCCGGTGCAGGCTCC
CGACCAGTGCTGCCCTGTTTGCCCTGAGAAACAAGATGTCAGAGACTTGCCAGGGCTGCCAAGGAGCCGGGACCC
AGGAGAGGGCTGCTATTTTGATGGTGACCGGAGCTGGCGGGCAGCGGGTACGCGGTGGCACCCCGTTGTGCCCCC
CTTTGGCTTAATTAAGTGTGCTGTCTGCACCTGCAAGGGGGCACTGGAGAGGTGCACTGTGAGAAGGTGCAGTG
TCCCCGGCTGGCCTGTGCCCAGCCTGTGCGTGTCAACCCCACCGACTGCTGCAAACAGTGTCCAGTGGGGTCGGG
GGCCCACCCCAGCTGGGGGACCCCATGCAGGCTGATGGGCCCCGGGGCTGCCGTTTTGCTGGGCAGTGGTTCCC
AGAGAGTCAGAGCTGGCACCCCTCAGTGCCCCCTTTTGGAGAGATGAGCTGTATCACCTGCAGATGTGGGGCAGG
GGTGCCCTCACTGTGAGCGGGATGACTGTTCACTGCCACTGTCCTGTGGCTCGGGGAAGGAGAGTCGATGCTGTTC
CCGCTGCACGGCCCACCGGCGGCCCCCAGAGACCAGAACTGATCCAGAGCTGGAGAAAGAAGCCGAAGGCTCTTA
GGGAGCAGCCAGAGGGCCAAGTGACCAAGAGGATGGGGCCTGAGCTGGGAAGGGGTGGCATCGAGGACCTTCTT
GCATTCTCCTGTGGGAAGCCCAGTGCCTTTGCTCCTCTGTCCTGCCTCTACTCCCACCCCCACTACCTCTGGGAA
CCACAGCTCCACAAGGGGGAGAGGCAGCTGGGCAGACCGAGGTCACAGCCACTCCAAGTCCTGCCCTGCCACCC
TCGGCCTCTGTCCTGGAAGCCCCACCCCTTTCCTCCTGTACATAATGTCACTGGCTTGTTGGGATTTTTAATTTA
TCTTCACTCAGCACCAAGGGCCCCCGACACTCCACTCCTGCTGCCCCTGAGCTGAGCAGAGTCATTATTGGAGAG
TTTTGTATTTATTAAAACATTTCTTTTTCAGTCAAAAAAAAAAAAAAAAAAAAAAAAAAAAAAAAAA
```

FIGURE 4

\><subunit 1 of 1, 954 aa, 1 stop

\><MW: 101960, pI: 8.21, NX(S/T): 5

MPSLPAPPAPLLLLGLLLLGSRPARGAGPEPPVLPIRSEKEPLPVRGAAGCTFGGKVYALDE
TWHPDLGQPFGVMRCVLCACEAPQWGRRTRGPGRVSCKNIKPECPTPACGQPRQLPGHCCQT
CPQERSSSERQPSGLSFEYPRDPEHRSYSDRGEPGAEERARGDGHTDFVALLTGPRSQAVAR
ARVSLLRSSLRFSISYRRLDRPTRIRFSDSNGSVLFEHPAAPTQDGLVCGVWRAVPRLSLRL
LRAEQLHVALVTLTHPSGEVWGPLIRHRALAAETFSAILTLEGPPQQGVGGITLLTLSDTED
SLHFLLLFRGLLEPRSGGLTQVPLRLQILHQGQLLRELQANVSAQEPGFAEVLPNLTVQEMD
WLVLGELQMALEWAGRPGLRISGHIAARKSCDVLQSVLCGADALIPVQTGAAGSASLTLLGN
GSLIYQVQVVGTSSEVVAMTLETKPQRRDQRTVLCHMAGLQPGGHTAVGICPGLGARGAHML
LQNELFLNVGTKDFPDGELRGHVAALPYCGHSARHDTLPVPLAGALVLPPVKSQAAGHAWLS
LDTHCHLHYEVLLAGLGGSEQGTVTAHLLGPPGTPGPRRLLKGFYGSEAQGVVKDLEPELLR
HLAKGMASLMITTKGSPRGELRGQVHIANQCEVGGLRLEAAGAEGVRALGAPDTASAAPPVV
PGLPALAPAKPGGPGRPRDPNTCFFEGQQRPHGARWAPNYDPLCSLCTCQRRTVICDPVVCP
PPSCPHPVQAPDQCCPVCPEKQDVRDLPGLPRSRDPGEGCYFDGDRSWRAAGTRWHPVVPPF
GLIKCAVCTCKGGTGEVHCEKVQCPRLACAQPVRVNPTDCCKQCPVGSGAHPQLGDPMQADG
PRGCRFAGQWFPESQSWHPSVPPFGEMSCITCRCGAGVPHCERDDCSLPLSCGSGKESRCCS
RCTAHRRPPETRTDPELEKEAEGS

Signal sequence.

amino acids 1-23

N-glycosylation sites.

amino acids 217-221, 351-355, 365-369, 434-438

Tyrosine kinase phosphorylation sites.

amino acids 145-153, 778-786

N-myristoylation sites.

amino acids 20-26, 47-53, 50-56, 69-75, 73-79, 232-238, 236-242, 390-396, 422-428, 473-479, 477-483, 483-489, 489-495, 573-579, 576-582, 580-586, 635-641, 670-676, 773-779, 807-813, 871-877, 905-911

Amidation site.

amino acids 87-91

Cell attachment sequence.

amino acids 165-168

Leucine zipper pattern.

amino acids 315-337

FIGURE 5

```
GGCGGAGCAGCCCTAGCCGCCACCGTCGCTCTCGCAGCTCTCGTCGCCACTGCCACCGCCGCCGCCGTCACTGCG
TCCTGGCTCCGGCTCCCGCGCCCTCCCGGCCGGCCATGCAGCCCCGCCGCGCCCAGGCGCCCGGTGCGCAGCTGC
TGCCCGCGCTGGCCCTGCTGCTGCTGCTGCTCGGAGCGGGGCCCCGAGGCAGCTCCCTGGCCAACCCGGTGCCCG
CCGCGCCCTTGTCTGCGCCCGGGCCGTGCGCCGCGCAGCCCTGCGGAATGGGGGTGTGTGCACCTCGCGCCCTG
AGCCGGACCCGCAGCACCCGGCCCCCGCCGGCGAGCCTGGCTACAGCTGCACCTGCCCCGCCGGGATCTCCGGCG
CCAACTGCCAGCTTGTTGCAGATCCTTGTGCCAGCAACCCTTGTCACCATGGCAACTGCAGCAGCAGCAGCAGCA
GCAGCAGCGATGGCTACCTCTGCATTTGCAATGAAGGCTATGAAGGTCCCAACTGTGAACAGGCACTTCCCAGTC
TCCCAGCCACTGGCTGGACCGAATCCATGGCACCCCGACAGCTTCAGCCTGTTCCTGCTACTCAGGAGCCTGACA
AAATCCTGCCTCGCTCTCAGGCAACGGTGACACTGCCTACCTGGCAGCCGAAAACAGGGCAGAAAGTTGTAGAAA
TGAAATGGGATCAAGTGGAGGTGATCCCAGATATTGCCTGTGGGAATGCCAGTTCTAACAGCTCTGCGGGTGGCC
GCCTGGTATCCTTTGAAGTGCCACAGAACACCTCAGTCAAGATTCGGCAAGATGCCACTGCCTCACTGATTTTGC
TCTGGAAGGTCACGGCCACAGGATTCCAACAGTGCTCCCTCATAGATGGACGAAGTGTGACCCCCCTTCAGGCTT
CAGGGGGACTGGTCCTCCTGGAGGAGATGCTCGCCTTGGGGAATAATCACTTTATTGGTTTTGTGAATGATTCTG
TGACTAAGTCTATTGTGGCTTTGCGCTTAACTCTGGTGGTGAAGGTCAGCACCTGTGTGCCGGGGGAGAGTCACG
CAAATGACTTGGAGTGTTCAGGAAAAGGAAAATGCACCACGAAGCCGTCAGAGGCAACTTTTTCCTGTACCTGTG
AGGAGCAGTACGTGGGTACTTTCTGTGAAGAATACGATGCTTGCCAGAGGAAACCTTGCCAAAACAACGCGAGCT
GTATTGATGCAAATGAAAAGCAAGATGGGAGCAATTTCACCTGTGTTTGCCTTCCTGGTTATACTGGAGAGCTTT
GCCAGTCCAAGATTGATTACTGCATCCTAGACCCATGCAGAAATGGAGCAACATGCATTTCCAGTCTCAGTGGAT
TCACCTGCCAGTGTCCAGAAGGATACTTCGGATCTGCTTGTGAAGAAAAGGTGGACCCCTGCGCCTCGTCTCCGT
GCCAGAACAACGGCACCTGCTATGTGGACGGGGTACACTTTACCTGCAACTGCAGCCCGGGCTTCACAGGGCCGA
CCTGTGCCCAGCTTATTGACTTCTGTGCCCTCAGCCCCTGTGCTCATGGCACGTGCCGCAGCGTGGGCACCAGCT
ACAAATGCCTCTGTGATCCAGGTTACCATGGCCTCTACTGTGAGGAGGAATATAATGAGTGCCTCTCCGCTCCAT
GCCTGAATGCAGCCACCTGCAGGGACCTCGTTAATGGCTATGAGTGTGTGTGCCTGGCAGAATACAAAGGAACAC
ACTGTGAATTGTACAAGGATCCCTGCGCTAACGTCAGCTGTCTGAACGGAGCCACCTGTGACAGCGACGGCCTGA
ATGGCACGTGCATCTGTGCACCCGGGTTTACAGGTGAAGAGTGCGACATTGACATAAATGAATGTGACAGTAACC
CCTGCCACCATGGTGGGAGCTGCCTGGACCAGCCCAATGGTTATAACTGCCACTGCCCGCATGGTTGGGTGGGAG
CAAACTGTGAGATCCACCTCCAATGGAAGTCCGGGCACATGGCGGAGAGCCTCACCAACATGCCACGGCACTCCC
TCTACATCATCATTGGAGCCCTCTGCGTGGCCTTCATCCTTATGCTGATCATCCTGATCGTGGGGATTTGCCGCA
TCAGCCGCATTGAATACCAGGGTTCTTCCAGGCCAGCCTATGAGGAGTTCTACAACTGCCGCAGCATCGACAGCG
AGTTCAGCAATGCCATTGCATCCATCCGGCATGCCAGGTTTGGAAAGAAATCCCGGCCTGCAATGTATGATGTGA
GCCCCATCGCCTATGAAGATTACAGTCCTGATGACAAACCCTTGGTCACACTGATTAAAACTAAAGATTTGTAAT
CTTTTTTTGGATTATTTTTCAAAAAGATGAGATACTACACTCATTTAAATATTTTTAAGAAAATAAAAAGCTTAA
GAAATTTAAAATGCTAGCTGCTCAAGAGTTTTCAGTAGAATATTTAAGAACTAATTTTCTGCAGCTTTTAGTTTG
GAAAAAATATTTTAAAAACAAAATTTGTGAAACCTATAGACGATGTTTTAATGTACCTTCAGCTCTCTAAACTGT
GTGCTTCTACTAGTGTGTGCTCTTTTCACTGTAGACACTATCACGAGACCCAGATTAATTTCTGTGGTTGTTACA
GAATAAGTCTAATCAAGGAGAAGTTTCTGTTTGACGTTTGAGTGCCGGCTTTCTGAGTAGAGTTAGGAAAACCAC
GTAACGTAGCATATGATGTATAATAGAGTATACCCGTTACTTAAAAAGAAGTCTGAAATGTTCGTTTTGTGGAAA
AGAAACTAGTTAAATTTACTATTCCTAACCCGAATGAAATTAGCCTTTGCCTTATTCTGTGCATGGGTAAGTAAC
TTATTTCTGCACTGTTTGTTGAACTTTGTGGAAACATTCTTTCGAGTTTGTTTTTGTCATTTTCGTAACAGTCG
TCGAACTAGGCCTCAAAAACATACGTAACGAAAAGGCCTAGCGAGGCAAATTCTGATTGATTTGAATCTATATTT
TTCTTTAAAAAGTCAAGGGTTCTATATTGTGAGTAAATTAAATTTACATTTGAGTTGTTTGTTGCTAAGAGGTAG
TAAATGTAAGAGAGTACTGGTTCCTTCAGTAGTGAGTATTTCTCATAGTGCAGCTTTATTTATCTCCAGGATGTT
TTTGTGGCTGTATTTGATTGATATGTGCTTCTTCTGATTCTTGCTAATTTCCAACCATATTGAATAAATGTGATC
AAGTCA
```

FIGURE 6

><subunit 1 of 1, 737 aa, 1 stop

><MW: 78475, pI: 5.09, NX(S/T): 11

MQPRRAQAPGAQLLPALALLLLLLGAGPRGSSLANPVPAAPLSAPGPCAAQPCRNGGVCTSR
PEPDPQHPAPAGEPGYSCTCPAGISGANCQLVADPCASNPCHHGNCSSSSSSSSDGYLCICN
EGYEGPNCEQALPSLPATGWTESMAPRQLQPVPATQEPDKILPRSQATVTLPTWQPKTGQKV
VEMKWDQVEVIPDIACGNASSNSSAGGRLVSFEVPQNTSVKIRQDATASLILLWKVTATGFQ
QCSLIDGRSVTPLQASGGLVLLEEMLALGNNHFIGFVNDSVTKSIVALRLTLVVKVSTCVPG
ESHANDLECSGKGKCTTKPSEATFSCTCEEQYVGTFCEEYDACQRKPCQNNASCIDANEKQD
GSNFTCVCLPGYTGELCQSKIDYCILDPCRNGATCISSLSGFTCQCPEGYFGSACEEKVDPC
ASSPCQNNGTCYVDGVHFTCNCSPGFTGPTCAQLIDFCALSPCAHGTCRSVGTSYKCLCDPG
YHGLYCEEEYNECLSAPCLNAATCRDLVNGYECVCLAEYKGTHCELYKDPCANVSCLNGATC
DSDGLNGTCICAPGFTGEECDIDINECDSNPCHHGGSCLDQPNGYNCHCPHGWVGANCEIHL
QWKSGHMAESLTNMPRHSLYIIIGALCVAFILMLIILIVGICRISRIEYQGSSRPAYEEFYN
CRSIDSEFSNAIASIRHARFGKKSRPAMYDVSPIAYEDYSPDDKPLVTLIKTKDL

Signal sequnce.

amino acids 1-28

Transmembrane domain.

amino acids 641-660

N-glycosylation sites.

amino acids 107-111, 204-208, 208-212, 223-227, 286-290, 361-365, 375-379, 442-446, 549-553, 564-568

Glycosaminoglycan attachment site.

amino acids 320-324

Tyrosine kinase phosphorylation sites.

amino acids 490-498, 674-682

N-myristoylation sites.

amino acids 30-36, 56-62, 57-63, 85-91, 106-112, 203-209, 373-379, 449-455, 480-486, 562-568, 565-571

Amidation site.

amino acids 702-706

Aspartic acid and asparagine hydroxylation site.

amino acids 520-532, 596-608

EGF-like domain cysteine pattern signatures.

amino acids 80-92, 121-133, 336-348, 378-390, 416-428, 454-466, 491-503, 529-541, 567-579, 605-617

FIGURE 7

CTCTGGAAGGTCACGGCCACAGGATTCCAACAGTGCTCCCTCATAGATGGACGAAAGTGTGA
CCCCCCTTTCAGGCTTTCAGGGGGACTGGTCCTCCTGGAGGAGATGCTCGCCTTGGGGAATA
ATCACTTTATTGGTTTTGTGAATGATTCTGTGACTAAGTCTATTGTGGCTTTGCGCTTAACT
CTGGTGGTGAAGGTCAGCACCTGTGTGCCGGGGAGAGTCACGCAAATGACTTGGAGTGTTC
AGGAAAAGGAAAATGCACCACGAAGCCGTCAGAGGCAACTTTTTCCTGTACCTGTGAGGAGC
AGTACGTGGGTACTTTCTGTGAAGAATACGATGCTTGCCAGAGGAAACCTTGCCAAAACAAC
GCGAGCTGTATTGATGCAAATGAAAAGCAAGATGGGAGCAATTTCACCTGTGTTTGCCTTCC
TGGTTATACTGGAGAGCTTTGCCAACCGAACTGAGATTGGAGCGAACGACCTACACCGAACT
GAGATAGGGGAG

FIGURE 8

CTCTGGAAGGTCACGGCCACAGGATTCCAACAGTGCTCCCTCATAGATGGACGAAAGTGTGA
CCCCCCTTTCAGGCTTTCAGGGGGACTGGTCCTCCTGGAGGAGATGCTCGCCTTGGGGAATA
ATCACTTTATTGGTTTTGTGAATGATTCTGTGACTAAGTCTATTGTGGCTTTGCGCTTAACT
CTGGTGGTGAAGGTCAGCACCTGTGTGCCGGGGAGAGTCACGCAAATGACTTGGAGTGTTC
AGGAAAAGGAAAATGCACCACGAAGCCGTCAGAGGCAACTTTTTCCTGTACCTGTGAGGAGC
AGTACGTGGGTACTTTCTGTGAAGAATACGATGCTTGCCAGAGGAAACCTTGCCAAAACAAC
GCGAGCTGTATTGATGCAAATGAAAAGCAAGATGGGAGCAATTTCACCTGTGTTTGCCTTCC
TGGTTATACTGGAGAGCTTTGCCAACCGAACTGAGATTGGAGCGAACGACCTACACCGAACT
GAGATAGGGGAG

FIGURE 9

GCTGAGTCTGCTGCTCCTGCTGCTGCTGCTCCAGCCTGTAACCTGTGCCTACACCACGCCAG
GCCCCCCAGAGCCCTCACCACGCTGGGCGCCCCAGAGCCCACAC<u>ATG</u>CCGGGCACCTAC
GCTCCCTCGACCACACTCAGTAGTCCCAGCACCCAGGGCCTGCAAGAGCAGGCACGGGCCCT
GATGCGGGACTTCCCGCTCGTGGACGGCCACAACGACCTGCCCCTGGTCCTAAGGCAGGTTT
ACCAGAAAGGGCTACAGGATGTTAACCTGCGCAATTTCAGCTACGGCCAGACCAGCCTGGAC
AGGCTTAGAGATGGCCTCGTGGGCGCCCAGTTCTGGTCAGCCTATGTGCCATGCCAGACCCA
GGACCGGGATGCCCTGCGCCTCACCCTGGAGCAGATTGACCTCATACGCCGCATGTGTGCCT
CCTATTCTGAGCTGGAGCTTGTGACCTCGGCTAAAGCTCTGAACGACACTCAGAAATTGGCC
TGCCTCATCGGTGTAGAGGGTGGCCACTCGCTGGACAATAGCCTCTCCATCTTACGTACCTT
CTACATGCTGGGAGTGCGCTACCTGACGCTCACCCACACCTGCAACACACCCTGGGCAGAGA
GCTCCGCTAAGGGCGTCCACTCCTTCTACAACAACATCAGCGGGCTGACTGACTTTGGTGAG
AAGGTGGTGGCAGAAATGAACCGCCTGGGCATGATGGTAGACTTATCCCATGTCTCAGATGC
TGTGGCACGGCGGGCCCTGGAAGTGTCACAGGCACCTGTGATCTTCTCCCACTCGGCTGCCC
GGGGTGTGTGCAACAGTGCTCGGAATGTTCCTGATGACATCCTGCAGCTTCTGAAGAAGAAC
GGTGGCGTCGTGATGGTGTCTTTGTCCATGGGAGTAATACAGTGCAACCCATCAGCCAATGT
GTCCACTGTGGCAGATCACTTCGACCACATCAAGGCTGTCATTGGATCCAAGTTCATCGGGA
TTGGTGGAGATTATGATGGGGCCGGCAAATTCCCTCAGGGGCTGGAAGACGTGTCCACATAC
CCGGTCCTGATAGAGGAGTTGCTGAGTCGTGGCTGGAGTGAGGAAGAGCTTCAGGGTGTCCT
TCGTGGAAACCTGCTGCGGGTCTTCAGACAAGTGGAAAAGGTACAGGAAGAAAACAAATGGC
AAAGCCCCTTGGAGGACAAGTTCCCGGATGAGCAGCTGAGCAGTTCCTGCCACTCCGACCTC
TCACGTCTGCGTCAGAGACAGAGTCTGACTTCAGGCCAGGAACTCACTGAGATTCCCATACA
CTGGACAGCCAAGTTACCAGCCAAGTGGTCAGTCTCAGAGTCCTCCCCCCACATGGCCCCAG
TCCTTGCAGTTGTGGCCACCTTCCCAGTCCTTATTCTGTGGCTC<u>TGA</u>TGACCCAGTTAGTCC
TGCCAGATGTCACTGTAGCAAGCCACAGACACCCCACAAAGTTCCCCTGTTGTGCAGGCACA
AATATTTCCTGAAATAAATGTTTTGGACATAG

FIGURE 10

```
</usr/seqdb2/sst/DNA/Dnaseqs.min/ss.DNA35595
<subunit 1 of 1, 433 aa, 1 stop
<MW: 47787, pI: 6.11, NX(S/T): 5
MPGTYAPSTTLSSPSTQGLQEQARALMRDFPLVDGHNDLPLVLRQVYQKGLQDVNLRNFSYG
QTSLDRLRDGLVGAQFWSAYVPCQTQDRDALRLTLEQIDLIRRMCASYSELELVTSAKALND
TQKLACLIGVEGGHSLDNSLSILRTFYMLGVRYLTLTHTCNTPWAESSAKGVHSFYNNISGL
TDFGEKVVAEMNRLGMMVDLSHVSDAVARRALEVSQAPVIFSHSAARGVCNSARNVPDDILQ
LLKKNGGVVMVSLSMGVIQCNPSANVSTVADHFDHIKAVIGSKFIGIGGDYDGAGKFPQGLE
DVSTYPVLIEELLSRGWSEEELQGVLRGNLLRVFRQVEKVQEENKWQSPLEDKFPDEQLSSS
CHSDLSRLRQRQSLTSGQELTEIPIHWTAKLPAKWSVSESSPHMAPVLAVVATFPVLILWL
```

N-glycosylation sites.
amino acids 58-62, 123-127, 182-186, 273-277

N-myristoylation sites.
amino acids 72-78, 133-139, 234-240, 264-270, 334-340, 389-395

Renal dipeptidase active site.
amino acids 134-157

FIGURE 11

AAAACCTATAAATATTCCGGATTATTCATACCGTCCCACCATCGGGCGCGGATCCGCGGCCG
CGAATTCTAAACCAACATGCCGGGCACCTACGCTCCCTCGACCACACTCAGTAGTCCCAGCA
CCCAGGGCCTGCAAGAGCAGGCACGGGCCCTGATGCGGGACTTCCCGCTCGTGGACGGCCAC
AACGACCTGCCCCTGGTCCTAAGGCAGGTTTACCAGAAAGGGCTACAGGATGTTAACCTGCG
CAATTTCAGCTACGGCCAGACCAGCCTGGACAGGCTTAGAGATGGCCTCGTGGGCGCCCAGT
TCTGGTCAGCCTATGTGCCATGCCAGACCCAGGACCGGGATGCCCTGCGCCTCACCCTGGAG
CAGATTGACCTCATACGCCGCATGTGTGCCTCCTATTCTGAGCTGGAGCTTGTGACCTCGGC
TAAAGCTCTGAACGACACTCAGAAATTGGCCTGCCTCATCGGTGTAGAGGGTGGCCACTCGC
TGGACAATAGCCTCTCCATCTTACGTACCTTCTACATGCTGGGAGTGCGCTACCTGACGCTC
ACCCACACCTGCAACACACCCTGGGCAGAGAGCTCCGCTAAGGGCGTCCACTCCTTCTACAA
CAACATCAGCGGGCTGACTGACTTTGGTGAGAAGGTGGTGGCAGAAATGAACCGCCTGGGCA
TGATGGTAGACTTATCCCATGTCTCAGATGCTGTGGCACGGCGGGCCCTGGAAGTGTCACAG
GCACCTGTGATCTTCTCCCACTCGGCTGCCCGGGGTGTGTGCAACAGTGCTCGGAATGTTCC
TGATGACATCCTGCAGCTTCTGAAGAAGAACGGTGGCGTCGTGATGGTGTCTTTGTCCATGG
GAGTAATACAGTGCAACCCATCAGCCAATGTGTCCACTGTGGCAGATCACTTCGACCACATC
AAGGCTGTCATTGGATCCAAGTTCATCGGGATTGGTGGAGATTATGATGGGGCCGGCAAATT
CCCTCAGGGGCTGGAAGACGTGTCCACATACCCGGTCCTGATAGAGGAGTTGCTGAGTCGTG
GCTGGAGTGAGGAAGAGCTTCAGGGTGTCCTTCGTGGAAACCTGCTGCGGGTCTTCAGACAA
GTGGAAAAGGTACAGGAAGAAAACAAATGGCAAAGCCCCTTGGAGGACAAGTTCCCGGATGA
GCAGCTGAGCAGTTCCTGCCACTCCGACCTCTCACGTCTGCGTCAGAGACAGAGTCTGACTT
CAGGCCAGGAACTCACTGAGATTCCCATACACTGGACAGCCAAGTTACCAGCCAAGTGGTCA
GTCTCAGAGTCCTCCCCCCACCCTGACAAAACTCACACATGCCCACCGTGCCCAGCACCTGA
ACTCCTGGGGGGACCGTCAGTCTTCCTCTTCCCCCAAAACCCAAGGACACC

FIGURE 12

```
></usr/seqdb2/sst/DNA/Dnaseqs.full/ss.DNA35872
><subunit 1 of 1, 446 aa, 0 stop
><NX(S/T): 5
MPGTYAPSTTLSSPSTQGLQEQARALMRDFPLVDGHNDLPLVLRQVYQKGLQDVNLRNFSYG
QTSLDRLRDGLVGAQFWSAYVPCQTQDRDALRLTLEQIDLIRRMCASYSELELVTSAKALND
TQKLACLIGVEGGHSLDNSLSILRTFYMLGVRYLTLTHTCNTPWAESSAKGVHSFYNNISGL
TDFGEKVVAEMNRLGMMVDLSHVSDAVARRALEVSQAPVIFSHSAARGVCNSARNVPDDILQ
LLKKNGGVVMVSLSMGVIQCNPSANVSTVADHFDHIKAVIGSKFIGIGGDYDGAGKFPQGLE
DVSTYPVLIEELLSRGWSEEELQGVLRGNLLRVFRQVEKVQEENKWQSPLEDKFPDEQLSSS
CHSDLSRLRQRQSLTSGQELTEIPIHWTAKLPAKWSVSESSPHPDKTHTCPPCPAPELLGGP
SVFLFPPKPKDT
```

FIGURE 13

CGCCCAGCGACGTGCGGGCGGCCTGGCCCGCGCCCTCCCGCGCCCGGCCTGCGTCCCGCGCC
CTGCGCCACCGCCGCCGAGCCGCAGCCCGCCGCGCGCCCCGGCAGCGCCGGCCCCATGCCC
GCCGGCCGCCGGGGCCCCGCCGCCCAATCCGCGCGGCGGCCGCCGCCGTTGCTGCCCCTGCT
GCTGCTGCTCTGCGTCCTCGGGGCGCCGCGAGCCGGATCAGGAGCCCACACAGCTGTGATCA
GTCCCCAGGATCCCACGCTTCTCATCGGCTCCTCCCTGCTGGCCACCTGCTCAGTGCACGGA
GACCCACCAGGAGCCACCGCCGAGGGCCTCTACTGGACCCTCAACGGGCGCCGCCTGCCCCC
TGAGCTCTCCCGTGTACTCAACGCCTCCACCTTGGCTCTGGCCCTGGCCAACCTCAATGGGT
CCAGGCAGCGGTCGGGGGACAACCTCGTGTGCCACGCCCGTGACGGCAGCATCCTGGCTGGC
TCCTGCCTCTATGTTGGCCTGCCCCAGAGAAACCCGTCAACATCAGCTGCTGGTCCAAGAA
CATGAAGGACTTGACCTGCCGCTGGACGCCAGGGGCCCACGGGGAGACCTTCCTCCACACCA
ACTACTCCCTCAAGTACAAGCTTAGGTGGTATGGCCAGGACAACACATGTGAGGAGTACCAC
ACAGTGGGGCCCCACTCCTGCCACATCCCCAAGGACCTGGCTCTCTTTACGCCCTATGAGAT
CTGGGTGGAGGCCACCAACCGCCTGGGCTCTGCCCGCTCCGATGTACTCACGCTGGATATCC
TGGATGTGGTGACCACGGACCCCCCGCCCGACGTGCACGTGAGCCGCGTCGGGGGCCTGGAG
GACCAGCTGAGCGTGCGCTGGGTGTCGCCACCCGCCCTCAAGGATTTCCTCTTTCAAGCCAA
ATACCAGATCCGCTACCGAGTGGAGGACAGTGTGGACTGGAAGGTGGTGGACGATGTGAGCA
ACCAGACCTCCTGCCGCCTGGCCGGCCTGAAACCCGGCACCGTGTACTTCGTGCAAGTGCGC
TGCAACCCCTTTGGCATCTATGGCTCCAAGAAAGCCGGGATCTGGAGTGAGTGGAGCCACCC
CACAGCCGCCTCCACTCCCCGCAGTGAGCGCCCGGGCCCGGGCGGCGGGGCGTGCGAACCGC
GGGGCGGAGAGCCGAGCTCGGGGCCGGTGCGGCGCGAGCTCAAGCAGTTCCTGGGCTGGCTC
AAGAAGCACGCGTACTGCTCCAACCTCAGCTTCCGCCTCTACGACCAGTGGCGAGCCTGGAT
GCAGAAGTCGCACAAGACCCGCAACCAGGACGAGGGGATCCTGCCCTCGGGCAGACGGGGCA
CGGCGAGAGGTCCTGCCAGATAAGCTGTAGGGGCTCAGGCCACCCTCCCTGCCACGTGGAGA
CGCAGAGGCCGAACCCAAACTGGGGCCACCTCTGTACCCTCACTTCAGGGCACCTGAGCCAC
CCTCAGCAGGAGCTGGGGTGGCCCCTGAGCTCCAACGGCCATAACAGCTCTGACTCCCACGT
GAGGCCACCTTTGGGTGCACCCCAGTGGGTGTGTGTGTGTGTGAGGGTTGGTTGAGTTGC
CTAGAACCCCTGCCAGGGCTGGGGGTGAGAAGGGGAGTCATTACTCCCCATTACCTAGGGCC
CCTCCAAAAGAGTCCTTTTAAATAAATGAGCTATTTAGGTGCTGTGATTGTGAAAAAAAAAA
AAAAAAAAAAAAAAAAAAAAAAAAAAAAAAAAAAACAAAAAAAAAAAAAA

FIGURE 14

```
><ss.DNA38113
><subunit 1 of 1, 422 aa, 1 stop
><MW: 46302, pI: 9.42, NX(S/T): 6
MPAGRRGPAAQSARRPPPLLPLLLLLCVLGAPRAGSGAHTAVISPQDPTLLIGSSLLATCSV
HGDPPGATAEGLYWTLNGRRLPPELSRVLNASTLALALANLNGSRQRSGDNLVCHARDGSIL
AGSCLYVGLPPEKPVNISCWSKNMKDLTCRWTPGAHGETFLHTNYSLKYKLRWYGQDNTCEE
YHTVGPHSCHIPKDLALFTPYEIWVEATNRLGSARSDVLTLDILDVVTTDPPPDVHVSRVGG
LEDQLSVRWVSPPALKDFLFQAKYQIRYRVEDSVDWKVVDDVSNQTSCRLAGLKPGTVYFVQ
VRCNPFGIYGSKKAGIWSEWSHPTAASTPRSERPGPGGGACEPRGGEPSSGPVRRELKQFLG
WLKKHAYCSNLSFRLYDQWRAWMQKSHKTRNQDEGILPSGRRGTARGPAR
```

Signal sequence.
amino acids 1-30

Transmembrane domain.
amino acids 44-61

N-glycosylation sites.
amino acids 92-96, 104-108, 140-144, 168-172, 292-296, 382-386 cAMP- and cGMP-dependent protein kinase phosphorylation site.
amino acids 413-417

N-myristoylation sites.
amino acids 30-36, 37-43, 73-79, 121-127, 179-185, 218-224, 300-306, 317-323, 320-326, 347-353, 355-361, 407-413

Amidation site.
amino acids 3-7, 79-83, 411-415

Growth factor and cytokines receptors family signature 2.
amino acids 325-331

FIGURE 15

CCCACGCGTCCGCTGGTGTTAGATCGAGCAACCCTCTAAAAGCAGTTTAGAGTGGTAAAAAA
AAAAAAAAACACACCAAACGCTCGCAGCCACAAAAGGG<u>ATG</u>AAATTTCTTCTGGACATCCTC
CTGCTTCTCCCGTTACTGATCGTCTGCTCCCTAGAGTCCTTCGTGAAGCTTTTTATTCCTAA
GAGGAGAAAATCAGTCACCGGCGAAATCGTGCTGATTACAGGAGCTGGGCATGGAATTGGGA
GACTGACTGCCTATGAATTTGCTAAACTTAAAAGCAAGCTGGTTCTCTGGGATATAAATAAG
CATGGACTGGAGGAAACAGCTGCCAAATGCAAGGGACTGGGTGCCAAGGTTCATACCTTTGT
GGTAGACTGCAGCAACCGAGAAGATATTTACAGCTCTGCAAAGAAGGTGAAGGCAGAAATTG
GAGATGTTAGTATTTTAGTAAATAATGCTGGTGTAGTCTATACATCAGATTTGTTTGCTACA
CAAGATCCTCAGATTGAAAAGACTTTTGAAGTTAATGTACTTGCACATTTCTGGACTACAAA
GGCATTTCTTCCTGCAATGACGAAGAATAACCATGGCCATATTGTCACTGTGGCTTCGGCAG
CTGGACATGTCTCGGTCCCCTTCTTACTGGCTTACTGTTCAAGCAAGTTTGCTGCTGTTGGA
TTTCATAAAACTTTGACAGATGAACTGGCTGCCTTACAAATAACTGGAGTCAAAACAACATG
TCTGTGTCCTAATTTCGTAAACACTGGCTTCATCAAAAATCCAAGTACAAGTTTGGGACCCA
CTCTGGAACCTGAGGAAGTGGTAAACAGGCTGATGCATGGATTCTGACTGAGCAGAAGATG
ATTTTTATTCCATCTTCTATAGCTTTTTTAACAACATTGGAAAGGATCCTTCCTGAGCGTTT
CCTGGCAGTTTTAAAACGAAAATCAGTGTTAAGTTTGATGCAGTTATTGGATATAAAATGA
AAGCGCAA<u>TAA</u>GCACCTAGTTTTCTGAAAACTGATTTACCAGGTTTAGGTTGATGTCATCTA
ATAGTGCCAGAATTTTAATGTTTGAACTTCTGTTTTTTCTAATTATCCCCATTTCTTCAATA
TCATTTTTGAGGCTTTGGCAGTCTTCATTTACTACCACTTGTTCTTTAGCCAAAAGCTGATT
ACATATGATATAAACAGAGAAATACCTTTAGAGGTGACTTTAAGGAAAATGAAGAAAAGAA
CCAAAATGACTTTATTAAAATAATTTCCAAGATTATTTGTGGCTCACCTGAAGGCTTTGCAA
AATTTGTACCATAACCGTTTATTTAACATATATTTTATTTTTGATTGCACTTAAATTTTGT
ATAATTTGTGTTTCTTTTTCTGTTCTACATAAAATCAGAAACTTCAAGCTCTCTAAATAAAA
TGAAGGACTATATCTAGTGGTATTTCACAATGAATATCATGAACTCTCAATGGGTAGGTTTC
ATCCTACCCATTGCCACTCTGTTTCCTGAGAGATACCTCACATTCCAATGCCAAACATTTCT
GCACAGGGAAGCTAGAGGTGGATACACGTGTTGCAAGTATAAAAGCATCACTGGGATTTAAG
GAGAATTGAGAGAATGTACCCACAAATGGCAGCAATAATAAATGGATCACACTTAAAAAAAA
AAAAAAAAAAAAAAAAAAAAAAAAAAAAAAAAAAAAAAAAAAAAAAAAAAAAAAAAAAAAAA
AAAAAAAAAAAAAAAAAAAAAAAAAAAAAAAA

FIGURE 16

```
</usr/seqdb2/sst/DNA/Dnaseqs.full/ss.DNA34436
<subunit 1 of 1, 300 aa, 1 stop
<MW: 32964, pI: 9.52, NX(S/T): 1
MKFLLDILLLLPLLIVCSLESFVKLFIPKRRKSVTGEIVLITGAGHGIGRLTAYEFAKLKSK
LVLWDINKHGLEETAAKCKGLGAKVHTFVVDCSNREDIYSSAKKVKAEIGDVSILVNNAGVV
YTSDLFATQDPQIEKTFEVNVLAHFWTTKAFLPAMTKNNHGHIVTVASAAGHVSVPFLLAYC
SSKFAAVGFHKTLTDELAALQITGVKTTCLCPNFVNTGFIKNPSTSLGPTLEPEEVVNRLMH
GILTEQKMIFIPSSIAFLTTLERILPERFLAVLKRKISVKFDAVIGYKMKAQ Signal sequence.
amino acids 1-19

Transmembrane domain.
amino acids 170-187 cAMP- and cGMP-dependent protein kinase phosphorylation sites.
amino acids 30-34, 283-287

N-myristoylation sites.
amino acids 43-49, 72-78, 122-128, 210-216
```

FIGURE 17

GACTAGTTCTCTTGGAGTCTGGGAGGAGGAAAGCGGAGCCGGCAGGGAGCGAACCAGGACTG
GGGTGACGGCAGGGCAGGGGGCGCCTGGCCGGGGAGAAGCGCGGGGGCTGGAGCACCACCAA
CTGGAGGGTCCGGAGTAGCGAGCGCCCCGAAGGAGGCCATCGGGGAGCCGGGAGGGGGACT
GCGAGAGGACCCCGGCGTCCGGGCTCCCGGTGCCAGCGCATGAGGCCACTCCTCGTCCTGC
TGCTCCTGGGCCTGGCGGCCGGCTCGCCCCACTGGACGACAACAAGATCCCCAGCCTCTGC
CCGGGGCACCCCGGCCTTCCAGGCACGCCGGGCCACCATGGCAGCCAGGGCTTGCCGGGCCG
CGATGGCCGCGACGGCCGCGACGGCGCGCCCGGGGCTCCGGGAGAGAAAGGCGAGGGCGGGA
GGCCGGGACTGCCGGGACCTCGAGGGGACCCCGGGCCGCGAGGAGAGGCGGGACCCGCGGGG
CCCACCGGGCCTGCCGGGGAGTGCTCGGTGCCTCCGCGATCCGCCTTCAGCGCCAAGCGCTC
CGAGAGCCGGGTGCCTCCGCCGTCTGACGCACCCTTGCCCTTCGACCGCGTGCTGGTGAACG
AGCAGGGACATTACGACGCCGTCACCGGCAAGTTCACCTGCCAGGTGCCTGGGGTCTACTAC
TTCGCCGTCCATGCCACCGTCTACCGGGCCAGCCTGCAGTTTGATCTGGTGAAGAATGGCGA
ATCCATTGCCTCTTTCTTCCAGTTTTTCGGGGGGTGGCCCAAGCCAGCCTCGCTCTCGGGGG
GGGCCATGGTGAGGCTGGAGCCTGAGGACCAAGTGTGGGTGCAGGTGGGTGTGGGTGACTAC
ATTGGCATCTATGCCAGCATCAAGACAGACAGCACCTTCTCCGGATTTCTGGTGTACTCCGA
CTGGCACAGCTCCCCAGTCTTTGCTTAGTGCCCACTGCAAAGTGAGCTCATGCTCTCACTCC
TAGAAGGAGGGTGTGAGGCTGACAACCAGGTCATCCAGGAGGGCTGGCCCCCTGGAATATT
GTGAATGACTAGGGAGGTGGGGTAGAGCACTCTCCGTCCTGCTGCTGGCAAGGAATGGGAAC
AGTGGCTGTCTGCGATCAGGTCTGGCAGCATGGGGCAGTGGCTGGATTTCTGCCCAAGACCA
GAGGAGTGTGCTGTGCTGGCAAGTGTAAGTCCCCAGTTGCTCTGGTCCAGGAGCCCACGGT
GGGGTGCTCTCTTCCTGGTCCTCTGCTTCTCTGGATCCTCCCCACCCCCTCCTGCTCCTGGG
GCCGGCCCTTTTCTCAGAGATCACTCAATAAACCTAAGAACCCTCATAAAAAAAAAAAAAA
AAAAAAAAAAAA

FIGURE 18

></usr/seqdb2/sst/DNA/Dnaseqs.min/ss.DNA40592

><subunit 1 of 1, 243 aa, 1 stop

><MW: 25298, pI: 6.44, NX(S/T): 0

MRPLLVLLLLGLAAGSPPLDDNKIPSLCPGHPGLPGTPGHHGSQGLPGRDGRDGRDGAPGAP

GEKGEGGRPGLPGPRGDPGPRGEAGPAGPTGPAGECSVPPRSAFSAKRSESRVPPPSDAPLP

FDRVLVNEQGHYDAVTGKFTCQVPGVYYFAVHATVYRASLQFDLVKNGESIASFFQFFGGWP

KPASLSGGAMVRLEPEDQVWVQVGVGDYIGIYASIKTDSTFSGFLVYSDWHSSPVFA

Signal sequence.

amino acids 1-15

N-myristoylation sites.

amino acids 11-17, 68-74, 216-222

Cell attachment sequence.

amino acids 77-80

FIGURE 19

CTCTTTTGTCCACCAGCCCAGCCTGACTCCTGGAGATTGTGAATAGCTCCATCCAGCCTGAG
AAACAAGCCGGGTGGCTGAGCCAGGCTGTGCACGGAGCACCTGACGGGCCCAACAGACCCAT
GCTGCATCCAGAGACCTCCCCTGGCCGGGGGCATCTCCTGGCTGTGCTCCTGGCCCTCCTTG
GCACCACCTGGGCAGAGGTGTGGCCACCCCAGCTGCAGGAGCAGGCTCCGATGGCCGGAGCC
CTGAACAGGAAGGAGAGTTTCTTGCTCCTCTCCCTGCACAACCGCCTGCGCAGCTGGGTCCA
GCCCCTGCGGCTGACATGCGGAGGCTGGACTGGAGTGACAGCCTGGCCCAACTGGCTCAAG
CCAGGGCAGCCCTCTGTGGAATCCCAACCCCGAGCCTGGCATCCGGCCTGTGGCGCACCCTG
CAAGTGGGCTGGAACATGCAGCTGCTGCCCGCGGGCTTGGCGTCCTTTGTTGAAGTGGTCAG
CCTATGGTTTGCAGAGGGGCAGCGGTACAGCCACGCGGCAGGAGAGTGTGCTCGCAACGCCA
CCTGCACCCACTACACGCAGCTCGTGTGGGCCACCTCAAGCCAGCTGGGCTGTGGGCGGCAC
CTGTGCTCTGCAGGCCAGACAGCGATAGAAGCCTTTGTCTGTGCCTACTCCCCGGAGGCAA
CTGGGAGGTCAACGGGAAGACAATCATCCCCTATAAGAAGGGTGCCTGGTGTTCGCTCTGCA
CAGCCAGTGTCTCAGGCTGCTTCAAAGCCTGGGACCATGCAGGGGGCTCTGTGAGGTCCCC
AGGAATCCTTGTCGCATGAGCTGCCAGAACCATGGACGTCTCAACATCAGCACCTGCCACTG
CCACTGTCCCCCTGGCTACACGGGCAGATACTGCCAAGTGAGGTGCAGCCTGCAGTGTGTGC
ACGGCCGGTTCCGGGAGGAGGAGTGCTCGTGCGTCTGTGACATCGGCTACGGGGAGCCCAG
TGTGCCACCAAGGTGCATTTTCCCTTCCACACCTGTGACCTGAGGATCGACGGAGACTGCTT
CATGGTGTCTTCAGAGGCAGACACCTATTACAGAGCCAGGATGAAATGTCAGAGGAAAGGCG
GGGTGCTGGCCCAGATCAAGAGCCAGAAAGTGCAGGACATCCTCGCCTTCTATCTGGGCCGC
CTGGAGACCACCAACGAGGTGACTGACAGTGACTTCGAGACCAGGAACTTCTGGATCGGGCT
CACCTACAAGACCGCCAAGGACTCCTTCCGCTGGGCCACAGGGGAGCACCAGGCCTTCACCA
GTTTTGCCTTTGGGCAGCCTGACAACCACGGGCTGGTGTGGCTGAGTGCTGCCATGGGGTTT
GGCAACTGCGTGGAGCTGCAGGCTTCAGCTGCCTTCAACTGGAACGACCAGCGCTGCAAAAC
CCGAAACCGTTACATCTGCCAGTTTGCCCAGGAGCACATCTCCCGGTGGGGCCCAGGGTCCT
GAGGCCTGACCACATGGCTCCCTCGCCTGCCCTGGGAGCACCGGCTCTGCTTACCTGTCTGC
CCACCTGTCTGGAACAAGGGCCAGGTTAAGACCACATGCCTCATGTCCAAAGAGGTCTCAGA
CCTTGCACAATGCCAGAAGTTGGGCAGAGAGAGGCAGGGAGGCCAGTGAGGGCCAGGGAGTG
AGTGTTAGAAGAAGCTGGGGCCCTTCGCCTGCTTTTGATTGGGAAGATGGGCTTCAATTAGA
TGGCGAAGGAGAGGACACCGCCAGTGGTCCAAAAAGGCTGCTCTCTTCCACCTGGCCCAGAC
CCTGTGGGGCAGCGGAGCTTCCCTGTGGCATGAACCCCACGGGGTATTAAATTATGAATCAG
CTGAAAAAAAAAAAAA

FIGURE 20

</usr/seqdb2/sst/DNA/Dnaseqs.min/ss.DNA44176

<subunit 1 of 1, 455 aa, 1 stop

<MW: 50478, pI: 8.44, NX(S/T): 2

MLHPETSPGRGHLLAVLLALLGTTWAEVWPPQLQEQAPMAGALNRKESFLLLSLHNRLRSWV
QPPAADMRRLDWSDSLAQLAQARAALCGIPTPSLASGLWRTLQVGWNMQLLPAGLASFVEVV
SLWFAEGQRYSHAAGECARNATCTHYTQLVWATSSQLGCGRHLCSAGQTAIEAFVCAYSPGG
NWEVNGKTIIPYKKGAWCSLCTASVSGCFKAWDHAGGLCEVPRNPCRMSCQNHGRLNISTCH
CHCPPGYTGRYCQVRCSLQCVHGRFREEECSCVCDIGYGGAQCATKVHFPFHTCDLRIDGDC
FMVSSEADTYYRARMKCQRKGGVLAQIKSQKVQDILAFYLGRLETTNEVTDSDFETRNFWIG
LTYKTAKDSFRWATGEHQAFTSFAFGQPDNHGLVWLSAAMGFGNCVELQASAAFNWNDQRCK
TRNRYICQFAQEHISRWGPGS

Signal sequence.

amino acids 1-26

Transmembrane domain.

amino acids 110-124

N-glycosylation sites.

amino acids 144-148, 243-247 cAMP- and cGMP-dependent protein kinase phosphorylation site.

amino acids 45-49

N-myristoylation sites.

amino acids 22-28, 99-105, 131-137, 201-207, 213-219, 287-293, 288-294, 331-337, 398-404

Prokaryotic membrane lipoprotein lipid attachment site.

amino acids 204-215

EGF-like domain cysteine pattern signature.

amino acids 249-261, 280-292

C-type lectin domain signature.

amino acids 417-442

FIGURE 21

CGGACGCGTGGGCTGGGCGCTGCAAAGCGTGTCCCGCCGGGTCCCCGAGCGTCCCGCGCCCT
CGCCCCGCCATGCTCCTGCTGCTGGGGCTGTGCCTGGGGCTGTCCCTGTGTGTGGGGTCGCA
GGAAGAGGCGCAGAGCTGGGGCCACTCTTCGGAGCAGGATGGACTCAGGGTCCCGAGGCAAG
TCAGACTGTTGCAGAGGCTGAAAACCAAACCTTTGATGACAGAATTCTCAGTGAAGTCTACC
ATCATTTCCCGTTATGCCTTCACTACGGTTTCCTGCAGAATGCTGAACAGAGCTTCTGAAGA
CCAGGACATTGAGTTCCAGATGCAGATTCCAGCTGCAGCTTTCATCACCAACTTCACTATGC
TTATTGGAGACAAGGTGTATCAGGGCGAAATTACAGAGAGAGAAAAGAAGAGTGGTGATAGG
GTAAAAGAGAAAAGGAATAAAACCACAGAAGAAAATGGAGAGAAGGGGACTGAAATATTCAG
AGCTTCTGCAGTGATTCCCAGCAAGGACAAAGCCGCCTTTTTCCTGAGTTATGAGGAGCTTC
TGCAGAGGCGCCTGGGCAAGTACGAGCACAGCATCAGCGTGCGGCCCCAGCAGCTGTCCGGG
AGGCTGAGCGTGGACGTGAATATCCTGGAGAGCGCGGGCATCGCATCCCTGGAGGTGCTGCC
GCTTCACAACAGCAGGCAGAGGGGCAGTGGGCGCGGGGAAGATGATTCTGGGCCTCCCCAT
CTACTGTCATTAACCAAAATGAAACATTTGCCAACATAATTTTTAAACCTACTGTAGTACAA
CAAGCCAGGATTGCCCAGAATGGAATTTTGGGAGACTTTATCATTAGATATGACGTCAATAG
AGAACAGAGCATTGGGGACATCCAGGTTCTAAATGGCTATTTTGTGCACTACTTTGCTCCTA
AAGACCTTCCTCCTTTACCCAAGAATGTGGTATTCGTGCTTGACAGCAGTGCTTCTATGGTG
GGAACCAAACTCCGGCAGACCAAGGATGCCCTCTTCACAATTCTCCATGACCTCCGACCCCA
GGACCGTTTCAGTATCATTGGATTTTCCAACCGGATCAAAGTATGGAAGGACCACTTGATAT
CAGTCACTCCAGACAGCATCAGGGATGGGAAAGTGTACATTCACCATATGTCACCCACTGGA
GGCACAGACATCAACGGGGCCCTGCAGAGGGCATCAGGCTCCTCAACAAGTACGTGGCCCA
CAGTGGCATTGGAGACCGGAGCGTGTCCCTCATCGTCTTCCTGACGGATGGGAAGCCCACGG
TCGGGGAGACGCACACCCTCAAGATCCTCAACAACACCCGAGAGGCCGCCCGAGGCCAAGTC
TGCATCTTCACCATTGGCATCGGCAACGACGTGGACTTCAGGCTGCTGGAGAAACTGTCGCT
GGAGAACTGTGGCCTCACACGGCGCGTGCACGAGGAGGAGGACGCAGGCTCGCAGCTCATCG
GGTTCTACGATGAAATCAGGACCCCGCTCCTCTCTGACATCCGCATCGATTATCCCCCCAGC
TCAGTGGTGCAGGCCACCAAGACCCTGTTCCCCAACTACTTCAACGGCTCGGAGATCATCAT
TGCGGGGAAGCTGGTGGACAGGAAGCTGGATCACCTGCACGTGGAGGTCACCGCCAGCAACA
GTAAGAAATTCATCATCCTGAAGACAGATGTGCCTGTGCGGCCTCAGAAGGCAGGGAAAGAT
GTCACAGGAAGCCCCAGGCCTGGAGGCGATGGAGAGGGGACACCAACCACATCGAGCGTCT
CTGGAGCTACCTCACCACAAAGGAGCTGCTGAGCTCCTGGCTGCAAAGTGACGATGAACCGG
AGAAGGAGCGGCTGCGGCAGCGGGCCCAGGCCCTGGCTGTGAGCTACCGCTTCCTCACTCCC
TTCACCTCCATGAAGCTGAGGGGGCCGGTCCCACGCATGGATGGCCTGGAGGAGGCCCACGG
CATGTCGGCTGCCATGGGACCCGAACCGGTGGTGCAGAGCGTGCGAGGAGCTGGCACGCAGC
CAGGACCTTTGCTCAAGAAGCCAAACTCCGTCAAAAAAAACAAAACAAAACAAAAAAAAGA
CATGGGAGAGATGGTGTTTTTCCTCTCCACCACCTGGGGATACGATGAGAAGATGGCCACCT
GCAAGCCAGGAAGACGGCCCTCACCAGACACCATGTCTGCTGGCACCTTGATCTTGGACCTC
CCAGCCTCCAGAACTGTGAGAAATAAATGTGTTTTGTTTAAGCTAAAAAAAAAAAAAAAAAA
AAAAAAAAAAAAAAAAAAAAAAAAAAAAAAAAA

FIGURE 22

```
</usr/seqdb2/sst/DNA/Dnaseqs.min/ss.DNA44192
<subunit 1 of 1, 694 aa, 1 stop
<MW: 77400, pI: 9.54, NX(S/T): 6
```

MLLLLGLCLGLSLCVGSQEEAQSWGHSSEQDGLRVPRQVRLLQRLKTKPLMTEFSVKSTIIS
RYAFTTVSCRMLNRASEDQDIEFQMQIPAAAFITNFTMLIGDKVYQGEITEREKKSGDRVKE
KRNKTTEENGEKGTEIFRASAVIPSKDKAAFFLSYEELLQRRLGKYEHSISVRPQQLSGRLS
VDVNILESAGIASLEVLPLHNSRQRGSGRGEDDSGPPPSTVINQNETFANIIFKPTVVQQAR
IAQNGILGDFIIRYDVNREQSIGDIQVLNGYFVHYFAPKDLPPLPKNVVFVLDSSASMVGTK
LRQTKDALFTILHDLRPQDRFSIIGFSNRIKVWKDHLISVTPDSIRDGKVYIHHMSPTGGTD
INGALQRAIRLLNKYVAHSGIGDRSVSLIVFLTDGKPTVGETHTLKILNNTREAARGQVCIF
TIGIGNDVDFRLLEKLSLENCGLTRRVHEEEDAGSQLIGFYDEIRTPLLSDIRIDYPPSSVV
QATKTLFPNYFNGSEIIIAGKLVDRKLDHLHVEVTASNSKKFIILKTDVPVRPQKAGKDVTG
SPRPGGDGEGDTNHIERLWSYLTTKELLSSWLQSDDEPEKERLRQRAQALAVSYRFLTPFTS
MKLRGPVPRMDGLEEAHGMSAAMGPEPVVQSVRGAGTQPGPLLKKPNSVKKKQNKTKKRHGR
DGVFPLHHLGIR

Signal sequence.
amino acids 1-14

N-glycosylation sites.
amino acids 97-101, 127-131, 231-235, 421-425, 508-512, 674-678

Glycosaminoglycan attachment sites.
amino acids 213-217, 391-395

N-myristoylation sites.
amino acids 6-12, 10-16, 212-218, 370-376, 632-638, 638-644

FIGURE 23

CGGACGCGTGGGGTGCCCGACATGGCGAGTGTAGTGCTGCCGAGCGGATCCCAGTGTGCGGC
GGCAGCGGCGGCGGCGGCGCCTCCCGGGCTCCGGCTTCTGCTGTTGCTCTTCTCCGCCGCGG
CACTGATCCCCACAGGTGATGGGCAGAATCTGTTTACGAAAGACGTGACAGTGATCGAGGGA
GAGGTTGCGACCATCAGTTGCCAAGTCAATAAGAGTGACGACTCTGTGATTCAGCTACTGAA
TCCCAACAGGCAGACCATTTATTTCAGGGACTTCAGGCCTTTGAAGGACAGCAGGTTTCAGT
TGCTGAATTTTTCTAGCAGTGAACTCAAAGTATCATTGACAAACGTCTCAATTTCTGATGAA
GGAAGATACTTTTGCCAGCTCTATACCGATCCCCCACAGGAAAGTTACACCACCATCACAGT
CCTGGTCCCACCACGTAATCTGATGATCGATATCCAGAAAGACACTGCGGTGGAAGGTGAGG
AGATTGAAGTCAACTGCACTGCTATGGCCAGCAAGCCAGCCACGACTATCAGGTGGTTCAAA
GGGAACACAGAGCTAAAAGGCAAATCGGAGGTGGAAGAGTGGTCAGACATGTACACTGTGAC
CAGTCAGCTGATGCTGAAGGTGCACAAGGAGGACGATGGGGTCCCAGTGATCTGCCAGGTGG
AGCACCCTGCGGTCACTGGAAACCTGCAGACCCAGCGGTATCTAGAAGTACAGTATAAGCCT
CAAGTGCACATTCAGATGACTTATCCTCTACAAGGCTTAACCCGGGAAGGGGACGCGCTTGA
GTTAACATGTGAAGCCATCGGGAAGCCCCAGCCTGTGATGGTAACTTGGGTGAGAGTCGATG
ATGAAATGCCTCAACACGCCGTACTGTCTGGGCCCAACCTGTTCATCAATAACCTAAACAAA
ACAGATAATGGTACATACCGCTGTGAAGCTTCAAACATAGTGGGGAAAGCTCACTCGGATTA
TATGCTGTATGTATACGATCCCCCCACAACTATCCCTCCTCCCACAACAACCACCACCACCA
CCACCACCACCACCACCATCCTTACCATCATCACAGATTCCCGAGCAGGTGAAGAAGGC
TCGATCAGGGCAGTGGATCATGCCGTGATCGGTGGCGTCGTGGCGGTGGTGGTGTTCGCCAT
GCTGTGCTTGCTCATCATTCTGGGGCGCTATTTTGCCAGACATAAAGGTACATACTTCACTC
ATGAAGCCAAAGGAGCCGATGACGCAGCAGACGCAGACACAGCTATAATCAATGCAGAAGGA
GGACAGAACAACTCCGAAGAAAAGAAAGAGTACTTCATCTAGATCAGCCTTTTTGTTTCAAT
GAGGTGTCCAACTGGCCCTATTTAGATGATAAAGAGACAGTGATATTGG

FIGURE 24

```
</usr/seqdb2/sst/DNA/Dnaseqs.min/ss.DNA39518
<subunit 1 of 1, 440 aa, 1 stop
<MW: 48240, pI: 4.93, NX(S/T): 7
MASVVLPSGSQCAAAAAAAAPPGLRLLLLLLFSAAALIPTGDGQNLFTKDVTVIEGEVATISC
QVNKSDDSVIQLLNPNRQTIYFRDFRPLKDSRFQLLNFSSSELKVSLTNVSISDEGRYFCQL
YTDPPQESYTTITVLVPPRNLMIDIQKDTAVEGEEIEVNCTAMASKPATTIRWFKGNTELKG
KSEVEEWSDMYTVTSQLMLKVHKEDDGVPVICQVEHPAVTGNLQTQRYLEVQYKPQVHIQMT
YPLQGLTREGDALELTCEAIGKPQPVMVTWVRVDDEMPQHAVLSGPNLFINNLNKTDNGTYR
CEASNIVGKAHSDYMLYVYDPPTTIPPPTTTTTTTTTTTTILTIITDSRAGEEGSIRAVDH
AVIGGVVAVVVFAMLCLLIILGRYFARHKGTYFTHEAKGADDAADADTAIINAEGGQNNSEE
KKEYFI Signal sequence.
amino acids 1-36

Transmembrane domain.
amino acids 372-393

N-glycosylation sites.
amino acids 65-69, 99-103, 111-115, 163-167, 302-306, 306-310,
430-434

Tyrosine kinase phosphorylation sites.
amino acids 233-240, 319-328

N-myristoylation sites.
amino acids 9-15, 227-233, 307-313, 365-371, 376-382, 402-408,
411-417, 427-433, 428-432
```

FIGURE 25

```
GGGGCGGGTGGACGCGGACTCGAACGCAGTTGCTTCGGGACCCAGGACCCCCTCGGGCCCGA
CCCGCCAGGAAAGACTGAGGCCGCGGCCTGCCCCGCCCGGCTCCCTGCGCCGCCGCCGCCTC
CCGGGACAGAAGATGTGCTCCAGGGTCCCTCTGCTGCTGCCGCTGCTCCTGCTACTGGCCCT
GGGGCCTGGGGTGCAGGGCTGCCCATCCGGCTGCCAGTGCAGCCAGCCACAGACAGTCTTCT
GCACTGCCCGCCAGGGGACCACGGTGCCCCGAGACGTGCCACCCGACACGGTGGGGCTGTAC
GTCTTTGAGAACGGCATCACCATGCTCGACGCAAGCAGCTTTGCCGGCCTGCCGGGCCTGCA
GCTCCTGGACCTGTCACAGAACCAGATCGCCAGCCTGCGCCTGCCCGCCTGCTGCTGCTGG
ACCTCAGCCACAACAGCCTCCTGGCCCTGGAGCCCGGCATCCTGGACACTGCCAACGTGGAG
GCGCTGCGGCTGGCTGGTCTGGGGCTGCAGCAGCTGGACGAGGGGCTCTTCAGCCGCTTGCG
CAACCTCCACGACCTGGATGTGTCCGACAACCAGCTGGAGCGAGTGCCACCTGTGATCCGAG
GCCTCCGGGGCCTGACGCGCCTGCGGCTGGCCGGCAACACCCGCATTGCCCAGCTGCGGCCC
GAGGACCTGGCCGGCCTGGCTGCCCTGCAGGAGCTGGATGTGAGCAACCTAAGCCTGCAGGC
CCTGCCTGGCGACCTCTCGGGCCTCTTCCCCGCCTGCGGCTGCTGGCAGCTGCCCGCAACC
CCTTCAACTGCGTGTGCCCCCTGAGCTGGTTTGGCCCCTGGGTGCGCGAGAGCCACGTCACA
CTGGCCAGCCCTGAGGAGACGCGCTGCCACTTCCCGCCCAAGAACGCTGGCCGGCTGCTCCT
GGAGCTTGACTACGCCGACTTTGGCTGCCCAGCCACCACCACCACAGCCACAGTGCCCACCA
CGAGGCCCGTGGTGCGGGAGCCCACAGCCTTGTCTTCTAGCTTGGCTCCTACCTGGCTTAGC
CCCACAGCGCCGGCCACTGAGGCCCCAGCCCGCCCTCCACTGCCCCACCGACTGTAGGGCC
TGTCCCCCAGCCCCAGGACTGCCCACCGTCCACCTGCCTCAATGGGGGCACATGCCACCTGG
GGACACGGCACCACCTGGCGTGCTTGTGCCCCGAAGGCTTCACGGGCCTGTACTGTGAGAGC
CAGATGGGGCAGGGGACACGGCCCAGCCCTACACCAGTCACGCCGAGGCCACCACGGTCCCT
GACCCTGGGCATCGAGCCGGTGAGCCCCACCTCCCTGCGCGTGGGGCTGCAGCGCTACCTCC
AGGGGAGCTCCGTGCAGCTCAGGAGCCTCCGTCTCACCTATCGCAACCTATCGGGCCCTGAT
AAGCGGCTGGTGACGCTGCGACTGCCTGCCTCGCTCGCTGAGTACACGGTCACCCAGCTGCG
GCCCAACGCCACTTACTCCGTCTGTGTCATGCCTTTGGGGCCCGGGCGGGTGCCGGAGGGCG
AGGAGGCCTGCGGGGAGGCCCATACACCCCAGCCGTCCACTCCAACCACGCCCCAGTCACC
CAGGCCCGCGAGGGCAACCTGCCGCTCCTCATTGCGCCCGCCCTGGCCGCGGTGCTCCTGGC
CGCGCTGGCTGCGGTGGGGGCAGCCTACTGTGTGCGGCGGGGCGGGCCATGGCAGCAGCGG
CTCAGGACAAAGGGCAGGTGGGGCCAGGGGCTGGGCCCCTGGAACTGGAGGGAGTGAAGGTC
CCCTTGGAGCCAGGCCCGAAGGCAACAGAGGGCGGTGGAGAGGCCCTGCCCAGCGGGTCTGA
GTGTGAGGTGCCACTCATGGGCTTCCCAGGGCCTGGCCTCCAGTCACCCCTCCACGCAAAGC
CCTACATCTAAGCCAGAGAGAGACAGGGCAGCTGGGGCCGGGCTCTCAGCCAGTGAGATGGC
CAGCCCCCTCCTGCTGCCACACCACGTAAGTTCTCAGTCCCAACCTCGGGGATGTGTGCAGA
CAGGGCTGTGTGACCACAGCTGGGCCCTGTTCCCTCTGGACCTCGGTCTCCTCATCTGTGAG
ATGCTGTGGCCCAGCTGACGAGCCCTAACGTCCCAGAACCGAGTGCCTATGAGGACAGTGT
CCGCCCTGCCCTCCGCAACGTGCAGTCCCTGGGCACGGCGGGCCCTGCCATGTGCTGGTAAC
GCATGCCTGGGCCCTGCTGGGCTCTCCCACTCCAGGCGGACCCTGGGGGCCAGTGAAGGAAG
CTCCCGGAAAGAGCAGAGGGAGAGCGGGTAGGCGGCTGTGTGACTCTAGTCTTGGCCCCAGG
AAGCGAAGGAACAAAAGAAACTGGAAAGGAAGATGCTTTAGGAACATGTTTGCTTTTTTAA
AATATATATATATTTATAAGAGATCCTTTCCCATTTATTCTGGGAAGATGTTTTTCAAACTC
AGAGACAAGGACTTTGGTTTTTGTAAGACAAACGATGATATGAAGGCCTTTTGTAAGAAAAA
ATAAAAAAAAAAA
```

FIGURE 26

</usr/seqdb2/sst/DNA/Dnaseqs.min/ss.DNA44804

<subunit 1 of 1, 598 aa, 1 stop

<MW: 63030, pI: 7.24, NX(S/T): 3

MCSRVPLLLPLLLLLALGPGVQGCPSGCQCSQPQTVFCTARQGTTVPRDVPPDTVGLYVFEN
GITMLDASSFAGLPGLQLLDLSQNQIASLRLPRLLLLDLSHNSLLALEPGILDTANVEALRL
AGLGLQQLDEGLFSRLRNLHDLDVSDNQLERVPPVIRGLRGLTRLRLAGNTRIAQLRPEDLA
GLAALQELDVSNLSLQALPGDLSGLFPRLRLLAAARNPFNCVCPLSWFGPWVRESHVTLASP
EETRCHFPPKNAGRLLLELDYADFGCPATTTTATVPTTRPVVREPTALSSSLAPTWLSPTAP
ATEAPSPPSTAPPTVGPVPQPQDCPPSTCLNGGTCHLGTRHHLACLCPEGFTGLYCESQMGQ
GTRPSPTPVTPRPPRSLTLGIEPVSPTSLRVGLQRYLQGSSVQLRSLRLTYRNLSGPDKRLV
TLRLPASLAEYTVTQLRPNATYSVCVMPLGPGRVPEGEEACGEAHTPPAVHSNHAPVTQARE
GNLPLLIAPALAAVLLAALAAVGAAYCVRRGRAMAAAAQDKGQVGPGAGPLELEGVKVPLEP
GPKATEGGGEALPSGSECEVPLMGFPGPGLQSPLHAKPYI

Signal sequence.

amino acids 1-23

Transmembrane domain.

amino acids 501-522

N-glycosylation sites.

amino acids 198-202, 425-429, 453-457

Tyrosine kinase phosphorylation site.

amino acids 262-270

N-myristoylation sites.

amino acids 23-29, 27-33, 112-118, 273-279, 519-525, 565-571

Prokaryotic membrane lipoprotein lipid attachment site.

amino acids 14-25

EGF-like domain cysteine pattern signature.

amino acids 355-367

Leucine zipper pattern.

amino acids 122-144, 194-216

FIGURE 27

GGCACTAGGACAACCTTCTTCCCTTCTGCACCACTGCCCGTACCCTTACCCGCCCCGCCACC
TCCTTGCTACCCCACTCTTGAAACCACAGCTGTTGGCAGGGTCCCCAGCTC<u>ATG</u>CCAGCCTC
ATCTCCTTTCTTGCTAGCCCCCAAAGGGCCTCCAGGCAACATGGGGGGCCCAGTCAGAGAGC
CGGCACTCTCAGTTGCCCTCTGGTTGAGTTGGGGGGCAGCTCTGGGGCCGTGGCTTGTGCC
ATGGCTCTGCTGACCCAACAAACAGAGCTGCAGAGCCTCAGGAGAGAGGTGAGCCGGCTGCA
GGGGACAGGAGGCCCCTCCCAGAATGGGGAAGGGTATCCCTGGCAGAGTCTCCCGGAGCAGA
GTTCCGATGCCCTGGAAGCCTGGGAGAATGGGGAGAGATCCCGGAAAAGGAGAGCAGTGCTC
ACCCAAAAACAGAAGAAGCAGCACTCTGTCCTGCACCTGGTTCCCATTAACGCCACCTCCAA
GGATGACTCCGATGTGACAGAGGTGATGTGGCAACCAGCTCTTAGGCGTGGGAGAGGCCTAC
AGGCCCAAGGATATGGTGTCCGAATCCAGGATGCTGGAGTTTATCTGCTGTATAGCCAGGTC
CTGTTTCAAGACGTGACTTTCACCATGGGTCAGGTGGTGTCTCGAGAAGGCCAAGGAAGGCA
GGAGACTCTATTCCGATGTATAAGAAGTATGCCCTCCCACCCGGACCGGGCCTACAACAGCT
GCTATAGCGCAGGTGTCTTCCATTTACACCAAGGGGATATTCTGAGTGTCATAATTCCCCGG
GCAAGGGCGAAACTTAACCTCTCTCCACATGGAACCTTCCTGGGGTTTGTGAAACTG<u>TGA</u>TT
GTGTTATAAAAAGTGGCTCCAGCTTGGAAGACCAGGGTGGGTACATACTGGAGACAGCCAA
GAGCTGAGTATATAAAGGAGAGGGAATGTGCAGGAACAGAGGCATCTTCCTGGGTTTGGCTC
CCCGTTCCTCACTTTTCCCTTTTCATTCCCACCCCCTAGACTTTGATTTTACGGATATCTTG
CTTCTGTTCCCCATGGAGCTCCG

FIGURE 28

```
</usr/seqdb2/sst/DNA/Dnaseqs.min/ss.DNA52722
<subunit 1 of 1, 250 aa, 1 stop
<MW: 27433, pI: 9.85, NX(S/T): 2
MPASSPFLLAPKGPPGNMGGPVREPALSVALWLSWGAALGAVACAMALLTQQTELQSLRREV
SRLQGTGGPSQNGEGYPWQSLPEQSSDALEAWENGERSRKRRAVLTQKQKKQHSVLHLVPIN
ATSKDDSDVTEVMWQPALRRGRGLQAQGYGVRIQDAGVYLLYSQVLFQDVTFTMGQVVSREG
QGRQETLFRCIRSMPSHPDRAYNSCYSAGVFHLHQGDILSVIIPRARAKLNLSPHGTFLGFVKL
```

Signal sequence.
amino acids 1-40

N-glycosylation site.
amino acids 124-128

Tyrosine kinase phosphorylation site.
amino acids 156-164

N-myristoylation site.
amino acids 36-42, 40-46, 179-185, 242-248

Prokaryotic membrane lipoprotein lipid attachment site.
amino acids 34-45

FIGURE 29

CACTTTCTCCCTCTCTTCCTTTACTTTCGAGAAACCGCGCTTCCGCTTCTGGTCGCAGAGAC
CTCGGAGACCGCGCCGGGGAGACGGAGGTGCTGTGGGTGGGGGGGACCTGTGGCTGCTCGTA
CCGCCCCCACCCTCCTCTTCTGCACTGCCGTCCTCCGGAAGACCTTTTCCCCTGCTCTGTT
TCCTTCACCGAGTCTGTGCATCGCCCCGGACCTGGCCGGGAGGAGGCTTGGCCGGCGGGAGA
TGCTCTAGGGGCGGCGCGGGAGGAGCGGCCGGCGGGACGGAGGGCCCGGCAGGAAG<u>ATG</u>GGC
TCCCGTGGACAGGGACTCTTGCTGGCGTACTGCCTGCTCCTTGCCTTTGCCTCTGGCCTGGT
CCTGAGTCGTGTGCCCCATGTCCAGGGGAACAGCAGGAGTGGGAGGGGACTGAGGAGCTGC
CGTCGCCTCCGGACCATGCCGAGAGGGCTGAAGAACAACATGAAAAATACAGGCCCAGTCAG
GACCAGGGGCTCCCTGCTTCCCGGTGCTTGCGCTGCTGTGACCCCGGTACCTCCATGTACCC
GGCGACCGCCGTGCCCCAGATCAACATCACTATCTTGAAAGGGGAGAAGGGTGACCGCGGAG
ATCGAGGCCTCCAAGGGAAATATGGCAAAACAGGCTCAGCAGGGGCCAGGGCCACACTGGA
CCCAAAGGGCAGAAGGGCTCCATGGGGCCCCTGGGGAGCGGTGCAAGAGCCACTACGCCGC
CTTTTCGGTGGGCCGGAAGAAGCCCATGCACAGCAACCACTACTACCAGACGGTGATCTTCG
ACACGGAGTTCGTGAACCTCTACGACCACTTCAACATGTTCACCGGCAAGTTCTACTGCTAC
GTGCCCGGCCTCTACTTCTTCAGCCTCAACGTGCACACCTGGAACCAGAAGGAGACCTACCT
GCACATCATGAAGAACGAGGAGGAGGTGGTGATCTTGTTCGCGCAGGTGGGCGACCGCAGCA
TCATGCAAAGCCAGAGCCTGATGCTGGAGCTGCGAGAGCAGGACCAGGTGTGGGTACGCCTC
TACAAGGGCGAACGTGAGAACGCCATCTTCAGCGAGGAGCTGGACACCTACATCACCTTCAG
TGGCTACCTGGTCAAGCACGCCACCGAGCCC<u>TAG</u>CTGGCCGGCCACCTCCTTTCCTCTCGCC
ACCTTCCACCCCTGCGCTGTGCTGACCCCACCGCCTCTTCCCCGATCCCTGGACTCCGACTC
CCTGGCTTTGGCATTCAGTGAGACGCCCTGCACACACAGAAAGCCAAAGCGATCGGTGCTCC
CAGATCCGCAGCCTCTGGAGAGAGCTGACGGCAGATGAAATCACCAGGGCGGGGCACCCGC
GAGAACCCTCTGGGACCTTCCGCGGCCCTCTCTGCACACATCCTCAAGTGACCCCGCACGGC
GAGACGCGGGTGGCGGCAGGGCGTCCCAGGGTGCGGCACCGCGGCTCCAGTCCTTGGAAATA
ATTAGGCAAATTCTAAAGGTCTCAAAAGGAGCAAAGTAAACCGTGGAGGACAAAGAAAAGGG
TTGTTATTTTTGTCTTTCCAGCCAGCCTGCTGGCTCCCAAGAGAGAGGCCTTTTCAGTTGAG
ACTCTGCTTAAGAGAAGATCCAAAGTTAAAGCTCTGGGGTCAGGGGAGGGGCCGGGGCAGG
AAACTACCTCTGGCTTAATTCTTTTAAGCCACGTAGGAACTTTCTTGAGGGATAGGTGGACC
CTGACATCCCTGTGGCCTTGCCCAAGGGCTCTGCTGGTCTTTCTGAGTCACAGCTGCGAGGT
GATGGGGGCTGGGGCCCCAGGCGTCAGCCTCCCAGAGGGACAGCTGAGCCCCCTGCCTTGGC
TCCAGGTTGGTAGAAGCAGCCGAAGGGCTCCTGACAGTGGCCAGGGACCCCTGGGTCCCCCA
GGCCTGCAGATGTTTCTATGAGGGCAGAGCTCCTTGGTACATCCATGTGTGGCTCTGCTCC
ACCCCTGTGCCACCCCAGAGCCCTGGGGGTGGTCTCCATGCCTGCCACCCTGGCATCGGCT
TTCTGTGCCGCCTCCCACACAAATCAGCCCCAGAAGGCCCCGGGGCCTTGGCTTCTGTTTTT
TATAAAACACCTCAAGCAGCACTGCAGTCTCCCATCTCCTCGTGGGCTAAGCATCACCGCTT
CCACGTGTGTTGTGTTGGTTGGCAGCAAGGCTGATCCAGACCCCTTCTGCCCCACTGCCCT
CATCCAGGCCTCTGACCAGTAGCCTGAGAGGGCTTTTCTAGGCTTCAGAGCAGGGAGAG
CTGGAAGGGGCTAGAAAGCTCCCGCTTGTCTGTTTCTCAGGCTCCTGTGAGCCTCAGTCCTG
AGACCAGAGTCAAGAGGAAGTACACGTCCCAATCACCCGTGTCAGGATTCACTCTCAGGAGC
TGGGTGGCAGGAGAGGCAATAGCCCCTGTGGCAATTGCAGGACCAGCTGGAGCAGGGTTGCG
GTGTCTCCACGGTGCTCTCGCCCTGCCCATGGCCACCCCAGACTCTGATCTCCAGGAACCCC
ATAGCCCCTCTCCACCTCACCCCATGTTGATGCCCAGGGTCACTCTTGCTACCCGCTGGGCC
CCCAAACCCCGCTGCCTCTCTTCCTTCCCCCCATCCCCCACCTGGTTTTGACTAATCCTGC
TTCCCTCTCTGGGCCTGGCTGCCGGGATCTGGGGTCCCTAAGTCCCTCTCTTTAAAGAACTT
CTGCGGGTCAGACTCTGAAGCCGAGTTGCTGTGGGCGTGCCCGGAAGCAGAGCGCCACACTC
GCTGCTTAAGCTCCCCCAGCTCTTTCCAGAAAACATTAAACTCAGAATTGTGTTTTCAA

FIGURE 30

></usr/seqdb2/sst/DNA/Dnaseqs.min/ss.DNA41234

><subunit 1 of 1, 281 aa, 1 stop

><MW: 31743, pI: 6.83, NX(S/T): 1

MGSRGQGLLLAYCLLLAFASGLVLSRVPHVQGEQQEWEGTEELPSPPDHAERAEEQHEKYRP

SQDQGLPASRCLRCCDPGTSMYPATAVPQINITILKGEKGDRGDRGLQGKYGKTGSAGARGH

TGPKGQKGSMGAPGERCKSHYAAFSVGRKKPMHSNHYYQTVIFDTEFVNLYDHFNMFTGKFY

CYVPGLYFFSLNVHTWNQKETYLHIMKNEEEVVILFAQVGDRSIMQSQSLMLELREQDQVWV

RLYKGERENAIFSEELDTYITFSGYLVKHATEP

Signal sequence.
amino acids 1-25

N-glycosylation site.
amino acids 93-97

N-myristoylation sites.
amino acids 7-13, 21-27, 67-73, 117-123, 129-135

Amidation site.
amino acids 150-154

Cell attachment sequence.
amino acids 104-107

FIGURE 31

GCGGAGCATCCGCTGCGGTCCTCGCCGAGACCCCGCGCGGATTCGCCGGTCCTTCCCGCGG
GCGCGACAGAGCTGTCCTCGCACCTGGATGGCAGCAGGGGCGCCGGGGTCCTCTCGACGCCA
GAGAGAAATCTCATCATCTGTGCAGCCTTCTTAAAGCAAACTAAGACCAGAGGGAGGATTAT
CCTTGACCTTTGAAGACCAAAACTAAACTGAAATTTAAA<u>ATG</u>TTCTTCGGGGGAGAAGGGAG
CTTGACTTACACTTTGGTAATAATTTGCTTCCTGACACTAAGGCTGTCTGCTAGTCAGAATT
GCCTCAAAAGAGTCTAGAAGATGTTGTCATTGACATCCAGTCATCTCTTTCTAAGGGAATC
AGAGGCAATGAGCCCGTATATACTTCAACTCAAGAAGACTGCATTAATTCTTGCTGTTCAAC
AAAAAACATATCAGGGGACAAAGCATGTAACTTGATGATCTTCGACACTCGAAAAACAGCTA
GACAACCCAACTGCTACCTATTTTCTGTCCCAACGAGGAAGCCTGTCCATTGAAACCAGCA
AAAGGACTTATGAGTTACAGGATAATTACAGATTTTCCATCTTTGACCAGAAATTTGCCAAG
CCAAGAGTTACCCCAGGAAGATTCTCTCTTACATGGCCAATTTTCACAAGCAGTCACTCCCC
TAGCCCATCATCACACAGATTATTCAAAGCCCACCGATATCTCATGGAGAGACACACTTTCT
CAGAAGTTTGGATCCTCAGATCACCTGGAGAAACTATTTAAGATGGATGAAGCAAGTGCCCA
GCTCCTTGCTTATAAGGAAAAAGGCCATTCTCAGAGTTCACAATTTTCCTCTGATCAAGAAA
TAGCTCATCTGCTGCCTGAAAATGTGAGTGCGCTCCAGCTACGGTGGCAGTTGCTTCTCCA
CATACCACCTCGGCTACTCCAAAGCCCGCCACCCTTCTACCCACCAATGCTTCAGTGACACC
TTCTGGGACTTCCCAGCCACAGCTGGCCACCACAGCTCCACCTGTAACCACTGTCACTTCTC
AGCCTCCCACGACCCTCATTTCTACAGTTTTTACACGGGCTGCGGCTACACTCCAAGCAATG
GCTACAACAGCAGTTCTGACTACCACCTTTCAGGCACCTACGGACTCGAAAGGCAGCTTAGA
AACCATACCGTTTACAGAAATCTCCAACTTAACTTTGAACACAGGGAATGTGTATAACCCTA
CTGCACTTTCTATGTCAAATGTGGAGTCTTCCACTATGAATAAAACTGCTTCCTGGGAAGGT
AGGGAGGCCAGTCCAGGCAGTTCCTCCCAGGGCAGTGTTCCAGAAAATCAGTACGGCCTTCC
ATTTGAAAAATGGCTTCTTATCGGGTCCCTGCTCTTTGGTGTCCTGTTCCTGGTGATAGGCC
TCGTCCTCCTGGGTAGAATCCTTTCGGAATCACTCCGCAGGAAACGTTACTCAAGACTGGAT
TATTTGATCAATGGGATCTATGTGGACATC<u>TAA</u>GGATGGAACTCGGTGTCTCTTAATTCATT
TAGTAACCAGAAGCCCAAATGCAATGAGTTTCTGCTGACTTGCTAGTCTTAGCAGGAGGTTG
TATTTTGAAGACAGGAAAATGCCCCCTTCTGCTTTCCTTTTTTTTTTGGAGACAGAGTCTT
GCTCTGTTGCCCAGGCTGGAGTGCAGTAGCACGATCTCGGCTCTCACCGCAACCTCCGTCTC
CTGGGTTCAAGCGATTCTCCTGCCTCAGCCTCCTAAGTATCTGGGATTACAGGCATGTGCCA
CCACACCTGGGTGATTTTGTATTTTTAGTAGAGACGGGGTTTCACCATGTTGGTCAGGCTG
GTCTCAAACTCCTGACCTAGTGATCCACCCTCCTCGGCCTCCCAAAGTGCTGGGATTACAGG
CATGAGCCACCACAGCTGGCCCCCTTCTGTTTTATGTTTGGTTTTGAGAAGGAATGAAGTG
GGAACCAAATTAGGTAATTTTGGGTAATCTGTCTCTAAAATATTAGCTAAAAACAAAGCTCT
ATGTAAAGTAATAAAGTATAATTGCCATATAAATTTCAAAATTCAACTGGCTTTTATGCAAA
GAAACAGGTTAGGACATCTAGGTTCCAATTCATTCACATTCTTGGTTCCAGATAAAATCAAC
TGTTTATATCAATTTCTAATGGATTTGCTTTTCTTTTTATATGGATTCCTTTAAAACTTATT
CCAGATGTAGTTCCTTCCAATTAAATATTTGAATAAATCTTTTGTTACTCAA

FIGURE 32

></usr/seqdb2/sst/DNA/Dnaseqs.min/ss.DNA45410
><subunit 1 of 1, 431 aa, 1 stop
><MW: 46810, pI: 6.45, NX(S/T): 6

MFFGGEGSLTYTLVIICFLTLRLSASQNCLKKSLEDVVIDIQSSLSKGIRGNEPVYTSTQED
CINSCCSTKNISGDKACNLMIFDTRKTARQPNCYLFFCPNEEACPLKPAKGLMSYRIITDFP
SLTRNLPSQELPQEDSLLHGQFSQAVTPLAHHHTDYSKPTDISWRDTLSQKFGSSDHLEKLF
KMDEASAQLLAYKEKGHSQSSQFSSDQEIAHLLPENVSALPATVAVASPHTTSATPKPATLL
PTNASVTPSGTSQPQLATTAPPVTTVTSQPPTTLISTVFTRAAATLQAMATTAVLTTTFQAP
TDSKGSLETIPFTEISNLTLNTGNVYNPTALSMSNVESSTMNKTASWEGREASPGSSSQGSV
PENQYGLPFEKWLLIGSLLFGVLFLVIGLVLLGRILSESLRRKRYSRLDYLINGIYVDI

Signal sequence.
amino acids 1-25

Transmembrane domain.
amino acids 384-405

N-glycosylation sites.
amino acids 72-76, 222-226, 251-255, 327-331, 352-356 cAMP- and cGMP-dependent protein kinase phosphorylation site.
amino acids 415-419

Tyrosine kinase phosphorylation site.
amino acids 50-57

N-myristoylation sites.
amino acids 4-10, 48-54, 315-321

FIGURE 33

GCGGCACCTGGAAG<u>ATG</u>CGCCCATTGGCTGGTGGCCTGCTCAAGGTGGTGTTCGTGGTCTTC
GCCTCCTTGTGTGCCTGGTATTCGGGGTACCTGCTCGCAGAGCTCATTCCAGATGCACCCCT
GTCCAGTGCTGCCTATAGCATCCGCAGCATCGGGGAGAGGCCTGTCCTCAAAGCTCCAGTCC
CCAAAAGGCAAAATGTGACCACTGGACTCCCTGCCCATCTGACACCTATGCCTACAGGTTA
CTCAGCGGAGGTGGCAGAAGCAAGTACGCCAAAATCTGCTTTGAGGATAACCTACTTATGGG
AGAACAGCTGGGAAATGTTGCCAGAGGAATAAACATTGCCATTGTCAACTATGTAACTGGGA
ATGTGACAGCAACACGATGTTTTGATATGTATGAAGGCGATAACTCTGGACCGATGACAAAG
TTTATTCAGAGTGCTGCTCCAAAATCCCTGCTCTTCATGGTGACCTATGACGACGGAAGCAC
AAGACTGAATAACGATGCCAAGAATGCCATAGAAGCACTTGGAAGTAAAGAAATCAGGAACA
TGAAATTCAGGTCTAGCTGGGTATTTATTGCAGCAAAAGGCTTGGAACTCCCTTCCGAAATT
CAGAGAGAAAAGATCAACCACTCTGATGCTAAGAACAACAGATATTCTGGCTGGCCTGCAGA
GATCCAGATAGAAGGCTGCATACCCAAAGAACGAAGC<u>TGA</u>CACTGCAGGGTCCTGAGTAAAT
GTGTTCTGTATAAACAAATGCAGCTGGAATCGCTCAAGAATCTTATTTTTCTAAATCCAACA
GCCCATATTTGATGAGTATTTTGGGTTTGTTGTAAACCAATGAACATTTGCTAGTTGTATCA
AATCTTGGTACGCAGTATTTTTATACCAGTATTTTATGTAGTGAAGATGTCAATTAGCAGGA
AACTAAAATGAATGGAAATTCTTAAAAAAAAAA

FIGURE 34

```
></usr/seqdb2/sst/DNA/Dnaseqs.min/ss.DNA46777
><subunit 1 of 1, 235 aa, 1 stop
><MW: 25982, pI: 9.09, NX(S/T): 2
MRPLAGGLLKVVFVVFASLCAWYSGYLLAELIPDAPLSSAAYSIRSIGERPVLKAPVPKRQK
CDHWTPCPSDTYAYRLLSGGGRSKYAKICFEDNLLMGEQLGNVARGINIAIVNYVTGNVTAT
RCFDMYEGDNSGPMTKFIQSAAPKSLLFMVTYDDGSTRLNNDAKNAIEALGSKEIRNMKFRS
SWVFIAAKGLELPSEIQREKINHSDAKNNRYSGWPAEIQIEGCIPKERS
```

Signal sequence.
amino acids 1-20

N-glycosylation sites.
amino acids 120-124, 208-212

Glycosaminoglycan attachment site.
amino acids 80-84

N-myristoylation sites.
amino acids 81-87, 108-114, 119-125

SEQUENCE LISTING

<160> NUMBER OF SEQ ID NOS: 120

<210> SEQ ID NO 1
<211> LENGTH: 2454
<212> TYPE: DNA
<213> ORGANISM: Homo Sapien

<400> SEQUENCE: 1

```
ggactaatct gtgggagcag tttattccag tatcacccag ggtgcagcca           50
caccaggact gtgttgaagg gtgttttttt tcttttaaat gtaatacctc          100
ctcatctttt cttcttacac agtgtctgag aacatttaca ttatagataa          150
gtagtacatg gtggataact tctacttta ggaggactac tctcttctga           200
cagtcctaga ctggtcttct acactaagac accatgaagg agtatgtgct          250
cctattattc ctggctttgt gctctgccaa acccttcttt agcccttcac          300
acatcgcact gaagaatatg atgctgaagg atatggaaga cacagatgat          350
gatgatgatg atgatgatga tgatgatgat gatgaggaca actctctttt          400
tccaacaaga gagccaagaa gccattttt tccatttgat ctgtttccaa           450
tgtgtccatt tggatgtcag tgctattcac gagttgtaca ttgctcagat          500
ttaggtttga cctcagtccc aaccaacatt ccatttgata ctcgaatgct          550
tgatcttcaa aacaataaaa ttaaggaaat caaagaaaat gattttaaag          600
gactcacttc actttatggt ctgatcctga acaacaacaa gctaacgaag          650
attcacccaa aagcctttct aaccacaaag aagttgcgaa ggctgtatct          700
gtcccacaat caactaagtg aaataccact taatcttccc aaatcattag          750
cagaactcag aattcatgaa aataaagtta agaaaataca aaaggacaca          800
ttcaaaggaa tgaatgcttt acacgtttg gaaatgagtg caaaccctct           850
tgataataat gggatagagc cagggggcatt tgaagggggtg acggtgttcc         900
atatcagaat tgcagaagca aaactgacct cagttcctaa aggcttacca          950
ccaactttat tggagcttca cttagattat aataaaattt caacagtgga         1000
acttgaggat tttaaacgat acaagaact acaaggctg ggcctaggaa           1050
acaacaaaat cacagatatc gaaatggga gtcttgctaa cataccacgt          1100
gtgagagaaa tacatttgga aaacaataaa ctaaaaaaaa tcccttcagg         1150
attaccagag ttgaaatacc tccagataat cttccttcat tctaattcaa         1200
```

-continued

```
ttgcaagagt gggagtaaat gacttctgtc caacagtgcc aaagatgaag        1250
aaatctttat acagtgcaat aagtttattc aacaacccgg tgaaatactg        1300
ggaaatgcaa cctgcaacat ttcgttgtgt tttgagcaga atgagtgttc        1350
agcttgggaa ctttggaatg taataattag taattggtaa tgtccattta        1400
atataagatt caaaaatccc tacatttgga atacttgaac tctattaata        1450
atggtagtat tatatataca agcaaatatc tattctcaag tggtaagtcc        1500
actgacttat tttatgacaa gaaatttcaa cggaattttg ccaaactatt        1550
gatacataag gggttgagag aaacaagcat ctattgcagt ttcctttttg        1600
cgtacaaatg atcttacata aatctcatgc ttgaccattc ctttcttcat        1650
aacaaaaaag taagatattc ggtatttaac actttgttat caagcacatt        1700
ttaaaagaa ctgtactgta aatggaatgc ttgacttagc aaaatttgtg        1750
ctctttcatt tgctgttaga aaaacagaat taacaaagac agtaatgtga        1800
agagtgcatt acactattct tattctttag taacttgggt agtactgtaa        1850
tatttttaat catcttaaag tatgatttga tataatctta ttgaaattac        1900
cttatcatgt cttagagccc gtctttatgt ttaaaactaa tttcttaaaa        1950
taaagccttc agtaaatgtt cattaccaac ttgataaatg ctactcataa        2000
gagctggttt ggggctatag catatgcttt ttttttttta attattacct        2050
gatttaaaaa tctctgtaaa aacgtgtagt gtttcataaa atctgtaact        2100
cgcattttaa tgatccgcta ttataagctt ttaatagcat gaaaattgtt        2150
aggctatata acattgccac ttcaactcta aggaatattt ttgagatatc        2200
cctttggaag accttgcttg aagagcctg acactaaca attctacacc         2250
aaattgtctc ttcaaatacg tatggactgg ataactctga aaacacatc         2300
tagtataact gaataagcag agcatcaaat taaacagaca gaaaccgaaa        2350
gctctatata aatgctcaga gttctttatg tatttcttat tggcattcaa        2400
catatgtaaa atcagaaaac agggaaattt tcattaaaaa tattggtttg        2450
aaat                                                          2454
```

<210> SEQ ID NO 2
<211> LENGTH: 379
<212> TYPE: PRT
<213> ORGANISM: Homo Sapien

<400> SEQUENCE: 2

```
Met Lys Glu Tyr Val Leu Leu Leu Phe Leu Ala Leu Cys Ser Ala
 1               5                  10                  15

Lys Pro Phe Phe Ser Pro Ser His Ile Ala Leu Lys Asn Met Met
                20                  25                  30

Leu Lys Asp Met Glu Asp Thr Asp Asp Asp Asp Asp Asp
                35                  40                  45

Asp Asp Asp Asp Asp Glu Asp Asn Ser Leu Phe Pro Thr Arg Glu
                50                  55                  60

Pro Arg Ser His Phe Phe Pro Phe Asp Leu Pro Met Cys Pro
                65                  70                  75

Phe Gly Cys Gln Cys Tyr Ser Arg Val Val His Cys Ser Asp Leu
                80                  85                  90

Gly Leu Thr Ser Val Pro Thr Asn Ile Pro Phe Asp Thr Arg Met
```

```
                         95                 100                 105
Leu Asp Leu Gln Asn Asn Lys Ile Lys Glu Ile Lys Glu Asn Asp
                        110                 115                 120

Phe Lys Gly Leu Thr Ser Leu Tyr Gly Leu Ile Leu Asn Asn Asn
                        125                 130                 135

Lys Leu Thr Lys Ile His Pro Lys Ala Phe Leu Thr Thr Lys Lys
                        140                 145                 150

Leu Arg Arg Leu Tyr Leu Ser His Asn Gln Leu Ser Glu Ile Pro
                        155                 160                 165

Leu Asn Leu Pro Lys Ser Leu Ala Glu Leu Arg Ile His Glu Asn
                        170                 175                 180

Lys Val Lys Lys Ile Gln Lys Asp Thr Phe Lys Gly Met Asn Ala
                        185                 190                 195

Leu His Val Leu Glu Met Ser Ala Asn Pro Leu Asp Asn Asn Gly
                        200                 205                 210

Ile Glu Pro Gly Ala Phe Glu Gly Val Thr Val Phe His Ile Arg
                        215                 220                 225

Ile Ala Glu Ala Lys Leu Thr Ser Val Pro Lys Gly Leu Pro Pro
                        230                 235                 240

Thr Leu Leu Glu Leu His Leu Asp Tyr Asn Lys Ile Ser Thr Val
                        245                 250                 255

Glu Leu Glu Asp Phe Lys Arg Tyr Lys Glu Leu Gln Arg Leu Gly
                        260                 265                 270

Leu Gly Asn Asn Lys Ile Thr Asp Ile Glu Asn Gly Ser Leu Ala
                        275                 280                 285

Asn Ile Pro Arg Val Arg Glu Ile His Leu Glu Asn Asn Lys Leu
                        290                 295                 300

Lys Lys Ile Pro Ser Gly Leu Pro Glu Leu Lys Tyr Leu Gln Ile
                        305                 310                 315

Ile Phe Leu His Ser Asn Ser Ile Ala Arg Val Gly Val Asn Asp
                        320                 325                 330

Phe Cys Pro Thr Val Pro Lys Met Lys Lys Ser Leu Tyr Ser Ala
                        335                 340                 345

Ile Ser Leu Phe Asn Asn Pro Val Lys Tyr Trp Glu Met Gln Pro
                        350                 355                 360

Ala Thr Phe Arg Cys Val Leu Ser Arg Met Ser Val Gln Leu Gly
                        365                 370                 375

Asn Phe Gly Met

<210> SEQ ID NO 3
<211> LENGTH: 20
<212> TYPE: DNA
<213> ORGANISM: Artificial Sequence
<220> FEATURE:
<223> OTHER INFORMATION: Synthetic Oligonucleotide Probe

<400> SEQUENCE: 3
ggaaatgagt gcaaaccctc                                                 20

<210> SEQ ID NO 4
<211> LENGTH: 24
<212> TYPE: DNA
<213> ORGANISM: Artificial Sequence
<220> FEATURE:
<223> OTHER INFORMATION: Synthetic Oligonucleotide Probe

<400> SEQUENCE: 4
```

```
tcccaagctg aacactcatt ctgc                                            24
```

<210> SEQ ID NO 5
<211> LENGTH: 50
<212> TYPE: DNA
<213> ORGANISM: Artificial Sequence
<220> FEATURE:
<223> OTHER INFORMATION: Synthetic Oligonucleotide Probe

<400> SEQUENCE: 5

```
gggtgacggt gttccatatc agaattgcag aagcaaaact gacctcagtt                50
```

<210> SEQ ID NO 6
<211> LENGTH: 3441
<212> TYPE: DNA
<213> ORGANISM: Homo Sapien

<400> SEQUENCE: 6

```
cggacgcgtg ggcggacgcg tgggcccgcs gcaccgcccc cggcccggcc                50
ctccgccctc cgcactcgcg cctccctccc tccgcccgct cccgcgccct               100
cctccctccc tcctccccag ctgtcccgtt cgcgtcatgc cgagcctccc               150
ggccccgccg gccccgctgc tgctcctcgg gctgctgctg ctcggctccc               200
ggccggcccg cggcgccggc ccagagcccc ccgtgctgcc catccgttct               250
gagaaggagc cgctgcccgt tcggggagcg gcaggctgca ccttcggcgg               300
gaaggtctat gccttggacg agacgtggca cccggaccta gggcagccat               350
tcggggtgat gcgctgcgtg ctgtgcgcct gcgaggcgcc tcagtggggt               400
cgccgtacca ggggccctgg cagggtcagc tgcaagaaca tcaaaccaga               450
gtgcccaacc ccggcctgtg ggcagccgcg ccagctgccg ggacactgct               500
gccagacctg cccccaggag cgcagcagtt cggagcggca gccgagcggc               550
ctgtccttcg agtatccgcg ggacccggag catcgcagtt atagcgaccg               600
cggggagcca ggcgctgagg agcgggcccg tggtgacggc cacacggact               650
tcgtggcgct gctgacaggg ccgaggtcgc aggcggtggc acgagcccga               700
gtctcgctgc tgcgctctag cctccgcttc tctatctcct acaggcggct               750
ggaccgccct accaggatcc gcttctcaga ctccaatggc agtgtcctgt               800
ttgagcaccc tgcagccccc acccaagatg gcctggtctg tggggtgtgg               850
cgggcagtgc ctcggttgtc tctgcggctc cttagggcag aacagctgca               900
tgtggcactt gtgacactca ctcacccttc aggggaggtc tgggggcctc               950
tcatccggca ccgggccctg ctgcagagac cttcagtgcc atcctgact               1000 ctagaaggcc cccacagca gggcgtaggg ggcatcaccc tgctcactct               1050
cagtgacaca gaggactcct tgcatttttt gctgctcttc cgagggctgc               1100
tggaacccag gagtggggga ctaacccagg ttcccttgag gctccagatt               1150
ctacaccagg ggcagctact gcgagaactt caggccaatg tctcagccca               1200
ggaaccaggc tttgctgagg tgctgcccaa cctgacagtc caggagatgg               1250
actggctggt gctgggggag ctgcagatgg ccctggagtg ggcaggcagg               1300
ccagggctgc gcatcagtgg acacattgct gccaggaaga gctgcgacgt               1350
cctgcaaagt gtcctttgtg gggctgatgc cctgatccca gtccagacgg               1400
```

```
gtgctgccgg ctcagccagc ctcacgctgc taggaaatgg ctccctgatc      1450
tatcaggtgc aagtggtagg gacaagcagt gaggtggtgg ccatgacact      1500
ggagaccaag cctcagcgga gggatcagcg cactgtcctg tgccacatgg      1550
ctggactcca gccaggagga cacacggccg tgggtatctg ccctgggctg      1600
ggtgcccgag gggctcatat gctgctgcag aatgagctct tcctgaacgt      1650
gggcaccaag gacttcccag acggagagct tcggggggcac gtggctgccc      1700
tgccctactg tgggcatagc gcccgccatg acacgctgcc cgtgcccta       1750
gcaggagccc tggtgctacc ccctgtgaag agccaagcag cagggcacgc      1800
ctggcttcc ttggataccc actgtcacct gcactatgaa gtgctgctgg       1850
ctgggcttgg tggctcagaa caaggcactg tcactgccca cctccttggg      1900
cctcctggaa cgccagggcc tcggcggctg ctgaagggat tctatggctc      1950
agaggcccag ggtgtggtga aggacctgga gccggaactg ctgcggcacc      2000
tggcaaaagg catggcctcc ctgatgatca ccaccaaggg tagccccaga      2050
ggggagctcc gagggcaggt gcacatagcc aaccaatgtg aggttggcgg      2100
actgcgcctg gaggcggccg gggccgaggg ggtgcgggcg ctggggggctc     2150
cggatacagc ctctgctgcg ccgcctgtgg tgcctggtct cccggcccta     2200
gcgcccgcca aacctggtgg tcctgggcgg ccccgagacc ccaacacatg     2250
cttcttcgag gggcagcagc gcccccacgg ggctcgctgg gcgcccaact     2300
acgacccgct ctgctcactc tgcacctgcc agagacgaac ggtgatctgt      2350
gacccggtgg tgtgcccacc gcccagctgc ccacacccgg tgcaggctcc     2400
cgaccagtgc tgccctgttt gccctgagaa acaagatgtc agagacttgc     2450
cagggctgcc aaggagccgg gacccaggag agggctgcta ttttgatggt     2500
gaccggagct ggcgggcagc gggtacgcgg tggcaccccg ttgtgccccc     2550
ctttggctta attaagtgtg ctgtctgcac ctgcaagggg ggcactggag     2600
aggtgcactg tgagaaggtg cagtgtcccc ggctggcctg tgcccagcct     2650
gtgcgtgtca accccaccga ctgctgcaaa cagtgtccag tggggtcggg     2700
ggcccacccc cagctggggg accccatgca ggctgatggg ccccggggct     2750
gccgttttgc tgggcagtgg ttcccagaga gtcagagctg gcacccctca     2800
gtgcccccct ttggagagat gagctgtatc acctgcagat gtggggcagg     2850
ggtgcctcac tgtgagcggg atgactgttc actgccactg tcctgtggct     2900
cggggaagga gagtcgatgc tgttcccgct gcacggccca ccggcggccc     2950
ccagagacca gaactgatcc agagctggag aaagaagccg aaggctctta     3000
gggagcagcc agagggccaa gtgaccaaga ggatggggcc tgagctgggg     3050
aaggggtggc atcgaggacc ttcttgcatt ctcctgtggg aagcccagtg     3100
cctttgctcc tctgtcctgc ctctactccc acccccacta cctctgggaa     3150
ccacagctcc acaaggggga gaggcagctg gccagaccg aggtcacagc       3200
cactccaagt cctgccctgc cacctcggc ctctgtcctg gaagcccac        3250
cccctttcctc ctgtacataa tgtcactggc ttgttgggat ttttaattta    3300
tcttcactca gcaccaaggg cccccgacac tccactcctg ctgcccctga     3350
gctgagcaga gtcattattg gagagttttg tatttattaa acatttcttc     3400
```
tttcagtcaa aaaaaaaaaa aaaaaaaaaa aaaaaaaaaa a               3441

<210> SEQ ID NO 7
<211> LENGTH: 954
<212> TYPE: PRT
<213> ORGANISM: Homo Sapien

<400> SEQUENCE: 7

Met Pro Ser Leu Pro Ala Pro Pro Ala Pro Leu Leu Leu Leu Gly
 1               5                  10                  15

Leu Leu Leu Leu Gly Ser Arg Pro Ala Arg Gly Ala Gly Pro Glu
                20                  25                  30

Pro Pro Val Leu Pro Ile Arg Ser Glu Lys Glu Pro Leu Pro Val
                35                  40                  45

Arg Gly Ala Ala Gly Cys Thr Phe Gly Gly Lys Val Tyr Ala Leu
                50                  55                  60

Asp Glu Thr Trp His Pro Asp Leu Gly Gln Pro Phe Gly Val Met
                65                  70                  75

Arg Cys Val Leu Cys Ala Cys Glu Ala Pro Gln Trp Gly Arg Arg
                80                  85                  90

Thr Arg Gly Pro Gly Arg Val Ser Cys Lys Asn Ile Lys Pro Glu
                95                 100                 105

Cys Pro Thr Pro Ala Cys Gly Gln Pro Arg Gln Leu Pro Gly His
               110                 115                 120

Cys Cys Gln Thr Cys Pro Gln Glu Arg Ser Ser Ser Glu Arg Gln
               125                 130                 135

Pro Ser Gly Leu Ser Phe Glu Tyr Pro Arg Asp Pro Glu His Arg
               140                 145                 150

Ser Tyr Ser Asp Arg Gly Glu Pro Gly Ala Glu Glu Arg Ala Arg
               155                 160                 165

Gly Asp Gly His Thr Asp Phe Val Ala Leu Leu Thr Gly Pro Arg
               170                 175                 180

Ser Gln Ala Val Ala Arg Ala Arg Val Ser Leu Leu Arg Ser Ser
               185                 190                 195

Leu Arg Phe Ser Ile Ser Tyr Arg Arg Leu Asp Arg Pro Thr Arg
               200                 205                 210

Ile Arg Phe Ser Asp Ser Asn Gly Ser Val Leu Phe Glu His Pro
               215                 220                 225

Ala Ala Pro Thr Gln Asp Gly Leu Val Cys Gly Val Trp Arg Ala
               230                 235                 240

Val Pro Arg Leu Ser Leu Arg Leu Leu Arg Ala Glu Gln Leu His
               245                 250                 255

Val Ala Leu Val Thr Leu Thr His Pro Ser Gly Glu Val Trp Gly
               260                 265                 270

Pro Leu Ile Arg His Arg Ala Leu Ala Ala Glu Thr Phe Ser Ala
               275                 280                 285

Ile Leu Thr Leu Glu Gly Pro Pro Gln Gln Gly Val Gly Gly Ile
               290                 295                 300

Thr Leu Leu Thr Leu Ser Asp Thr Glu Asp Ser Leu His Phe Leu
               305                 310                 315

Leu Leu Phe Arg Gly Leu Leu Glu Pro Arg Ser Gly Gly Leu Thr
               320                 325                 330

Gln Val Pro Leu Arg Leu Gln Ile Leu His Gln Gly Gln Leu Leu
               335                 340                 345

-continued

```
Arg Glu Leu Gln Ala Asn Val Ser Ala Gln Glu Pro Gly Phe Ala
                350                 355                 360
Glu Val Leu Pro Asn Leu Thr Val Gln Glu Met Asp Trp Leu Val
            365                 370                 375
Leu Gly Glu Leu Gln Met Ala Leu Glu Trp Ala Gly Arg Pro Gly
        380                 385                 390
Leu Arg Ile Ser Gly His Ile Ala Ala Arg Lys Ser Cys Asp Val
    395                 400                 405
Leu Gln Ser Val Leu Cys Gly Ala Asp Ala Leu Ile Pro Val Gln
410                 415                 420
Thr Gly Ala Ala Gly Ser Ala Ser Leu Thr Leu Leu Gly Asn Gly
                425                 430                 435
Ser Leu Ile Tyr Gln Val Gln Val Val Gly Thr Ser Ser Glu Val
            440                 445                 450
Val Ala Met Thr Leu Glu Thr Lys Pro Gln Arg Arg Asp Gln Arg
        455                 460                 465
Thr Val Leu Cys His Met Ala Gly Leu Gln Pro Gly Gly His Thr
    470                 475                 480
Ala Val Gly Ile Cys Pro Gly Leu Gly Ala Arg Gly Ala His Met
485                 490                 495
Leu Leu Gln Asn Glu Leu Phe Leu Asn Val Gly Thr Lys Asp Phe
                500                 505                 510
Pro Asp Gly Glu Leu Arg Gly His Val Ala Ala Leu Pro Tyr Cys
            515                 520                 525
Gly His Ser Ala Arg His Asp Thr Leu Pro Val Pro Leu Ala Gly
        530                 535                 540
Ala Leu Val Leu Pro Pro Val Lys Ser Gln Ala Ala Gly His Ala
    545                 550                 555
Trp Leu Ser Leu Asp Thr His Cys His Leu His Tyr Glu Val Leu
560                 565                 570
Leu Ala Gly Leu Gly Gly Ser Glu Gln Gly Thr Val Thr Ala His
                575                 580                 585
Leu Leu Gly Pro Pro Gly Thr Pro Gly Pro Arg Arg Leu Leu Lys
            590                 595                 600
Gly Phe Tyr Gly Ser Glu Ala Gln Gly Val Val Lys Asp Leu Glu
        605                 610                 615
Pro Glu Leu Leu Arg His Leu Ala Lys Gly Met Ala Ser Leu Met
    620                 625                 630
Ile Thr Thr Lys Gly Ser Pro Arg Gly Glu Leu Arg Gly Gln Val
635                 640                 645
His Ile Ala Asn Gln Cys Glu Val Gly Gly Leu Arg Leu Glu Ala
                650                 655                 660
Ala Gly Ala Glu Gly Val Arg Ala Leu Gly Ala Pro Asp Thr Ala
            665                 670                 675
Ser Ala Ala Pro Pro Val Val Pro Gly Leu Pro Ala Leu Ala Pro
        680                 685                 690
Ala Lys Pro Gly Gly Pro Gly Arg Pro Arg Asp Pro Asn Thr Cys
    695                 700                 705
Phe Phe Glu Gly Gln Gln Arg Pro His Gly Ala Arg Trp Ala Pro
710                 715                 720
Asn Tyr Asp Pro Leu Cys Ser Leu Cys Thr Cys Gln Arg Arg Thr
                725                 730                 735
```

-continued

Val Ile Cys Asp Pro Val Val Cys Pro Pro Ser Cys Pro His
            740                 745                 750

Pro Val Gln Ala Pro Asp Gln Cys Cys Pro Val Cys Pro Glu Lys
            755                 760                 765

Gln Asp Val Arg Asp Leu Pro Gly Leu Pro Arg Ser Arg Asp Pro
            770                 775                 780

Gly Glu Gly Cys Tyr Phe Asp Gly Asp Arg Ser Trp Arg Ala Ala
            785                 790                 795

Gly Thr Arg Trp His Pro Val Val Pro Pro Phe Gly Leu Ile Lys
            800                 805                 810

Cys Ala Val Cys Thr Cys Lys Gly Gly Thr Gly Glu Val His Cys
            815                 820                 825

Glu Lys Val Gln Cys Pro Arg Leu Ala Cys Ala Gln Pro Val Arg
            830                 835                 840

Val Asn Pro Thr Asp Cys Cys Lys Gln Cys Pro Val Gly Ser Gly
            845                 850                 855

Ala His Pro Gln Leu Gly Asp Pro Met Gln Ala Asp Gly Pro Arg
            860                 865                 870

Gly Cys Arg Phe Ala Gly Gln Trp Phe Pro Glu Ser Gln Ser Trp
            875                 880                 885

His Pro Ser Val Pro Pro Phe Gly Glu Met Ser Cys Ile Thr Cys
            890                 895                 900

Arg Cys Gly Ala Gly Val Pro His Cys Glu Arg Asp Asp Cys Ser
            905                 910                 915

Leu Pro Leu Ser Cys Gly Ser Gly Lys Glu Ser Arg Cys Cys Ser
            920                 925                 930

Arg Cys Thr Ala His Arg Arg Pro Pro Glu Thr Arg Thr Asp Pro
            935                 940                 945

Glu Leu Glu Lys Glu Ala Glu Gly Ser
            950

<210> SEQ ID NO 8
<211> LENGTH: 44
<212> TYPE: DNA
<213> ORGANISM: Artificial Sequence
<220> FEATURE:
<223> OTHER INFORMATION: Synthetic Oligonucleotide probe

<400> SEQUENCE: 8
gactagttct agatcgcgag cggccgccct tttttttttt tttt        44

<210> SEQ ID NO 9
<211> LENGTH: 28
<212> TYPE: DNA
<213> ORGANISM: Artificial Sequence
<220> FEATURE:
<223> OTHER INFORMATION: Synthetic oligonucleotide probe

<400> SEQUENCE: 9
cggacgcgtg gggcctgcgc acccagct        28

<210> SEQ ID NO 10
<211> LENGTH: 36
<212> TYPE: DNA
<213> ORGANISM: Artificial Sequence
<220> FEATURE:
<223> OTHER INFORMATION: Synthetic oligonucleotide probe

<400> SEQUENCE: 10
gccgctcccc gaacgggcag cggctccttc tcagaa                                    36

<210> SEQ ID NO 11
<211> LENGTH: 36
<212> TYPE: DNA
<213> ORGANISM: Artificial Sequence
<220> FEATURE:
<223> OTHER INFORMATION: Synthetic oligonucleotide probe

<400> SEQUENCE: 11
ggcgcacagc acgcagcgca tcaccccgaa tggctc                                    36

<210> SEQ ID NO 12
<211> LENGTH: 26
<212> TYPE: DNA
<213> ORGANISM: Artificial Sequence
<220> FEATURE:
<223> OTHER INFORMATION: Synthetic Oligonucleotide Probe

<400> SEQUENCE: 12
gtgctgccca tccgttctga gaagga                                               26

<210> SEQ ID NO 13
<211> LENGTH: 22
<212> TYPE: DNA
<213> ORGANISM: Artificial Sequence
<220> FEATURE:
<223> OTHER INFORMATION: Synthetic oligonucleotide probe

<400> SEQUENCE: 13
gcagggtgct caaacaggac ac                                                   22

<210> SEQ ID NO 14
<211> LENGTH: 3231
<212> TYPE: DNA
<213> ORGANISM: Homo Sapien

<400> SEQUENCE: 14
ggcggagcag ccctagccgc caccgtcgct ctcgcagctc tcgtcgccac                      50
tgccaccgcc gccgccgtca ctgcgtcctg gctccggctc ccgcgccctc                     100
ccggccggcc atgcagcccc gccgcgccca ggcgcccggt gcgcagctgc                     150
tgcccgcgct ggccctgctg ctgctgctgc tcggagcggg gccccgaggc                     200
agctccctgg ccaacccggt gcccgccgcg cccttgtctg cgcccgggcc                     250
gtgcgccgcg cagccctgcc ggaatggggg tgtgtgcacc tcgcgccctg                     300
agccggaccc gcagcacccg gccccgccg gcgagcctgg ctacagctgc                      350
acctgccccg ccgggatctc cggcgccaac tgccagcttg ttgcagatcc                     400
ttgtgccagc aacccttgtc accatggcaa ctgcagcagc agcagcagca                     450
gcagcagcga tggctacctc tgcatttgca atgaaggcta tgaaggtccc                     500
aactgtgaac aggcacttcc cagtctccca gccactggct ggaccgaatc                     550
catggcaccc cgacagcttc agcctgttcc tgctactcag gagcctgaca                     600
aaatcctgcc tcgctctcag gcaacggtga cactgcctac ctggcagccg                     650 aaaacgggc agaaagttgt agaaatgaaa tgggatcaag tggaggtgat                      700
cccagatatt gcctgtggga atgccagttc taacagctct gcgggtggcc                     750
gcctggtatc ctttgaagtg ccacagaaca cctcagtcaa gattcggcaa                     800
gatgccactg cctcactgat tttgctctgg aaggtcacgg ccacaggatt                     850

| | |
|---|---|
| ccaacagtgc tccctcatag atggacgaag tgtgacccccc cttcaggctt | 900 |
| caggggggact ggtcctcctg gaggagatgc tcgccttggg gaataatcac | 950 |
| tttattggtt ttgtgaatga ttctgtgact aagtctattg tggctttgcg | 1000 |
| cttaactctg gtggtgaagg tcagcacctg tgtgccgggg gagagtcacg | 1050 |
| caaatgactt ggagtgttca ggaaaaggaa aatgcaccac gaagccgtca | 1100 |
| gaggcaactt tttcctgtac ctgtgaggag cagtacgtgg gtactttctg | 1150 |
| tgaagaatac gatgcttgcc agaggaaacc ttgccaaaac aacgcgagct | 1200 |
| gtattgatgc aaatgaaaag caagatggga gcaatttcac ctgtgtttgc | 1250 |
| cttcctggtt atactggaga gctttgccag tccaagattg attactgcat | 1300 |
| cctagaccca tgcagaaatg gagcaacatg catttccagt ctcagtggat | 1350 |
| tcacctgcca gtgtccagaa ggatacttcg gatctgcttg tgaagaaaag | 1400 |
| gtggaccccct gcgcctcgtc tccgtgccag aacaacggca cctgctatgt | 1450 |
| ggacggggta cactttacct gcaactgcag cccgggcttc acagggccga | 1500 |
| cctgtgccca gcttattgac ttctgtgccc tcagcccctg tgctcatggc | 1550 |
| acgtgccgca gcgtgggcac cagctacaaa tgcctctgtg atccaggtta | 1600 |
| ccatggcctc tactgtgagg aggaatataa tgagtgcctc tccgctccat | 1650 |
| gcctgaatgc agccacctgc agggacctcg ttaatggcta tgagtgtgtg | 1700 |
| tgcctggcag aatacaaagg aacacactgt gaattgtaca aggatccctg | 1750 |
| cgctaacgtc agctgtctga acggagccac ctgtgacagc gacggcctga | 1800 |
| atggcacgtg catctgtgca cccgggttta caggtgaaga gtgcgacatt | 1850 |
| gacataaatg aatgtgacag taaccctgc caccatggtg ggagctgcct | 1900 |
| ggaccagccc aatggttata actgccactg cccgcatggt tgggtgggag | 1950 |
| caaactgtga gatccacctc aatggaagt ccgggcacat ggcggagagc | 2000 |
| ctcaccaaca tgccacggca ctccctctac atcatcattg gagccctctg | 2050 |
| cgtggccttc atccttatgc tgatcatcct gatcgtgggg atttgccgca | 2100 |
| tcagccgcat tgaataccag ggttcttcca ggccagccta tgaggagttc | 2150 |
| tacaactgcc gcagcatcga cagcgagttc agcaatgcca ttgcatccat | 2200 |
| ccggcatgcc aggtttggaa agaaatcccg gcctgcaatg tatgatgtga | 2250 |
| gccccatcgc ctatgaagat tacagtcctg atgacaaacc cttggtcaca | 2300 |
| ctgattaaaa ctaaagattt gtaatctttt tttggattat ttttcaaaaa | 2350 |
| gatgagatac tacactcatt taaatatttt taagaaaata aaaagcttaa | 2400 |
| gaaatttaaa atgctagctg ctcaagagtt ttcagtagaa tatttaagaa | 2450 |
| ctaattttct gcagctttta gtttggaaaa atatttaa aaacaaaatt | 2500 |
| tgtgaaacct atagacgatg ttttaatgta ccttcagctc tctaaactgt | 2550 |
| gtgcttctac tagtgtgtgc tcttttcact gtagacacta tcacgagacc | 2600 |
| cagattaatt tctgtggttg ttacagaata agtctaatca aggagaagtt | 2650 |
| tctgtttgac gtttgagtgc cggctttctg agtagagtta ggaaaaccac | 2700 |
| gtaacgtagc atatgatgta taatagagta tacccgttac ttaaaaagaa | 2750 |
| gtctgaaaatg ttcgttttgt ggaaaagaaa ctagttaaat ttactattcc | 2800 |

-continued

| | |
|---|---|
| taacccgaat gaaattagcc tttgccttat tctgtgcatg ggtaagtaac | 2850 |
| ttatttctgc actgttttgt tgaactttgt ggaaacattg tttcgagttt | 2900 |
| gttttttgtca ttttcgtaac agtcgtcgaa ctaggcctca aaaacatacg | 2950 |
| taacgaaaag gcctagcgag gcaaattctg attgatttga atctatattt | 3000 |
| ttctttaaaa agtcaagggt tctatattgt gagtaaatta aatttacatt | 3050 |
| tgagttgttt gttgctaaga ggtagtaaat gtaagagagt actggttcct | 3100 |
| tcagtagtga gtatttctca tagtgcagct ttatttatct ccaggatgtt | 3150 |
| tttgtggctg tatttgattg atatgtgctt cttctgattc ttgctaattt | 3200 |
| ccaaccatat tgaataaatg tgatcaagtc a | 3231 |

<210> SEQ ID NO 15
<211> LENGTH: 737
<212> TYPE: PRT
<213> ORGANISM: Homo Sapien

<400> SEQUENCE: 15

```
Met Gln Pro Arg Arg Ala Gln Ala Pro Gly Ala Gln Leu Leu Pro
 1               5                   10                  15

Ala Leu Ala Leu Leu Leu Leu Leu Gly Ala Gly Pro Arg Gly
                20                  25                  30

Ser Ser Leu Ala Asn Pro Val Pro Ala Pro Leu Ser Ala Pro
                35                  40                  45

Gly Pro Cys Ala Ala Gln Pro Cys Arg Asn Gly Gly Val Cys Thr
                50                  55                  60

Ser Arg Pro Glu Pro Asp Pro Gln His Pro Ala Pro Ala Gly Glu
                65                  70                  75

Pro Gly Tyr Ser Cys Thr Cys Pro Ala Gly Ile Ser Gly Ala Asn
                80                  85                  90

Cys Gln Leu Val Ala Asp Pro Cys Ala Ser Asn Pro Cys His His
                95                  100                 105

Gly Asn Cys Ser Ser Ser Ser Ser Ser Ser Ser Asp Gly Tyr Leu
                110                 115                 120

Cys Ile Cys Asn Glu Gly Tyr Glu Gly Pro Asn Cys Glu Gln Ala
                125                 130                 135

Leu Pro Ser Leu Pro Ala Thr Gly Trp Thr Glu Ser Met Ala Pro
                140                 145                 150

Arg Gln Leu Gln Pro Val Pro Ala Thr Gln Glu Pro Asp Lys Ile
                155                 160                 165

Leu Pro Arg Ser Gln Ala Thr Val Thr Leu Pro Thr Trp Gln Pro
                170                 175                 180

Lys Thr Gly Gln Lys Val Val Glu Met Lys Trp Asp Gln Val Glu
                185                 190                 195

Val Ile Pro Asp Ile Ala Cys Gly Asn Ala Ser Ser Asn Ser Ser
                200                 205                 210

Ala Gly Gly Arg Leu Val Ser Phe Glu Val Pro Gln Asn Thr Ser
                215                 220                 225

Val Lys Ile Arg Gln Asp Ala Thr Ala Ser Leu Ile Leu Leu Trp
                230                 235                 240

Lys Val Thr Ala Thr Gly Phe Gln Gln Cys Ser Leu Ile Asp Gly
                245                 250                 255

Arg Ser Val Thr Pro Leu Gln Ala Ser Gly Gly Leu Val Leu Leu
                260                 265                 270
```

-continued

```
Glu Glu Met Leu Ala Leu Gly Asn Asn His Phe Ile Gly Phe Val
            275                 280                 285

Asn Asp Ser Val Thr Lys Ser Ile Val Ala Leu Arg Leu Thr Leu
            290                 295                 300

Val Val Lys Val Ser Thr Cys Val Pro Gly Glu Ser His Ala Asn
            305                 310                 315

Asp Leu Glu Cys Ser Gly Lys Gly Lys Cys Thr Thr Lys Pro Ser
            320                 325                 330

Glu Ala Thr Phe Ser Cys Thr Cys Glu Gln Tyr Val Gly Thr
            335                 340                 345

Phe Cys Glu Glu Tyr Asp Ala Cys Gln Arg Lys Pro Cys Gln Asn
            350                 355                 360

Asn Ala Ser Cys Ile Asp Ala Asn Glu Lys Gln Asp Gly Ser Asn
            365                 370                 375

Phe Thr Cys Val Cys Leu Pro Gly Tyr Thr Gly Glu Leu Cys Gln
            380                 385                 390

Ser Lys Ile Asp Tyr Cys Ile Leu Asp Pro Cys Arg Asn Gly Ala
            395                 400                 405

Thr Cys Ile Ser Ser Leu Ser Gly Phe Thr Cys Gln Cys Pro Glu
            410                 415                 420

Gly Tyr Phe Gly Ser Ala Cys Glu Glu Lys Val Asp Pro Cys Ala
            425                 430                 435

Ser Ser Pro Cys Gln Asn Asn Gly Thr Cys Tyr Val Asp Gly Val
            440                 445                 450

His Phe Thr Cys Asn Cys Ser Pro Gly Phe Thr Gly Pro Thr Cys
            455                 460                 465

Ala Gln Leu Ile Asp Phe Cys Ala Leu Ser Pro Cys Ala His Gly
            470                 475                 480

Thr Cys Arg Ser Val Gly Thr Ser Tyr Lys Cys Leu Cys Asp Pro
            485                 490                 495

Gly Tyr His Gly Leu Tyr Cys Glu Glu Glu Tyr Asn Glu Cys Leu
            500                 505                 510

Ser Ala Pro Cys Leu Asn Ala Ala Thr Cys Arg Asp Leu Val Asn
            515                 520                 525

Gly Tyr Glu Cys Val Cys Leu Ala Glu Tyr Lys Gly Thr His Cys
            530                 535                 540

Glu Leu Tyr Lys Asp Pro Cys Ala Asn Val Ser Cys Leu Asn Gly
            545                 550                 555

Ala Thr Cys Asp Ser Asp Gly Leu Asn Gly Thr Cys Ile Cys Ala
            560                 565                 570

Pro Gly Phe Thr Gly Glu Glu Cys Asp Ile Asp Asn Glu Cys
            575                 580                 585

Asp Ser Asn Pro Cys His His Gly Gly Ser Cys Leu Asp Gln Pro
            590                 595                 600

Asn Gly Tyr Asn Cys His Cys Pro His Gly Trp Val Gly Ala Asn
            605                 610                 615

Cys Glu Ile His Leu Gln Trp Lys Ser Gly His Met Ala Glu Ser
            620                 625                 630

Leu Thr Asn Met Pro Arg His Ser Leu Tyr Ile Ile Gly Ala
            635                 640                 645

Leu Cys Val Ala Phe Ile Leu Met Leu Ile Ile Leu Ile Val Gly
            650                 655                 660
```

```
Ile Cys Arg Ile Ser Arg Ile Glu Tyr Gln Gly Ser Ser Arg Pro
            665                 670                 675

Ala Tyr Glu Glu Phe Tyr Asn Cys Arg Ser Ile Asp Ser Glu Phe
            680                 685                 690

Ser Asn Ala Ile Ala Ser Ile Arg His Ala Arg Phe Gly Lys Lys
            695                 700                 705

Ser Arg Pro Ala Met Tyr Asp Val Ser Pro Ile Ala Tyr Glu Asp
            710                 715                 720

Tyr Ser Pro Asp Asp Lys Pro Leu Val Thr Leu Ile Lys Thr Lys
            725                 730                 735

Asp Leu

<210> SEQ ID NO 16
<211> LENGTH: 43
<212> TYPE: DNA
<213> ORGANISM: Artificial Sequence
<220> FEATURE:
<223> OTHER INFORMATION: Synthetic Oligonucleotide Probe

<400> SEQUENCE: 16
tgtaaaacga cggccagtta aatagacctg caattattaa tct                  43

<210> SEQ ID NO 17
<211> LENGTH: 41
<212> TYPE: DNA
<213> ORGANISM: Artificial Sequence
<220> FEATURE:
<223> OTHER INFORMATION: Synthetic Oligonucleotide Probe

<400> SEQUENCE: 17
caggaaacag ctatgaccac ctgcacacct gcaaatccat t                    41

<210> SEQ ID NO 18
<211> LENGTH: 508
<212> TYPE: DNA
<213> ORGANISM: Homo Sapien

<400> SEQUENCE: 18
ctctggaagg tcacggccac aggattccaa cagtgctccc tcatagatgg            50
acgaaagtgt gaccccccctt tcaggctttc aggggggactg gtcctcctgg         100 aggagatgct cgccttgggg aataatcact ttattggttt tgtgaatgat           150
tctgtgacta agtctattgt ggctttgcgc ttaactctgg tggtgaaggt           200
cagcacctgt gtgccggggg agagtcacgc aaatgacttg gagtgttcag           250
gaaaaggaaa atgcaccacg aagccgtcag aggcaacttt ttcctgtacc           300
tgtgaggagc agtacgtggg tactttctgt gaagaatacg atgcttgcca           350
gaggaaacct tgccaaaaca acgcgagctg tattgatgca aatgaaaagc           400
aagatgggag caatttcacc tgtgtttgcc ttcctggtta tactggagag           450
ctttgccaac cgaactgaga ttggagcgaa cgacctacac cgaactgaga           500
tagggggag                                                       508

<210> SEQ ID NO 19
<211> LENGTH: 508
<212> TYPE: DNA
<213> ORGANISM: Homo Sapien

<400> SEQUENCE: 19
```

```
ctctggaagg tcacggccac aggattccaa cagtgctccc tcatagatgg        50
acgaaagtgt gacccccctt tcaggctttc aggggggactg gtcctcctgg       100 aggagatgct cgccttgggg aataatcact ttattggttt tgtgaatgat       150
tctgtgacta agtctattgt ggcttttgcgc ttaactctgg tggtgaaggt      200
cagcacctgt gtgccggggg agagtcacgc aaatgacttg gagtgttcag       250
gaaaaggaaa atgcaccacg aagccgtcag aggcaacttt ttcctgtacc       300
tgtgaggagc agtacgtggg tactttctgt gaagaatacg atgcttgcca       350
gaggaaacct tgccaaaaca acgcgagctg tattgatgca aatgaaaagc       400
aagatgggag caatttcacc tgtgtttgcc ttcctggtta tactggagag       450 cttttgccaac cgaactgaga ttggagcgaa cgacctacac cgaactgaga      500
taggggag                                                     508
```

<210> SEQ ID NO 20
<211> LENGTH: 23
<212> TYPE: DNA
<213> ORGANISM: Artificial Sequence
<220> FEATURE:
<223> OTHER INFORMATION: Synthetic Oligonucleotide Probe

<400> SEQUENCE: 20

```
ctctggaagg tcacggccac agg                                     23
```

<210> SEQ ID NO 21
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 21

```
ctcagttcgg ttggcaaagc tctc                                    24
```

<210> SEQ ID NO 22
<211> LENGTH: 69
<212> TYPE: DNA
<213> ORGANISM: Artificial Sequence
<220> FEATURE:
<223> OTHER INFORMATION: Synthetic oligonucleotide probe

<400> SEQUENCE: 22

```
cagtgctccc tcatagatgg acgaaagtgt gacccccctt tcaggcgaga        50
gctttgccaa ccgaactga                                          69
```

<210> SEQ ID NO 23
<211> LENGTH: 1520
<212> TYPE: DNA
<213> ORGANISM: Homo Sapien

<400> SEQUENCE: 23

```
gctgagtctg ctgctcctgc tgctgctgct ccagcctgta acctgtgcct        50
acaccacgcc aggccccccc agagccctca ccacgctggg cgccccccaga      100 gcccacacca tgccgggcac ctacgctccc tcgaccacac tcagtagtcc       150
cagcacccag ggcctgcaag agcaggcacg ggccctgatg cgggacttcc       200
cgctcgtgga cggccacaac gacctgcccc tggtcctaag gcaggtttac       250
cagaaagggc tacaggatgt taacctgcgc aatttcagct acggccagac       300
```

-continued

```
cagcctggac aggcttagag atggcctcgt gggcgcccag ttctggtcag        350
cctatgtgcc atgccagacc caggaccggg atgccctgcg cctcaccctg        400
gagcagattg acctcatacg ccgcatgtgt gcctcctatt ctgagctgga        450
gcttgtgacc tcggctaaag ctctgaacga cactcagaaa ttggcctgcc        500
tcatcggtgt agagggtggc cactcgctgg acaatagcct ctccatctta        550
cgtaccttct acatgctggg agtgcgctac ctgacgctca cccacacctg        600
caacacaccc tgggcagaga gctccgctaa gggcgtccac tccttctaca        650
acaacatcag cgggctgact gactttggtg agaaggtggt ggcagaaatg        700
aaccgcctgg gcatgatggt agacttatcc catgtctcag atgctgtggc        750
acggcgggcc ctggaagtgt cacaggcacc tgtgatcttc tcccactcgg        800
ctgcccgggg tgtgtgcaac agtgctcgga atgttcctga tgacatcctg        850
cagcttctga agaagaacgg tggcgtcgtg atggtgtctt tgtccatggg        900
agtaatacag tgcaacccat cagccaatgt gtccactgtg gcagatcact        950
tcgaccacat caaggctgtc attggatcca agttcatcgg gattggtgga       1000
gattatgatg gggccggcaa attccctcag gggctggaag acgtgtccac       1050
atacccggtc ctgatagagg agttgctgag tcgtggctgg agtgaggaag       1100
agcttcaggg tgtccttcgt ggaaacctgc tgcgggtctt cagacaagtg       1150
gaaaaggtac aggaagaaaa caatggcaa agccccttgg aggacaagtt        1200
cccggatgag cagctgagca gttcctgcca ctccgacctc tcacgtctgc       1250
gtcagagaca gagtctgact tcaggccagg aactcactga gattcccata       1300
cactggacag ccaagttacc agccaagtgg tcagtctcag agtcctcccc       1350
ccacatggcc ccagtccttg cagttgtggc accttcccca gtccttattc       1400
tgtggctctg atgacccagt tagtcctgcc agatgtcact gtagcaagcc       1450
acagacaccc cacaaagttc ccctgttgtg caggcacaaa tatttcctga       1500
aataaatgtt ttggacatag                                        1520
```

<210> SEQ ID NO 24
<211> LENGTH: 433
<212> TYPE: PRT
<213> ORGANISM: Homo Sapien

<400> SEQUENCE: 24

```
Met Pro Gly Thr Tyr Ala Pro Ser Thr Thr Leu Ser Ser Pro Ser
  1               5                  10                  15

Thr Gln Gly Leu Gln Glu Gln Ala Arg Ala Leu Met Arg Asp Phe
                 20                  25                  30

Pro Leu Val Asp Gly His Asn Asp Leu Pro Leu Val Leu Arg Gln
                 35                  40                  45

Val Tyr Gln Lys Gly Leu Gln Asp Val Asn Leu Arg Asn Phe Ser
                 50                  55                  60

Tyr Gly Gln Thr Ser Leu Asp Arg Leu Arg Asp Gly Leu Val Gly
                 65                  70                  75

Ala Gln Phe Trp Ser Ala Tyr Val Pro Cys Gln Thr Gln Asp Arg
                 80                  85                  90

Asp Ala Leu Arg Leu Thr Leu Glu Gln Ile Asp Leu Ile Arg Arg
                 95                 100                 105
```

-continued

```
Met Cys Ala Ser Tyr Ser Glu Leu Glu Leu Val Thr Ser Ala Lys
            110                 115                 120

Ala Leu Asn Asp Thr Gln Lys Leu Ala Cys Leu Ile Gly Val Glu
        125                 130                 135

Gly Gly His Ser Leu Asp Asn Ser Leu Ser Ile Leu Arg Thr Phe
        140                 145                 150

Tyr Met Leu Gly Val Arg Tyr Leu Thr Leu Thr His Thr Cys Asn
        155                 160                 165

Thr Pro Trp Ala Glu Ser Ser Ala Lys Gly Val His Ser Phe Tyr
        170                 175                 180

Asn Asn Ile Ser Gly Leu Thr Asp Phe Gly Glu Lys Val Val Ala
        185                 190                 195

Glu Met Asn Arg Leu Gly Met Met Val Asp Leu Ser His Val Ser
        200                 205                 210

Asp Ala Val Ala Arg Arg Ala Leu Glu Val Ser Gln Ala Pro Val
        215                 220                 225

Ile Phe Ser His Ser Ala Ala Arg Gly Val Cys Asn Ser Ala Arg
        230                 235                 240

Asn Val Pro Asp Asp Ile Leu Gln Leu Leu Lys Lys Asn Gly Gly
        245                 250                 255

Val Val Met Val Ser Leu Ser Met Gly Val Ile Gln Cys Asn Pro
        260                 265                 270

Ser Ala Asn Val Ser Thr Val Ala Asp His Phe Asp His Ile Lys
        275                 280                 285

Ala Val Ile Gly Ser Lys Phe Ile Gly Ile Gly Gly Asp Tyr Asp
        290                 295                 300

Gly Ala Gly Lys Phe Pro Gln Gly Leu Glu Asp Val Ser Thr Tyr
        305                 310                 315

Pro Val Leu Ile Glu Glu Leu Leu Ser Arg Gly Trp Ser Glu Glu
        320                 325                 330

Glu Leu Gln Gly Val Leu Arg Gly Asn Leu Leu Arg Val Phe Arg
        335                 340                 345

Gln Val Glu Lys Val Gln Glu Glu Asn Lys Trp Gln Ser Pro Leu
        350                 355                 360

Glu Asp Lys Phe Pro Asp Glu Gln Leu Ser Ser Ser Cys His Ser
        365                 370                 375

Asp Leu Ser Arg Leu Arg Gln Arg Gln Ser Leu Thr Ser Gly Gln
        380                 385                 390

Glu Leu Thr Glu Ile Pro Ile His Trp Thr Ala Lys Leu Pro Ala
        395                 400                 405

Lys Trp Ser Val Ser Glu Ser Ser Pro His Met Ala Pro Val Leu
        410                 415                 420

Ala Val Val Ala Thr Phe Pro Val Leu Ile Leu Trp Leu
        425                 430
```

<210> SEQ ID NO 25
<211> LENGTH: 22
<212> TYPE: DNA
<213> ORGANISM: Artificial Sequence
<220> FEATURE:
<223> OTHER INFORMATION: Synthetic oligonucleotide probe

<400> SEQUENCE: 25
agttctggtc agcctatgtg cc                                          22

```
<210> SEQ ID NO 26
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 26
cgtgatggtg tctttgtcca tggg                                         24

<210> SEQ ID NO 27
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 27
ctccaccaat cccgatgaac ttgg                                         24

<210> SEQ ID NO 28
<211> LENGTH: 50
<212> TYPE: DNA
<213> ORGANISM: Artificial Sequence
<220> FEATURE:
<223> OTHER INFORMATION: Synthetic oligonucleotide probe

<400> SEQUENCE: 28
gagcagattg acctcatacg ccgcatgtgt gcctcctatt ctgagctgga             50

<210> SEQ ID NO 29
<211> LENGTH: 1416
<212> TYPE: DNA
<213> ORGANISM: Homo Sapien

<400> SEQUENCE: 29
aaaacctata atattccgg attattcata ccgtcccacc atcgggcgcg              50
gatccgcggc cgcgaattct aaaccaacat gccgggcacc tacgctccct            100
cgaccacact cagtagtccc agcacccagg gcctgcaaga gcaggcacgg            150
gccctgatgc gggacttccc gctcgtggac ggccacaacg acctgcccct            200
ggtcctaagg caggtttacc agaaagggct acaggatgtt aacctgcgca            250
atttcagcta cggccagacc agcctggaca ggcttagaga tggcctcgtg            300
ggcgcccagt tctggtcagc ctatgtgcca tgccagaccc aggaccggga            350
tgccctgcgc ctcaccctgg agcagattga cctcatacgc cgcatgtgtg            400
cctcctattc tgagctggag cttgtgacct cggctaaagc tctgaacgac            450
actcagaaat tggcctgcct catcggtgta gagggtggcc actcgctgga            500
caatagcctc tccatcttac gtaccttcta catgctggga gtgcgctacc            550
tgacgctcac ccacacctgc aacacaccct gggcagagag ctccgctaag            600
ggcgtccact ccttctacaa caacatcagc gggctgactg actttggtga            650
gaaggtggtg gcagaaatga accgcctggg catgatggta gacttatccc            700
atgtctcaga tgctgtggca cggcgggccc tggaagtgtc acaggcacct            750
gtgatcttct cccactcggc tgcccggggt gtgtgcaaca gtgctcggaa            800
tgttcctgat gacatcctgc agcttctgaa gaagaacggt ggcgtcgtga            850
tggtgtcttt gtccatggga gtaatacagt gcaacccatc agccaatgtg            900
```

```
tccactgtgg cagatcactt cgaccacatc aaggctgtca ttggatccaa         950
gttcatcggg attggtggag attatgatgg ggccggcaaa ttccctcagg         1000
ggctggaaga cgtgtccaca tacccggtcc tgatagagga gttgctgagt         1050
cgtggctgga gtgaggaaga gcttcagggt gtccttcgtg aaacctgct          1100
gcgggtcttc agacaagtgg aaaaggtaca ggaagaaaac aaatggcaaa         1150
gccccttgga ggacaagttc ccggatgagc agctgagcag ttcctgccac         1200
tccgacctct cacgtctgcg tcagagacag agtctgactt caggccagga         1250
actcactgag attcccatac actggacagc caagttacca gccaagtggt         1300
cagtctcaga gtcctccccc caccctgaca aaactcacac atgcccaccg         1350
tgcccagcac ctgaactcct gggggaccg tcagtcttcc tcttcccccc          1400
aaaacccaag gacacc                                              1416
```

<210> SEQ ID NO 30
<211> LENGTH: 446
<212> TYPE: PRT
<213> ORGANISM: Homo Sapien

<400> SEQUENCE: 30

```
Met Pro Gly Thr Tyr Ala Pro Ser Thr Thr Leu Ser Ser Pro Ser
 1               5                  10                  15

Thr Gln Gly Leu Gln Glu Gln Ala Arg Ala Leu Met Arg Asp Phe
            20                  25                  30

Pro Leu Val Asp Gly His Asn Asp Leu Pro Leu Val Leu Arg Gln
            35                  40                  45

Val Tyr Gln Lys Gly Leu Gln Asp Val Asn Leu Arg Asn Phe Ser
            50                  55                  60

Tyr Gly Gln Thr Ser Leu Asp Arg Leu Arg Asp Gly Leu Val Gly
            65                  70                  75

Ala Gln Phe Trp Ser Ala Tyr Val Pro Cys Gln Thr Gln Asp Arg
            80                  85                  90

Asp Ala Leu Arg Leu Thr Leu Glu Gln Ile Asp Leu Ile Arg Arg
            95                 100                 105

Met Cys Ala Ser Tyr Ser Glu Leu Glu Leu Val Thr Ser Ala Lys
           110                 115                 120

Ala Leu Asn Asp Thr Gln Lys Leu Ala Cys Leu Ile Gly Val Glu
           125                 130                 135

Gly Gly His Ser Leu Asp Asn Ser Leu Ser Ile Leu Arg Thr Phe
           140                 145                 150

Tyr Met Leu Gly Val Arg Tyr Leu Thr Leu Thr His Thr Cys Asn
           155                 160                 165

Thr Pro Trp Ala Glu Ser Ser Ala Lys Gly Val His Ser Phe Tyr
           170                 175                 180

Asn Asn Ile Ser Gly Leu Thr Asp Phe Gly Glu Lys Val Val Ala
           185                 190                 195

Glu Met Asn Arg Leu Gly Met Met Val Asp Leu Ser His Val Ser
           200                 205                 210

Asp Ala Val Ala Arg Arg Ala Leu Glu Val Ser Gln Ala Pro Val
           215                 220                 225

Ile Phe Ser His Ser Ala Ala Arg Gly Val Cys Asn Ser Ala Arg
           230                 235                 240
```

-continued

```
Asn Val Pro Asp Asp Ile Leu Gln Leu Leu Lys Lys Asn Gly Gly
            245                 250                 255

Val Val Met Val Ser Leu Ser Met Gly Val Ile Gln Cys Asn Pro
            260                 265                 270

Ser Ala Asn Val Ser Thr Val Ala Asp His Phe Asp His Ile Lys
            275                 280                 285

Ala Val Ile Gly Ser Lys Phe Ile Gly Ile Gly Gly Asp Tyr Asp
            290                 295                 300

Gly Ala Gly Lys Phe Pro Gln Gly Leu Glu Asp Val Ser Thr Tyr
            305                 310                 315

Pro Val Leu Ile Glu Glu Leu Ser Arg Gly Trp Ser Glu Glu
            320                 325                 330

Glu Leu Gln Gly Val Leu Arg Gly Asn Leu Leu Arg Val Phe Arg
            335                 340                 345

Gln Val Glu Lys Val Gln Glu Glu Asn Lys Trp Gln Ser Pro Leu
            350                 355                 360

Glu Asp Lys Phe Pro Asp Glu Gln Leu Ser Ser Ser Cys His Ser
            365                 370                 375

Asp Leu Ser Arg Leu Arg Gln Arg Gln Ser Leu Thr Ser Gly Gln
            380                 385                 390

Glu Leu Thr Glu Ile Pro Ile His Trp Thr Ala Lys Leu Pro Ala
            395                 400                 405

Lys Trp Ser Val Ser Glu Ser Ser Pro His Pro Asp Lys Thr His
            410                 415                 420

Thr Cys Pro Pro Cys Pro Ala Pro Glu Leu Leu Gly Gly Pro Ser
            425                 430                 435

Val Phe Leu Phe Pro Pro Lys Pro Lys Asp Thr
            440                 445

<210> SEQ ID NO 31
<211> LENGTH: 1790
<212> TYPE: DNA
<213> ORGANISM: Homo Sapien

<400> SEQUENCE: 31
cgcccagcga cgtgcgggcg gcctggcccg cgccctcccg cgcccggcct          50
gcgtcccgcg ccctgcgcca ccgccgccga gccgcagccc gccgcgcgcc         100
cccggcagcg ccggccccat gcccgccggc cgccggggcc ccgccgccca         150
atccgcgcgg cggccgccgc cgttgctgcc cctgctgctg ctgctctgcg         200
tcctcggggc gccgcgagcc ggatcaggag cccacacagc tgtgatcagt         250
ccccaggatc ccacgcttct catcggctcc tccctgctgg ccacctgctc         300
agtgcacgga gacccaccag gagccaccgc cgagggcctc tactggaccc         350
tcaacgggcg ccgcctgccc cctgagctct cccgtgtact caacgcctcc         400
accttggctc tggccctggc caacctcaat gggtccaggc agcggtcggg         450
ggacaacctc gtgtgccacg cccgtgacgg cagcatcctg ctggctcct          500 gcctctatgt tggcctgccc ccagagaaac ccgtcaacat cagctgctgg         550
tccaagaaca tgaaggactt gacctgccgc tggacgccag ggcccacgg          600 ggagaccttc ctccacacca actactccct caagtacaag cttaggtggt         650
atggccagga caacacatgt gaggagtacc acacagtggg gccccactcc         700
tgccacatcc ccaaggacct ggctctcttt acgccctatg agatctgggt         750
```

-continued

```
ggaggccacc aaccgcctgg gctctgcccg ctccgatgta ctcacgctgg          800
atatcctgga tgtggtgacc acggaccccc cgcccgacgt gcacgtgagc          850
cgcgtcgggg gcctggagga ccagctgagc gtgcgctggg tgtcgccacc          900
cgccctcaag gatttcctct ttcaagccaa ataccagatc cgctaccgag          950
tggaggacag tgtggactgg aaggtggtgg acgatgtgag caaccagacc         1000
tcctgccgcc tggccggcct gaaacccggc accgtgtact tcgtgcaagt         1050
gcgctgcaac ccctttggca tctatggctc aagaaagcc gggatctgga          1100
gtgagtggag ccaccccaca gccgcctcca ctccccgcag tgagcgcccg         1150
ggcccgggcg gcggggcgtg cgaaccgcgg ggcggagagc cgagctcggg         1200
gccggtgcgg cgcgagctca agcagttcct gggctggctc aagaagcacg         1250
cgtactgctc caacctcagc ttccgcctct acgaccagtg gcgagcctgg         1300
atgcagaagt cgcacaagac ccgcaaccag gacgagggga tcctgccctc         1350
gggcagacgg ggcacggcga gaggtcctgc cagataagct gtaggggctc         1400
aggccaccct ccctgccacg tggagacgca gaggccgaac ccaaactggg         1450
gccacctctg taccctcact tcagggcacc tgagccaccc tcagcaggag         1500
ctggggtggc ccctgagctc caacggccat aacagctctg actcccacgt         1550
gaggccacct ttgggtgcac cccagtgggt gtgtgtgtgt gtgtgagggt         1600
tggttgagtt gcctagaacc cctgccaggg ctggggtga gaaggggagt          1650
cattactccc cattacctag ggcccctcca aagagtcct tttaaataaa          1700
tgagctattt aggtgctgtg attgtgaaaa aaaaaaaaa aaaaaaaaa           1750
aaaaaaaaaa aaaaaaaaaa aaaacaaaa aaaaaaaaa                      1790
```

<210> SEQ ID NO 32
<211> LENGTH: 422
<212> TYPE: PRT
<213> ORGANISM: Homo Sapien

<400> SEQUENCE: 32

```
Met Pro Ala Gly Arg Arg Gly Pro Ala Ala Gln Ser Ala Arg Arg
  1               5                  10                  15

Pro Pro Pro Leu Leu Pro Leu Leu Leu Leu Cys Val Leu Gly
                 20                  25                  30

Ala Pro Arg Ala Gly Ser Gly Ala His Thr Ala Val Ile Ser Pro
                 35                  40                  45

Gln Asp Pro Thr Leu Leu Ile Gly Ser Ser Leu Leu Ala Thr Cys
                 50                  55                  60

Ser Val His Gly Asp Pro Pro Gly Ala Thr Ala Glu Gly Leu Tyr
                 65                  70                  75

Trp Thr Leu Asn Gly Arg Arg Leu Pro Pro Glu Leu Ser Arg Val
                 80                  85                  90

Leu Asn Ala Ser Thr Leu Ala Leu Ala Leu Ala Asn Leu Asn Gly
                 95                 100                 105

Ser Arg Gln Arg Ser Gly Asp Asn Leu Val Cys His Ala Arg Asp
                110                 115                 120

Gly Ser Ile Leu Ala Gly Ser Cys Leu Tyr Val Gly Leu Pro Pro
                125                 130                 135

Glu Lys Pro Val Asn Ile Ser Cys Trp Ser Lys Asn Met Lys Asp
```

```
                    140                 145                 150
Leu Thr Cys Arg Trp Thr Pro Gly Ala His Gly Glu Thr Phe Leu
            155                 160                 165
His Thr Asn Tyr Ser Leu Lys Tyr Lys Leu Arg Trp Tyr Gly Gln
            170                 175                 180
Asp Asn Thr Cys Glu Glu Tyr His Thr Val Gly Pro His Ser Cys
            185                 190                 195
His Ile Pro Lys Asp Leu Ala Leu Phe Thr Pro Tyr Glu Ile Trp
            200                 205                 210
Val Glu Ala Thr Asn Arg Leu Gly Ser Ala Arg Ser Asp Val Leu
            215                 220                 225
Thr Leu Asp Ile Leu Asp Val Val Thr Thr Asp Pro Pro Pro Asp
            230                 235                 240
Val His Val Ser Arg Val Gly Gly Leu Glu Asp Gln Leu Ser Val
            245                 250                 255
Arg Trp Val Ser Pro Pro Ala Leu Lys Asp Phe Leu Phe Gln Ala
            260                 265                 270
Lys Tyr Gln Ile Arg Tyr Arg Val Glu Asp Ser Val Asp Trp Lys
            275                 280                 285
Val Val Asp Asp Val Ser Asn Gln Thr Ser Cys Arg Leu Ala Gly
            290                 295                 300
Leu Lys Pro Gly Thr Val Tyr Phe Val Gln Val Arg Cys Asn Pro
            305                 310                 315
Phe Gly Ile Tyr Gly Ser Lys Lys Ala Gly Ile Trp Ser Glu Trp
            320                 325                 330
Ser His Pro Thr Ala Ala Ser Thr Pro Arg Ser Glu Arg Pro Gly
            335                 340                 345
Pro Gly Gly Gly Ala Cys Glu Pro Arg Gly Gly Glu Pro Ser Ser
            350                 355                 360
Gly Pro Val Arg Arg Glu Leu Lys Gln Phe Leu Gly Trp Leu Lys
            365                 370                 375
Lys His Ala Tyr Cys Ser Asn Leu Ser Phe Arg Leu Tyr Asp Gln
            380                 385                 390
Trp Arg Ala Trp Met Gln Lys Ser His Lys Thr Arg Asn Gln Asp
            395                 400                 405
Glu Gly Ile Leu Pro Ser Gly Arg Arg Gly Thr Ala Arg Gly Pro
            410                 415                 420
Ala Arg

<210> SEQ ID NO 33
<211> LENGTH: 23
<212> TYPE: DNA
<213> ORGANISM: Artificial Sequence
<220> FEATURE:
<223> OTHER INFORMATION: Synthetic oligonucleotide probe

<400> SEQUENCE: 33
cccgcccgac gtgcacgtga gcc                                     23

<210> SEQ ID NO 34
<211> LENGTH: 23
<212> TYPE: DNA
<213> ORGANISM: Artificial Sequence
<220> FEATURE:
<223> OTHER INFORMATION: Synthetic oligonucleotide probe

<400> SEQUENCE: 34
```

```
<210> SEQ ID NO 35
<211> LENGTH: 50
<212> TYPE: DNA
<213> ORGANISM: Artificial Sequence
<220> FEATURE:
<223> OTHER INFORMATION: Synthetic oligonucleotide probe

<400> SEQUENCE: 35
caagtgcgct gcaaccccctt tggcatctat ggctccaaga aagccgggat         50

<210> SEQ ID NO 36
<211> LENGTH: 1771
<212> TYPE: DNA
<213> ORGANISM: Homo Sapien

<400> SEQUENCE: 36
cccacgcgtc cgctggtgtt agatcgagca accctctaaa agcagtttag         50
agtggtaaaa aaaaaaaaaa acacaccaaa cgctcgcagc cacaaaaggg        100
atgaaatttc ttctggacat cctcctgctt ctcccgttac tgatcgtctg        150
ctccctagag tccttcgtga agcttttttat tcctaagagg agaaaatcag        200
tcaccggcga aatcgtgctg attacaggag ctgggcatgg aattgggaga        250
ctgactgcct atgaatttgc taaacttaaa agcaagctgg ttctctggga        300
tataaataag catggactgg aggaaacagc tgccaaatgc aagggactgg        350
gtgccaaggt tcataccttt gtggtagact gcagcaaccg agaagatatt        400
tacagctctg caaagaaggt gaaggcagaa attggagatg ttagtatttt        450
agtaaataat gctggtgtag tctatacatc agatttgttt gctacacaag        500
atcctcagat tgaaaagact tttgaagtta atgtacttgc acatttctgg        550
actacaaagg catttcttcc tgcaatgacg aagaataacc atggccatat        600
tgtcactgtg gcttcggcag ctggacatgt ctcggtcccc ttcttactgg        650
cttactgttc aagcaagttt gctgctgttg gatttcataa aactttgaca        700
gatgaactgg ctgccttaca aataactgga gtcaaaacaa catgtctgtg        750
tcctaatttc gtaaacactg gcttcatcaa aaatccaagt acaagtttgg        800
gacccactct ggaacctgag gaagtggtaa acaggctgat gcatgggatt        850
ctgactgagc agaagatgat ttttattcca tcttctatag cttttttaac        900
aacattggaa aggatccttc ctgagcgttt cctggcagtt ttaaaacgaa        950
aaatcagtgt taagtttgat gcagttattg gatataaaat gaaagcgcaa       1000
taagcaccta gttttctgaa aactgattta ccaggtttag gttgatgtca       1050
tctaatagtg ccagaatttt aatgtttgaa cttctgtttt ttctaattat       1100
ccccatttct tcaatatcat ttttgaggct ttggcagtct tcatttacta       1150
ccacttgttc tttagccaaa agctgattac atatgatata aacagagaaa       1200 taccttttaga ggtgactttta aggaaaatga agaaaaagaa ccaaaatgac       1250
tttattaaaa taatttccaa gattatttgt ggctcacctg aaggctttgc       1300
aaaatttgta ccataaccgt ttatttaaca tatattttta tttttgattg       1350
cacttaaatt ttgtataatt tgtgtttctt tttctgttct acataaaatc       1400
```

```
-continued agaaacttca agctctctaa ataaaatgaa ggactatatc tagtggtatt         1450
tcacaatgaa tatcatgaac tctcaatggg taggtttcat cctacccatt         1500
gccactctgt ttcctgagag atacctcaca ttccaatgcc aaacatttct         1550
gcacagggaa gctagaggtg gatacacgtg ttgcaagtat aaaagcatca         1600
ctgggattta aggagaattg agagaatgta cccacaaatg gcagcaataa         1650
taaatggatc acacttaaaa aaaaaaaaaa aaaaaaaaaa aaaaaaaaaa         1700
aaaaaaaaaa aaaaaaaaaa aaaaaaaaaa aaaaaaaaaa aaaaaaaaaa         1750
aaaaaaaaaa aaaaaaaaa a                                        1771

<210> SEQ ID NO 37
<211> LENGTH: 300
<212> TYPE: PRT
<213> ORGANISM: Homo Sapien

<400> SEQUENCE: 37

Met Lys Phe Leu Leu Asp Ile Leu Leu Leu Pro Leu Leu Ile
  1               5                  10                  15

Val Cys Ser Leu Glu Ser Phe Val Lys Leu Phe Ile Pro Lys Arg
                 20                  25                  30

Arg Lys Ser Val Thr Gly Glu Ile Val Leu Ile Thr Gly Ala Gly
                 35                  40                  45

His Gly Ile Gly Arg Leu Thr Ala Tyr Glu Phe Ala Lys Leu Lys
                 50                  55                  60

Ser Lys Leu Val Leu Trp Asp Ile Asn Lys His Gly Leu Glu Glu
                 65                  70                  75

Thr Ala Ala Lys Cys Lys Gly Leu Gly Ala Lys Val His Thr Phe
                 80                  85                  90

Val Val Asp Cys Ser Asn Arg Glu Asp Ile Tyr Ser Ser Ala Lys
                 95                 100                 105

Lys Val Lys Ala Glu Ile Gly Asp Val Ser Ile Leu Val Asn Asn
                110                 115                 120

Ala Gly Val Val Tyr Thr Ser Asp Leu Phe Ala Thr Gln Asp Pro
                125                 130                 135

Gln Ile Glu Lys Thr Phe Glu Val Asn Val Leu Ala His Phe Trp
                140                 145                 150

Thr Thr Lys Ala Phe Leu Pro Ala Met Thr Lys Asn Asn His Gly
                155                 160                 165

His Ile Val Thr Val Ala Ser Ala Ala Gly His Val Ser Val Pro
                170                 175                 180

Phe Leu Leu Ala Tyr Cys Ser Ser Lys Phe Ala Ala Val Gly Phe
                185                 190                 195

His Lys Thr Leu Thr Asp Glu Leu Ala Ala Leu Gln Ile Thr Gly
                200                 205                 210

Val Lys Thr Thr Cys Leu Cys Pro Asn Phe Val Asn Thr Gly Phe
                215                 220                 225

Ile Lys Asn Pro Ser Thr Ser Leu Gly Pro Thr Leu Glu Pro Glu
                230                 235                 240

Glu Val Val Asn Arg Leu Met His Gly Ile Leu Thr Glu Gln Lys
                245                 250                 255

Met Ile Phe Ile Pro Ser Ser Ile Ala Phe Leu Thr Thr Leu Glu
                260                 265                 270

Arg Ile Leu Pro Glu Arg Phe Leu Ala Val Leu Lys Arg Lys Ile
```

275              280              285
Ser Val Lys Phe Asp Ala Val Ile Gly Tyr Lys Met Lys Ala Gln
         290              295              300

<210> SEQ ID NO 38
<211> LENGTH: 23
<212> TYPE: DNA
<213> ORGANISM: Artificial Sequence
<220> FEATURE:
<223> OTHER INFORMATION: Synthetic oligonucleotide probe

<400> SEQUENCE: 38
ggtgaaggca gaaattggag atg                                         23

<210> SEQ ID NO 39
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 39
atcccatgca tcagcctgtt tacc                                        24

<210> SEQ ID NO 40
<211> LENGTH: 48
<212> TYPE: DNA
<213> ORGANISM: Artificial Sequence
<220> FEATURE:
<223> OTHER INFORMATION: Synthetic oligonucleotide probe

<400> SEQUENCE: 40
gctggtgtag tctatacatc agatttgttt gctacacaag atcctcag              48

<210> SEQ ID NO 41
<211> LENGTH: 1377
<212> TYPE: DNA
<213> ORGANISM: Homo Sapien

<400> SEQUENCE: 41
gactagttct cttggagtct gggaggagga aagcggagcc ggcagggagc             50
gaaccaggac tggggtgacg gcagggcagg gggcgcctgg ccggggagaa            100 gcgcggggc tggagcacca ccaactggag ggtccggagt agcgagcgcc             150
ccgaaggagg ccatcgggga gccgggaggg gggactgcga gaggaccccg            200
gcgtccgggc tcccggtgcc agcgctatga ggccactcct cgtcctgctg            250
ctcctgggcc tggcggccgg ctcgccccca ctggacgaca caagatccc              300 cagcctctgc ccggggcacc ccggccttcc aggcacgccg ggccaccatg            350
gcagccaggg cttgccgggc cgcgatggcc gcgacggccg cgacgcgcg              400 cccgggggctc cgggagagaa aggcgagggc gggaggccgg gactgccggg            450
acctcgaggg gaccccgggc cgcgaggaga ggcgggaccc gcggggccca             500
ccgggcctgc cggggagtgc tcggtgcctc cgcgatccgc cttcagcgcc             550
aagcgctccg agagcgggt gcctccgccg tctgacgcac ccttgccctt              600
cgaccgcgtg ctggtgaacg agcagggaca ttacgacgcc gtcaccggca             650
agttcacctg ccaggtgcct ggggtctact acttcgccgt ccatgccacc             700
gtctaccggg ccagcctgca gtttgatctg gtgaagaatg gcgaatccat             750

```
tgcctctttc ttccagtttt tcggggggtg gcccaagcca gcctcgctct              800 cgggggggc  catggtgagg  ctggagcctg aggaccaagt  gtgggtgcag            850
gtgggtgtgg gtgactacat tggcatctat gccagcatca agacagacag              900
caccttctcc ggatttctgg tgtactccga ctggcacagc tccccagtct              950
ttgcttagtg cccactgcaa agtgagctca tgctctcact cctagaagga             1000
gggtgtgagg ctgacaacca ggtcatccag gagggctggc ccccctggaa             1050
tattgtgaat gactagggag gtggggtaga gcactctccg tcctgctgct             1100
ggcaaggaat gggaacagtg gctgtctgcg atcaggtctg gcagcatggg             1150
gcagtggctg gatttctgcc aagaccaga  ggagtgtgct gtgctggcaa             1200
gtgtaagtcc cccagttgct ctggtccagg agcccacggt ggggtgctct             1250
cttcctggtc ctctgcttct ctggatcctc cccaccccct cctgctcctg             1300
gggccggccc ttttctcaga gatcactcaa taaacctaag aaccctcata             1350
aaaaaaaaaa aaaaaaaaa  aaaaaaa                                      1377

<210> SEQ ID NO 42
<211> LENGTH: 243
<212> TYPE: PRT
<213> ORGANISM: Homo Sapien

<400> SEQUENCE: 42

Met Arg Pro Leu Leu Val Leu Leu Leu Gly Leu Ala Ala Gly
 1               5                  10                  15

Ser Pro Pro Leu Asp Asp Asn Lys Ile Pro Ser Leu Cys Pro Gly
                20                  25                  30

His Pro Gly Leu Pro Gly Thr Pro Gly His His Gly Ser Gln Gly
                35                  40                  45

Leu Pro Gly Arg Asp Gly Arg Asp Gly Arg Asp Gly Ala Pro Gly
                50                  55                  60

Ala Pro Gly Glu Lys Gly Glu Gly Gly Arg Gly Leu Pro Gly
                65                  70                  75

Pro Arg Gly Asp Pro Gly Pro Arg Gly Glu Ala Gly Pro Ala Gly
                80                  85                  90

Pro Thr Gly Pro Ala Gly Glu Cys Ser Val Pro Pro Arg Ser Ala
                95                 100                 105

Phe Ser Ala Lys Arg Ser Glu Ser Arg Val Pro Pro Ser Asp
               110                 115                 120

Ala Pro Leu Pro Phe Asp Arg Val Leu Val Asn Glu Gln Gly His
               125                 130                 135

Tyr Asp Ala Val Thr Gly Lys Phe Thr Cys Gln Val Pro Gly Val
               140                 145                 150

Tyr Tyr Phe Ala Val His Ala Thr Val Tyr Arg Ala Ser Leu Gln
               155                 160                 165

Phe Asp Leu Val Lys Asn Gly Glu Ser Ile Ala Ser Phe Gln
               170                 175                 180

Phe Phe Gly Gly Trp Pro Lys Pro Ala Ser Leu Ser Gly Gly Ala
               185                 190                 195

Met Val Arg Leu Glu Pro Glu Asp Gln Val Trp Val Gln Val Gly
               200                 205                 210

Val Gly Asp Tyr Ile Gly Ile Tyr Ala Ser Ile Lys Thr Asp Ser
               215                 220                 225
```

```
Thr Phe Ser Gly Phe Leu Val Tyr Ser Asp Trp His Ser Ser Pro
        230                 235                 240
Val Phe Ala

<210> SEQ ID NO 43
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 43
tacaggccca gtcaggacca gggg                                          24

<210> SEQ ID NO 44
<211> LENGTH: 18
<212> TYPE: DNA
<213> ORGANISM: Artificial Sequence
<220> FEATURE:
<223> OTHER INFORMATION: Synthetic oligonucleotide probe

<400> SEQUENCE: 44
agccagcctc gctctcgg                                                 18

<210> SEQ ID NO 45
<211> LENGTH: 18
<212> TYPE: DNA
<213> ORGANISM: Artificial Sequence
<220> FEATURE:
<223> OTHER INFORMATION: Synthetic oligonucleotide probe

<400> SEQUENCE: 45
gtctgcgatc aggtctgg                                                 18

<210> SEQ ID NO 46
<211> LENGTH: 20
<212> TYPE: DNA
<213> ORGANISM: Artificial Sequence
<220> FEATURE:
<223> OTHER INFORMATION: Synthetic oligonucleotide probe

<400> SEQUENCE: 46
gaaagaggca atggattcgc                                               20

<210> SEQ ID NO 47
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 47
gacttacact tgccagcaca gcac                                          24

<210> SEQ ID NO 48
<211> LENGTH: 45
<212> TYPE: DNA
<213> ORGANISM: Artificial Sequence
<220> FEATURE:
<223> OTHER INFORMATION: Synthetic oligonucleotide probe

<400> SEQUENCE: 48
ggagcaccac caactggagg gtccggagta gcgagcgccc cgaag                   45

<210> SEQ ID NO 49
```

<211> LENGTH: 1876
<212> TYPE: DNA
<213> ORGANISM: Homo Sapien

<400> SEQUENCE: 49

| | |
|---|---:|
| ctcttttgtc caccagccca gcctgactcc tggagattgt gaatagctcc | 50 |
| atccagcctg agaaacaagc cgggtggctg agccaggctg tgcacggagc | 100 |
| acctgacggg cccaacagac ccatgctgca tccagagacc tcccctggcc | 150 |
| gggggcatct cctggctgtg ctcctggccc tccttggcac cacctgggca | 200 |
| gaggtgtggc caccccagct gcaggagcag gctccgatgg ccggagccct | 250 |
| gaacaggaag gagagtttct tgctcctctc cctgcacaac cgcctgcgca | 300 |
| gctgggtcca gccccctgcg gctgacatgc ggaggctgga ctggagtgac | 350 |
| agcctggccc aactggctca agccagggca gccctctgtg gaatcccaac | 400 |
| cccgagcctg gcatccggcc tgtggcgcac cctgcaagtg ggctggaaca | 450 |
| tgcagctgct gcccgcgggc ttggcgtcct tgttgaagt ggtcagccta | 500 |
| tggttttgcag aggggcagcg gtacagccac gcggcaggag agtgtgctcg | 550 |
| caacgccacc tgcacccact acacgcagct cgtgtgggcc acctcaagcc | 600 |
| agctgggctg tgggcggcac ctgtgctctg caggccagac agcgatagaa | 650 |
| gcctttgtct gtgcctactc ccccggaggc aactgggagg tcaacgggaa | 700 |
| gacaatcatc ccctataaga agggtgcctg gtgttcgctc tgcacagcca | 750 |
| gtgtctcagg ctgcttcaaa gcctgggacc atgcaggggg gctctgtgag | 800 |
| gtccccagga atccttgtcg catgagctgc cagaaccatg gacgtctcaa | 850 |
| catcagcacc tgccactgcc actgtccccc tggctacacg ggcagatact | 900 |
| gccaagtgag gtgcagcctg cagtgtgtgc acggccggtt ccgggaggag | 950 |
| gagtgctcgt gcgtctgtga catcggctac ggggagccc agtgtgccac | 1000 |
| caaggtgcat tttcccttcc acacctgtga cctgaggatc gacggagact | 1050 |
| gcttcatggt gtcttcagag gcagacacct attacagagc caggatgaaa | 1100 |
| tgtcagagga aggcggggt gctggcccag atcaagagcc agaaagtgca | 1150 |
| ggacatcctc gccttctatc tgggccgcct ggagaccacc aacgaggtga | 1200 |
| ctgacagtga cttcgagacc aggaacttct ggatcgggct cacctacaag | 1250 |
| accgccaagg actccttccg ctgggccaca ggggagcacc aggccttcac | 1300 |
| cagttttgcc tttgggcagc ctgacaacca cgggctggtg tggctgagtg | 1350 |
| ctgccatggg gtttggcaac tgcgtggagc tgcaggcttc agctgccttc | 1400 |
| aactggaacg accagcgctg caaaacccga accgttaca tctgccagtt | 1450 |
| tgcccaggag cacatctccc ggtgggggcc agggtcctga ggcctgacca | 1500 |
| catggctccc tcgcctgccc tgggagcacc ggctctgctt acctgtctgc | 1550 |
| ccacctgtct ggaacaaggg ccaggttaag accacatgcc tcatgtccaa | 1600 |
| agaggtctca gaccttgcac aatgccagaa gttgggcaga gagaggcagg | 1650 |
| gaggccagtg agggcaggg agtgagtgtt agaagaagct ggggcccttc | 1700 |
| gcctgctttt gattgggaag atgggcttca attagatggc gaaggagagg | 1750 |
| acaccgccag tggtccaaaa aggctgctct cttccacctg gcccagaccc | 1800 |
| tgtggggcag cggagcttcc ctgtggcatg aaccccacgg ggtattaaat | 1850 | tatgaatcag ctgaaaaaaa aaaaaa                                                    1876

<210> SEQ ID NO 50
<211> LENGTH: 455
<212> TYPE: PRT
<213> ORGANISM: Homo Sapien

<400> SEQUENCE: 50

Met Leu His Pro Glu Thr Ser Pro Gly Arg Gly His Leu Leu Ala
 1               5                  10                  15

Val Leu Leu Ala Leu Leu Gly Thr Thr Trp Ala Glu Val Trp Pro
                20                  25                  30

Pro Gln Leu Gln Glu Gln Ala Pro Met Ala Gly Ala Leu Asn Arg
                35                  40                  45

Lys Glu Ser Phe Leu Leu Ser Leu His Asn Arg Leu Arg Ser
                50                  55                  60

Trp Val Gln Pro Pro Ala Ala Asp Met Arg Arg Leu Asp Trp Ser
                65                  70                  75

Asp Ser Leu Ala Gln Leu Ala Gln Ala Arg Ala Ala Leu Cys Gly
                80                  85                  90

Ile Pro Thr Pro Ser Leu Ala Ser Gly Leu Trp Arg Thr Leu Gln
                95                 100                 105

Val Gly Trp Asn Met Gln Leu Leu Pro Ala Gly Leu Ala Ser Phe
               110                 115                 120

Val Glu Val Val Ser Leu Trp Phe Ala Glu Gly Gln Arg Tyr Ser
               125                 130                 135

His Ala Ala Gly Glu Cys Ala Arg Asn Ala Thr Cys Thr His Tyr
               140                 145                 150

Thr Gln Leu Val Trp Ala Thr Ser Ser Gln Leu Gly Cys Gly Arg
               155                 160                 165

His Leu Cys Ser Ala Gly Gln Thr Ala Ile Glu Ala Phe Val Cys
               170                 175                 180

Ala Tyr Ser Pro Gly Gly Asn Trp Glu Val Asn Gly Lys Thr Ile
               185                 190                 195

Ile Pro Tyr Lys Lys Gly Ala Trp Cys Ser Leu Cys Thr Ala Ser
               200                 205                 210

Val Ser Gly Cys Phe Lys Ala Trp Asp His Ala Gly Gly Leu Cys
               215                 220                 225

Glu Val Pro Arg Asn Pro Cys Arg Met Ser Cys Gln Asn His Gly
               230                 235                 240

Arg Leu Asn Ile Ser Thr Cys His Cys His Cys Pro Pro Gly Tyr
               245                 250                 255

Thr Gly Arg Tyr Cys Gln Val Arg Cys Ser Leu Gln Cys Val His
               260                 265                 270

Gly Arg Phe Arg Glu Glu Cys Ser Cys Val Cys Asp Ile Gly
               275                 280                 285

Tyr Gly Gly Ala Gln Cys Ala Thr Lys Val His Phe Pro Phe His
               290                 295                 300

Thr Cys Asp Leu Arg Ile Asp Gly Asp Cys Phe Met Val Ser Ser
               305                 310                 315

Glu Ala Asp Thr Tyr Tyr Arg Ala Arg Met Lys Cys Gln Arg Lys
               320                 325                 330

Gly Gly Val Leu Ala Gln Ile Lys Ser Gln Lys Val Gln Asp Ile
               335                 340                 345

```
Leu Ala Phe Tyr Leu Gly Arg Leu Glu Thr Thr Asn Glu Val Thr
            350                 355                 360

Asp Ser Asp Phe Glu Thr Arg Asn Phe Trp Ile Gly Leu Thr Tyr
        365                 370                 375

Lys Thr Ala Lys Asp Ser Phe Arg Trp Ala Thr Gly Glu His Gln
    380                 385                 390

Ala Phe Thr Ser Phe Ala Phe Gly Gln Pro Asp Asn His Gly Leu
395                 400                 405

Val Trp Leu Ser Ala Ala Met Gly Phe Gly Asn Cys Val Glu Leu
            410                 415                 420

Gln Ala Ser Ala Ala Phe Asn Trp Asn Asp Gln Arg Cys Lys Thr
        425                 430                 435

Arg Asn Arg Tyr Ile Cys Gln Phe Ala Gln Glu His Ile Ser Arg
    440                 445                 450

Trp Gly Pro Gly Ser
            455

<210> SEQ ID NO 51
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 51
aggaacttct ggatcgggct cacc                                       24

<210> SEQ ID NO 52
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 52
gggtctgggc caggtggaag agag                                       24

<210> SEQ ID NO 53
<211> LENGTH: 45
<212> TYPE: DNA
<213> ORGANISM: Artificial Sequence
<220> FEATURE:
<223> OTHER INFORMATION: Synthetic oligonucleotide probe

<400> SEQUENCE: 53
gccaaggact ccttccgctg ggccacaggg gagcaccagg ccttc                45

<210> SEQ ID NO 54
<211> LENGTH: 2331
<212> TYPE: DNA
<213> ORGANISM: Homo Sapien

<400> SEQUENCE: 54
cggacgcgtg ggctgggcgc tgcaaagcgt gtcccgccgg gtccccgagc            50
gtcccgcgcc ctcgcccgc catgctcctg ctgctggggc tgtgcctggg            100
gctgtccctg tgtgtggggt cgcaggaaga ggcgcagagc tggggccact           150
cttcggagca ggatggactc agggtcccga ggcaagtcag actgttgcag           200
aggctgaaaa ccaaaccttt gatgacagaa ttctcagtga agtctaccat           250
```

-continued

```
catttcccgt tatgccttca ctacggtttc ctgcagaatg ctgaacagag        300
cttctgaaga ccaggacatt gagttccaga tgcagattcc agctgcagct        350
ttcatcacca acttcactat gcttattgga gacaaggtgt atcagggcga        400
aattacagag agagaaaaga agagtggtga tagggtaaaa gagaaaagga        450
ataaaaccac agaagaaaat ggagagaagg ggactgaaat attcagagct        500
tctgcagtga ttcccagcaa ggacaaagcc gccttttcc tgagttatga         550 ggagcttctg cagaggcgcc tgggcaagta cgagcacagc atcagcgtgc        600
ggccccagca gctgtccggg aggctgagcg tggacgtgaa tatcctggag        650
agcgcgggca tcgcatccct ggaggtgctg ccgcttcaca acagcaggca        700
gaggggcagt gggcgcgggg aagatgattc tgggcctccc ccatctactg        750
tcattaacca aaatgaaaca tttgccaaca taatttttaa acctactgta        800
gtacaacaag ccaggattgc ccagaatgga attttgggag actttatcat        850
tagatatgac gtcaatagag aacagagcat tggggacatc caggttctaa        900
atggctattt tgtgcactac tttgctccta aagaccttcc tcctttaccc        950
aagaatgtgg tattcgtgct tgacagcagt gcttctatgg tgggaaccaa        1000
actccggcag accaaggatg ccctcttcac aattctccat gacctccgac        1050
cccaggaccg tttcagtatc attggatttt ccaaccggat caaagtatgg        1100
aaggaccact tgatatcagt cactccagac agcatcaggg atgggaaagt        1150
gtacattcac catatgtcac ccactggagg cacagacatc aacggggccc        1200
tgcagagggc catcaggctc ctcaacaagt acgtggccca cagtggcatt        1250
ggagaccgga gcgtgtccct catcgtcttc ctgacggatg ggaagcccac        1300
ggtcggggag acgcacaccc tcaagatcct caacaacacc cgagaggccg        1350
cccgaggcca agtctgcatc ttcaccattg gcatcggcaa cgacgtggac        1400
ttcaggctgc tggagaaact gtcgctggag aactgtggcc tcacacggcg        1450
cgtgcacgag gaggaggacg caggctcgca gctcatcggg ttctacgatg        1500
aaatcaggac cccgctcctc tctgacatcc gcatcgatta ccccccagc         1550 tcagtggtgc aggccaccaa gaccctgttc cccaactact caacggctc         1600 ggagatcatc attgcgggga agctggtgga caggaagctg gatcacctgc        1650
acgtggaggt caccgccagc aacagtaaga aattcatcat cctgaagaca        1700
gatgtgcctg tgcggcctca gaaggcaggg aaagatgtca caggaagccc        1750
caggcctgga ggcgatggag agggggacac caacccatc gagcgtctct         1800 ggagctacct caccacaaag gagctgctga gctcctggct gcaaagtgac        1850
gatgaaccgg agaaggagcg gctgcggcag cgggcccagg ccctggctgt        1900
gagctaccgc ttcctcactc ccttcacctc catgaagctg agggggccgg        1950
tcccacgcat ggatggcctg gaggaggccc acggcatgtc ggctgccatg        2000
ggacccgaac cggtggtgca gagcgtgcga ggagctggca cgcagccagg        2050
acctttgctc aagaagccaa actccgtcaa aaaaaaacaa acaaaacaa         2100 aaaaaagaca tgggagagat ggtgttttc ctctccacca cctggggata         2150
cgatgagaag atggccacct gcaagccagg aagacggccc tcaccagaca        2200
ccatgtctgc tggcaccttg atcttggacc tcccagcctc cagaactgtg        2250
```

```
agaaataaat gtgttttgtt taagctaaaa aaaaaaaaaa aaaaaaaaaa         2300
aaaaaaaaaa aaaaaaaaaa aaaaaaaaaa a                             2331
```

<210> SEQ ID NO 55
<211> LENGTH: 694
<212> TYPE: PRT
<213> ORGANISM: Homo Sapien

<400> SEQUENCE: 55

```
Met Leu Leu Leu Leu Gly Leu Cys Leu Gly Leu Ser Leu Cys Val
 1               5                  10                  15

Gly Ser Gln Glu Glu Ala Gln Ser Trp Gly His Ser Ser Glu Gln
                20                  25                  30

Asp Gly Leu Arg Val Pro Arg Gln Val Arg Leu Leu Gln Arg Leu
            35                  40                  45

Lys Thr Lys Pro Leu Met Thr Glu Phe Ser Val Lys Ser Thr Ile
        50                  55                  60

Ile Ser Arg Tyr Ala Phe Thr Thr Val Ser Cys Arg Met Leu Asn
    65                  70                  75

Arg Ala Ser Glu Asp Gln Asp Ile Glu Phe Gln Met Gln Ile Pro
                80                  85                  90

Ala Ala Ala Phe Ile Thr Asn Phe Thr Met Leu Ile Gly Asp Lys
            95                  100                 105

Val Tyr Gln Gly Glu Ile Thr Glu Arg Glu Lys Lys Ser Gly Asp
        110                 115                 120

Arg Val Lys Glu Lys Arg Asn Lys Thr Thr Glu Glu Asn Gly Glu
    125                 130                 135

Lys Gly Thr Glu Ile Phe Arg Ala Ser Ala Val Ile Pro Ser Lys
                140                 145                 150

Asp Lys Ala Ala Phe Phe Leu Ser Tyr Glu Glu Leu Leu Gln Arg
            155                 160                 165

Arg Leu Gly Lys Tyr Glu His Ser Ile Ser Val Arg Pro Gln Gln
        170                 175                 180

Leu Ser Gly Arg Leu Ser Val Asp Val Asn Ile Leu Glu Ser Ala
    185                 190                 195

Gly Ile Ala Ser Leu Glu Val Leu Pro Leu His Asn Ser Arg Gln
                200                 205                 210

Arg Gly Ser Gly Arg Gly Glu Asp Asp Ser Gly Pro Pro Ser
        215                 220                 225

Thr Val Ile Asn Gln Asn Glu Thr Phe Ala Asn Ile Ile Phe Lys
    230                 235                 240

Pro Thr Val Val Gln Gln Ala Arg Ile Ala Gln Asn Gly Ile Leu
                245                 250                 255

Gly Asp Phe Ile Ile Arg Tyr Asp Val Asn Arg Glu Gln Ser Ile
            260                 265                 270

Gly Asp Ile Gln Val Leu Asn Gly Tyr Phe Val His Tyr Phe Ala
        275                 280                 285

Pro Lys Asp Leu Pro Pro Leu Pro Lys Asn Val Val Phe Val Leu
    290                 295                 300

Asp Ser Ser Ala Ser Met Val Gly Thr Lys Leu Arg Gln Thr Lys
                305                 310                 315

Asp Ala Leu Phe Thr Ile Leu His Asp Leu Arg Pro Gln Asp Arg
            320                 325                 330
```

-continued

```
Phe Ser Ile Ile Gly Phe Ser Asn Arg Ile Lys Val Trp Lys Asp
                335                 340                 345
His Leu Ile Ser Val Thr Pro Asp Ser Ile Arg Asp Gly Lys Val
            350                 355                 360
Tyr Ile His His Met Ser Pro Thr Gly Thr Asp Ile Asn Gly
        365                 370                 375
Ala Leu Gln Arg Ala Ile Arg Leu Leu Asn Lys Tyr Val Ala His
        380                 385                 390
Ser Gly Ile Gly Asp Arg Ser Val Ser Leu Ile Val Phe Leu Thr
            395                 400                 405
Asp Gly Lys Pro Thr Val Gly Glu Thr His Thr Leu Lys Ile Leu
            410                 415                 420
Asn Asn Thr Arg Glu Ala Ala Arg Gly Gln Val Cys Ile Phe Thr
            425                 430                 435
Ile Gly Ile Gly Asn Asp Val Asp Phe Arg Leu Leu Glu Lys Leu
            440                 445                 450
Ser Leu Glu Asn Cys Gly Leu Thr Arg Arg Val His Glu Glu Glu
            455                 460                 465
Asp Ala Gly Ser Gln Leu Ile Gly Phe Tyr Asp Glu Ile Arg Thr
            470                 475                 480
Pro Leu Leu Ser Asp Ile Arg Ile Asp Tyr Pro Pro Ser Ser Val
            485                 490                 495
Val Gln Ala Thr Lys Thr Leu Phe Pro Asn Tyr Phe Asn Gly Ser
            500                 505                 510
Glu Ile Ile Ile Ala Gly Lys Leu Val Asp Arg Lys Leu Asp His
            515                 520                 525
Leu His Val Glu Val Thr Ala Ser Asn Ser Lys Lys Phe Ile Ile
            530                 535                 540
Leu Lys Thr Asp Val Pro Val Arg Pro Gln Lys Ala Gly Lys Asp
            545                 550                 555
Val Thr Gly Ser Pro Arg Pro Gly Gly Asp Gly Glu Gly Asp Thr
            560                 565                 570
Asn His Ile Glu Arg Leu Trp Ser Tyr Leu Thr Thr Lys Glu Leu
            575                 580                 585
Leu Ser Ser Trp Leu Gln Ser Asp Asp Glu Pro Glu Lys Glu Arg
            590                 595                 600
Leu Arg Gln Arg Ala Gln Ala Leu Ala Val Ser Tyr Arg Phe Leu
            605                 610                 615
Thr Pro Phe Thr Ser Met Lys Leu Arg Gly Pro Val Pro Arg Met
            620                 625                 630
Asp Gly Leu Glu Glu Ala His Gly Met Ser Ala Ala Met Gly Pro
            635                 640                 645
Glu Pro Val Val Gln Ser Val Arg Gly Ala Gly Thr Gln Pro Gly
            650                 655                 660
Pro Leu Leu Lys Lys Pro Asn Ser Val Lys Lys Gln Asn Lys
            665                 670                 675
Thr Lys Lys Arg His Gly Arg Asp Gly Val Phe Pro Leu His His
            680                 685                 690
Leu Gly Ile Arg
```

<210> SEQ ID NO 56
<211> LENGTH: 24
<212> TYPE: DNA
<213> ORGANISM: Artificial Sequence

```
<220> FEATURE:
<223> OTHER INFORMATION: Synthetic oligonucleotide probe

<400> SEQUENCE: 56
gtgggaacca aactccggca gacc                                              24

<210> SEQ ID NO 57
<211> LENGTH: 18
<212> TYPE: DNA
<213> ORGANISM: Artificial Sequence
<220> FEATURE:
<223> OTHER INFORMATION: Synthetic oligonucleotide probe

<400> SEQUENCE: 57
cacatcgagc gtctctgg                                                     18

<210> SEQ ID NO 58
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 58
agccgctcct tctccggttc atcg                                              24

<210> SEQ ID NO 59
<211> LENGTH: 48
<212> TYPE: DNA
<213> ORGANISM: Artificial Sequence
<220> FEATURE:
<223> OTHER INFORMATION: Synthetic oligonucleotide probe

<400> SEQUENCE: 59
tggaaggacc acttgatatc agtcactcca gacagcatca gggatggg                    48

<210> SEQ ID NO 60
<211> LENGTH: 1413
<212> TYPE: DNA
<213> ORGANISM: Homo Sapien

<400> SEQUENCE: 60
cggacgcgtg gggtgcccga catggcgagt gtagtgctgc cgagcggatc                  50
ccagtgtgcg gcggcagcgg cggcggcggc gcctcccggg ctccggcttc                 100
tgctgttgct cttctccgcc gcggcactga tccccacagg tgatgggcag                 150
aatctgttta cgaaagacgt gacagtgatc gagggagagg ttgcgaccat                 200
cagttgccaa gtcaataaga gtgacgactc tgtgattcag ctactgaatc                 250
ccaacaggca gaccatttat ttcagggact tcaggccttt gaaggacagc                 300
aggtttcagt tgctgaattt ttctagcagt gaactcaaag tatcattgac                 350
aaacgtctca atttctgatg aaggaagata cttttgccag ctctataccg                 400
atccccacac ggaaagttac accaccatca cagtcctggt cccaccacgt                 450
aatctgatga tcgatatcca gaaagacact gcggtggaag gtgaggagat                 500
tgaagtcaac tgcactgcta tggccagcaa gccagccacg actatcaggt                 550
ggttcaaagg gaacacagag ctaaaaggca aatcggaggt ggaagagtgg                 600
tcagacatgt acactgtgac cagtcagctg atgctgaagg tgcacaagga                 650
ggacgatggg gtcccagtga tctgccaggt ggagcaccct gcggtcactg                 700
```

-continued

| | |
|---|---|
| gaaacctgca gacccagcgg tatctagaag tacagtataa gcctcaagtg | 750 |
| cacattcaga tgacttatcc tctacaaggc ttaacccggg aaggggacgc | 800 |
| gcttgagtta acatgtgaag ccatcgggaa gccccagcct gtgatggtaa | 850 |
| cttgggtgag agtcgatgat gaaatgcctc aacacgccgt actgtctggg | 900 |
| cccaacctgt tcatcaataa cctaaacaaa acagataatg gtacataccg | 950 |
| ctgtgaagct tcaaacatag tggggaaagc tcactcggat tatatgctgt | 1000 |
| atgtatacga tcccccacac actatccctc ctcccacaac aaccaccacc | 1050 |
| accaccacca ccaccaccac caccatcctt accatcatca cagattcccg | 1100 |
| agcaggtgaa gaaggctcga tcagggcagt ggatcatgcc gtgatcggtg | 1150 |
| gcgtcgtggc ggtggtggtg ttcgccatgc tgtgcttgct catcattctg | 1200 |
| gggcgctatt ttgccagaca taaaggtaca tacttcactc atgaagccaa | 1250 |
| aggagccgat gacgcagcag acgcagacac agctataatc aatgcagaag | 1300 |
| gaggacagaa caactccgaa gaaaagaaag agtacttcat ctagatcagc | 1350 |
| cttttttgttt caatgaggtg tccaactggc cctatttaga tgataaagag | 1400 |
| acagtgatat tgg | 1413 |

```
<210> SEQ ID NO 61
<211> LENGTH: 440
<212> TYPE: PRT
<213> ORGANISM: Homo Sapien

<400> SEQUENCE: 61
```

```
Met Ala Ser Val Val Leu Pro Ser Gly Ser Gln Cys Ala Ala Ala
  1               5                  10                  15

Ala Ala Ala Ala Ala Pro Pro Gly Leu Arg Leu Leu Leu Leu Leu
                 20                  25                  30

Phe Ser Ala Ala Ala Leu Ile Pro Thr Gly Asp Gly Gln Asn Leu
                 35                  40                  45

Phe Thr Lys Asp Val Thr Val Ile Glu Gly Glu Val Ala Thr Ile
                 50                  55                  60

Ser Cys Gln Val Asn Lys Ser Asp Asp Ser Val Ile Gln Leu Leu
                 65                  70                  75

Asn Pro Asn Arg Gln Thr Ile Tyr Phe Arg Asp Phe Arg Pro Leu
                 80                  85                  90

Lys Asp Ser Arg Phe Gln Leu Leu Asn Phe Ser Ser Ser Glu Leu
                 95                 100                 105

Lys Val Ser Leu Thr Asn Val Ser Ile Ser Asp Glu Gly Arg Tyr
                110                 115                 120

Phe Cys Gln Leu Tyr Thr Asp Pro Pro Gln Glu Ser Tyr Thr Thr
                125                 130                 135

Ile Thr Val Leu Val Pro Pro Arg Asn Leu Met Ile Asp Ile Gln
                140                 145                 150

Lys Asp Thr Ala Val Glu Gly Glu Glu Ile Glu Val Asn Cys Thr
                155                 160                 165

Ala Met Ala Ser Lys Pro Ala Thr Thr Ile Arg Trp Phe Lys Gly
                170                 175                 180

Asn Thr Glu Leu Lys Gly Lys Ser Glu Val Glu Glu Trp Ser Asp
                185                 190                 195

Met Tyr Thr Val Thr Ser Gln Leu Met Leu Lys Val His Lys Glu
                200                 205                 210
```

```
Asp Asp Gly Val Pro Val Ile Cys Gln Val Glu His Pro Ala Val
            215                 220                 225

Thr Gly Asn Leu Gln Thr Gln Arg Tyr Leu Glu Val Gln Tyr Lys
            230                 235                 240

Pro Gln Val His Ile Gln Met Thr Tyr Pro Leu Gln Gly Leu Thr
            245                 250                 255

Arg Glu Gly Asp Ala Leu Glu Leu Thr Cys Glu Ala Ile Gly Lys
            260                 265                 270

Pro Gln Pro Val Met Val Thr Trp Val Arg Val Asp Asp Glu Met
            275                 280                 285

Pro Gln His Ala Val Leu Ser Gly Pro Asn Leu Phe Ile Asn Asn
            290                 295                 300

Leu Asn Lys Thr Asp Asn Gly Thr Tyr Arg Cys Glu Ala Ser Asn
            305                 310                 315

Ile Val Gly Lys Ala His Ser Asp Tyr Met Leu Tyr Val Tyr Asp
            320                 325                 330

Pro Pro Thr Thr Ile Pro Pro Pro Thr Thr Thr Thr Thr Thr Thr
            335                 340                 345

Thr Thr Thr Thr Thr Thr Ile Leu Thr Ile Ile Thr Asp Ser Arg
            350                 355                 360

Ala Gly Glu Glu Gly Ser Ile Arg Ala Val Asp His Ala Val Ile
            365                 370                 375

Gly Gly Val Val Ala Val Val Val Phe Ala Met Leu Cys Leu Leu
            380                 385                 390

Ile Ile Leu Gly Arg Tyr Phe Ala Arg His Lys Gly Thr Tyr Phe
            395                 400                 405

Thr His Glu Ala Lys Gly Ala Asp Asp Ala Ala Asp Ala Asp Thr
            410                 415                 420

Ala Ile Ile Asn Ala Glu Gly Gly Gln Asn Asn Ser Glu Glu Lys
            425                 430                 435

Lys Glu Tyr Phe Ile
            440
```

```
<210> SEQ ID NO 62
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 62
ggcttctgct gttgctcttc tccg                                  24

<210> SEQ ID NO 63
<211> LENGTH: 20
<212> TYPE: DNA
<213> ORGANISM: Artificial Sequence
<220> FEATURE:
<223> OTHER INFORMATION: Synthetic oligonucleotide probe

<400> SEQUENCE: 63
gtacactgtg accagtcagc                                       20

<210> SEQ ID NO 64
<211> LENGTH: 20
<212> TYPE: DNA
<213> ORGANISM: Artificial Sequence
<220> FEATURE:
```

-continued

<223> OTHER INFORMATION: Synthetic oligonucleotide probe

<400> SEQUENCE: 64
atcatcacag attcccgagc                                                    20

<210> SEQ ID NO 65
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 65
ttcaatctcc tcaccttcca ccgc                                               24

<210> SEQ ID NO 66
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 66
atagctgtgt ctgcgtctgc tgcg                                               24

<210> SEQ ID NO 67
<211> LENGTH: 50
<212> TYPE: DNA
<213> ORGANISM: Artificial Sequence
<220> FEATURE:
<223> OTHER INFORMATION: Synthetic oligonucleotide probe

<400> SEQUENCE: 67
cgcggcactg atccccacag gtgatgggca gaatctgttt acgaaagacg                   50

<210> SEQ ID NO 68
<211> LENGTH: 2555
<212> TYPE: DNA
<213> ORGANISM: Homo Sapien

<400> SEQUENCE: 68
ggggcgggtg gacgcggact cgaacgcagt tgcttcggga cccaggaccc                   50
cctcgggccc gacccgccag gaaagactga ggccgcggcc tgccccgccc                  100
ggctccctgc gccgccgccg cctcccggga cagaagatgt gctccagggt                  150
ccctctgctg ctgccgctgc tcctgctact ggccctgggg cctggggtgc                  200
agggctgccc atccggctgc cagtgcagcc agccacagac agtcttctgc                  250
actgcccgcc aggggaccac ggtgcccga gacgtgccac ccgacacggt                   300
ggggctgtac gtctttgaga acggcatcac catgctcgac gcaagcagct                  350
ttgccggcct gccgggcctg cagctcctgg acctgtcaca gaaccagatc                  400
gccagcctgc gcctgccccg cctgctgctg ctggacctca gccacaacag                  450
cctcctggcc ctggagcccg gcatcctgga cactgccaac gtggaggcgc                  500
tgcggctggc tggtctgggg ctgcagcagc tggacgaggg gctcttcagc                  550
cgcttgcgca acctccacga cctggatgtg tccgacaacc agctggagcg                  600
agtgccacct gtgatccgag gcctccgggg cctgacgcgc ctgcggctgg                  650
ccggcaacac ccgcattgcc agctgcggcc cgaggaccct ggccggcctg                  700
gctgccctgc aggagctgga tgtgagcaac ctaagcctgc aggccctgcc                  750

-continued

| | |
|---|---|
| tggcgacctc tcgggcctct tcccccgcct gcggctgctg cagctgccc | 800 |
| gcaacccctt caactgcgtg tgccccctga gctggtttgg ccccctgggtg | 850 |
| cgcgagagcc acgtcacact ggccagccct gaggagacgc gctgccactt | 900 |
| cccgcccaag aacgctggcc ggctgctcct ggagcttgac tacgccgact | 950 |
| ttggctgccc agccaccacc accacagcca cagtgcccac cacgaggccc | 1000 |
| gtggtgcggg agcccacagc cttgtcttct agcttggctc ctacctggct | 1050 |
| tagccccaca cgccggcca ctgaggcccc cagcccgccc tccactgccc | 1100 |
| caccgactgt agggcctgtc cccagcccc aggactgccc accgtccacc | 1150 |
| tgcctcaatg ggggcacatg ccacctgggg acacggcacc acctggcgtg | 1200 |
| cttgtgcccc gaaggcttca cgggcctgta ctgtgagagc cagatggggc | 1250 |
| aggggacacg gccagcccct acaccagtca cgccgaggcc accacggtcc | 1300 |
| ctgaccctgg gcatcgagcc ggtgagcccc acctccctgc gcgtggggct | 1350 |
| gcagcgctac ctccagggga gctccgtgca gctcaggagc ctccgtctca | 1400 |
| cctatcgcaa cctatcgggc cctgataagc ggctggtgac gctgcgactg | 1450 |
| cctgcctcgc tcgctgagta cacggtcacc cagctgcggc caacgccac | 1500 |
| ttactccgtc tgtgtcatgc ctttggggcc cgggcgggtg ccggagggcg | 1550 |
| aggaggcctg cggggaggcc catacacccc cagccgtcca ctccaaccac | 1600 |
| gccccagtca cccaggcccg cgagggcaac ctgccgctcc tcattgcgcc | 1650 |
| cgccctggcc gcggtgctcc tggccgcgct ggctgcggtg ggggcagcct | 1700 |
| actgtgtgcg gcggggggcgg gccatggcag cagcggctca ggacaaaggg | 1750 |
| caggtggggc caggggctgg gcccctggaa ctggagggag tgaaggtccc | 1800 |
| cttggagcca ggcccgaagg caacagaggg cggtggagag gccctgccca | 1850 |
| gcgggtctga gtgtgaggtg ccactcatgg gcttcccagg gcctggcctc | 1900 |
| cagtcacccc tccacgcaaa gccctacatc taagccagag agagacaggg | 1950 |
| cagctggggc cgggctctca gccagtgaga tggccagccc cctcctgctg | 2000 |
| ccacaccacg taagttctca gtcccaacct cggggatgtg tgcagacagg | 2050 |
| gctgtgtgac cacagctggg ccctgttccc tctggacctc ggtctcctca | 2100 |
| tctgtgagat gctgtggccc agctgacgag ccctaacgtc cccagaaccg | 2150 |
| agtgcctatg aggacagtgt ccgccctgcc ctccgcaacg tgcagtccct | 2200 |
| gggcacggcg ggccctgcca tgtgctggta acgcatgcct gggccctgct | 2250 |
| gggctctccc actccaggcg gaccctgggg gccagtgaag gaagctcccg | 2300 |
| gaaagagcag agggagagcg ggtaggcggc tgtgtgactc tagtcttggc | 2350 |
| cccaggaagc gaaggaacaa agaaactgg aaggaagat gctttaggaa | 2400 |
| catgttttgc ttttttaaaa tatatatata tttataagag atccttttccc | 2450 |
| atttattctg ggaagatgtt tttcaaactc agagacaagg actttggttt | 2500 |
| ttgtaagaca acgatgata tgaaggcctt ttgtaagaaa aaataaaaaa | 2550 |
| aaaaa | 2555 |

<210> SEQ ID NO 69
<211> LENGTH: 598
<212> TYPE: PRT

-continued

<213> ORGANISM: Homo Sapien

<400> SEQUENCE: 69

```
Met Cys Ser Arg Val Pro Leu Leu Pro Leu Leu Leu Leu Leu Leu
  1               5                  10                  15

Ala Leu Gly Pro Gly Val Gln Gly Cys Pro Ser Gly Cys Gln Cys
                 20                  25                  30

Ser Gln Pro Gln Thr Val Phe Cys Thr Ala Arg Gln Gly Thr Thr
                 35                  40                  45

Val Pro Arg Asp Val Pro Pro Asp Thr Val Gly Leu Tyr Val Phe
                 50                  55                  60

Glu Asn Gly Ile Thr Met Leu Asp Ala Ser Ser Phe Ala Gly Leu
                 65                  70                  75

Pro Gly Leu Gln Leu Leu Asp Leu Ser Gln Asn Gln Ile Ala Ser
                 80                  85                  90

Leu Arg Leu Pro Arg Leu Leu Leu Leu Asp Leu Ser His Asn Ser
                 95                 100                 105

Leu Leu Ala Leu Glu Pro Gly Ile Leu Asp Thr Ala Asn Val Glu
                110                 115                 120

Ala Leu Arg Leu Ala Gly Leu Gly Leu Gln Gln Leu Asp Glu Gly
                125                 130                 135

Leu Phe Ser Arg Leu Arg Asn Leu His Asp Leu Asp Val Ser Asp
                140                 145                 150

Asn Gln Leu Glu Arg Val Pro Pro Val Ile Arg Gly Leu Arg Gly
                155                 160                 165

Leu Thr Arg Leu Arg Leu Ala Gly Asn Thr Arg Ile Ala Gln Leu
                170                 175                 180

Arg Pro Glu Asp Leu Ala Gly Leu Ala Ala Leu Gln Glu Leu Asp
                185                 190                 195

Val Ser Asn Leu Ser Leu Gln Ala Leu Pro Gly Asp Leu Ser Gly
                200                 205                 210

Leu Phe Pro Arg Leu Arg Leu Leu Ala Ala Arg Asn Pro Phe
                215                 220                 225

Asn Cys Val Cys Pro Leu Ser Trp Phe Gly Pro Trp Val Arg Glu
                230                 235                 240

Ser His Val Thr Leu Ala Ser Pro Glu Glu Thr Arg Cys His Phe
                245                 250                 255

Pro Pro Lys Asn Ala Gly Arg Leu Leu Leu Glu Leu Asp Tyr Ala
                260                 265                 270

Asp Phe Gly Cys Pro Ala Thr Thr Thr Ala Thr Val Pro Thr
                275                 280                 285

Thr Arg Pro Val Val Arg Glu Pro Thr Ala Leu Ser Ser Ser Leu
                290                 295                 300

Ala Pro Thr Trp Leu Ser Pro Thr Ala Pro Thr Glu Ala Pro
                305                 310                 315

Ser Pro Pro Ser Thr Ala Pro Thr Val Gly Pro Val Pro Gln
                320                 325                 330

Pro Gln Asp Cys Pro Pro Ser Thr Cys Leu Asn Gly Gly Thr Cys
                335                 340                 345

His Leu Gly Thr Arg His His Leu Ala Cys Leu Cys Pro Glu Gly
                350                 355                 360

Phe Thr Gly Leu Tyr Cys Glu Ser Gln Met Gly Gln Gly Thr Arg
                365                 370                 375
```

-continued

```
Pro Ser Pro Thr Pro Val Thr Pro Arg Pro Pro Arg Ser Leu Thr
            380                 385                 390

Leu Gly Ile Glu Pro Val Ser Pro Thr Ser Leu Arg Val Gly Leu
            395                 400                 405

Gln Arg Tyr Leu Gln Gly Ser Ser Val Gln Leu Arg Ser Leu Arg
            410                 415                 420

Leu Thr Tyr Arg Asn Leu Ser Gly Pro Asp Lys Arg Leu Val Thr
            425                 430                 435

Leu Arg Leu Pro Ala Ser Leu Ala Glu Tyr Thr Val Thr Gln Leu
            440                 445                 450

Arg Pro Asn Ala Thr Tyr Ser Val Cys Val Met Pro Leu Gly Pro
            455                 460                 465

Gly Arg Val Pro Glu Gly Glu Glu Ala Cys Gly Glu Ala His Thr
            470                 475                 480

Pro Pro Ala Val His Ser Asn His Ala Pro Val Thr Gln Ala Arg
            485                 490                 495

Glu Gly Asn Leu Pro Leu Leu Ile Ala Pro Ala Leu Ala Ala Val
            500                 505                 510

Leu Leu Ala Ala Leu Ala Ala Val Gly Ala Ala Tyr Cys Val Arg
            515                 520                 525

Arg Gly Arg Ala Met Ala Ala Ala Ala Gln Asp Lys Gly Gln Val
            530                 535                 540

Gly Pro Gly Ala Gly Pro Leu Glu Leu Glu Gly Val Lys Val Pro
            545                 550                 555

Leu Glu Pro Gly Pro Lys Ala Thr Glu Gly Gly Gly Glu Ala Leu
            560                 565                 570

Pro Ser Gly Ser Glu Cys Glu Val Pro Leu Met Gly Phe Pro Gly
            575                 580                 585

Pro Gly Leu Gln Ser Pro Leu His Ala Lys Pro Tyr Ile
            590                 595

<210> SEQ ID NO 70
<211> LENGTH: 22
<212> TYPE: DNA
<213> ORGANISM: Artificial Sequence
<220> FEATURE:
<223> OTHER INFORMATION: Synthetic oligonucleotide probe

<400> SEQUENCE: 70
ccctccactg ccccaccgac tg                                              22

<210> SEQ ID NO 71
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 71
cggttctggg gacgttaggg ctcg                                            24

<210> SEQ ID NO 72
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 72
```

```
ctgcccaccg tccacctgcc tcaat                                           25
```

```
<210> SEQ ID NO 73
<211> LENGTH: 45
<212> TYPE: DNA
<213> ORGANISM: Artificial Sequence
<220> FEATURE:
<223> OTHER INFORMATION: Synthetic oligonucleotide probe

<400> SEQUENCE: 73
aggactgccc accgtccacc tgcctcaatg ggggcacatg ccacc                     45
```

```
<210> SEQ ID NO 74
<211> LENGTH: 45
<212> TYPE: DNA
<213> ORGANISM: Artificial Sequence
<220> FEATURE:
<223> OTHER INFORMATION: Synthetic Oligonucleotide Probe

<400> SEQUENCE: 74
acgcaaagcc ctacatctaa gccagagaga gacagggcag ctggg                     45
```

```
<210> SEQ ID NO 75
<211> LENGTH: 1077
<212> TYPE: DNA
<213> ORGANISM: Homo Sapien

<400> SEQUENCE: 75
ggcactagga caaccttctt cccttctgca ccactgcccg tacccttacc                50
cgccccgcca cctccttgct accccactct tgaaaccaca gctgttggca              100
gggtccccag ctcatgccag cctcatctcc tttcttgcta gccccaaag               150
ggcctccagg caacatgggg ggcccagtca gagagccggc actctcagtt              200
gccctctggt tgagttgggg ggcagctctg ggggccgtgg cttgtgccat              250
ggctctgctg acccaacaaa cagagctgca gagcctcagg agagaggtga              300
gccggctgca ggggacagga ggcccctccc agaatgggga agggtatccc              350
tggcagagtc tcccggagca gagttccgat gccctggaag cctgggagaa              400
tggggagaga tcccggaaaa ggagagcagt gctcacccaa aaacagaaga              450
agcagcactc tgtcctgcac ctggttccca ttaacgccac ctccaaggat              500
gactccgatg tgacagaggt gatgtggcaa ccagctctta ggcgtgggag              550
aggcctacag gcccaaggat atggtgtccg aatccaggat gctggagttt              600
atctgctgta tagccaggtc ctgtttcaag acgtgacttt caccatgggt              650
caggtggtgt ctcgagaagg ccaaggaagg caggagactc tattccgatg              700
tataagaagt atgccctccc acccggaccg ggcctacaac agctgctata              750
gcgcaggtgt cttccattta caccaagggg atattctgag tgtcataatt              800
ccccgggcaa gggcgaaact taacctctct ccacatggaa ccttcctggg              850
gtttgtgaaa ctgtgattgt gttataaaaa gtggctccca gcttggaaga              900
ccagggtggg tacatactgg agacagccaa gagctgagta tataaggag               950
agggaatgtg caggaacaga ggcatcttcc tgggtttggc tccccgttcc             1000
tcacttttcc cttttcattc ccaccccta gactttgatt ttacggatat              1050
cttgcttctg ttccccatgg agctccg                                       1077
```

<210> SEQ ID NO 76
<211> LENGTH: 250
<212> TYPE: PRT
<213> ORGANISM: Homo Sapien

<400> SEQUENCE: 76

```
Met Pro Ala Ser Ser Pro Phe Leu Leu Ala Pro Lys Gly Pro Pro
 1               5                  10                  15

Gly Asn Met Gly Gly Pro Val Arg Glu Pro Ala Leu Ser Val Ala
                20                  25                  30

Leu Trp Leu Ser Trp Gly Ala Ala Leu Gly Ala Val Ala Cys Ala
                35                  40                  45

Met Ala Leu Leu Thr Gln Gln Thr Glu Leu Gln Ser Leu Arg Arg
                50                  55                  60

Glu Val Ser Arg Leu Gln Gly Thr Gly Gly Pro Ser Gln Asn Gly
                65                  70                  75

Glu Gly Tyr Pro Trp Gln Ser Leu Pro Glu Gln Ser Ser Asp Ala
                80                  85                  90

Leu Glu Ala Trp Glu Asn Gly Glu Arg Ser Arg Lys Arg Arg Ala
                95                  100                 105

Val Leu Thr Gln Lys Gln Lys Lys Gln His Ser Val Leu His Leu
                110                 115                 120

Val Pro Ile Asn Ala Thr Ser Lys Asp Asp Ser Asp Val Thr Glu
                125                 130                 135

Val Met Trp Gln Pro Ala Leu Arg Arg Gly Arg Gly Leu Gln Ala
                140                 145                 150

Gln Gly Tyr Gly Val Arg Ile Gln Asp Ala Gly Val Tyr Leu Leu
                155                 160                 165

Tyr Ser Gln Val Leu Phe Gln Asp Val Thr Phe Thr Met Gly Gln
                170                 175                 180

Val Val Ser Arg Glu Gly Gln Gly Arg Gln Glu Thr Leu Phe Arg
                185                 190                 195

Cys Ile Arg Ser Met Pro Ser His Pro Asp Arg Ala Tyr Asn Ser
                200                 205                 210

Cys Tyr Ser Ala Gly Val Phe His Leu His Gln Gly Asp Ile Leu
                215                 220                 225

Ser Val Ile Ile Pro Arg Ala Arg Ala Lys Leu Asn Leu Ser Pro
                230                 235                 240

His Gly Thr Phe Leu Gly Phe Val Lys Leu
                245                 250
```

<210> SEQ ID NO 77
<211> LENGTH: 2849
<212> TYPE: DNA
<213> ORGANISM: Homo Sapien

<400> SEQUENCE: 77

| | |
|---|---:|
| cactttctcc ctctcttcct ttactttcga gaaaccgcgc ttccgcttct | 50 |
| ggtcgcagag acctcggaga ccgcgccggg gagacggagg tgctgtgggt | 100 |
| gggggggacc tgtggctgct cgtaccgccc cccaccctcc tcttctgcac | 150 |
| tgccgtcctc cggaagacct tttcccctgc tctgtttcct tcaccgagtc | 200 |
| tgtgcatcgc cccggacctg gccgggagga ggcttggccg gcgggagatg | 250 |
| ctctaggggc ggcgcgggag gagcggccgg cgggacggag ggcccggcag | 300 |
| gaagatgggc tcccgtggac agggactctt gctggcgtac tgcctgctcc | 350 |

-continued

| | |
|---|---|
| ttgcctttgc ctctggcctg gtcctgagtc gtgtgcccca tgtccagggg | 400 |
| gaacagcagg agtgggaggg gactgaggag ctgccgtcgc ctccggacca | 450 |
| tgccgagagg gctgaagaac aacatgaaaa atacaggccc agtcaggacc | 500 |
| aggggctccc tgcttcccgg tgcttgcgct gctgtgaccc cggtacctcc | 550 |
| atgtacccgg cgaccgccgt gccccagatc aacatcacta tcttgaaagg | 600 |
| ggagaagggt gaccgcggag atcgaggcct ccaagggaaa tatggcaaaa | 650 |
| caggctcagc aggggccagg ggccacactg gacccaaagg gcagaagggc | 700 |
| tccatggggg cccctgggga gcggtgcaag agccactacg ccgccttttc | 750 |
| ggtgggccgg aagaagccca tgcacagcaa ccactactac cagacggtga | 800 |
| tcttcgacac ggagttcgtg aacctctacg accacttcaa catgttcacc | 850 |
| ggcaagttct actgctacgt gcccggcctc tacttcttca gcctcaacgt | 900 |
| gcacacctgg aaccagaagg agacctacct gcacatcatg aagaacgagg | 950 |
| aggaggtggt gatcttgttc gcgcaggtgg gcgaccgcag catcatgcaa | 1000 |
| agccagagcc tgatgctgga gctgcgagag caggaccagg tgtgggtacg | 1050 |
| cctctacaag ggcgaacgtg agaacgccat cttcagcgag gagctggaca | 1100 |
| cctacatcac cttcagtggc tacctggtca agcacgccac cgagccctag | 1150 |
| ctggccggcc acctcctttc ctctcgccac cttccacccc tgcgctgtgc | 1200 |
| tgaccccacc gcctcttccc cgatccctgg actccgactc cctggctttg | 1250 |
| gcattcagtg agacgccctg cacacacaga aagccaaagc gatcggtgct | 1300 |
| cccagatccc gcagcctctg gagagagctg acggcagatg aaatcaccag | 1350 |
| ggcggggcac ccgcgagaac cctctgggac cttccgcggc cctctctgca | 1400 |
| cacatcctca agtgaccccg cacggcgaga cgcgggtggc ggcagggcgt | 1450 |
| cccagggtgc ggcaccgcgg ctccagtcct tggaaataat taggcaaatt | 1500 |
| ctaaaggtct caaaaggagc aaagtaaacc gtggaggaca agaaaagggg | 1550 |
| ttgttatttt tgtctttcca gccagcctgc tggctcccaa gagagaggcc | 1600 |
| ttttcagttg agactctgct taagagaaga tccaaagtta aagctctggg | 1650 |
| gtcaggggag gggccggggg caggaaacta cctctggctt aattctttta | 1700 |
| agccacgtag gaactttctt gagggatagg tggaccctga catccctgtg | 1750 |
| gccttgccca agggctctgc tggtctttct gagtcacagc tgcgaggtga | 1800 |
| tgggggctgg ggccccaggc gtcagcctcc cagagggaca gctgagcccc | 1850 |
| ctgccttggc tccaggttgg tagaagcagc cgaagggctc ctgacagtgg | 1900 |
| ccagggaccc ctgggtcccc caggcctgca gatgtttcta tgaggggcag | 1950 |
| agctccttgg tacatccatg tgtggctctg ctccacccct gtgccacccc | 2000 |
| agagccctgg ggggtggtct ccatgcctgc caccctggca tcggcttttct | 2050 |
| gtgccgcctc ccacacaaat cagccccaga aggcccgggg gccttggctt | 2100 |
| ctgttttttta taaacaccct caagcagcac tgcagtctcc catctcctcg | 2150 |
| tgggctaagc atcaccgctt ccacgtgtgt tgtgttggtt ggcagcaagg | 2200 |
| ctgatccaga cccttctgc ccccactgcc ctcatccagg cctctgacca | 2250 |
| gtagcctgag aggggctttt tctaggcttc agagcagggg agagctggaa | 2300 |

-continued

| | |
|---|---|
| ggggctagaa agctcccgct tgtctgtttc tcaggctcct gtgagcctca | 2350 |
| gtcctgagac cagagtcaag aggaagtaca cgtcccaatc acccgtgtca | 2400 |
| ggattcactc tcaggagctg ggtggcagga gaggcaatag ccctgtggc | 2450 |
| aattgcagga ccagctggag cagggttgcg gtgtctccac ggtgctctcg | 2500 |
| ccctgcccat ggccacccca gactctgatc tccaggaacc ccatagcccc | 2550 |
| tctccacctc accccatgtt gatgcccagg gtcactcttg ctacccgctg | 2600 |
| ggccccaaa ccccgctgc ctctcttcct tcccccatc ccccacctgg | 2650 |
| ttttgactaa tcctgcttcc ctctctgggc ctggctgccg ggatctgggg | 2700 |
| tccctaagtc cctctcttta aagaacttct gcgggtcaga ctctgaagcc | 2750 |
| gagttgctgt gggcgtgccc ggaagcagag cgccacactc gctgcttaag | 2800 |
| ctcccccagc tctttccaga aaacattaaa ctcagaattg tgttttcaa | 2849 |

<210> SEQ ID NO 78
<211> LENGTH: 281
<212> TYPE: PRT
<213> ORGANISM: Homo Sapien

<400> SEQUENCE: 78

Met Gly Ser Arg Gly Gln Gly Leu Leu Leu Ala Tyr Cys Leu Leu
1               5                   10                  15

Leu Ala Phe Ala Ser Gly Leu Val Leu Ser Arg Val Pro His Val
                20                  25                  30

Gln Gly Glu Gln Gln Glu Trp Glu Gly Thr Glu Leu Pro Ser
            35                  40                  45

Pro Pro Asp His Ala Glu Arg Ala Glu Gln His Glu Lys Tyr
        50                  55                  60

Arg Pro Ser Gln Asp Gln Gly Leu Pro Ala Ser Arg Cys Leu Arg
        65                  70                  75

Cys Cys Asp Pro Gly Thr Ser Met Tyr Pro Ala Thr Ala Val Pro
        80                  85                  90

Gln Ile Asn Ile Thr Ile Leu Lys Gly Glu Lys Gly Asp Arg Gly
        95                  100                 105

Asp Arg Gly Leu Gln Gly Lys Tyr Gly Lys Thr Gly Ser Ala Gly
        110                 115                 120

Ala Arg Gly His Thr Gly Pro Lys Gly Gln Lys Gly Ser Met Gly
        125                 130                 135

Ala Pro Gly Glu Arg Cys Lys Ser His Tyr Ala Ala Phe Ser Val
        140                 145                 150

Gly Arg Lys Lys Pro Met His Ser Asn His Tyr Tyr Gln Thr Val
        155                 160                 165

Ile Phe Asp Thr Glu Phe Val Asn Leu Tyr Asp His Phe Asn Met
        170                 175                 180

Phe Thr Gly Lys Phe Tyr Cys Tyr Val Pro Gly Leu Tyr Phe Phe
        185                 190                 195

Ser Leu Asn Val His Thr Trp Asn Gln Lys Glu Thr Tyr Leu His
        200                 205                 210

Ile Met Lys Asn Glu Glu Val Val Ile Leu Phe Ala Gln Val
        215                 220                 225

Gly Asp Arg Ser Ile Met Gln Ser Gln Ser Leu Met Leu Glu Leu
        230                 235                 240

Arg Glu Gln Asp Gln Val Trp Val Arg Leu Tyr Lys Gly Glu Arg

```
                245                 250                 255
Glu Asn Ala Ile Phe Ser Glu Glu Leu Asp Thr Tyr Ile Thr Phe
            260                 265                 270

Ser Gly Tyr Leu Val Lys His Ala Thr Glu Pro
            275                 280

<210> SEQ ID NO 79
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 79
tacaggccca gtcaggacca gggg                                           24

<210> SEQ ID NO 80
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 80
ctgaagaagt agaggccggg cacg                                           24

<210> SEQ ID NO 81
<211> LENGTH: 45
<212> TYPE: DNA
<213> ORGANISM: Artificial Sequence
<220> FEATURE:
<223> OTHER INFORMATION: Synthetic oligonucleotide probe

<400> SEQUENCE: 81
cccggtgctt gcgctgctgt gaccccggta cctccatgta cccgg                    45

<210> SEQ ID NO 82
<211> LENGTH: 2284
<212> TYPE: DNA
<213> ORGANISM: Homo Sapien

<400> SEQUENCE: 82
gcggagcatc cgctgcggtc ctcgccgaga ccccgcgcg gattcgccgg                50 tccttcccgc gggcgcgaca gagctgtcct cgcacctgga tggcagcagg              100
ggcgccgggg tcctctcgac gccagagaga aatctcatca tctgtgcagc              150
cttcttaaag caaactaaga ccagagggag gattatcctt gacctttgaa              200
gaccaaaact aaactgaaat ttaaaatgtt cttcggggga aagggagct               250 tgacttacac tttggtaata atttgcttcc tgacactaag gctgtctgct              300
agtcagaatt gcctcaaaaa gagtctagaa gatgttgtca ttgacatcca              350
gtcatctctt tctaagggaa tcagaggcaa tgagcccgta tatacttcaa              400
ctcaagaaga ctgcattaat tcttgctgtt caacaaaaaa catatcaggg              450
gacaaagcat gtaacttgat gatcttcgac actcgaaaaa cagctagaca              500
acccaactgc tacctatttt tctgtcccaa cgaggaagcc tgtccattga              550
aaccagcaaa aggacttatg agttacagga taattacaga ttttccatct              600
ttgaccagaa atttgccaag ccaagagtta ccccaggaag attctctctt              650
acatggccaa ttttcacaag cagtcactcc cctagcccat catcacacag              700
```

```
attattcaaa gcccaccgat atctcatgga gagacacact ttctcagaag      750
tttggatcct cagatcacct ggagaaacta tttaagatgg atgaagcaag      800
tgcccagctc cttgcttata aggaaaaagg ccattctcag agttcacaat      850
tttcctctga tcaagaaata gctcatctgc tgcctgaaaa tgtgagtgcg      900
ctcccagcta cggtggcagt tgcttctcca cataccacct cggctactcc      950
aaagcccgcc acccttctac ccaccaatgc ttcagtgaca ccttctggga     1000
cttcccagcc acagctggcc accacagctc cacctgtaac cactgtcact     1050
tctcagcctc ccacgaccct catttctaca gtttttacac gggctgcggc     1100
tacactccaa gcaatggcta acacagcagt tctgactacc acctttcagg     1150
cacctacgga ctcgaaaggc agcttagaaa ccataccgtt tacagaaatc     1200
tccaacttaa ctttgaacac agggaatgtg tataaccta ctgcactttc      1250 tatgtcaaat gtggagtctt ccactatgaa taaaactgct tcctgggaag     1300
gtagggaggc cagtccaggc agttcctccc agggcagtgt tccagaaaat     1350
cagtacggcc ttccatttga aaaatggctt cttatcgggt ccctgctctt     1400
tggtgtcctg ttcctggtga taggcctcgt cctcctgggt agaatccttt     1450
cggaatcact ccgcaggaaa cgttactcaa gactggatta tttgatcaat     1500
gggatctatg tggacatcta aggatggaac tcggtgtctc ttaattcatt     1550
tagtaaccag aagcccaaat gcaatgagtt tctgctgact tgctagtctt     1600
agcaggaggt tgtattttga agacaggaaa atgcccccctt ctgctttcct    1650 ttttttttt  ggagacagag tcttgctctg ttgcccaggc tggagtgcag     1700
tagcacgatc tcggctctca ccgcaacctc cgtctcctgg gttcaagcga     1750
ttctcctgcc tcagcctcct aagtatctgg gattacaggc atgtgccacc     1800
acacctgggt gattttgta  ttttagtag agacggggtt tcaccatgtt      1850
ggtcaggctg gtctcaaact cctgacctag tgatccaccc tcctcggcct     1900
cccaaagtgc tgggattaca ggcatgagcc accacagctg ccccccttct     1950
gttttatgtt tggttttga  gaaggaatga agtgggaacc aaattaggta     2000
attttgggta atctgtctct aaaatattag ctaaaaacaa agctctatgt     2050
aaagtaataa agtataattg ccatataaat ttcaaaattc aactggcttt     2100
tatgcaaaga aacaggttag gacatctagg ttccaattca ttcacattct     2150
tggttccaga taaatcaac  tgtttatatc aatttctaat ggatttgctt     2200 ttcttttttat atggattcct ttaaaactta ttccagatgt agttccttcc    2250 aattaaaatat ttgaataaat cttttgttac tcaa                     2284
```

<210> SEQ ID NO 83
<211> LENGTH: 431
<212> TYPE: PRT
<213> ORGANISM: Homo Sapien

<400> SEQUENCE: 83

Met Phe Phe Gly Gly Glu Gly Ser Leu Thr Tyr Thr Leu Val Ile
 1               5                  10                  15

Ile Cys Phe Leu Thr Leu Arg Leu Ser Ala Ser Gln Asn Cys Leu
                20                  25                  30

```
Lys Lys Ser Leu Glu Asp Val Val Ile Asp Ile Gln Ser Ser Leu
                35                  40                  45

Ser Lys Gly Ile Arg Gly Asn Glu Pro Val Tyr Thr Ser Thr Gln
                50                  55                  60

Glu Asp Cys Ile Asn Ser Cys Cys Ser Thr Lys Asn Ile Ser Gly
                65                  70                  75

Asp Lys Ala Cys Asn Leu Met Ile Phe Asp Thr Arg Lys Thr Ala
                80                  85                  90

Arg Gln Pro Asn Cys Tyr Leu Phe Phe Cys Pro Asn Glu Glu Ala
                95                  100                 105

Cys Pro Leu Lys Pro Ala Lys Gly Leu Met Ser Tyr Arg Ile Ile
                110                 115                 120

Thr Asp Phe Pro Ser Leu Thr Arg Asn Leu Pro Ser Gln Glu Leu
                125                 130                 135

Pro Gln Glu Asp Ser Leu Leu His Gly Gln Phe Ser Gln Ala Val
                140                 145                 150

Thr Pro Leu Ala His His His Thr Asp Tyr Ser Lys Pro Thr Asp
                155                 160                 165

Ile Ser Trp Arg Asp Thr Leu Ser Gln Lys Phe Gly Ser Ser Asp
                170                 175                 180

His Leu Glu Lys Leu Phe Lys Met Asp Glu Ala Ser Ala Gln Leu
                185                 190                 195

Leu Ala Tyr Lys Glu Lys Gly His Ser Gln Ser Ser Gln Phe Ser
                200                 205                 210

Ser Asp Gln Glu Ile Ala His Leu Leu Pro Glu Asn Val Ser Ala
                215                 220                 225

Leu Pro Ala Thr Val Ala Val Ala Ser Pro His Thr Thr Ser Ala
                230                 235                 240

Thr Pro Lys Pro Ala Thr Leu Leu Pro Thr Asn Ala Ser Val Thr
                245                 250                 255

Pro Ser Gly Thr Ser Gln Pro Gln Leu Ala Thr Thr Ala Pro Pro
                260                 265                 270

Val Thr Thr Val Thr Ser Gln Pro Pro Thr Thr Leu Ile Ser Thr
                275                 280                 285

Val Phe Thr Arg Ala Ala Ala Thr Leu Gln Ala Met Ala Thr Thr
                290                 295                 300

Ala Val Leu Thr Thr Thr Phe Gln Ala Pro Thr Asp Ser Lys Gly
                305                 310                 315

Ser Leu Glu Thr Ile Pro Phe Thr Glu Ile Ser Asn Leu Thr Leu
                320                 325                 330

Asn Thr Gly Asn Val Tyr Asn Pro Thr Ala Leu Ser Met Ser Asn
                335                 340                 345

Val Glu Ser Ser Thr Met Asn Lys Thr Ala Ser Trp Glu Gly Arg
                350                 355                 360

Glu Ala Ser Pro Gly Ser Ser Gln Gly Ser Val Pro Glu Asn
                365                 370                 375

Gln Tyr Gly Leu Pro Phe Glu Lys Trp Leu Leu Ile Gly Ser Leu
                380                 385                 390

Leu Phe Gly Val Leu Phe Leu Val Ile Gly Leu Val Leu Leu Gly
                395                 400                 405

Arg Ile Leu Ser Glu Ser Leu Arg Arg Lys Arg Tyr Ser Arg Leu
                410                 415                 420

Asp Tyr Leu Ile Asn Gly Ile Tyr Val Asp Ile
```

<210> SEQ ID NO 84
<211> LENGTH: 30
<212> TYPE: DNA
<213> ORGANISM: Artificial Sequence
<220> FEATURE:
<223> OTHER INFORMATION: Synthetic oligonucleotide probe

<400> SEQUENCE: 84
agggaggatt atccttgacc tttgaagacc                                    30

<210> SEQ ID NO 85
<211> LENGTH: 18
<212> TYPE: DNA
<213> ORGANISM: Artificial Sequence
<220> FEATURE:
<223> OTHER INFORMATION: Synthetic oligonucleotide probe

<400> SEQUENCE: 85
gaagcaagtg cccagctc                                                 18

<210> SEQ ID NO 86
<211> LENGTH: 18
<212> TYPE: DNA
<213> ORGANISM: Artificial Sequence
<220> FEATURE:
<223> OTHER INFORMATION: Synthetic oligonucleotide probe

<400> SEQUENCE: 86
cgggtccctg ctctttgg                                                 18

<210> SEQ ID NO 87
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 87
caccgtagct gggagcgcac tcac                                          24

<210> SEQ ID NO 88
<211> LENGTH: 18
<212> TYPE: DNA
<213> ORGANISM: Artificial Sequence
<220> FEATURE:
<223> OTHER INFORMATION: Synthetic oligonucleotide probe

<400> SEQUENCE: 88
agtgtaagtc aagctccc                                                 18

<210> SEQ ID NO 89
<211> LENGTH: 49
<212> TYPE: DNA
<213> ORGANISM: Artificial Sequence
<220> FEATURE:
<223> OTHER INFORMATION: Synthetic oligonucleotide probe

<400> SEQUENCE: 89
gcttcctgac actaaggctg tctgctagtc agaattgcct caaaaagag               49

<210> SEQ ID NO 90
<211> LENGTH: 957
<212> TYPE: DNA
<213> ORGANISM: Homo Sapien

<400> SEQUENCE: 90

```
cctggaagat gcgcccattg gctggtggcc tgctcaaggt ggtgttcgtg         50
gtcttcgcct ccttgtgtgc ctggtattcg gggtacctgc tcgcagagct        100
cattccagat gcacccctgt ccagtgctgc ctatagcatc cgcagcatcg        150
gggagaggcc tgtcctcaaa gctccagtcc ccaaaaggca aaatgtgac         200
cactggactc cctgcccatc tgacacctat gcctacaggt tactcagcgg        250
aggtggcaga agcaagtacg ccaaaatctg ctttgaggat aacctactta        300
tgggagaaca gctgggaaat gttgccagag aataaacat tgccattgtc         350
aactatgtaa ctgggaatgt gacagcaaca cgatgttttg atatgtatga        400
aggcgataac tctggaccga tgacaaagtt tattcagagt gctgctccaa        450
aatccctgct cttcatggtg acctatgacg acggaagcac aagactgaat        500
aacgatgcca agaatgccat agaagcactt ggaagtaaag aaatcaggaa        550
catgaaattc aggtctagct gggtatttat tgcagcaaaa ggcttggaac        600
tcccttccga aattcagaga gaaaagatca accactctga tgctaagaac        650
aacagatatt ctggctggcc tgcagagatc cagatagaag gctgcatacc        700
caaagaacga agctgacact gcagggtcct gagtaaatgt gttctgtata        750
aacaaatgca gctggaatcg ctcaagaatc ttatttttct aaatccaaca        800
gcccatattt gatgagtatt ttgggtttgt tgtaaaccaa tgaacatttg        850
ctagttgtat caaatcttgg tacgcagtat ttttataccaa gtattttatg        900
tagtgaagat gtcaattagc aggaaactaa atgaatgga aattcttaaa         950
aaaaaaa                                                       957
```

<210> SEQ ID NO 91
<211> LENGTH: 235
<212> TYPE: PRT
<213> ORGANISM: Homo Sapien

<400> SEQUENCE: 91

```
Met Arg Pro Leu Ala Gly Gly Leu Leu Lys Val Val Phe Val Val
  1               5                  10                  15

Phe Ala Ser Leu Cys Ala Trp Tyr Ser Gly Tyr Leu Leu Ala Glu
                 20                  25                  30

Leu Ile Pro Asp Ala Pro Leu Ser Ser Ala Ala Tyr Ser Ile Arg
                 35                  40                  45

Ser Ile Gly Glu Arg Pro Val Leu Lys Ala Pro Val Pro Lys Arg
                 50                  55                  60

Gln Lys Cys Asp His Trp Thr Pro Cys Pro Ser Asp Thr Tyr Ala
                 65                  70                  75

Tyr Arg Leu Leu Ser Gly Gly Arg Ser Lys Tyr Ala Lys Ile
                 80                  85                  90

Cys Phe Glu Asp Asn Leu Leu Met Gly Glu Gln Leu Gly Asn Val
                 95                 100                 105

Ala Arg Gly Ile Asn Ile Ala Ile Val Asn Tyr Val Thr Gly Asn
                110                 115                 120

Val Thr Ala Thr Arg Cys Phe Asp Met Tyr Glu Gly Asp Asn Ser
                125                 130                 135

Gly Pro Met Thr Lys Phe Ile Gln Ser Ala Ala Pro Lys Ser Leu
```

-continued

```
                    140                 145                 150
Leu Phe Met Val Thr Tyr Asp Asp Gly Ser Thr Arg Leu Asn Asn
                155                 160                 165

Asp Ala Lys Asn Ala Ile Glu Ala Leu Gly Ser Lys Glu Ile Arg
            170                 175                 180

Asn Met Lys Phe Arg Ser Ser Trp Val Phe Ile Ala Ala Lys Gly
        185                 190                 195

Leu Glu Leu Pro Ser Glu Ile Gln Arg Glu Lys Ile Asn His Ser
    200                 205                 210

Asp Ala Lys Asn Arg Tyr Ser Gly Trp Pro Ala Glu Ile Gln
215                 220                 225

Ile Glu Gly Cys Ile Pro Lys Glu Arg Ser
            230                 235

<210> SEQ ID NO 92
<211> LENGTH: 20
<212> TYPE: DNA
<213> ORGANISM: Artificial Sequence
<220> FEATURE:
<223> OTHER INFORMATION: Synthetic oligonucleotide probe

<400> SEQUENCE: 92
aatgtgacca ctggactccc                                              20

<210> SEQ ID NO 93
<211> LENGTH: 18
<212> TYPE: DNA
<213> ORGANISM: Artificial Sequence
<220> FEATURE:
<223> OTHER INFORMATION: Synthetic oligonucleotide probe

<400> SEQUENCE: 93
aggcttggaa ctcccttc                                                18

<210> SEQ ID NO 94
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 94
aagattcttg agcgattcca gctg                                         24

<210> SEQ ID NO 95
<211> LENGTH: 47
<212> TYPE: DNA
<213> ORGANISM: Artificial Sequence
<220> FEATURE:
<223> OTHER INFORMATION: Synthetic oligonucleotide probe

<400> SEQUENCE: 95
aatccctgct cttcatggtg acctatgacg acggaagcac aagactg                47

<210> SEQ ID NO 96
<211> LENGTH: 21
<212> TYPE: DNA
<213> ORGANISM: Artificial Sequence
<220> FEATURE:
<223> OTHER INFORMATION: Synthetic oligonucleotide probe

<400> SEQUENCE: 96
ctcaagaagc acgcgtactg c                                            21
```

```
<210> SEQ ID NO 97
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 97
ccaacctcag cttccgcctc tacga                                          25

<210> SEQ ID NO 98
<211> LENGTH: 18
<212> TYPE: DNA
<213> ORGANISM: Artificial Sequence
<220> FEATURE:
<223> OTHER INFORMATION: Synthetic oligonucleotide probe

<400> SEQUENCE: 98
catccaggct cgccactg                                                  18

<210> SEQ ID NO 99
<211> LENGTH: 20
<212> TYPE: DNA
<213> ORGANISM: Artificial Sequence
<220> FEATURE:
<223> OTHER INFORMATION: Synthetic oligonucleotide probe

<400> SEQUENCE: 99
tggcaaggaa tgggaacagt                                                20

<210> SEQ ID NO 100
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 100
atgctgccag acctgatcgc agaca                                          25

<210> SEQ ID NO 101
<211> LENGTH: 19
<212> TYPE: DNA
<213> ORGANISM: Artificial Sequence
<220> FEATURE:
<223> OTHER INFORMATION: Synthetic oligonucleotide probe

<400> SEQUENCE: 101
gggcagaaat ccagccact                                                 19

<210> SEQ ID NO 102
<211> LENGTH: 18
<212> TYPE: DNA
<213> ORGANISM: Artificial Sequence
<220> FEATURE:
<223> OTHER INFORMATION: Synthetic oligonucleotide probe

<400> SEQUENCE: 102
cccttcgcct gcttttga                                                  18

<210> SEQ ID NO 103
<211> LENGTH: 27
<212> TYPE: DNA
<213> ORGANISM: Artificial Sequence
<220> FEATURE:
```

<223> OTHER INFORMATION: Synthetic oligonucleotide probe

<400> SEQUENCE: 103
gccatctaat tgaagcccat cttccca                                27

<210> SEQ ID NO 104
<211> LENGTH: 19
<212> TYPE: DNA
<213> ORGANISM: Artificial Sequence
<220> FEATURE:
<223> OTHER INFORMATION: Synthetic oligonucleotide probe

<400> SEQUENCE: 104
ctggcggtgt cctctcctt                                         19

<210> SEQ ID NO 105
<211> LENGTH: 21
<212> TYPE: DNA
<213> ORGANISM: Artificial Sequence
<220> FEATURE:
<223> OTHER INFORMATION: Synthetic oligonucleotide probe

<400> SEQUENCE: 105
cctcggtctc ctcatctgtg a                                      21

<210> SEQ ID NO 106
<211> LENGTH: 20
<212> TYPE: DNA
<213> ORGANISM: Artificial Sequence
<220> FEATURE:
<223> OTHER INFORMATION: Synthetic oligonucleotide probe

<400> SEQUENCE: 106
tggcccagct gacgagccct                                        20

<210> SEQ ID NO 107
<211> LENGTH: 21
<212> TYPE: DNA
<213> ORGANISM: Artificial Sequence
<220> FEATURE:
<223> OTHER INFORMATION: Synthetic oligonucleotide probe

<400> SEQUENCE: 107
ctcataggca ctcggttctg g                                      21

<210> SEQ ID NO 108
<211> LENGTH: 19
<212> TYPE: DNA
<213> ORGANISM: Artificial Sequence
<220> FEATURE:
<223> OTHER INFORMATION: Synthetic oligonucleotide probe

<400> SEQUENCE: 108
tggctcccag cttggaaga                                         19

<210> SEQ ID NO 109
<211> LENGTH: 30
<212> TYPE: DNA
<213> ORGANISM: Artificial Sequence
<220> FEATURE:
<223> OTHER INFORMATION: Synthetic oligonucleotide probe

<400> SEQUENCE: 109
cagctcttgg ctgtctccag tatgtaccca                             30

```
<210> SEQ ID NO 110
<211> LENGTH: 21
<212> TYPE: DNA
<213> ORGANISM: Artificial Sequence
<220> FEATURE:
<223> OTHER INFORMATION: Synthetic oligonucleotide probe

<400> SEQUENCE: 110
gatgcctctg ttcctgcaca t                                            21

<210> SEQ ID NO 111
<211> LENGTH: 48
<212> TYPE: DNA
<213> ORGANISM: Artificial Sequence
<220> FEATURE:
<223> OTHER INFORMATION: Synthetic oligonucleotide probe

<400> SEQUENCE: 111
ggattctaat acgactcact atagggctgc ccgcaacccc ttcaactg               48

<210> SEQ ID NO 112
<211> LENGTH: 48
<212> TYPE: DNA
<213> ORGANISM: Artificial Sequence
<220> FEATURE:
<223> OTHER INFORMATION: Synthetic oligonucleotide probe

<400> SEQUENCE: 112
ctatgaaatt aaccctcact aaagggaccg cagctgggtg accgtgta               48

<210> SEQ ID NO 113
<211> LENGTH: 43
<212> TYPE: DNA
<213> ORGANISM: Artificial Sequence
<220> FEATURE:
<223> OTHER INFORMATION: Synthetic oligonucleotide probe

<400> SEQUENCE: 113
ggattctaat acgactcact atagggccgc cccgccacct cct                    43

<210> SEQ ID NO 114
<211> LENGTH: 48
<212> TYPE: DNA
<213> ORGANISM: Artificial Sequence
<220> FEATURE:
<223> OTHER INFORMATION: Synthetic oligonucleotide probe

<400> SEQUENCE: 114
ctatgaaatt aaccctcact aaagggactc gagacaccac ctgaccca               48

<210> SEQ ID NO 115
<211> LENGTH: 48
<212> TYPE: DNA
<213> ORGANISM: Artificial Sequence
<220> FEATURE:
<223> OTHER INFORMATION: Synthetic oligonucleotide probe

<400> SEQUENCE: 115
ggattctaat acgactcact atagggccca aggaaggcag gagactct               48

<210> SEQ ID NO 116
<211> LENGTH: 48
<212> TYPE: DNA
<213> ORGANISM: Artificial Sequence
<220> FEATURE:
<223> OTHER INFORMATION: Synthetic Oligonucleotide probe
```

```
<400> SEQUENCE: 116
ctatgaaatt aaccctcact aaagggacta gggggtggga atgaaaag                         48

<210> SEQ ID NO 117
<211> LENGTH: 48
<212> TYPE: DNA
<213> ORGANISM: Artificial Sequence
<220> FEATURE:
<223> OTHER INFORMATION: Synthetic oligonucleotide probe

<400> SEQUENCE: 117
ggattctaat acgactcact atagggcccc cctgagctct cccgtgta                         48

<210> SEQ ID NO 118
<211> LENGTH: 48
<212> TYPE: DNA
<213> ORGANISM: Artificial Sequence
<220> FEATURE:
<223> OTHER INFORMATION: Synthetic oligonucleotide probe

<400> SEQUENCE: 118
ctatgaaatt aaccctcact aaagggaagg ctcgccactg gtcgtaga                         48

<210> SEQ ID NO 119
<211> LENGTH: 48
<212> TYPE: DNA
<213> ORGANISM: Artificial Sequence
<220> FEATURE:
<223> OTHER INFORMATION: Synthetic oligonucleotide probe

<400> SEQUENCE: 119
ggattctaat acgactcact atagggcaag gagccgggac ccaggaga                         48

<210> SEQ ID NO 120
<211> LENGTH: 47
<212> TYPE: DNA
<213> ORGANISM: Artificial Sequence
<220> FEATURE:
<223> OTHER INFORMATION: Synthetic oligonucleotide probe

<400> SEQUENCE: 120
ctatgaaatt aaccctcact aaagggaggg ggcccttggt gctgagt                          47
```

ANTIBODIES TO PRO361 POLYPEPTIDE

This application is a continuation of U.S. application Ser. No. 09/944,852 filed Aug. 31, 2001, now abandoned which is a continuation of and claims priority under 35 USC §120 to U.S. application Ser. No. 09/866,028 filed May 25, 2001, now U.S. Pat. No. 6,642,360 which is a continuation of, and claims priority under 35 USC §120 to, PCT Application PCT/US99/28301 filed Dec. 1, 1999, which is a continuation-in-part of, and claims priority under 35 USC §120 to, U.S. application Ser. No. 09/254,311 filed Mar. 3, 1999, now abandoned, which is the National Stage filed under 35 USC §371 of PCT Application PCT/US98/25108 filed Dec. 1, 1998, which claims priority under 35 USC §119 to U.S. Provisional Application 60/075,945 filed Feb. 25, 1998.

FIELD OF THE INVENTION

The present invention relates generally to the identification and isolation of novel DNA and to the recombinant production of novel polypeptides.

BACKGROUND OF THE INVENTION

Extracellular proteins play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. These secreted polypeptides or signaling molecules normally pass through the cellular secretory pathway to reach their site of action in the extracellular environment.

Secreted proteins have various industrial applications, including as pharmaceuticals, diagnostics, biosensors and bioreactors. Most protein drugs available at present, such as thrombolytic agents, interferons, interleukins, erythropoietins, colony stimulating factors, and various other cytokines, are secretory proteins. Their receptors, which are membrane proteins, also have potential as therapeutic or diagnostic agents. Efforts are being undertaken by both industry and academia to identify new, native secreted proteins. Many efforts are focused on the screening of mammalian recombinant DNA libraries to identify the coding sequences for novel secreted proteins. Examples of screening methods and techniques are described in the literature [see, for example, Klein et al., *Proc. Natl. Acad. Sci.* 93:7108-7113 (1996); U.S. Pat. No. 5,536,637)].

Membrane-bound proteins and receptors can play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. Such membrane-bound proteins and cell receptors include, but are not limited to, cytokine receptors, receptor kinases, receptor phosphatases, receptors involved in cell-cell interactions, and cellular adhesin molecules like selectins and integrins. For instance, transduction of signals that regulate cell growth and differentiation is regulated in part by phosphorylation of various cellular proteins. Protein tyrosine kinases, enzymes that catalyze that process, can also act as growth factor receptors. Examples include fibroblast growth factor receptor and nerve growth factor receptor.

Membrane-bound proteins and receptor molecules have various industrial applications, including as pharmaceutical and diagnostic agents. Receptor immunoadhesins, for instance, can be employed as therapeutic agents to block receptor-ligand interactions. The membrane-bound proteins can also be employed for screening of potential peptide or small molecule inhibitors of the relevant receptor/ligand interaction.

Efforts are being undertaken by both industry and academia to identify new, native receptor or membrane-bound proteins. Many efforts are focused on the screening of mammalian recombinant DNA libraries to identify the coding sequences for novel receptor or membrane-bound proteins.

1. PRO241

Cartilage is a specialized connective tissue with a large extracellular matrix containing a dense network of collagen fibers and a high content of proteoglycan. While the majority of the proteoglycan in cartilage is aggrecan, which contains many chondroitin sulphate and keratin sulphate chains and forms multimolecular aggregates by binding with link protein to hyaluronan, cartilage also contains a number of smaller molecular weight proteoglycans. One of these smaller molecular weight proteoglycans is a protein called biglycan, a proteoglycan which is widely distributed in the extracellular matrix of various other connective tissues including tendon, sclera, skin, and the like. Biglycan is known to possess leucine-rich repeat sequences and two chondroitin sulphate/dermatan sulphate chains and functions to bind to the cell-binding domain of fibronectin so as to inhibit cellular attachment thereto. It is speculated that the small molecular weight proteoglycans such as biglycan may play important roles in the growth and/or repair of cartilage and in degenrative diseases such as arthritis. As such, there is an interest in identifying and characterizing novel polypeptides having homology to biglycan protein.

We herein describe the identification and characterization of novel polypeptides having homology to the biglycan protein, wherein those polypeptides are herein designated PRO241 polypeptides.

2. PRO243

Chordin (*Xenopus*, Xchd) is a soluble factor secreted by the Spemann organizer which has potent dorsalizing activity (Sasai et al., *Cell* 79: 779-90 (1994); Sasai et al., *Nature* 376: 333-36 (1995). Other dorsalizing factors secreted by the organizer are noggin (Smith and Harlan, *Cell* 70: 829-840 (1992); Lamb et al, *Science* 262: 713-718 (1993) and follistatin (Hemmanti-Brivartou et al., *Cell* 77: 283-295 (1994). Chordin subdivides primitive ectoderm into neural versus nonneural domains, and induces notochord and muscle formation by the dorsalization of the mesoderm. It does this by functioning as an antagonist of the ventralizing BMP-4 signals. This inhibition is mediated by direct binding of chordin to BMP-4 in the extracellular space, thereby preventing BMP-4 receptor activation by BMP-4 (Piccolo et al., *Develop. Biol.* 182: 5-20 (1996).

BMP-4 is expressed in a gradient from the ventral side of the embryo, while chordin is expressed in a gradient complementary to that of BMP-4. Chordin antagonizes BMP-4 to establish the low end of the BMP-4 gradient. Thus, the balance between the signal from chordin and other organizer-derived factors versus the BMP signal provides the ectodermal germ layer with its dorsal-ventral positional information Chordin may also be involved in the dorsal-ventral patterning of the central nervous system (Sasai et al, Cell 79: 779-90 (1994). It also induces exclusively anterior neural tissues (forebrain-type), thereby anteriorizing the neural type (Sasai et al, Cell 79: 779-90 (1997). Given its role in neuronal induction and patterning, chordin may prove useful in the treatment of neurodegenerative disorders and neural damage, e.g., due to trauma or after chemotherapy.

We herein describe the identification and characterization of novel polypeptides having homology to the chordin protein, wherein those polypeptides are herein designated PRO243 polypeptides.

3. PRO299

The notch proteins are involved in signaling during development. They may effect asymmetric development potential and may signal expression of other proteins involved in development [See Robey, E., Curr. Opin. Genet. Dev., 7(4):551 (1997), Simpson, P., Curr. Opin. Genet. Dev., 7(4):537 (1997), Blobel, C P., Cell, 90(4):589 (1997)], Nakayama, H. et al., Dev. Genet., 21(1):21 (1997), Nakayama, H. et al., Dev. Genet., 21(1):21 (1997), Sullivan, S. A. et al., Dev. Genet., 20(3):208 (1997) and Hayashi, H. et al., Int. J. Dev. Biol., 40(6):1089 (1996).] Serrate-mediated activation of notch has been observed in the dorsal compartment of the Drosophila wing imaginal disc. Fleming et al., Development, 124(15): 2973 (1997). Notch is of interest for both its role in development as well as its signaling abilities. Also of interest are novel polypeptides which may have a role in development and/or signaling.

We herein describe the identification and characterization of novel polypeptides having homology to the notch protein, wherein those polypeptides are herein designated PRO299 polypeptides.

4. PRO323

Dipeptidases are enzymatic proteins which function to cleave a large variety of different dipeptides and which are involved in an enormous number of very important biological processes in mammalian and non-mammalian organisms. Numerous different dipeptidase enzymes from a variety of different mammalian and non-mammalian organisms have been both identified and characterized. The mammalian dipeptidase enzymes play important roles in many different biological processes including, for example, protein digestion, activation, inactivation, or modulation of dipeptide hormone activity, and alteration of the physical properties of proteins and enzymes.

In light of the important physiological roles played by dipeptidase enzymes, efforts are being undertaken by both industry and academia to identify new, native dipeptidase homologs. Many efforts are focused on the screening of mammalian recombinant DNA libraries to identify the coding sequences for novel secreted and membrane-bound receptor proteins. Examples of screening methods and techniques are described in the literature [see, for example, Klein et al., Proc. Natl. Acad. Sci., 93:7108-7113 (1996); U.S. Pat. No. 5,536, 637)].

We herein describe the identification and characterization of novel polypeptides having homology to various dipeptidase enzymes, designated herein as PRO323 polypeptides.

5. PRO327

The anterior pituitary hormone prolactin is encoded by a member of the growth hormone/prolactin/placental lactogen gene family. In mammals, prolactin is primarily responsible for the development of the mammary gland and lactation. Prolactin functions to stimulate the expression of milk protein genes by increasing both gene transcription and mRNA half-life.

The physiological effects of the prolactin protein are mediated through the ability of prolactin to bind to a cell surface prolactin receptor. The prolactin receptor is found in a variety of different cell types, has a molecular mass of approximately 40,000 and is apparently not linked by disulfide bonds to itself or to other subunits. Prolactin receptor levels are differentially regulated depending upon the tissue studied.

Given the important physiological roles played by cell surface receptor molecules in vivo, efforts are currently being undertaken by both industry and academia to identify new, native membrane-bound receptor proteins, including those which share sequence homology with the prolactin receptor. Many of these efforts are focused on the screening of mammalian recombinant DNA libraries to identify the coding sequences for novel membrane-bound receptor proteins. Examples of screening methods and techniques are described in the literature [see, for example, Klein et al., Proc. Natl. Acad. Sci., 93:7108-7113 (1996); U.S. Pat. No. 5,536,637)].

We herein describe the identification and characterization of novel polypeptides having significant homology to the prolactin receptor protein, designated herein as PRO327 polypeptides.

6. PRO233

Studies have reported that the redox state of the cell is an important determinant of the fate of the cell. Furthermore, reactive oxygen species have been reported to be cytotoxic, causing inflammatory disease, including tissue necrosis, organ failure, atherosclerosis, infertility, birth defects, premature aging, mutations and malignancy. Thus, the control of oxidation and reduction is important for a number of reasons, including the control and prevention of strokes, heart attacks, oxidative stress and hypertension.

Oxygen free radicals and antioxidants appear to play an important role in the central nervous system after cerebral ischemia and reperfusion. Moreover, cardiac injury, related to ischaemia and reperfusion has been reported to be caused by the action of free radicals. In this regard, reductases, and particularly, oxidoreductases, are of interest. In addition, the transcription factors, NF-kappa B and AP-1, are known to be regulated by redox state and to affect the expression of a large variety of genes thought to be involved in the pathogenesis of AIDS, cancer, atherosclerosis and diabetic complications. Publications further describing this subject matter include Kelsey et al., Br. J. Cancer, 76(7):852-854 (1997); Friedrich and Weiss, J. Theor. Biol., 187(4):529-540 (1997) and Pieulle et al., J. Bacteriol., 179(18):5684-5692 (1997). Given the physiological importance of redox reactions in vivo, efforts are currently being under taken to identify new, native proteins which are involved in redox reactions. We describe herein the identification and characterization of novel polypeptides which have homology to reductase, designated herein as PRO233 polypeptides.

7. PRO344

The complement proteins comprise a large group of serum proteins some of which act in an enzymatic cascade, producing effector molecules involved in inflammation. The complement proteins are of particular physiological importance in regulating movement and function of cells involved in inflammation. Given the physiological importance of inflammation and related mechanisms in vivo, efforts are currently being under taken to identify new, native proteins which are involved in inflammation. We describe herein the identification and characterization of novel polypeptides which have homology to complement proteins, wherein those polypeptides are herein designated as PRO344 polypeptides.

8. PRO347

Cysteine-rich proteins are generally proteins which have intricate three-dimensional structures and/or exist in multimeric forms due to the presence of numerous cysteine residues which are capable of forming disulfide bridges. One well known cysteine-rich protein is the mannose receptor which is expressed in, among other tissues, liver where it serves to bind to mannose and transport it into liver cells. Other cysteine-rich proteins are known to play important roles in many other physiological and biochemical processes. As such, there is an interest in identifying novel cysteine-rich proteins. In this regard, Applicants describe herein the identification and characterization of novel cysteine-rich polypeptides that has significant sequence homology to the cysteine-rich secretory protein-3, designated herein as PRO347 polypeptides.

9. PRO354

Inter-alpha-trypsin inhibitor (ITI) is a large (Mr approximately 240,000) circulating protease inhibitor found in the plasma of many mammalian species. The intact inhibitor is a glycoprotein and consists of three glycosylated subunits that interact through a strong glycosaminoglycan linkage. The anti-trypsin activity of ITI is located on the smallest subunit (i.e., the light chain) of the complex, wherein that light chain is now known as the protein bikunin. The mature light chain consists of a 21-amino acid N-terminal sequence, glycosylated at Ser-10, followed by two tandem Kunitz-type domains, the first of which is glycosylated at Asn-45 and the second of which is capable of inhibiting trypsin, chymotrypsin and plasmin. The remaining two chains of the ITI complex are heavy chains which function to interact with the enzymatically active light chain of the complex.

Efforts are being undertaken by both industry and academia to identify new, native proteins. Many efforts are focused on the screening of mammalian recombinant DNA libraries to identify the coding sequences for novel secreted and membrane-bound receptor proteins. Examples of screening methods and techniques are described in the literature [see, for example, Klein et al., *Proc. Natl. Acad. Sci.* 93:7108-7113 (1996); U.S. Pat. No. 5,536,637)]. We herein describe the identification and characterization of novel polypeptides having significant homology to the ITI heavy chain, designated in the present application as PRO354 polypeptides.

10. PRO355

Cytotoxic or regulatory T cell associated molecule or "CRTAM" protein is structurally related to the immunoglobulin superfamily. The CRTAM protein should be capable of mediating various immune responses. Antibodies typically bind to CRTAM proteins with high affinity. Zlotnik, A., *Faseb*, 10(6): A1037, Abr. 216, June 1996. Given the physiological importance of T cell antigens and immune processes in vivo, efforts are currently being under taken to identify new, native proteins which are involved in immune responses. See also Kennedy et al., U.S. Pat. No. 5,686,257 (1997). We describe herein the identification and characterization of novel polypeptides which have homology to CRTAM, designated in the present application as PRO355 polypeptides.

11. PRO357

Protein-protein interactions include receptor and antigen complexes and signaling mechanisms. As more is known about the structural and functional mechanisms underlying protein-protein interactions, protein-protein interactions can be more easily manipulated to regulate the particular result of the protein-protein interaction. Thus, the underlying mechanisms of protein-protein interactions are of interest to the scientific and medical community.

All proteins containing leucine-rich repeats are thought to be involved in protein-protein interactions Leucine-rich repeats are short sequence motifs present in a number of proteins with diverse functions and cellular locations. The crystal structure of ribonuclease inhibitor protein has revealed that leucine-rich repeats correspond to beta-alpha structural units. These units are arranged so that they form a parallel beta-sheet with one surface exposed to solvent, so that the protein acquires an unusual, nonglobular shape. These two features have been indicated as responsible for the protein-binding functions of proteins containing leucine-rich repeats. See, Kobe and Deisenhofer, *Trends Biochem. Sci.*, 19(10):415-421 (October 1994).

A study has been reported on leucine-rich proteoglycans which serve as tissue organizers, orienting and ordering collagen fibrils during ontogeny and are involved in pathological processes such as wound healing, tissue repair, and tumor stroma formation. Iozzo, R. V., *Crit. Rev. Biochem. Mol. Biol.*, 32(2):141-174 (1997). Others studies implicating leucine rich proteins in wound healing and tissue repair are De La Salle, C., et al., *Vouv. Rev. Fr. Hematol.* (Germany), 37(4): 215-222 (1995), reporting mutations in the leucine rich motif in a complex associated with the bleeding disorder Bernard-Soulier syndrome, Chlemetson, K. J., *Thromb. Haemost.* (Germany), 74(1):111-116 (July 1995), reporting that platelets have leucine rich repeats and Ruoslahti, E. I., et al., WO9110727-A by La Jolla Cancer Research Foundation reporting that decorin binding to transforming growth factorβ has involvement in a treatment for cancer, wound healing and scarring. Related by function to this group of proteins is the insulin like growth factor (IGF), in that it is useful in wound-healing and associated therapies concerned with re-growth of tissue, such as connective tissue, skin and bone; in promoting body growth in humans and animals; and in stimulating other growth-related processes. The acid labile subunit (ALS) of IGF is also of interest in that it increases the half-life of IGF and is part of the IGF complex in vivo.

Another protein which has been reported to have leucine-rich repeats is the SLIT protein which has been reported to be useful in treating neuro-degenerative diseases such as Alzheimer's disease, nerve damage such as in Parkinson's disease, and for diagnosis of cancer, see, Artavanistsakonas, S. and Rothberg, J. M., WO9210518-A1 by Yale University. Also of interest is LIG-1, a membrane glycoprotein that is expressed specifically in glial cells in the mouse brain, and has leucine rich repeats and immunoglobulin-like domains. Suzuki, et al., J. Biol. Chem. (U.S.), 271(37):22522 (1996). Other studies reporting on the biological functions of proteins having leucine rich repeats include: Tayar, N., et al., *Mol. Cell Endocrinol.*, (Ireland), 125(1-2):65-70 (December 1996) (gonadotropin receptor involvement); Miura, Y., et al., *Nippon Rinsho* (Japan), 54(7):1784-1789 (July 1996) (apoptosis involvement); Harris, P. C., et al., *J. Am. Soc. Nephrol.*, 6(4): 1125-1133 (October 1995) (kidney disease involvement).

Efforts are therefore being undertaken by both industry and academia to identify new proteins having leucine rich repeats to better understand protein-protein interactions. Of particular interest are those proteins having leucine rich repeats and homology to known proteins having leucine rich repeats such as the acid labile subunit of insulin-like growth factor. Many efforts are focused on the screening of mammalian recombinant DNA libraries to identify the coding sequences for novel secreted and membrane-bound proteins having leucine rich repeats. Examples of screening methods and techniques are described in the literature [see, for example, Klein et al., *Proc. Natl. Acad. Sci.,* 93:7108-7113 (1996); U.S. Pat. No. 5,536, 637)].

We describe herein the identification and characterization of novel polypeptides having homology to the acid labile subunit of insulin-like growth factor, designated in the present application as PRO357 polypeptides.

12. PRO715

Control of cell numbers in mammals is believed to be determined, in part, by a balance between cell proliferation and cell death. One form of cell death, sometimes referred to as necrotic cell death, is typically characterized as a pathologic form of cell death resulting from some trauma or cellular injury. In contrast, there is another, "physiologic" form of cell death which usually proceeds in an orderly or controlled manner. This orderly or controlled form of cell death is often referred to as "apoptosis" [see, e.g., Barr et al., *Bio/Technology,* 12:487-493 (1994); Steller et al., *Science,* 267:1445-1449 (1995)]. Apoptotic cell death naturally occurs in many physiological processes, including embryonic development and clonal selection in the immune system [Itoh et al., *Cell,* 66:233-243 (1991)]. Decreased levels of apoptotic cell death have been associated with a variety of pathological conditions, including cancer, lupus, and herpes virus infection [Thompson, *Science,* 267:1456-1462 (1995)]. Increased levels of apoptotic cell death may be associated with a variety of other pathological conditions, including AIDS, Alzheimer's disease, Parkinson's disease, amyotrophic lateral sclerosis, multiple sclerosis, retinitis pigmentosa, cerebellar degeneration, aplastic anemia, myocardial infarction, stroke, reperfusion injury, and toxin-induced liver disease [see, Thompson, supra].

Apoptotic cell death is typically accompanied by one or more characteristic morphological and biochemical changes in cells, such as condensation of cytoplasm, loss of plasma membrane microvilli, segmentation of the nucleus, degradation of chromosomal DNA or loss of mitochondrial function. A variety of extrinsic and intrinsic signals are believed to trigger or induce such morphological and biochemical cellular changes [Raff, *Nature,* 356:397-400 (1992); Steller, supra; Sachs et al., *Blood,* 82:15 (1993)]. For instance, they can be triggered by hormonal stimuli, such as glucocorticoid hormones for immature thymocytes, as well as withdrawal of certain growth factors [Watanabe-Fukunaga et al., *Nature,* 356:314-317 (1992)]. Also, some identified oncogenes such as myc, rel, and EIA, and tumor suppressors, like p53, have been reported to have a role in inducing apoptosis. Certain chemotherapy drugs and some forms of radiation have likewise been observed to have apoptosis-inducing activity [Thompson, supra].

Various molecules, such as tumor necrosis factor-α" ("TNF-α"), tumor necrosis factor-β ("TNF-β" or "lymphotoxin-α"), lymphotoxin-β ("LT-β"), CD30 ligand, CD27 ligand. CD40 ligand, OX-40 ligand, 4-IBB ligand, Apo-1 ligand (also referred to as Fas ligand or CD95 ligand), and Apo-2 ligand (also referred to as TRAIL) have been identified as members of the tumor necrosis factor ('TNF') family of cytokines [See, e.g., Gruss and Dower, *Blood,* 85:3378-3404 (1995); Pitti et al., *J. Biol. Chem.,* 271:12687-12690 (1996); Wiley et al., *Immunity,* 3:673-682 (1995); Browning et al., *Cell,* 72:847-856 (1993); Armitage et al. *Nature,* 357:80-82 (1992)]. Among these molecules, TNF-α, TNF-β, CD30 ligand, 4-IBB ligand, Apo-1 ligand, and Apo-2 ligand (TRAIL) have been reported to be involved in apoptotic cell death. Both TNF-α and TNF-β have been reported to induce apoptotic death in susceptible tumor cells [Schmid et al., *Proc. Natl. Acad. Sci,* 83:1881 (1986); Dealtry et al., *Eur. J. Immunol.,* 17:689 (1987)]. Zheng et al. have reported that TNF-α is involved in post-stimulation apoptosis of CD8-positive T cells [Zheng et al., *Nature,* 377:348-351 (1995)]. Other investigators have reported that CD30 ligand may be involved in deletion of self-reactive T cells in the thymus [Amakawa et al., Cold Spring Harbor Laboratory Symposium on Programmed Cell Death, Abstr. No. 10, (1995)].

Mutations in the mouse Fas/Apo-1 receptor or ligand genes (called lpr and gld, respectively) have been associated with some autoimmune disorders, indicating that Apo-1 ligand may play a role in regulating the clonal deletion of self-reactive lymphocytes in the periphery [Krammer et al., *Curr. Op. Immunol.,* 6:279-289 (1994); Nagata et al., *Science,* 267: 1449-1456 (1995)]. Apo-1 ligand is also reported to induce post-stimulation apoptosis in CD4-positive T lymphocytes and in B lymphocytes, and may be involved in the elimination of activated lymphocytes when their function is no longer needed [Krammer et al., supra; Nagata et al., supra]. Agonist mouse monoclonal antibodies specifically binding to the Apo-1 receptor have been reported to exhibit cell killing activity that is comparable to or similar to that of TNF-α [Yonehara et al., *J. Exp. Med.* 169:1747-1756 (1989)].

Induction of various cellular responses mediated by such TNF family cytokines is believed to be initiated by their binding to specific cell receptors. Two distinct TNF receptors of approximately 55-kDa (TNFR1) and 75-kDa (TNFR2) have been identified [Hohman et al., *J. Biol. Chem.,* 264: 14927-14934 (1989); Brockhaus et al., *Proc. Natl. Acad. Sci.,* 87:3127-3131 (1990); EP 417,563, published Mar. 20, 1991] and human and mouse cDNAs corresponding to both receptor types have been isolated and characterized [Loetscher et al., *Cell,* 61:351 (1990); Schall et al., *Cell,* 61:361 (1990); Smith et al., *Science,* 248:1019-1023 (1990); Lewis et al., *Proc. Natl. Acad. Sci.,* 88:2830-2834 (1991); Goodwin et al., *Mol. Cell. Biol.,* 11:3020-3026 (1991)]. The TNF family ligands identified to date, with the exception of lymphotoxin-α, are type II transmembrane proteins, whose C-terminus is extracellular. In contrast, most receptors in the TNF receptor (TNFR) family identified to date are type I transmembrane proteins. In both the TNF ligand and receptor families, however, homology identified between family members has been found mainly in the extracellular domain ("ECD"). Several of the TNF family cytokines, including TNF-α, Apo-1 ligand and CD40 ligand, are cleaved proteolytically at the cell surface; the resulting protein in each case typically forms a homotrimeric molecule that functions as a soluble cytokine. TNF receptor family proteins are also usually cleaved proteolytically to release soluble receptor ECDs that can function as inhibitors of the cognate cytokines.

Recently, other members of the TNFR family have been identified. Such newly identified members of the TNFR family include CAR1, HVEM and osteoprolegerin (OPG) [Brojatsch et al., *Cell,* 87:845-855 (1996); Montgomery et al., *Cell,* 87:427-436 (1996); Marsters et al., *J. Biol Chem.,* 272: 14029-14032 (1997); Simonet et al., *Cell,* 89:309-319 (1997)]. Unlike other known TNFR-like molecules, Simonet et al., supra, report that OPG contains no hydrophobic transmembrane-spanning sequence.

For a review of the TNF family of cytokines and their receptors, see Gruss and Dower, supra.

Applicants herein describe the identification and characterization of novel polypeptides having homology to members of the tumor necrosis factor family of polypeptides, designated herein as PRO715 polypeptides.

9

13. PRO353

The complement proteins comprise a large group of serum proteins some of which act in an enzymatic cascade, producing effector molecules involved in inflammation. The complement proteins are of particular importance in regulating movement and function of cells involved in inflammation. Given the physiological importance of inflammation and related mechanisms in vivo, efforts are currently being under taken to identify new, native proteins which are involved in inflammation. We describe herein the identification and characterization of novel polypeptides which have homology to complement proteins, designated herein as PRO353 polypeptides.

14. PRO361

The mucins comprise a family of glycoproteins which have been implicated in carcinogenesis. Mucin and mucin-like proteins are secreted by both normal and transformed cells. Both qualitative and quantitative changes in mucins have been implicated in various types of cancer. Given the medical importance of cancer, efforts are currently being under taken to identify new, native proteins which may be useful for the diagnosis or treatment of cancer.

The chitinase proteins comprise a family of which have been implicated in pathogenesis responses in plants. Chitinase proteins are produced by plants and microorganisms and may play a role in the defense of plants to injury. Given the importance of plant defense mechanisms, efforts are currently being under taken to identify new, native proteins which may be useful for modulation of pathogenesis-related responses in plants. We describe herein the identification and characterization of novel polypeptides which have homology to mucin and chitinase, designated in the present application as PRO361 polypeptides.

15. PRO365

Polypeptides such as human 2-19 protein may function as cytokines. Cytokines are low molecular weight proteins which function to stimulate or inhibit the differentiation, proliferation or function of immune cells. Cytokines often act as intercellular messengers and have multiple physiological effects. Given the physiological importance of immune mechanisms in vivo, efforts are currently being under taken to identify new, native proteins which are involved in effecting the immune system. We describe herein the identification and characterization of novel polypeptides which have homology to the human 2-19 protein, designated herein as PRO365 polypeptides.

SUMMARY OF THE INVENTION

1. PRO241

Applicants have identified a cDNA clone that encodes a novel polypeptide having homology to biglycan protein, wherein the polypeptide is designated in the present application as "PRO241".

In one embodiment, the invention provides an isolated nucleic acid molecule comprising DNA encoding a PRO241 polypeptide. In one aspect, the isolated nucleic acid comprises DNA encoding the PRO241 polypeptide having amino acid residues 1 to 379 of FIG. 2 (SEQ ID NO:2), or is complementary to such encoding nucleic acid sequence, and remains stably bound to it under at least moderate, and optionally, under high stringency conditions.

In another embodiment, the invention provides isolated PRO241 polypeptide. In particular, the invention provides isolated native sequence PRO241 polypeptide, which in one embodiment, includes an amino acid sequence comprising residues 1 to 379 of FIG. 2 (SEQ ID NO:2). Another embodiment of the present invention is directed to a PRO241 polypeptide lacking the N-terminal signal peptide, wherein the PRO241 polypeptide comprises about amino acids 16 to 379 of the full-length PRO241 amino acid sequence (SEQ ID NO:2).

2. PRO243

Applicants have identified a cDNA clone (DNA35917-1207) that encodes a novel polypeptide, designated in the present application as "PRO243".

In one embodiment, the invention provides an isolated nucleic acid molecule having at least about 80% sequence identity to (a) a DNA molecule encoding a PRO243 polypeptide comprising the sequence of amino acids 1 or about 24 to 954 of FIG. 4 (SEQ ID NO:7), or (b) the complement of the DNA molecule of (a). The sequence identity preferably is about 85%, more preferably about 90%, most preferably about 95%. In one aspect, the isolated nucleic acid has at least about 80%, preferably at least about 85%, more preferably at least about 90%, and most preferably at least about 95% sequence identity with a polypeptide having amino acid residues 1 or about 24 to 954 of FIG. 4 (SEQ ID NO:7). Preferably, the highest degree of sequence identity occurs within the four (4) conserved cysteine clusters (amino acids 51 to 125; amino acids 705 to 761; amino acids 784 to 849; and amino acids 897 to 931) of FIG. 4 (SEQ ID NO:7). In a further embodiment, the isolated nucleic acid molecule comprises DNA encoding a PRO243 polypeptide having amino acid residues 1 or about 24 to 954 of FIG. 4 (SEQ ID NO:7), or is complementary to such encoding nucleic acid sequence, and remains stably bound to it under at least moderate, and optionally, under high stringency conditions. In another aspect, the invention provides a nucleic acid of the full length protein of clone DNA35917-1207, deposited with the ATCC under accession number ATCC 209508, alternatively the coding sequence of clone DNA35917-1207, deposited under accession number ATCC 209508.

In yet another embodiment, the invention provides isolated PRO243 polypeptide. In particular, the invention provides isolated native sequence PRO243 polypeptide, which in one embodiment, includes an amino acid sequence comprising residues 1 or about 24 to 954 of FIG. 4 (SEQ ID NO:7). Native PRO243 polypeptides with or without the native signal sequence (amino acids 1 to 23 in FIG. 4 (SEQ ID NO:7)), and with or without the initiating methionine are specifically included. Alternatively, the invention provides a PRO243 polypeptide encoded by the nucleic acid deposited under accession number ATCC 209508.

3. PRO299

Applicants have identified a cDNA clone that encodes a novel polypeptide, wherein the polypeptide is designated in the present application as "PRO299".

In one embodiment, the invention provides an isolated nucleic acid molecule comprising DNA encoding a PRO299 polypeptide. In one aspect, the isolated nucleic acid comprises DNA encoding the PRO299 polypeptide having amino acid residues 1 to 737 of FIG. 6 (SEQ ID NO:15), or is complementary to such encoding nucleic acid sequence, and remains stably bound to it under at least moderate, and optionally, under high stringency conditions.

In another embodiment, the invention provides isolated PRO299 polypeptide. In particular, the invention provides isolated native sequence PRO299 polypeptide, which in one embodiment, includes an amino acid sequence comprising residues 1 to 737 of FIG. 6 (SEQ ID NO:15). An additional embodiment of the present invention is directed to an isolated extracellular domain of a PRO299 polypeptide.

4. PRO323

Applicants have identified a cDNA clone that encodes a novel polypeptide having homology to a microsomal dipeptidase protein, wherein the polypeptide is designated in the present application as "PRO323".

In one embodiment, the invention provides an isolated nucleic acid molecule comprising DNA encoding a PRO323 polypeptide. In one aspect, the isolated nucleic acid comprises DNA encoding the PRO323 polypeptide having amino acid residues 1 to 433 of FIG. 10 (SEQ ID NO:24), or is complementary to such encoding nucleic acid sequence, and remains stably bound to it under at least moderate, and optionally, under high stringency conditions.

In another embodiment, the invention provides isolated PRO323 polypeptide. In particular, the invention provides isolated native sequence PRO323 polypeptide, which in one embodiment, includes an amino acid sequence comprising residues 1 to 433 of FIG. 10 (SEQ ID NO:24).

5. PRO327

Applicants have identified a cDNA clone that encodes a novel polypeptide having homology to prolactin receptor, wherein the polypeptide is designated in the present application as "PRO327".

In one embodiment, the invention provides an isolated nucleic acid molecule comprising DNA encoding a PRO327 polypeptide. In one aspect, the isolated nucleic acid comprises DNA encoding the PRO327 polypeptide having amino acid residues 1 to 422 of FIG. 14 (SEQ ID NO:32), or is complementary to such encoding nucleic acid sequence, and remains stably bound to it under at least moderate, and optionally, under high stringency conditions.

In another embodiment, the invention provides isolated PRO327 polypeptide. In particular, the invention provides isolated native sequence PRO327 polypeptide, which in one embodiment, includes an amino acid sequence comprising residues 1 to 422 of FIG. 14 (SEQ ID NO:32).

6. PRO233

Applicants have identified a cDNA clone that encodes a novel polypeptide, wherein the polypeptide is designated in the present application as "PRO233".

In one embodiment, the invention provides an isolated nucleic acid molecule comprising DNA encoding a PRO233 polypeptide. In one aspect, the isolated nucleic acid comprises DNA encoding the PRO233 polypeptide having amino acid residues 1 to 300 of FIG. 16 (SEQ ID NO:37), or is complementary to such encoding nucleic acid sequence, and remains stably bound to it under at least moderate, and optionally, under high stringency conditions.

In another embodiment, the invention provides isolated PRO233 polypeptide. In particular, the invention provides isolated native sequence PRO233 polypeptide, which in one embodiment, includes an amino acid sequence comprising residues 1 to 300 of FIG. 16 (SEQ ID NO:37).

7. PRO344

Applicants have identified a cDNA clone that encodes a novel polypeptide, wherein the polypeptides are designated in the present application as "PRO344".

In one embodiment, the invention provides an isolated nucleic acid molecule comprising DNA encoding a PRO344 polypeptide. In one aspect, the isolated nucleic acid comprises DNA encoding the PRO344 polypeptide having amino acid residues 1 to 243 of FIG. 18 (SEQ ID NO:42), or is complementary to such encoding nucleic acid sequence, and remains stably bound to it under at least moderate, and optionally, under high stringency conditions.

In another embodiment, the invention provides isolated PRO344 polypeptide. In particular, the invention provides isolated native sequence PRO344 polypeptide, which in one embodiment, includes an amino acid sequence comprising residues 1 to 243 of FIG. 18 (SEQ ID NO:42).

8. PRO347

Applicants have identified a cDNA clone that encodes a novel polypeptide having homology to cysteine-rich secretory protein-3, wherein the polypeptide is designated in the present application as "PRO347".

In one embodiment, the invention provides an isolated nucleic acid molecule comprising DNA encoding a PRO347 polypeptide. In one aspect, the isolated nucleic acid comprises DNA encoding the PRO347 polypeptide having amino acid residues 1 to 455 of FIG. 20 (SEQ ID NO:50), or is complementary to such encoding nucleic acid sequence, and remains stably bound to it under at least moderate, and optionally, under high stringency conditions.

In another embodiment, the invention provides isolated PRO347 polypeptide. In particular, the invention provides isolated native sequence PRO347 polypeptide, which in one embodiment, includes an amino acid sequence comprising residues 1 to 455 of FIG. 20 (SEQ ID NO:50).

9. PRO354

Applicants have identified a cDNA clone that encodes a novel polypeptide having homology to the heavy chain of the inter-alpha-trypsin inhibitor (ITI), wherein the polypeptide is designated in the present application as "PRO354".

In one embodiment, the invention provides an isolated nucleic acid molecule comprising DNA encoding a PRO354 polypeptide. In one aspect, the isolated nucleic acid comprises DNA encoding the PRO354 polypeptide having amino acid residues 1 to 694 of FIG. 22 (SEQ ID NO:55), or is complementary to such encoding nucleic acid sequence, and remains stably bound to it under at least moderate, and optionally, under high stringency conditions.

In another embodiment, the invention provides isolated PRO354 polypeptide. In particular, the invention provides isolated native sequence PRO354 polypeptide, which in one embodiment, includes an amino acid sequence comprising residues 1 to 694 of FIG. 22 (SEQ ID NO:55).

10. PRO355

Applicants have identified a cDNA clone that encodes a novel polypeptide, wherein the polypeptide is designated in the present application as "PRO355".

In one embodiment, the invention provides an isolated nucleic acid molecule comprising DNA encoding a PRO355 polypeptide. In one aspect, the isolated nucleic acid comprises DNA encoding the PRO355 polypeptide having amino acid residues 1 to 440 of FIG. 24 (SEQ ID NO:61), or is complementary to such encoding nucleic acid sequence, and remains stably bound to it under at least moderate, and optionally, under high stringency conditions.

In another embodiment, the invention provides isolated PRO355 polypeptide. In particular, the invention provides isolated native sequence PRO355 polypeptide, which in one embodiment, includes an amino acid sequence comprising residues 1 to 440 of FIG. 24 (SEQ ID NO:61). An additional embodiment of the present invention is directed to an isolated extracellular domain of a PRO355 polypeptide.

11. PRO357

Applicants have identified a cDNA clone that encodes a novel polypeptide having homology to insulin-like growth factor (IGF) acid labile subunit (ALS), wherein the polypeptide is designated in the present application as "PRO357".

In one embodiment, the invention provides an isolated nucleic acid molecule comprising DNA encoding a PRO357 polypeptide. In one aspect, the isolated nucleic acid comprises DNA encoding the PRO357 polypeptide having amino acid residues 1 through 598 of FIG. 26 (SEQ ID NO:69), or is complementary to such encoding nucleic acid sequence, and remains stably bound to it under at least moderate, and optionally, under high stringency conditions.

In another embodiment, the invention provides isolated PRO357 polypeptide. In particular, the invention provides isolated native sequence PRO357 polypeptide, which in one embodiment, includes an amino acid sequence comprising residues 1 through 598 of FIG. 26 (SEQ ID NO:69). An additional embodiment of the present invention is directed to an isolated extracellular domain of a PRO357 polypeptide.

12. PRO715

Applicants have identified cDNA clones that encode novel polypeptides having homology to tumor necrosis factor family polypeptides, wherein the polypeptides are designated in the present application as "PRO715".

In one embodiment, the invention provides an isolated nucleic acid molecule comprising DNA encoding a PRO715 polypeptide. In one aspect, the isolated nucleic acid comprises DNA encoding the PRO715 polypeptide having amino acid residues 1 to 250 of FIG. 28 (SEQ ID NO:76), or is complementary to such encoding nucleic acid sequence, and remains stably bound to it under at least moderate, and optionally, under high stringency conditions.

In another embodiment, the invention provides isolated PRO715 polypeptide. In particular, the invention provides isolated native sequence PRO715 polypeptide, which in one embodiment, includes an amino acid sequence comprising residues 1 to 250 of FIG. 28 (SEQ ID NO:76). An additional embodiment of the present invention is directed to an isolated extracellular domain of a PRO715 polypeptide.

13. PRO353

Applicants have identified a cDNA clone that encodes a novel polypeptide, wherein the polypeptides are designated in the present application as "PRO353".

In one embodiment, the invention provides an isolated nucleic acid molecule comprising DNA encoding a PRO353 polypeptide. In one aspect, the isolated nucleic acid comprises DNA encoding the PRO353 polypeptide having amino acid residues 1 to 281 of FIG. 30 (SEQ ID NO:78), or is complementary to such encoding nucleic acid sequence, and remains stably bound to it under at least moderate, and optionally, under high stringency conditions.

In another embodiment, the invention provides isolated PRO353 polypeptide. In particular, the invention provides isolated native sequence PRO353 polypeptide, which in one embodiment, includes an amino acid sequence comprising residues 1 to 281 of FIG. 30 (SEQ ID NO:78).

14. PRO361

Applicants have identified a cDNA clone that encodes a novel polypeptide, wherein the polypeptide is designated in the present application as "PRO361".

In one embodiment, the invention provides an isolated nucleic acid molecule comprising DNA encoding a PRO361 polypeptide. In one aspect, the isolated nucleic acid comprises DNA encoding the PRO361 polypeptide having amino acid residues 1 to 431 of FIG. 32 (SEQ ID NO:83), or is complementary to such encoding nucleic acid sequence, and remains stably bound to it under at least moderate, and optionally, under high stringency conditions. The isolated nucleic acid sequence may comprise the cDNA insert of the vector deposited on Feb. 5, 1998 as ATCC 209621 which includes the nucleotide sequence encoding PRO361.

In another embodiment, the invention provides isolated PRO361 polypeptide. In particular, the invention provides isolated native sequence PRO361 polypeptide, which in one embodiment, includes an amino acid sequence comprising residues 1 to 431 of FIG. 32 (SEQ ID NO:83). An additional embodiment of the present invention is directed to an isolated extracellular domain of a PRO361 polypeptide having amino acids 1 to 379 of the amino acids sequence shown in FIG. 32 (SEQ ID NO:83). Optionally, the PRO361 polypeptide is obtained or is obtainable by expressing the polypeptide encoded by the cDNA insert of the vector deposited on Feb. 5, 1998 as ATCC 209621.

15. PRO365

Applicants have identified a cDNA clone that encodes a novel polypeptide, wherein the polypeptide is designated in the present application as "PRO365".

In one embodiment, the invention provides an isolated nucleic acid molecule comprising DNA encoding a PRO365 polypeptide. In one aspect, the isolated nucleic acid comprises DNA encoding the PRO365 polypeptide having amino acid residues 1 to 235 of FIG. 34 (SEQ ID NO:91), or is complementary to such encoding nucleic acid sequence, and remains stably bound to it under at least moderate, and optionally, under high stringency conditions. In another aspect, the isolated nucleic acid comprises DNA encoding the PRO365 polypeptide having amino acid residues 21 to 235 of FIG. 34 (SEQ ID NO:91), or is complementary to such encoding nucleic acid sequence, and remains stably bound to it under at least moderate, and optionally, under high stringency conditions.

In another embodiment, the invention provides isolated PRO365 polypeptide. In particular, the invention provides isolated native sequence PRO365 polypeptide, which in one embodiment, includes an amino acid sequence comprising residues 1 to 235 of FIG. 34 (SEQ ID NO:91). An additional embodiment of the present invention is directed to an amino acid sequence comprising residues 21 to 235 of FIG. 34 (SEQ ID NO:91).

16. Additional Embodiments

In other embodiments of the present invention, the invention provides vectors comprising DNA encoding any of the herein described polypeptides. Host cell comprising any such vector are also provided. By way of example, the host cells may be CHO cells, *E. coli*, or yeast. A process for producing any of the herein described polypeptides is further provided and comprises culturing host cells under conditions suitable for expression of the desired polypeptide and recovering the desired polypeptide from the cell culture.

In other embodiments, the invention provides chimeric molecules comprising any of the herein described polypeptides fused to a heterologous polypeptide or amino acid sequence. Example of such chimeric molecules comprise any of the herein described polypeptides fused to an epitope tag sequence or a Fc region of an immunoglobulin.

In another embodiment, the invention provides an antibody which specifically binds to any of the above or below described polypeptides. Optionally, the antibody is a monoclonal antibody, humanized antibody, antibody fragment or single-chain antibody.

In yet other embodiments, the invention provides oligonucleotide probes useful for isolating genomic and cDNA nucleotide sequences or as antisense probes, wherein those probes may be derived from any of the above or below described nucleotide sequences.

In other embodiments, the invention provides an isolated nucleic acid molecule comprising a nucleotide sequence that encodes a PRO polypeptide.

In one aspect, the isolated nucleic acid molecule comprises a nucleotide sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to (a) a DNA molecule encoding a PRO polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein, or (b) the complement of the DNA molecule of (a).

In other aspects, the isolated nucleic acid molecule comprises a nucleotide sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to (a) a DNA molecule comprising the coding sequence of a full-length PRO polypeptide cDNA as disclosed herein, the coding sequence of a PRO polypeptide lacking the signal peptide as disclosed herein, the coding sequence of an extracellular domain of a transmembrane PRO polypeptide, with or without the signal peptide, as disclosed herein or the coding sequence of any other specifically defined fragment of the full-length amino acid sequence as disclosed herein, or (b) the complement of the DNA molecule of (a).

In a further aspect, the invention concerns an isolated nucleic acid molecule comprising a nucleotide sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to (a) a DNA molecule that encodes the same mature polypeptide encoded by any of the human protein cDNAs deposited with the ATCC as disclosed herein, or (b) the complement of the DNA molecule of (a).

Another aspect the invention provides an isolated nucleic acid molecule comprising a nucleotide sequence encoding a PRO polypeptide which is either transmembrane domain-deleted or transmembrane domain-inactivated, or is complementary to such encoding nucleotide sequence, wherein the transmembrane domain(s) of such polypeptide are disclosed herein. Therefore, soluble extracellular domains of the herein described PRO polypeptides are contemplated.

Another embodiment is directed to fragments of a PRO polypeptide coding sequence, or the complement thereof, that may find use as, for example, hybridization probes, for encoding fragments of a PRO polypeptide that may optionally encode a polypeptide comprising a binding site for an anti-PRO antibody or as antisense oligonucleotide probes. Such nucleic acid fragments are usually at least about 20 nucleotides in length, preferably at least about 30 nucleotides in length, more preferably at least about 40 nucleotides in length, yet more preferably at least about 50 nucleotides in length, yet more preferably at least about 60 nucleotides in length, yet more preferably at least about 70 nucleotides in length, yet more preferably at least about 80 nucleotides in length, yet more preferably at least about 90 nucleotides in length, yet more preferably at least about 100 nucleotides in length, yet more preferably at least about 110 nucleotides in length, yet more preferably at least about 120 nucleotides in length, yet more preferably at least about 130 nucleotides in length, yet more preferably at least about 140 nucleotides in length, yet more preferably at least about 150 nucleotides in length, yet more preferably at least about 160 nucleotides in length, yet more preferably at least about 170 nucleotides in length, yet more preferably at least about 180 nucleotides in length, yet more preferably at least about 190 nucleotides in length, yet more preferably at least about 200 nucleotides in length, yet more preferably at least about 250 nucleotides in length, yet more preferably at least about 300 nucleotides in length, yet more preferably at least about 350 nucleotides in length, yet more preferably at least about 400 nucleotides in length, yet more preferably at least about 450 nucleotides in length, yet more preferably at least about 500 nucleotides in length, yet more preferably at least about 600 nucleotides in length, yet more preferably at least about 700 nucleotides in length, yet more preferably at least about 800 nucleotides in length, yet more preferably at least about 900 nucleotides in length and yet more preferably at least about 1000 nucleotides in length, wherein in this context the term "about"

means the referenced nucleotide sequence length plus or minus 10% of that referenced length. It is noted that novel fragments of a PRO polypeptide-encoding nucleotide sequence may be determined in a routine manner by aligning the PRO polypeptide-encoding nucleotide sequence with other known nucleotide sequences using any of a number of well known sequence alignment programs and determining which PRO polypeptide-encoding nucleotide sequence fragment(s) are novel. All of such PRO polypeptide-encoding nucleotide sequences are contemplated herein. Also contemplated are the PRO polypeptide fragments encoded by these nucleotide molecule fragments, preferably those PRO polypeptide fragments that comprise a binding site for an anti-PRO antibody.

In another embodiment, the invention provides isolated PRO polypeptide encoded by any of the isolated nucleic acid sequences hereinabove identified.

In a certain aspect, the invention concerns an isolated PRO polypeptide, comprising an amino acid sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to a PRO polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein.

In a further aspect, the invention concerns an isolated PRO polypeptide comprising an amino acid sequence having at least about 80% sequence identity, preferably at least about 0.81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to an amino acid sequence encoded by any of the human protein cDNAs deposited with the ATCC as disclosed herein.

In a further aspect, the invention concerns an isolated PRO polypeptide comprising an amino acid sequence scoring at least about 80% positives, preferably at least about 81% positives, more preferably at least about 82% positives, yet more preferably at least about 83% positives, yet more preferably at least about 84% positives, yet more preferably at least about 85% positives, yet more preferably at least about 86% positives, yet more preferably at least about 87% positives, yet more preferably at least about 88% positives, yet more preferably at least about 89% positives, yet more preferably at least about 90% positives, yet more preferably at least about 91% positives, yet more preferably at least about 92% positives, yet more preferably at least about 93% positives, yet more preferably at least about 94% positives, yet more preferably at least about 95% positives, yet more preferably at least about 96% positives, yet more preferably at least about 97% positives, yet more preferably at least about 98% positives and yet more preferably at least about 99% positives when compared with the amino acid sequence of a PRO polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein.

In a specific aspect, the invention provides an isolated PRO polypeptide without the N-terminal signal sequence and/or the initiating methionine and is encoded by a nucleotide sequence that encodes such an amino acid sequence as hereinbefore described. Processes for producing the same are also herein described, wherein those processes comprise culturing a host cell comprising a vector which comprises the appropriate encoding nucleic acid molecule under conditions suitable for expression of the PRO polypeptide and recovering the PRO polypeptide from the cell culture.

Another aspect the invention provides an isolated PRO polypeptide which is either transmembrane domain-deleted or transmembrane domain-inactivated. Processes for producing the same are also herein described, wherein those processes comprise culturing a host cell comprising a vector which comprises the appropriate encoding nucleic acid molecule under conditions suitable for expression of the PRO polypeptide and recovering the PRO polypeptide from the cell culture.

In yet another embodiment, the invention concerns agonists and antagonists of a native PRO polypeptide as defined herein. In a particular embodiment, the agonist or antagonist is an anti-PRO antibody or a small molecule.

In a further embodiment, the invention concerns a method of identifying agonists or antagonists to a PRO polypeptide which comprise contacting the PRO polypeptide with a candidate molecule and monitoring a biological activity mediated by said PRO polypeptide. Preferably, the PRO polypeptide is a native PRO polypeptide.

In a still further embodiment, the invention concerns a composition of matter comprising a PRO polypeptide, or an agonist or antagonist of a PRO polypeptide as herein described, or an anti-PRO antibody, in combination with a carrier. Optionally, the carrier is a pharmaceutically acceptable carrier.

Another embodiment of the present invention is directed to the use of a PRO polypeptide, or an agonist or antagonist thereof as hereinbefore described, or an anti-PRO antibody, for the preparation of a medicament useful in the treatment of a condition which is responsive to the PRO polypeptide, an agonist or antagonist thereof or an anti-PRO antibody.

BRIEF DESCRIPTION OF THE DRAWINGS

FIG. 1 shows a nucleotide sequence (SEQ ID NO:1) of a native sequence PRO241 cDNA, wherein SEQ ID NO:1 is a clone designated herein as "DNA34392-1170".

FIG. 2 shows the amino acid sequence (SEQ ID NO:2) derived from the coding sequence of SEQ ID NO:1 shown in FIG. 1.

FIG. 3 shows a nucleotide sequence (SEQ ID NO:6) of a native sequence PRO243 cDNA, wherein SEQ ID NO:6 is a clone designated herein as "DNA35917-1207".

FIG. 4 shows the amino acid sequence (SEQ ID NO:7) derived from the coding sequence of SEQ ID NO:6 shown in FIG. 3.

FIG. 5 shows a nucleotide sequence (SEQ ID NO:14) of a native sequence PRO299 cDNA, wherein SEQ ID NO:14 is a clone designated herein as "DNA39976-1215".

FIG. 6 shows the amino acid sequence (SEQ ID NO:15) derived from the coding sequence of SEQ ID NO:14 shown in FIG. 5.

FIG. 7 shows a nucleotide sequence designated herein as DNA28847 (SEQ ID NO:18)

FIG. 8 shows a nucleotide sequence designated herein as DNA35877 (SEQ ID NO:19).

FIG. 9 shows a nucleotide sequence (SEQ ID NO:23) of a native sequence PRO323 cDNA, wherein SEQ ID NO:23 is a clone designated herein as "DNA35595-1228".

FIG. 10 shows the amino acid sequence (SEQ ID NO:24) derived from the coding sequence of SEQ ID NO:23 shown in FIG. 9.

FIG. 11 shows a single-stranded nucleotide sequence (SEQ ID NO:29) containing the nucleotide sequence (nucleotides 79-1416) of a chimeric fusion protein between a PRO323-derived polypeptide and a portion of an IgG constant domain, wherein the chimeric fusion protein is designated herein as "PRO454". The single-stranded nucleotide sequence (SEQ ID NO:29) encoding the PRO323/IgG fusion protein (PRO454) is designated herein as "DNA35872".

FIG. 12 shows the amino acid sequence (SEQ ID NO:30) derived from nucleotides 79-1416 of the nucleotide sequence shown in FIG. 11. The junction in the PRO454 amino acid sequence between the PRO323-derived sequences and the IgG-derived sequences appears between amino acids 415-416 in the figure.

FIG. 13 shows a nucleotide sequence (SEQ ID NO:31) of a native sequence PRO327 cDNA, wherein SEQ ID NO:31 is a clone designated herein as "DNA38113-1230".

FIG. 14 shows the amino acid sequence (SEQ ID NO:32) derived from the coding sequence of SEQ ID NO:31 shown in FIG. 13.

FIG. 15 shows a nucleotide sequence (SEQ ID NO:36) of a native sequence PRO233 cDNA, wherein SEQ ID NO:36 is a clone designated herein as "DNA34436-1238".

FIG. 16 shows the amino acid sequence (SEQ ID NO:37) derived from the coding sequence of SEQ ID NO:36 shown in FIG. 15.

FIG. 17 shows a nucleotide sequence (SEQ ID NO:41) of a native sequence PRO344 cDNA, wherein SEQ ID NO:41 is a clone designated herein as "DNA40592-1242".

FIG. 18 shows the amino acid sequence (SEQ ID NO:42) derived from the coding sequence of SEQ ID NO:41 shown in FIG. 17.

FIG. 19 shows a nucleotide sequence (SEQ ID NO:49) of a native sequence PRO347 cDNA, wherein SEQ ID NO:49 is a clone designated herein as "DNA44176-1244".

FIG. 20 shows the amino acid sequence (SEQ ID NO:50) derived from the coding sequence of SEQ ID NO:49 shown in FIG. 19.

FIG. 21 shows a nucleotide sequence (SEQ ID NO:54) of a native sequence PRO354 cDNA, wherein SEQ ID NO:54 is a clone designated herein as "DNA44192-1246".

FIG. 22 shows the amino acid sequence (SEQ ID NO:55) derived from the coding sequence of SEQ ID NO:54 shown in FIG. 21.

FIG. 23 shows a nucleotide sequence (SEQ ID NO:60) of a native sequence PRO355 cDNA, wherein SEQ ID NO:60 is a clone designated herein as "DNA39518-1247".

FIG. 24 shows the amino acid sequence (SEQ ID NO:61) derived from the coding sequence of SEQ ID NO:60 shown in FIG. 23.

FIG. 25 shows a nucleotide sequence (SEQ ID NO:68) of a native sequence PRO357 cDNA, wherein SEQ ID NO:68 is a clone designated herein as "DNA44804-1248".

FIG. 26 shows the amino acid sequence (SEQ ID NO:69) derived from the coding sequence of SEQ ID NO:68 shown in FIG. 25.

FIG. 27 shows a nucleotide sequence (SEQ ID NO:75) of a native sequence PRO715 cDNA, wherein SEQ ID NO:75 is a clone designated herein as "DNA52722-1229".

FIG. 28 shows the amino acid sequence (SEQ ID NO:76) derived from the coding sequence of SEQ ID NO:75 shown in FIG. 27.

FIG. 29 shows a nucleotide sequence (SEQ ID NO:77) of a native sequence PRO353 cDNA, wherein SEQ ID NO:77 is a clone designated herein as "DNA41234-1242".

FIG. 30 shows the amino acid sequence (SEQ ID NO:78) derived from the coding sequence of SEQ ID NO:77 shown in FIG. 29.

FIG. 31 shows a nucleotide sequence (SEQ ID NO:82) of a native sequence PRO361 cDNA, wherein SEQ ID NO:82 is a clone designated herein as "DNA45410-1250".

FIG. 32 shows the amino acid sequence (SEQ ID NO:83) derived from the coding sequence of SEQ ID NO:82 shown in FIG. 31.

FIG. 33 shows a nucleotide sequence (SEQ ID NO:90) of a native sequence PRO365 cDNA, wherein SEQ ID NO:90 is a clone designated herein as "DNA46777-1253".

FIG. 34 shows the amino acid sequence (SEQ ID NO:91) derived from the coding sequence of SEQ ID NO:90 shown in FIG. 33.

DETAILED DESCRIPTION OF THE PREFERRED EMBODIMENTS

The terms "PRO polypeptide" and "PRO" as used herein and when immediately followed by a numerical designation refer to various polypeptides, wherein the complete designation (i.e., PRO/number) refers to specific polypeptide sequences as described herein. The terms "PRO/number polypeptide" and "PRO/number" wherein the term "number" is provided as an actual numerical designation as used herein encompass native sequence polypeptides and polypeptide variants (which are further defined herein). The PRO polypeptides described herein may be isolated from a variety of sources, such as from human tissue types or from another source, or prepared by recombinant or synthetic methods.

A "native sequence PRO polypeptide" comprises a polypeptide having the same amino acid sequence as the corresponding PRO polypeptide derived from nature. Such native sequence PRO polypeptides can be isolated from nature or can be produced by recombinant or synthetic means. The term "native sequence PRO polypeptide" specifically encompasses naturally-occurring truncated or secreted forms of the specific PRO polypeptide (e.g., an extracellular domain sequence), naturally-occurring variant forms (e.g., alternatively spliced forms) and naturally-occurring allelic variants of the polypeptide. In various embodiments of the invention, the native sequence PRO polypeptides disclosed herein are mature or full-length native sequence polypeptides comprising the full-length amino acids sequences shown in the accompanying figures. Start and stop codons are shown in bold font and underlined in the figures. However, while the PRO polypeptide disclosed in the accompanying figures are shown to begin with methionine residues designated herein as amino acid position 1 in the figures, it is conceivable and possible that other methionine residues located either upstream or downstream from the amino acid position 1 in the figures may be employed as the starting amino acid residue for the PRO polypeptides.

The PRO polypeptide "extracellular domain" or "ECD" refers to a form of the PRO polypeptide which is essentially free of the transmembrane and cytoplasmic domains. Ordinarily, a PRO polypeptide ECD will have less than 1% of such transmembrane and/or cytoplasmic domains and preferably, will have less than 0.5% of such domains. It will be understood that any transmembrane domains identified for the PRO polypeptides of the present invention are identified pursuant to criteria routinely employed in the art for identifying that type of hydrophobic domain. The exact boundaries of a transmembrane domain may vary but most likely by no more than about 5 amino acids at either end of the domain as initially identified herein. Optionally, therefore, an extracellular domain of a PRO polypeptide may contain from about 5 or fewer amino acids on either side of the transmembrane domain/extracellular domain boundary as identified in the Examples or specification and such polypeptides, with or without the associated signal peptide, and nucleic acid encoding them, are comtemplated by the present invention.

The approximate location of the "signal peptides" of the various PRO polypeptides disclosed herein are shown in the present specification and/or the accompanying figures. It is noted, however, that the C-terminal boundary of a signal peptide may vary, but most likely by no more than about 5 amino acids on either side of the signal peptide C-terminal boundary as initially identified herein, wherein the C-terminal boundary of the signal peptide may be identified pursuant to criteria routinely employed in the art for identifying that type of amino acid sequence element (e.g., Nielsen et al., *Prot. Eng.* 10:1-6 (1997) and von Heinje et al., *Nucl. Acids. Res.* 14:4683-4690 (1986)). Moreover, it is also recognized that, in some cases, cleavage of a signal sequence from a secreted polypeptide is not entirely uniform, resulting in more than one secreted species. These mature polypeptides, where the signal peptide is cleaved within no more than about 5 amino acids on either side of the C-terminal boundary of the signal peptide as identified herein, and the polynucleotides encoding them, are contemplated by the present invention.

"PRO polypeptide variant" means an active PRO polypeptide as defined above or below having at least about 80% amino acid sequence identity with a full-length native sequence PRO polypeptide sequence as disclosed herein, a PRO polypeptide sequence lacking the signal peptide as disclosed herein, an extracellular domain of a PRO polypeptide, with or without the signal peptide, as disclosed herein or any other fragment of a full-length PRO polypeptide sequence as disclosed herein. Such PRO polypeptide variants include, for instance, PRO polypeptides wherein one or more amino acid residues are added, or deleted, at the N- or C-terminus of the full-length native amino acid sequence. Ordinarily, a PRO polypeptide variant will have at least about 80% amino acid sequence identity, preferably at least about 81% amino acid sequence identity, more preferably at least about 82% amino acid sequence identity, more preferably at least about 83% amino acid sequence identity, more preferably at least about 84% amino acid sequence identity, more preferably at least about 85% amino acid sequence identity, more preferably at least about 86% amino acid sequence identity, more preferably at least about 87% amino acid sequence identity, more preferably at least about 88% amino acid sequence identity, more preferably at least about 89% amino acid sequence identity, more preferably at least about 90% amino acid sequence identity, more preferably at least about 91% amino acid sequence identity, more preferably at least about 92% amino acid sequence identity, more preferably at least about 93% amino acid sequence identity, more preferably at least about 94% amino acid sequence identity, more preferably at least about 95% amino acid sequence identity, more preferably at least about 96% amino acid sequence identity, more preferably at least about 97% amino acid sequence identity, more preferably at least about 98% amino acid sequence identity and most preferably at least about 99% amino acid sequence identity with a full-length native sequence PRO polypeptide sequence as disclosed herein, a PRO polypeptide sequence lacking the signal peptide as disclosed herein, an extracellular domain of a PRO polypeptide, with or without the signal peptide, as disclosed herein or any other specifically defined fragment of a full-length PRO polypeptide sequence as disclosed herein. Ordinarily, PRO variant polypeptides are at least about 10 amino acids in length, often at least about 20 amino acids in length, more often at least about 30 amino acids in length, more often at least about 40 amino acids in length, more often at least about 50 amino acids in length, more often at least about 60 amino acids in length, more often at least about 70 amino acids in length, more often at least about 80 amino acids in length, more often at least about 90 amino acids in length, more often at least about 100 amino acids in length, more often at least about 150 amino acids in length, more often at least about 200 amino acids in length, more often at least about 300 amino acids in length, or more.

"Percent (%) amino acid sequence identity" with respect to the PRO polypeptide sequences identified herein is defined as the percentage of amino acid residues in a candidate sequence that are identical with the amino acid residues in the specific PRO polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations using this method, Tables 2 and 3 demonstrate how to calculate the % amino acid sequence identity of the amino acid sequence designated "Comparison Protein" to the amino acid sequence designated "PRO", wherein "PRO" represents the amino acid sequence of a hypothetical PRO polypeptide of interest, "Comparison Protein" represents the amino acid sequence of a polypeptide against which the "PRO" polypeptide of interest is being compared, and "X," "Y" and "Z" each represent different hypothetical amino acid residues.

Unless specifically stated otherwise, all % amino acid sequence identity values used herein are obtained as described in the immediately preceding paragraph using the ALIGN-2 computer program. However, % amino acid sequence identity values may also be obtained as described below by using the WU-BLAST-2 computer program (Altschul et al., *Methods in Enzymology* 266:460-480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % amino acid sequence identity value is determined by dividing (a) the number of matching identical amino acid residues between the amino acid sequence of the PRO polypeptide of interest having a sequence derived from the native PRO polypeptide and the comparison amino acid sequence of interest (i.e., the sequence against which the PRO polypeptide of interest is being compared which may be a PRO variant polypeptide) as determined by WU-BLAST-2 by (b) the total number of amino acid residues of the PRO polypeptide of interest. For example, in the statement "a polypeptide comprising an the amino acid sequence A which has or having at least 80% amino acid sequence identity to the amino acid sequence B", the amino acid sequence A is the comparison amino acid sequence of interest and the amino acid sequence B is the amino acid sequence of the PRO polypeptide of interest.

Percent amino acid sequence identity may also be determined using the sequence comparison program NCBI-BLAST2 (Altschul et al., *Nucleic Acids Res.* 25:3389-3402 (1997)). NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

"PRO variant polynucleotide" or "PRO variant nucleic acid sequence" means a nucleic acid molecule which encodes an active PRO polypeptide as defined below and which has at least about 80% nucleic acid sequence identity with a nucleotide acid sequence encoding a full-length native sequence PRO polypeptide sequence as disclosed herein, a full-length native sequence PRO polypeptide sequence lacking the signal peptide as disclosed herein, an extracellular domain of a PRO polypeptide, with or without the signal peptide, as disclosed herein or any other fragment of a full-length PRO polypeptide sequence as disclosed herein. Ordinarily, a PRO variant polynucleotide will have at least about 80% nucleic acid sequence identity, more preferably at least about 81% nucleic acid sequence identity, more preferably at least about 82% nucleic acid sequence identity, more preferably at least about 83% nucleic acid sequence identity, more preferably at least about 84% nucleic acid sequence identity, more preferably at least about 85% nucleic acid sequence identity, more preferably at least about 86% nucleic acid sequence identity, more preferably at least about 87% nucleic acid sequence identity, more preferably at least about 88% nucleic acid sequence identity, more preferably at least about 89% nucleic acid sequence identity, more preferably at least about 90% nucleic acid sequence identity, more preferably at least about 91% nucleic acid sequence identity, more preferably at least about 92% nucleic acid sequence identity, more preferably at least about 93% nucleic acid sequence identity, more preferably at least about 94% nucleic acid sequence identity, more preferably at least about 95% nucleic acid sequence identity, more preferably at least about 96% nucleic acid sequence identity, more preferably at least about 97% nucleic acid sequence identity, more preferably at least about 98% nucleic acid sequence identity and yet more preferably at least about 99% nucleic acid sequence identity with a nucleic acid sequence encoding a full-length native sequence PRO polypeptide sequence as disclosed herein, a full-length native sequence PRO polypeptide sequence lacking the signal peptide as disclosed herein, an extracellular domain of a PRO polypeptide, with or without the signal sequence, as disclosed herein or any other fragment of a full-length PRO polypeptide sequence as disclosed herein. Variants do not encompass the native nucleotide sequence.

Ordinarily, PRO variant polynucleotides are at least about 30 nucleotides in length, often at least about 60 nucleotides in length, more often at least about 90 nucleotides in length, more often at least about 120 nucleotides in length, more often at least about 150 nucleotides in length, more often at least about 180 nucleotides in length, more often at least about 210 nucleotides in length, more often at least about 240 nucleotides in length, more often at least about 270 nucleotides in length, more often at least about 300 nucleotides in length, more often at least about 450 nucleotides in length, more often at least about 600 nucleotides in length, more often at least about 900 nucleotides in length, or more.

"Percent (%) nucleic acid sequence identity" with respect to PRO-encoding nucleic acid sequences identified herein is defined as the percentage of nucleotides in a candidate sequence that are identical with the nucleotides in the PRO nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. For purposes herein, however, % nucleic acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for nucleic acid sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 4 and 5, demonstrate how to calculate the % nucleic acid sequence identity of the nucleic acid sequence designated "Comparison DNA" to the nucleic acid sequence designated "PRO-DNA", wherein "PRO-DNA" represents a hypothetical PRO-encoding nucleic acid sequence of interest, "Comparison DNA" represents the nucleotide sequence of a nucleic acid molecule against which the "PRO-DNA" nucleic acid molecule of interest is being compared, and "N", "L" and "V" each represent different hypothetical nucleotides.

Unless specifically stated otherwise, all % nucleic acid sequence identity values used herein are obtained as described in the immediately preceding paragraph using the ALIGN-2 computer program. However, % nucleic acid sequence identity values may also be obtained as described below by using the WU-BLAST-2 computer program (Altschul et al., *Methods in Enzymology* 266:460-480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % nucleic acid sequence identity value is determined by dividing (a) the number of matching identical nucleotides between the nucleic acid sequence of the PRO polypeptide-encoding nucleic acid molecule of interest having a sequence derived from the native sequence PRO polypeptide-encoding nucleic acid and the comparison nucleic acid molecule of interest (i.e., the sequence against which the PRO polypeptide-encoding nucleic acid molecule of interest is being compared which may be a variant PRO polynucleotide) as determined by WU-BLAST-2 by (b) the total number of nucleotides of the PRO polypeptide-encoding nucleic acid molecule of interest. For example, in the statement "an isolated nucleic acid molecule comprising a nucleic acid sequence A which has or having at least 80% nucleic acid sequence identity to the nucleic acid sequence B", the nucleic acid sequence A is the comparison nucleic acid molecule of interest and the nucleic acid sequence B is the nucleic acid sequence of the PRO polypeptide-encoding nucleic acid molecule of interest.

Percent nucleic acid sequence identity may also be determined using the sequence comparison program NCBI-BLAST2 (Altschul et al., *Nucleic Acids Res.* 25:3389-3402 (1997)). NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program NCBI-BLAST2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

In other embodiments, PRO variant polynucleotides are nucleic acid molecules that encode an active PRO polypeptide and which are capable of hybridizing, preferably under stringent hybridization and wash conditions, to nucleotide sequences encoding a full-length PRO polypeptide as disclosed herein. PRO variant polypeptides may be those that are encoded by a PRO variant polynucleotide.

The term "positives", in the context of sequence comparison performed as described above, includes residues in the sequences compared that are not identical but have similar properties (e.g. as a result of conservative substitutions, see Table 6 below). For purposes herein, the % value of positives is determined by dividing (a) the number of amino acid residues scoring a positive value between the PRO polypeptide amino acid sequence of interest having a sequence derived from the native PRO polypeptide sequence and the comparison amino acid sequence of interest (i.e., the amino acid sequence against which the PRO polypeptide sequence is being compared) as determined in the BLOSUM62 matrix of WU-BLAST-2 by (b) the total number of amino acid residues of the PRO polypeptide of interest.

Unless specifically stated otherwise, the % value of positives is calculated as described in the immediately preceding paragraph. However, in the context of the amino acid sequence identity comparisons performed as described for ALIGN-2 and NCBI-BLAST-2 above, includes amino acid residues in the sequences compared that are not only identical, but also those that have similar properties. Amino acid residues that score a positive value to an amino acid residue of interest are those that are either identical to the amino acid residue of interest or are a preferred substitution (as defined in Table 6 below) of the amino acid residue of interest.

For amino acid sequence comparisons using ALIGN-2 or NCBI-BLAST2, the % value of positives of a given amino acid sequence A to, with, or against a given amino acid sequence B (which can alternatively be phrased as a given amino acid sequence A that has or comprises a certain % positives to, with, or against a given amino acid sequence B) is calculated as follows:

100 times the fraction X/Y where X is the number of amino acid residues scoring a positive value as defined above by the sequence alignment program ALIGN-2 or NCBI-BLAST2 in that program's alignment of A and B, and where Y is the total number of amino acid residues in B. It will be appreciated that where the length of amino acid sequence A is not equal to the length of amino acid sequence B, the % positives of A to B will not equal the % positives of B to A.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the PRO polypeptide natural environment will not be present. Ordinarily, however, isolated polypeptide will be prepared by at least one purification step.

An "isolated" PRO polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers, for example, single anti-PRO monoclonal antibodies (including agonist, antagonist, and neutralizing antibodies), anti-PRO antibody compositions with poly-epitopic specificity, single chain anti-PRO antibodies, and fragments of anti-PRO antibodies (see below). The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/ml), 01% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising a PRO polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

"Active" or "activity" for the purposes herein refers to form(s) of a PRO polypeptide which retain a biological and/or an immunological activity of native or naturally-occurring PRO, wherein "biological" activity refers to a biological function (either inhibitory or stimulatory) caused by a native or naturally-occurring PRO other than the ability to induce the production of an antibody against an antigenic epitope possessed by a native or naturally-occurring PRO and an "immunological" activity refers to the ability to induce the production of an antibody against an antigenic epitope possessed by a native or naturally-occurring PRO.

The term "antagonist" is used in the broadest sense, and includes any molecule that partially or fully blocks, inhibits, or neutralizes a biological activity of a native PRO polypeptide disclosed herein. In a similar manner, the term "agonist" is used in the broadest sense and includes any molecule that mimics a biological activity of a native PRO polypeptide disclosed herein. Suitable agonist or antagonist molecules specifically include agonist or antagonist antibodies or antibody fragments, fragments or amino acid sequence variants of native PRO polypeptides, peptides, antisense oligonucleotides, small organic molecules, etc. Methods for identifying agonists or antagonists of a PRO polypeptide may comprise contacting a PRO polypeptide with a candidate agonist or antagonist molecule and measuring a detectable change in one or more biological activities normally associated with the PRO polypeptide.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al., *Protein Eng.* 8(10): 1057-1062 [1995]); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The word 'label' when used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a PRO polypeptide or antibody thereto) to a mammal. The components of the liposome are commonly arranged in a bilayer formation, similar to the lipid arrangement of biological membranes.

A "small molecule" is defined herein to have a molecular weight below about 500 Daltons.

Table 1

```
/*
 *
 * C-C increased from 12 to 15
 * Z is average of EQ
 * B is average of ND
 * match with stop is _M; stop-stop = 0; J (joker) match = 0
 */
define  _M    -8      /* value of a match with a stop */ int     _day[26][26] = {
/*       A  B  C  D  E  F  G  H  I  J  K  L  M  N  O  P  Q  R  S  T  U  V  W  X  Y  Z */
/* A */  { 2, 0,-2, 0, 0,-4, 1,-1,-1, 0,-1,-2,-1, 0,_M, 1, 0,-2, 1, 1, 0, 0,-6, 0,-3, 0},
/* B */  { 0, 3,-4, 3, 2,-5, 0, 1,-2, 0, 0,-3,-2, 2,_M,-1, 1, 0, 0, 0, 0,-2,-5, 0,-3, 1},
/* C */  {-2,-4,15,-5,-5,-4,-3,-3,-2, 0,-5,-6,-5,-4,_M,-3,-5,-4, 0,-2, 0,-2,-8, 0, 0,-5},
/* D */  { 0, 3,-5, 4, 3,-6, 1, 1,-2, 0, 0,-4,-3, 2,_M,-1, 2,-1, 0, 0, 0,-2,-7, 0,-4, 2},
/* E */  { 0, 2,-5, 3, 4,-5, 0, 1,-2, 0, 0,-3,-2, 1,_M,-1, 2,-1, 0, 0, 0,-2,-7, 0,-4, 3},
/* F */  {-4,-5,-4,-6,-5, 9,-5,-2, 1, 0,-5, 2, 0,-4,_M,-5,-5,-4,-3,-3, 0,-1, 0, 0, 7,-5},
/* G */  { 1, 0,-3, 1, 0,-5, 5,-2,-3, 0,-2,-4,-3, 0,_M,-1,-1,-3, 1, 0, 0,-1,-7, 0,-5, 0},
/* H */  {-1, 1,-3, 1, 1,-2,-2, 6,-2, 0, 0,-2,-2, 2,_M, 0, 3, 2,-1,-1, 0,-2,-3, 0, 0, 2},
/* I */  {-1,-2,-2,-2,-2, 1,-3,-2, 5, 0,-2, 2, 2,-2,_M,-2,-2,-2,-1, 0, 0, 4,-5, 0,-1,-2},
/* J */  { 0, 0, 0, 0, 0, 0, 0, 0, 0, 0, 0, 0, 0, 0,_M, 0, 0, 0, 0, 0, 0, 0, 0, 0, 0, 0},
/* K */  {-1, 0,-5, 0, 0,-5,-2, 0,-2, 0, 5,-3, 0, 1,_M,-1, 1, 3, 0, 0, 0,-2,-3, 0,-4, 0},
/* L */  {-2,-3,-6,-4,-3, 2,-4,-2, 2, 0,-3, 6, 4,-3,_M,-3,-2,-3,-3,-1, 0, 2,-2, 0,-1,-2},
/* M */  {-1,-2,-5,-3,-2, 0,-3,-2, 2, 0, 0, 4, 6,-2,_M,-2,-1, 0,-2,-1, 0, 2,-4, 0,-2,-1},
/* N */  { 0, 2,-4, 2, 1,-4, 0, 2,-2, 0, 1,-3,-2, 2,_M,-1, 1, 0, 1, 0, 0,-2,-4, 0,-2, 1},
/* O */  {_M,_M,_M,_M,_M,_M,_M,_M,_M,_M,_M,_M,_M,_M, 0,_M,_M,_M,_M,_M,_M,_M,_M,_M,_M,_M},
/* P */  { 1,-1,-3,-1,-1,-5,-1, 0,-2, 0,-1,-3,-2,-1,_M, 6, 0, 0, 1, 0, 0,-1,-6, 0,-5, 0},
/* Q */  { 0, 1,-5, 2, 2,-5,-1, 3,-2, 0, 1,-2,-1, 1,_M, 0, 4, 1,-1,-1, 0,-2,-5, 0,-4, 3},
/* R */  {-2, 0,-4,-1,-1,-4,-3, 2,-2, 0, 3,-3, 0, 0,_M, 0, 1, 6, 0,-1, 0,-2, 2, 0,-4, 0},
/* S */  { 1, 0, 0, 0, 0,-3, 1,-1,-1, 0, 0,-3,-2, 1,_M, 1,-1, 0, 2, 1, 0,-1,-2, 0,-3, 0},
/* T */  { 1, 0,-2, 0, 0,-3, 0,-1, 0, 0, 0,-1,-1, 0,_M, 0,-1,-1, 1, 3, 0, 0,-5, 0,-3, 0},
/* U */  { 0, 0, 0, 0, 0, 0, 0, 0, 0, 0, 0, 0, 0, 0,_M, 0, 0, 0, 0, 0, 0, 0, 0, 0, 0, 0},
/* V */  { 0,-2,-2,-2,-2,-1,-1,-2, 4, 0,-2, 2, 2,-2,_M,-1,-2,-2,-1, 0, 0, 4,-6, 0,-2,-2},
/* W */  {-6,-5,-8,-7,-7, 0,-7,-3,-5, 0,-3,-2,-4,-4,_M,-6,-5, 2,-2,-5, 0,-6,17, 0, 0,-6},
/* X */  { 0, 0, 0, 0, 0, 0, 0, 0, 0, 0, 0, 0, 0, 0,_M, 0, 0, 0, 0, 0, 0, 0, 0, 0, 0, 0},
/* Y */  {-3,-3, 0,-4,-4, 7,-5, 0,-1, 0,-4,-1,-2,-2,_M,-5,-4,-4,-3,-3, 0,-2, 0, 0,10,-4},
/* Z */  { 0, 1,-5, 2, 3,-5, 0, 2,-2, 0, 0,-2,-1, 1,_M, 0, 3, 0, 0, 0, 0,-2,-6, 0,-4, 4}
};
```

Table 1 (cont')

```
/*
*/
#include <stdio.h>
include <ctype.h> define  MAXJMP    16      /* max jumps in a diag */
define  MAXGAP    24      /* don't continue to penalize gaps larger than this */
#define  JMPS      1024    /* max jmps in an path */
define  MX        4       /* save if there's at least MX-1 bases since last jmp */ define  DMAT      3       /* value of matching bases */
define  DMIS      0       /* penalty for mismatched bases */
#define  DINS0     8       /* penalty for a gap */
#define  DINS1     1       /* penalty per base */
#define  PINS0     8       /* penalty for a gap */
define  PINS1     4       /* penalty per residue */ struct jmp {
        short           n[MAXJMP];      /* size of jmp (neg for dely) */
        unsigned short  x[MAXJMP];      /* base no. of jmp in seq x */
};                                      /* limits seq to 2^16 -1 */ struct diag {
        int         score;      /* score at last jmp */
        long        offset;     /* offset of prev block */
        short       ijmp;       /* current jmp index */
        struct jmp  jp;         /* list of jmps */
};

struct path {
        int     spc;            /* number of leading spaces */
        short   n[JMPS];        /* size of jmp (gap) */
        int     x[JMPS];        /* loc of jmp (last elem before gap) */
};

char          *ofile;           /* output file name */
char          *namex[2];        /* seq names: getseqs() */
char          *prog;            /* prog name for err msgs */
char          *seqx[2];         /* seqs: getseqs() */
int           dmax;             /* best diag: nw() */
int           dmax0;            /* final diag */
int           dna;              /* set if dna: main() */
int           endgaps;          /* set if penalizing end gaps */
int           gapx, gapy;       /* total gaps in seqs */
int           len0, len1;       /* seq lens */
int           ngapx, ngapy;     /* total size of gaps */
int           smax;             /* max score: nw() */
int           *xbm;             /* bitmap for matching */
long          offset;           /* current offset in jmp file */
struct  diag  *dx;              /* holds diagonals */
struct  path  pp[2];            /* holds path for seqs */ char          *calloc(), *malloc(), *index(), *strcpy();
char          *getseq(), *g_calloc();
```

Table 1 (cont')

```
/* Needleman-Wunsch alignment program
 *
 * usage: progs file1 file2
 *   where file1 and file2 are two dna or two protein sequences.
 *   The sequences can be in upper- or lower-case an may contain ambiguity
 *   Any lines beginning with ';', '>' or '<' are ignored
 *   Max file length is 65535 (limited by unsigned short x in the jmp struct)
 *   A sequence with 1/3 or more of its elements ACGTU is assumed to be DNA
 *   Output is in the file "align.out"
 *
 * The program may create a tmp file in /tmp to hold info about traceback.
 * Original version developed under BSD 4.3 on a vax 8650
 */
include "nw.h"
#include "day.h"

static   _dbval[26] = {
         1,14,2,13,0,0,4,11,0,0,12,0,3,15,0,0,0,5,6,8,8,7,9,0,10,0
};

static   _pbval[26] = {
         1, 2|(1<<('D'-'A'))|(1<<('N'-'A')), 4, 8, 16, 32, 64,
         128, 256, 0xFFFFFFF, 1<<10, 1<<11, 1<<12, 1<<13, 1<<14,
         1<<15, 1<<16, 1<<17, 1<<18, 1<<19, 1<<20, 1<<21, 1<<22,
         1<<23, 1<<24, 1<<25|(1<<('E'-'A'))|(1<<('Q'-'A'))
};

main(ac, av)                                                                main
         int    ac;
         char   *av[];
{
         prog = av[0];
         if (ac != 3) {
                  fprintf(stderr,"usage: %s file1 file2\n", prog);
                  fprintf(stderr,"where file1 and file2 are two dna or two protein sequences.\n");
                  fprintf(stderr,"The sequences can be in upper- or lower-case\n");
                  fprintf(stderr,"Any lines beginning with ';' or '<' are ignored\n");
                  fprintf(stderr,"Output is in the file \"align.out\"\n");
                  exit(1);
         }
         namex[0] = av[1];
         namex[1] = av[2];
         seqx[0] = getseq(namex[0], &len0);
         seqx[1] = getseq(namex[1], &len1);
         xbm = (dna)? _dbval : _pbval;

endgaps = 0;                 /* 1 to penalize endgaps */
         ofile = "align.out";         /* output file */ nw();                        /* fill in the matrix, get the possible jmps */
         readjmps();                  /* get the actual jmps */
         print();                     /* print stats, alignment */ cleanup(0);                  /* unlink any tmp files */
}
```

Table 1 (cont')

```
/* do the alignment, return best score: main()
 * dna: values in Fitch and Smith, PNAS, 80, 1382-1386, 1983
 * pro: PAM 250 values
 * When scores are equal, we prefer mismatches to any gap, prefer
 * a new gap to extending an ongoing gap, and prefer a gap in seqx
 * to a gap in seq y.
 */
nw()                                                                                nw
{
        char       *px, *py;              /* seqs and ptrs */
        int        *ndely, *dely;         /* keep track of dely */
        int        ndelx, delx;           /* keep track of delx */
        int        *tmp;                  /* for swapping row0, row1 */
        int        mis;                   /* score for each type */
        int        ins0, ins1;            /* insertion penalties */
        register   id;                    /* diagonal index */
        register   ij;                    /* jmp index */
        register   *col0, *col1;          /* score for curr, last row */
        register   xx, yy;                /* index into seqs */ dx = (struct diag *)g_calloc("to get diags", len0+len1+1, sizeof(struct diag));

ndely = (int *)g_calloc("to get ndely", len1+1, sizeof(int));
        dely  = (int *)g_calloc("to get dely", len1+1, sizeof(int));
        col0  = (int *)g_calloc("to get col0", len1+1, sizeof(int));
        col1  = (int *)g_calloc("to get col1", len1+1, sizeof(int));
        ins0  = (dna)? DINS0 : PINS0;
        ins1  = (dna)? DINS1 : PINS1;

smax = -10000;
        if (endgaps) {
                for (col0[0] = dely[0] = -ins0, yy = 1; yy <= len1; yy++) {
                        col0[yy] = dely[yy] = col0[yy-1] - ins1;
                        ndely[yy] = yy;
                }
                col0[0] = 0;         /* Waterman Bull Math Biol 84 */
        }
        else
                for (yy = 1; yy <= len1; yy++)
                        dely[yy] = -ins0;

/* fill in match matrix
         */
        for (px = seqx[0], xx = 1; xx <= len0; px++, xx++) {
                /* initialize first entry in col
                 */
                if (endgaps) {
                        if (xx == 1)
                                col1[0] = delx = -(ins0+ins1);
                        else
                                col1[0] = delx = col0[0] - ins1;
                        ndelx = xx;
                }
                else {
                        col1[0] = 0;
                        delx = -ins0;
                        ndelx = 0;
                }
```

Table 1 (cont')

...nw

```
for (py = seqx[1], yy = 1; yy <= lenl; py++, yy++) {
        mis = col0[yy-1];
        if (dna)
                mis += (xbm[*px-'A']&xbm[*py-'A'])? DMAT : DMIS;
        else
                mis += _day[*px-'A'][*py-'A'];

/* update penalty for del in x seq;
         * favor new del over ongong del
         * ignore MAXGAP if weighting endgaps
         */
        if (endgaps || ndely[yy] < MAXGAP) {
                if (col0[yy] - ins0 >= dely[yy]) {
                        dely[yy] = col0[yy] - (ins0+ins1);
                        ndely[yy] = 1;
                } else {
                        dely[yy] -= ins1;
                        ndely[yy]++;
                }
        } else {
                if (col0[yy] - (ins0+ins1) >= dely[yy]) {
                        dely[yy] = col0[yy] - (ins0+ins1);
                        ndely[yy] = 1;
                } else
                        ndely[yy]++;
        }

/* update penalty for del in y seq;
         * favor new del over ongong del
         */
        if (endgaps || ndelx < MAXGAP) {
                if (col1[yy-1] - ins0 >= delx) {
                        delx = col1[yy-1] - (ins0+ins1);
                        ndelx = 1;
                } else {
                        delx -= ins1;
                        ndelx++;
                }
        } else {
                if (col1[yy-1] - (ins0+ins1) >= delx) {
                        delx = col1[yy-1] - (ins0+ins1);
                        ndelx = 1;
                } else
                        ndelx++;
        }

/* pick the maximum score; we're favoring
         * mis over any del and delx over dely
         */
```

Table 1 (cont')

...nw

```
                    id = xx - yy + len1 - 1;
                    if (mis > = delx && mis > = dely[yy])
                            col1[yy] = mis;
                    else if (delx > = dely[yy]) {
                            col1[yy] = delx;
                            ij = dx[id].ijmp;
                            if (dx[id].jp.n[0] && (!dna || (ndelx > = MAXJMP
                                && xx > dx[id].jp.x[ij]+MX) || mis > dx[id].score+DINS0)) {
                                    dx[id].ijmp++;
                                    if (++ij > = MAXJMP) {
                                            writejmps(id);
                                            ij = dx[id].ijmp = 0;
                                            dx[id].offset = offset;
                                            offset += sizeof(struct jmp) + sizeof(offset);
                                    }
                            }
                            dx[id].jp.n[ij] = ndelx;
                            dx[id].jp.x[ij] = xx;
                            dx[id].score = delx;
                    }
                    else {
                            col1[yy] = dely[yy];
                            ij = dx[id].ijmp;
    if (dx[id].jp.n[0] && (!dna || (ndely[yy] > = MAXJMP
                                && xx > dx[id].jp.x[ij]+MX) || mis > dx[id].score+DINS0)) {
                                    dx[id].ijmp++;
                                    if (++ij > = MAXJMP) {
                                            writejmps(id);
                                            ij = dx[id].ijmp = 0;
                                            dx[id].offset = offset;
                                            offset += sizeof(struct jmp) + sizeof(offset);
                                    }
                            }
                            dx[id].jp.n[ij] = -ndely[yy];
                            dx[id].jp.x[ij] = xx;
                            dx[id].score = dely[yy];
                    }
                    if (xx == len0 && yy < len1) {
                            /* last col
                             */
                            if (endgaps)
                                    col1[yy] -= ins0+ins1*(len1-yy);
                            if (col1[yy] > smax) {
                                    smax = col1[yy];
                                    dmax = id;
                            }
                    }
            }
            if (endgaps && xx < len0)
                    col1[yy-1] -= ins0+ins1*(len0-xx);
            if (col1[yy-1] > smax) {
                    smax = col1[yy-1];
                    dmax = id;
            }
            tmp = col0; col0 = col1; col1 = tmp;
    }
    (void) free((char *)ndely);
    (void) free((char *)dely);
    (void) free((char *)col0);
    (void) free((char *)col1);
}
```

Table 1 (cont')

```
/*
 *
 * print() -- only routine visible outside this module
 *
 * static:
 * getmat() -- trace back best path, count matches: print()
 * pr_align() -- print alignment of described in array p[]: print()
 * dumpblock() -- dump a block of lines with numbers, stars: pr_align()
 * nums() -- put out a number line: dumpblock()
 * putline() -- put out a line (name, [num], seq, [num]): dumpblock()
 * stars() - -put a line of stars: dumpblock()
 * stripname() -- strip any path and prefix from a seqname
 */ include "nw.h"

define SPC     3
#define P_LINE  256     /* maximum output line */
define P_SPC   3       /* space between name or num and seq */ extern    _day[26][26];
int       olen;          /* set output line length */
FILE      *fx;           /* output file */ print()
{
        int     lx, ly, firstgap, lastgap;      /* overlap */ if ((fx = fopen(ofile, "w")) == 0) {
                fprintf(stderr," %s: can't write %s\n", prog, ofile);
                cleanup(1);
        }
        fprintf(fx, " <first sequence: %s (length = %d)\n", namex[0], len0);
        fprintf(fx, " <second sequence: %s (length = %d)\n", namex[1], len1);
        olen = 60;
        lx = len0;
        ly = len1;
        firstgap = lastgap = 0;
        if (dmax < len1 - 1) {          /* leading gap in x */
                pp[0].spc = firstgap = len1 - dmax - 1;
                ly -= pp[0].spc;
        }
        else if (dmax > len1 - 1) {     /* leading gap in y */
                pp[1].spc = firstgap = dmax - (len1 - 1);
                lx -= pp[1].spc;
        }
        if (dmax0 < len0 - 1) {         /* trailing gap in x */
                lastgap = len0 - dmax0 -1;
                lx -= lastgap;
        }
        else if (dmax0 > len0 - 1) {    /* trailing gap in y */
                lastgap = dmax0 - (len0 - 1);
                ly -= lastgap;
        }
        getmat(lx, ly, firstgap, lastgap);
        pr_align();
}
```

Table 1 (cont')

```
/*
 * trace back the best path, count matches
 */
static
getmat(lx, ly, firstgap, lastgap)                                               getmat
        int     lx, ly;                 /* "core" (minus endgaps) */
        int     firstgap, lastgap;      /* leading trailing overlap */
{
        int             nm, i0, i1, siz0, siz1;
        char            outx[32];
        double          pct;
        register        n0, n1;
        register char   *p0, *p1;

/* get total matches, score
         */
        i0 = i1 = siz0 = siz1 = 0;
        p0 = seqx[0] + pp[1].spc;
        p1 = seqx[1] + pp[0].spc;
        n0 = pp[1].spc + 1;
        n1 = pp[0].spc + 1;

nm = 0;
        while ( *p0 && *p1 ) {
                if (siz0) {
                        p1++;
                        n1++;
                        siz0--;
                }
                else if (siz1) {
                        p0++;
                        n0++;
                        siz1--;
                }
                else {
                        if (xbm[*p0-'A']&xbm[*p1-'A'])
                                nm++;
                        if (n0++ == pp[0].x[i0])
                                siz0 = pp[0].n[i0++];
                        if (n1++ == pp[1].x[i1])
                                siz1 = pp[1].n[i1++];
                        p0++;
                        p1++;
                }
        }

/* pct homology:
         * if penalizing endgaps, base is the shorter seq
         * else, knock off overhangs and take shorter core
         */
        if (endgaps)
                lx = (len0 < len1)? len0 : len1;
        else
                lx = (lx < ly)? lx : ly;
        pct = 100.*(double)nm/(double)lx;
        fprintf(fx, "\n");
        fprintf(fx, " <%d match%s in an overlap of %d: %.2f percent similarity\n",
                nm, (nm == 1)? "" : "es", lx, pct);
```

Table 1 (cont')

```
            fprintf(fx, " <gaps in first sequence: %d", gapx);                          ...getmat
            if (gapx) {
                    (void) sprintf(outx, " (%d %s%s)",
                            ngapx, (dna)? "base":"residue", (ngapx == 1)? "":"s");
                    fprintf(fx,"%s", outx);

fprintf(fx, ", gaps in second sequence: %d", gapy);
            if (gapy) {
                    (void) sprintf(outx, " (%d %s%s)",
                            ngapy, (dna)? "base":"residue", (ngapy == 1)? "":"s");
                    fprintf(fx,"%s", outx);
            }
            if (dna)
                    fprintf(fx,
                    "\n<score: %d (match = %d, mismatch = %d, gap penalty = %d + %d per base)\n",
                    smax, DMAT, DMIS, DINS0, DINS1);
            else
                    fprintf(fx,
                    "\n<score: %d (Dayhoff PAM 250 matrix, gap penalty = %d + %d per residue)\n",
                    smax, PINS0, PINS1);
            if (endgaps)
                    fprintf(fx,
                    " <endgaps penalized. left endgap: %d %s%s, right endgap: %d %s%s\n",
                    firstgap, (dna)? "base" : "residue", (firstgap == 1)? "" : "s",
                    lastgap, (dna)? "base" : "residue", (lastgap == 1)? "" : "s");
            else
                    fprintf(fx, " <endgaps not penalized\n");
} static          nm;             /* matches in core -- for checking */
static          lmax;           /* lengths of stripped file names */
static          ij[2];          /* jmp index for a path */
static          nc[2];          /* number at start of current line */
static          ni[2];          /* current elem number -- for gapping */
static          siz[2];
static char     *ps[2];         /* ptr to current element */
static char     *po[2];         /* ptr to next output char slot */
static char     out[2][P_LINE]; /* output line */
static char     star[P_LINE];   /* set by stars() */

/*
 * print alignment of described in struct path pp[]
 */
static
pr_align()                                                                              pr_align
{
        int     nn;     /* char count */
        int     more;
        register i;

for (i = 0, lmax = 0; i < 2; i++) {
                nn = stripname(namex[i]);
                if (nn > lmax)
                        lmax = nn;

nc[i] = 1;
                ni[i] = 1;
                siz[i] = ij[i] = 0;
                ps[i] = seqx[i];
                po[i] = out[i];
        }
```

Table 1 (cont')

```
    for (nn = nm = 0, more = 1; more; ) {                                          ...pr_align
        for (i = more = 0; i < 2; i++) {
            /*
             * do we have more of this sequence?
             */
            if (!*ps[i])
                    continue;

more++;

if (pp[i].spc) {        /* leading space */
                    *po[i]++ = ' ';
                    pp[i].spc--;
            }
            else if (siz[i]) {      /* in a gap */
                    *po[i]++ = '-';
                    siz[i]--;
            }
            else {                  /* we're putting a seq element
                                     */
                    *po[i] = *ps[i];
                    if (islower(*ps[i]))
                            *ps[i] = toupper(*ps[i]);
                    po[i]++;
                    ps[i]++;

/*
                     * are we at next gap for this seq?
                     */
                    if (ni[i] == pp[i].x[ij[i]]) {
                            /*
                             * we need to merge all gaps
                             * at this location
                             */
                            siz[i] = pp[i].n[ij[i]++];
                            while (ni[i] == pp[i].x[ij[i]])
                                    siz[i] += pp[i].n[ij[i]++];
                    }
                    ni[i]++;
            }
        }
        if (++nn == olen || !more && nn) {
                dumpblock();
                for (i = 0; i < 2; i++)
                        po[i] = out[i];
                nn = 0;
        }
    }
}

/*
 * dump a block of lines, including numbers, stars: pr_align()
 */
static
dumpblock()                                                                        dumpblock
{
    register i;

for (i = 0; i < 2; i++)
            *po[i]-- = '\0';
```

Table 1 (cont')

...dumpblock

```
                (void) putc('\n', fx);
                for (i = 0; i < 2; i++) {
                        if (*out[i] && (*out[i] != ' ' || *(po[i]) != ' ')) {
                                if (i == 0)
                                        nums(i);
                                if (i == 0 && *out[1])
                                        stars();
                                putline(i);
                                if (i == 0 && *out[1])
                                        fprintf(fx, star);
                                if (i == 1)
                                        nums(i);
                        }
                }
        }

/*
 * put out a number line: dumpblock()
 */
static
nums(ix)                                                                    nums
        int     ix;     /* index in out[] holding seq line */
{
        char            nline[P_LINE];
        register        i, j;
        register char   *pn, *px, *py;

for (pn = nline, i = 0; i < lmax+P_SPC; i++, pn++)
                *pn = ' ';
        for (i = nc[ix], py = out[ix]; *py; py++, pn++) {
                if (*py == ' ' || *py == '-')
                        *pn = ' ';
                else {
                        if (i%10 == 0 || (i == 1 && nc[ix] != 1)) {
                                j = (i < 0)? -i : i;
                                for (px = pn; j; j /= 10, px--)
                                        *px = j%10 + '0';
                                if (i < 0)
                                        *px = '-';
                        }
                        else
                                *pn = ' ';
                        i++;
                }
        }
        *pn = '\0';
        nc[ix] = i;
        for (pn = nline; *pn; pn++)
                (void) putc(*pn, fx);
        (void) putc('\n', fx);
}

/*
 * put out a line (name, [num], seq, [num]): dumpblock()
 */
static
putline(ix)                                                                 putline
        int     ix;
{
```

Table 1 (cont')

```
        int         i;
        register char   *px;

for (px = namex[ix], i = 0; *px && *px != ':'; px++, i++)
                (void) putc(*px, fx);
        for (; i < lmax+P_SPC; i++)
                (void) putc(' ', fx);

/* these count from 1:
         * ni[] is current element (from 1)
         * nc[] is number at start of current line
         */
        for (px = out[ix]; *px; px++)
                (void) putc(*px&0x7F, fx);
        (void) putc('\n', fx);
}

/*
 * put a line of stars (seqs always in out[0], out[1]): dumpblock()
 */
static
stars()
{
        int         i;
        register char   *p0, *p1, cx, *px;

if (!*out[0] || (*out[0] == ' ' && *(po[0]) == ' ') ||
            !*out[1] || (*out[1] == ' ' && *(po[1]) == ' '))
                return;
        px = star;
        for (i = lmax+P_SPC; i; i--)
                *px++ = ' ';

for (p0 = out[0], p1 = out[1]; *p0 && *p1; p0++, p1++) {
                if (isalpha(*p0) && isalpha(*p1)) { if (xbm[*p0-'A']&xbm[*p1-'A']) {
                                cx = '*';
                                nm++;
                        }
                        else if (!dna && _day[*p0-'A'][*p1-'A'] > 0)
                                cx = '.';
                        else
                                cx = ' ';
                }
                else
                        cx = ' ';
                *px++ = cx;
        }
        *px++ = '\n';
        *px = '\0';

}
```

...putline stars

Table 1 (cont')

```
/*
 * strip path or prefix from pn, return len: pr_align()
 */
static
stripname(pn)
        char    *pn;    /* file name (may be path) */
{
        register char   *px, *py;

py = 0;
        for (px = pn; *px; px++)
                if (*px == '/')
                        py = px + 1;
        if (py)
                (void) strcpy(pn, py);
        return(strlen(pn));

}
``` stripname

Table 1 (cont')

```
/*
 * cleanup() -- cleanup any tmp file
 * getseq() -- read in seq, set dna, len, maxlen
 * g_calloc() -- calloc() with error checkin
 * readjmps() -- get the good jmps, from tmp file if necessary
 * writejmps() -- write a filled array of jmps to a tmp file: nw()
 */
include "nw.h"
include <sys/file.h> char      *jname = "/tmp/homgXXXXXX";      /* tmp file for jmps */
FILE      *fj;

int       cleanup();                        /* cleanup tmp file */
long      lseek();

/*
 * remove any tmp file if we blow
 */
cleanup(i)                                                                          cleanup
        int     i;
{
        if (fj)
                (void) unlink(jname);
        exit(i);
}

/*
 * read, return ptr to seq, set dna, len, maxlen
 * skip lines starting with ';', '<', or '>'
 * seq in upper or lower case
 */
char    *
getseq(file, len)                                                                   getseq
        char    *file;    /* file name */
        int     *len;     /* seq len */
{
        char              line[1024], *pseq;
        register char     *px, *py;
        int               natgc, tlen;
        FILE              *fp;

if ((fp = fopen(file,"r")) == 0) {
                fprintf(stderr,"%s: can't read %s\n", prog, file);
                exit(1);
        }
        tlen = natgc = 0;
        while (fgets(line, 1024, fp)) {
                if (*line == ';' || *line == '<' || *line == '>')
                        continue;
                for (px = line; *px != '\n'; px++)
                        if (isupper(*px) || islower(*px))
                                tlen++;
        }
        if ((pseq = malloc((unsigned)(tlen+6))) == 0) {
                fprintf(stderr,"%s: malloc() failed to get %d bytes for %s\n", prog, tlen+6, file);
                exit(1);
        }
        pseq[0] = pseq[1] = pseq[2] = pseq[3] = '\0';
```

Table 1 (cont')

...getseq

```
            py = pseq + 4;
            *len = tlen;
            rewind(fp);

while (fgets(line, 1024, fp)) {
                    if (*line == ';' || *line == '<' || *line == '>')
                            continue;
                    for (px = line; *px != '\n'; px++) {
                            if (isupper(*px))
                                    *py++ = *px;
                            else if (islower(*px))
                                    *py++ = toupper(*px);
                            if (index("ATGCU",*(py-1)))
                                    natgc++;
                    }
            }
            *py++ = '\0';
            *py = '\0';
            (void) fclose(fp);
            dna = natgc > (tlen/3);
            return(pseq+4);
    } char    *
    g_calloc(msg, nx, sz)
``` g_calloc

```
            char    *msg;           /* program, calling routine */
            int     nx, sz;        /* number and size of elements */
    {
            char    *px, *calloc();

if ((px = calloc((unsigned)nx, (unsigned)sz)) == 0) {
                    if (*msg) {
                            fprintf(stderr, "%s: g_calloc() failed %s (n=%d, sz=%d)\n", prog, msg, nx, sz);
                            exit(1);
                    }
            }
            return(px);
    }

/*
     * get final jmps from dx[] or tmp file, set pp[], reset dmax: main()
     */
    readjmps()
``` readjmps

```
    {
            int     fd = -1;
            int     siz, i0, i1;
            register i, j, xx;

if (fj) {
                    (void) fclose(fj);
                    if ((fd = open(jname, O_RDONLY, 0)) < 0) {
                            fprintf(stderr, "%s: can't open() %s\n", prog, jname);
                            cleanup(1);
                    }
            }
            for (i = i0 = i1 = 0, dmax0 = dmax, xx = len0; ; i++) {
                    while (1) {
                            for (j = dx[dmax].ijmp; j >= 0 && dx[dmax].jp.x[j] >= xx; j--)
                                    ;
```

Table 1 (cont')

...readjmps

```
                if (j < 0 && dx[dmax].offset && fj) {
                        (void) lseek(fd, dx[dmax].offset, 0);
                        (void) read(fd, (char *)&dx[dmax].jp, sizeof(struct jmp));
                        (void) read(fd, (char *)&dx[dmax].offset, sizeof(dx[dmax].offset));
                        dx[dmax].ijmp = MAXJMP-1;
                }
                else
                        break;
        }
        if (i >= JMPS) {
                fprintf(stderr, "%s: too many gaps in alignment\n", prog);
                cleanup(1);
        }
        if (j >= 0) {
                siz = dx[dmax].jp.n[j];
                xx = dx[dmax].jp.x[j];
                dmax += siz;
                if (siz < 0) {                  /* gap in second seq */
                        pp[1].n[i1] = -siz;
                        xx += siz;
                        /* id = xx - yy + len1 - 1
                        */
                        pp[1].x[i1] = xx - dmax + len1 - 1;
                        gapy++;
                        ngapy -= siz;
/* ignore MAXGAP when doing endgaps */
                        siz = (-siz < MAXGAP || endgaps)? -siz : MAXGAP;
                        i1++;
                }
                else if (siz > 0) {             /* gap in first seq */
                        pp[0].n[i0] = siz;
                        pp[0].x[i0] = xx;
                        gapx++;
                        ngapx += siz;
/* ignore MAXGAP when doing endgaps */
                        siz = (siz < MAXGAP || endgaps)? siz : MAXGAP;
                        i0++;
                }
        }
        else
                break;
}

/* reverse the order of jmps
*/
for (j = 0, i0--; j < i0; j++, i0--) {
        i = pp[0].n[j]; pp[0].n[j] = pp[0].n[i0]; pp[0].n[i0] = i;
        i = pp[0].x[j]; pp[0].x[j] = pp[0].x[i0]; pp[0].x[i0] = i;
}
for (j = 0, i1--; j < i1; j++, i1--) {
        i = pp[1].n[j]; pp[1].n[j] = pp[1].n[i1]; pp[1].n[i1] = i;
        i = pp[1].x[j]; pp[1].x[j] = pp[1].x[i1]; pp[1].x[i1] = i;
}
if (fd >= 0)
        (void) close(fd);
if (fj) {
        (void) unlink(jname);
        fj = 0;
        offset = 0;
}
}
```

Table 1 (cont')

```
/*
 * write a filled jmp struct offset of the prev one (if any): nw()
 */
writejmps(ix)                                                              writejmps
        int     ix;
{
        char    *mktemp();

if (!fj) {
                if (mktemp(jname) < 0) {
                        fprintf(stderr, "%s: can't mktemp() %s\n", prog, jname);
                        cleanup(1);
                }
                if ((fj = fopen(jname, "w")) = = 0) {
                        fprintf(stderr, "%s: can't write %s\n", prog, jname);
                        exit(1);
                }
        }
        (void) fwrite((char *)&dx[ix].jp, sizeof(struct jmp), 1, fj);
        (void) fwrite((char *)&dx[ix].offset, sizeof(dx[ix].offset), 1, fj);
}
```

TABLE 2

| PRO | XXXXXXXXXXXXXXX | (Length = 15 amino acids) |
|---|---|---|
| Comparison Protein | XXXXXYYYYYYY | (Length = 12 amino acids) |

% amino acid sequence identity = (the number of identically matching amino acid residues between the two polypeptide sequences as determined by ALIGN-2) divided by (the total number of amino acid residues of the PRO polypeptide) = 5 divided by 15 = 33.3%

TABLE 3

| PRO | XXXXXXXXXX | (Length = 10 amino acids) |
|---|---|---|
| Comparison Protein | XXXXXYYYYYYZZYZ | (Length = 15 amino acids) |

% amino acid sequence identity = (the number of identically matching amino acid residues between the two polypeptide sequences as determined by ALIGN-2) divided by (the total number of amino acid residues of the PRO polypeptide) = 5 divided by 10 = 50%

TABLE 4

| PRO-DNA | NNNNNNNNNNNNNN | (Length = 14 nucleotides) |
|---|---|---|
| Comparison DNA | NNNNNNLLLLLLLLLL | (Length = 16 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 6 divided by 14 = 42.9%

TABLE 5

| PRO-DNA | NNNNNNNNNNNN | (Length = 12 nucleotides) |
|---|---|---|
| Comparison DNA | NNNNLLLVV | (Length = 9 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 4 divided by 12 = 33.3%

II. Compositions and Methods of the Invention

A. Full-Length PRO Polypeptides

The present invention provides newly identified and isolated nucleotide sequences encoding polypeptides referred to in the present application as PRO polypeptides. In particular, cDNAs encoding various PRO polypeptides have been identified and isolated, as disclosed in further detail in the Examples below. It is noted that proteins produced in separate expression rounds may be given different PRO numbers but the UNQ number is unique for any given DNA and the encoded protein, and will not be changed. However, for sake of simplicity, in the present specification the protein encoded by the full length native nucleic acid molecules disclosed herein as well as all further native homologues and variants included in the foregoing definition of PRO, will be referred to as "PRO/number", regardless of their origin or mode of preparation.

As disclosed in the Examples below, various cDNA clones have been deposited with the ATCC. The actual nucleotide sequences of those clones can readily be determined by the skilled artisan by sequencing of the deposited clone using routine methods in the art. The predicted amino acid sequence can be determined from the nucleotide sequence using routine skill. For the PRO polypeptides and encoding nucleic acids described herein, Applicants have identified what is believed to be the reading frame best identifiable with the sequence information available at the time.

1. Full-length PRO241 Polypeptides

The present invention provides newly identified and isolated nucleotide sequences encoding polypeptides referred to in the present application as PRO241. In particular, Applicants have identified and isolated cDNA encoding a PRO241 polypeptide, as disclosed in further detail in the Examples below. Using BLAST and FastA sequence alignment computer programs, Applicants found that portions of the PRO241 polypeptide have certain homology with the various biglycan proteins. Accordingly, it is presently believed that PRO241 polypeptide disclosed in the present application is a newly identified biglycan homolog polypeptide and may possess activity typical of biglycan proteins.

2. Full-length PRO243 Polypeptides

The present invention provides newly identified and isolated nucleotide sequences encoding polypeptides referred to in the present application as PRO243. In particular, Applicants have identified and isolated cDNA encoding a PRO243 polypeptide, as disclosed in further detail in the Examples below. Using BLAST, BLAST-2 and FastA sequence alignment computer programs, Applicants found that a full-length native sequence PRO243 (shown in FIG. 4 and SEQ ID NO:7) has certain amino acid sequence identity with African clawed frog and *Xenopus* chordin and certain homology with rat chordin. Accordingly, it is presently believed that PRO243 disclosed in the present application is a newly identified member of the chordin protein family and may possess ability to influence notochord and muscle formation by the dorsalization of the mesoderm.

3. Full-length PRO299

The present invention provides newly identified and isolated nucleotide sequences encoding polypeptides referred to in the present application as PRO299. In particular, Applicants have identified and isolated cDNA encoding a PRO299 polypeptide, as disclosed in further detail in the Examples below. Using BLAST and FastA sequence alignment computer programs, Applicants found that various portions of the PRO299 polypeptide have certain homology with the notch protein. Accordingly, it is presently believed that PRO299 polypeptide disclosed in the present application is a newly identified member of the notch protein family and possesses signaling properties typical of the notch protein family.

4. Full-length PRO323 Polypeptides

The present invention provides newly identified and isolated nucleotide sequences encoding polypeptides referred to in the present application as PRO323. In particular, Applicants have identified and isolated cDNA encoding a PRO323 polypeptide, as disclosed in further detail in the Examples below. Using BLAST and FastA sequence alignment computer programs, Applicants found that various portions of the PRO323 polypeptide have certain homology with various dipeptidase proteins. Accordingly, it is presently believed that PRO323 polypeptide disclosed in the present application is a newly identified dipeptidase homolog that has dipeptidase activity 5. Full-length PRO327 Polypeptides The present invention provides newly identified and isolated nucleotide sequences encoding polypeptides referred to in the present application as PRO327. In particular, Applicants have identified and isolated cDNA encoding a PRO327 polypeptide, as disclosed in further detail in the Examples below. Using BLAST and FastA sequence alignment computer programs, Applicants found that portions of the PRO327 polypeptide have certain homology with various prolactin receptor proteins. Accordingly, it is presently believed that PRO327 polypeptide disclosed in the present application is a newly identified prolactin receptor homolog and has activity typical of a prolactin receptor protein.

6. Full-length PRO233 Polypeptides

The present invention provides newly identified and isolated nucleotide sequences encoding polypeptides referred to in the present application as PRO233. In particular, Applicants have identified and isolated cDNA encoding a PRO233 polypeptide, as disclosed in further detail in the Examples below. Using BLAST and FastA sequence alignment computer programs, Applicants found that various portions of the PRO233 polypeptide have certain homology with various reductase proteins. Applicants have also found that the DNA encoding the PRO233 polypeptide has significant homology with proteins from *Caenorhabditis elegans*. Accordingly, it is presently believed that PRO233 polypeptide disclosed in the present application is a newly identified member of the reductase family and possesses the ability to effect the redox state of a cell typical of the reductase family.

7. Full-length PRO344 Polypeptides

The present invention provides newly identified and isolated nucleotide sequences encoding polypeptides referred to in the present application as PRO344. In particular, Applicants have identified and isolated cDNA encoding PRO344 polypeptides, as disclosed in further detail in the Examples below. Using BLAST and FastA sequence alignment computer programs, Applicants found that various portions of the PRO344 polypeptide have certain homology with the human and mouse complement proteins. Accordingly, it is presently believed that the PRO344 polypeptide disclosed in the present application is a newly identified member of the complement family and possesses the ability to affect the inflammation process as is typical of the complement family of proteins.

8. Full-length PRO347 Polypeptides

The present invention provides newly identified and isolated nucleotide sequences encoding polypeptides referred to in the present application as PRO347. In particular, Applicants have identified and isolated cDNA encoding a PRO347 polypeptide, as disclosed in further detail in the Examples below. Using BLAST and FastA sequence alignment computer programs, Applicants found that portions of the PRO347 polypeptide have certain homology with various cysteine-rich secretory proteins. Accordingly, it is presently believed that PRO347 polypeptide disclosed in the present application is a newly identified cysteine-rich secretory protein and may possess activity typical of the cysteine-rich secretory protein family.

9. Full-length PRO354 Polypeptides

The present invention provides newly identified and isolated nucleotide sequences encoding polypeptides referred to in the present application as PRO354. In particular, Applicants have identified and isolated cDNA encoding a PRO354 polypeptide, as disclosed in further detail in the Examples below. Using BLAST and FastA sequence alignment computer programs, Applicants found that portions of the PRO354 polypeptide have certain homology with the inter-alpha-trypsin inhibitor heavy chain protein. Accordingly, it is presently believed that PRO354 polypeptide disclosed in the present application is a newly identified inter-alpha-trypsin inhibitor heavy chain homolog.

10. Full-length PRO355 Polypeptides

The present invention provides newly identified and isolated nucleotide sequences encoding polypeptides referred to in the present application as PRO355. In particular, Applicants have identified and isolated cDNA encoding a PRO355 polypeptide, as disclosed in further detail in the Examples below. Using BLAST and FastA sequence alignment computer programs, Applicants found that various portions of the PRO355 polypeptide have certain homology with the CRTAM protein. Applicants have also found that the DNA encoding the PRO355 polypeptide also has homology to the thymocyte activation and developmental protein, the H20A receptor, the H20B receptor, the poliovirus receptor and the *Cercopithecus aethiops* AGM delta 1 protein. Accordingly, it is presently believed that PRO355 polypeptide disclosed in the present application is a newly identified member of the CRTAM protein family.

11. Full-length PRO357 Polypeptides

The present invention provides newly identified and isolated nucleotide sequences encoding polypeptides referred to in the present application as PRO357. In particular, Applicants have identified and isolated cDNA encoding a PRO357 polypeptide, as disclosed in further detail in the Examples below. Using BLAST and FastA sequence alignment computer programs, Applicants found that various portions of the PRO357 polypeptide have certain homology with the acid labile subunit of insulin-like growth factor Applicants have also found that non-coding regions of the DNA44804-1248 align with a human gene signature as described in WO 95/14772. Applicants have further found that non-coding regions of the DNA44804-1248 align with the adenovirus type 12/human recombinant viral DNA as described in Deuring and Doerfler, *Gene*, 26:283-289 (1983). Based on the coding region homology, it is presently believed that PRO357 polypeptide disclosed in the present application is a newly identified member of the leucine rich repeat family of proteins, and particularly, is related to the acid labile subunit of insulin-like growth factor. As such, PRO357 is likely to be involved in binding mechanisms, and may be part of a complex.

12. Full-length PRO715 Polypeptides

The present invention provides newly identified and isolated nucleotide sequences encoding polypeptides referred to in the present application as PRO715. In particular, Applicants have identified and isolated cDNA molecules encoding PRO715 polypeptides, as disclosed in further detail in the Examples below. Using BLAST and FastA sequence alignment computer programs, Applicants found that various portions of the PRO715 polypeptides have certain homology with the various members of the tumor necrosis family of proteins. Accordingly, it is presently believed that the PRO715 polypeptides disclosed in the present application are newly identified members of the tumor necrosis factor family of proteins.

13. Full-length PRO353 Polypeptides

The present invention provides newly identified and isolated nucleotide sequences encoding polypeptides referred to in the present application as PRO353. In particular, Applicants have identified and isolated cDNA encoding PRO353 polypeptides, as disclosed in further detail in the Examples below. Using BLAST and, FastA sequence alignment computer programs, Applicants found that various portions of the PRO353 polypeptides have certain homology with the human and mouse complement proteins. Accordingly, it is presently believed that the PRO353 polypeptides disclosed in the present application are newly identified members of the complement protein family and possesses the ability to effect the inflammation process as is typical of the complement family of proteins.

14. Full-length PRO361 Polypeptides

The present invention provides newly identified and isolated nucleotide sequences encoding polypeptides referred to in the present application as PRO361. In particular, Applicants have identified and isolated cDNA encoding a PRO361 polypeptide, as disclosed in further detail in the Examples below. Using BLAST and FastA sequence alignment computer programs, Applicants found that various portions of the PRO361 polypeptide have certain homology with the mucin and chitinase proteins. Accordingly, it is presently believed that PRO361 polypeptide disclosed in the present application is a newly identified member of the mucin and/or chitinase protein families and may be associated with cancer, plant pathogenesis or receptor functions typical of the mucin and chitinase protein families, respectively.

15. Full-length PRO365 Polypeptides

The present invention provides newly identified and isolated nucleotide sequences encoding polypeptides referred to in the present application as PRO365. In particular, Applicants have identified and isolated cDNA encoding a PRO365 polypeptide, as disclosed in further detail in the Examples below. Using BLAST and FastA sequence alignment computer programs, Applicants found that various portions of the PRO365 polypeptide have certain homology with the human 2-19 protein. Accordingly, it is presently believed that PRO365 polypeptide disclosed in the present application is a newly identified member of the human 2-19 protein family.

2. PRO Polypeptide Variants

In addition to the full-length native sequence PRO polypeptides described herein, it is contemplated that PRO variants can be prepared. PRO variants can be prepared by introducing appropriate nucleotide changes into the PRO DNA, and/or by synthesis of the desired PRO polypeptide. Those skilled in the art will appreciate that amino acid changes may alter post-translational processes of the PRO, such as changing the number or position of glycosylation sites or altering the membrane anchoring characteristics.

Variations in the native full-length sequence PRO or in various domains of the PRO described herein, can be made, for example, using any of the techniques and guidelines for conservative and non-conservative mutations set forth, for instance, in U.S. Pat. No. 5,364,934. Variations may be a substitution, deletion or insertion of one or more codons encoding the PRO that results in a change in the amino acid sequence of the PRO as compared with the native sequence PRO. Optionally the variation is by substitution of at least one amino acid with any other amino acid in one or more of the domains of the PRO. Guidance in determining which amino acid residue may be inserted, substituted or deleted without adversely affecting the desired activity may be found by comparing the sequence of the PRO with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

PRO polypeptide fragments are provided herein. Such fragments may be truncated at the N-terminus or C-terminus, or may lack internal residues, for example, when compared with a full length native protein. Certain fragments lack amino acid residues that are not essential for a desired biological activity of the PRO polypeptide.

PRO fragments may be prepared by any of a number of conventional techniques. Desired peptide fragments may be chemically synthesized. An alternative approach involves generating PRO fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, PRO polypeptide fragments share at least one biological and/or immunological activity with the native PRO polypeptide disclosed herein.

In particular embodiments, conservative substitutions of interest are shown in Table 1 under the heading of preferred substitutions. If such substitutions result in a change in biological activity, then more substantial changes, denominated exemplary substitutions in Table 6, or as further described below in reference to amino acid classes, are introduced and the products screened.

TABLE 6

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the PRO polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl Acids Res.*, 10:6487 (1987)], cassette mutagenesis [Wells et al., *Gene*, 34:315 (1985)], restriction selection mutagenesis [Wells et al., *Philos. Trans. R. Soc. London SerA*, 317:415 (1986)] or other known techniques can be performed on the cloned DNA to produce the PRO variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to after the main-chain conformation of the variant [Cunningham and Wells, *Science*, 244: 1081-1085 (1989)]. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol.*, 150:1 (1976)]. If alanine substitution does not yield adequate amounts of variant, an isoteric amino acid can be used.

C. Modifications of PRO

Covalent modifications of PRO are included within the scope of this invention. One type of covalent modification includes reacting targeted amino acid residues of a PRO polypeptide with an organic derivatizing agent that is capable of reacting with selected side chains or the N- or C-terminal residues of the PRO. Derivatization with bifunctional agents is useful, for instance, for crosslinking PRO to a water-insoluble support matrix or surface for use in the method for purifying anti-PRO antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W.H. Freeman & Co., San Francisco, pp. 79-86 (1983)], acetylation of the N-terminal amine, and amidation of any C-terminal carboxyl group.

Another type of covalent modification of the PRO polypeptide included within the scope of this invention comprises altering the native glycosylation pattern of the polypeptide. "Altering the native glycosylation pattern" is intended for purposes herein to mean deleting one or more carbohydrate moieties found in native sequence PRO (either by removing the underlying glycosylation site or by deleting the glycosylation by chemical and/or enzymatic means), and/or adding one or more glycosylation sites that are not present in the native sequence PRO. In addition, the phrase includes qualitative changes in the glycosylation of the native proteins, involving a change in the nature and proportions of the various carbohydrate moieties present.

Addition of glycosylation sites to the PRO polypeptide may be accomplished by altering the amino acid sequence. The alteration may be made, for example, by the addition of, or substitution by, one or more serine or threonine residues to the native sequence PRO (for O-linked glycosylation sites). The PRO amino acid sequence may optionally be altered through changes at the DNA level, particularly by mutating the DNA encoding the PRO polypeptide at preselected bases such that codons are generated that will translate into the desired amino acids.

Another means of increasing the number of carbohydrate moieties on the PRO polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.*, pp. 259-306 (1981).

Removal of carbohydrate moieties present on the PRO polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of PRO comprises linking the PRO polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The PRO of the present invention may also be modified in a way to form a chimeric molecule comprising PRO fused to another, heterologous polypeptide or amino acid sequence.

In one embodiment, such a chimeric molecule comprises a fusion of the PRO with a tag polypeptide which provides an epitope to which an anti-tag antibody can selectively bind. The epitope tag is generally placed at the amino- or carboxyl-terminus of the PRO. The presence of such epitope-tagged forms of the PRO can be detected using an antibody against the tag polypeptide. Also, provision of the epitope tag enables the PRO to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 6:1204-1210 (1988)]; the KT3 epitope peptide [Martin et al., *Science*, 255:192-194 (1992)]; an α-tubulin epitope peptide [Skinner et al., *J. Biol. Chem.*, 266:15163-15166 (1991)]; and the T7 gene 10 protein peptide tag [Lutz-Freyermuth et al., *Proc. Natl. Acad. Sci. USA*, 87:6393-6397 (1990)].

In an alternative embodiment, the chimeric molecule may comprise a fusion of the PRO with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a PRO polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

D. Preparation of PRO

The description below relates primarily to production of PRO by culturing cells transformed or transfected with a vector containing PRO nucleic acid. It is, of course, contemplated that alternative methods, which are well known in the art, may be employed to prepare PRO. For instance, the PRO sequence, or portions thereof, may be produced by direct peptide synthesis using solid-phase techniques [see, e.g., Stewart et al., *Solid-Phase Peptide Synthesis*. W.H. Freeman Co, San Francisco, Calif. (1969); Merrifield, *J. Am. Chem. Soc.*, 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the PRO may be chemically synthesized separately and combined using chemical or enzymatic methods to produce the full-length PRO.

1. Isolation of DNA Encoding PRO

DNA encoding PRO may be obtained from a cDNA library prepared from tissue believed to possess the PRO mRNA and to express it at a detectable level. Accordingly, human PRO DNA can be conveniently obtained from a cDNA library prepared from human tissue, such as described in the Examples. The PRO-encoding gene may also be obtained from a genomic library or by known synthetic procedures (e.g., automated nucleic acid synthesis).

Libraries can be screened with probes (such as antibodies to the PRO or oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding PRO is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for PRO production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacierium tumefaciens* is used for transformation of certain plant cells, as described by Shaw et al., *Gene*, 23:315 (1983) and WO89/05859 published 29 Jun. 1989. For mammalian cells without such cell walls, the calcium phosphate precipitation method of Graham and van der Eb, *Virology*, 52:456-457 (1978) can be employed. General aspects of mammalian cell host system transfections have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527-537 (1990) and Mansour et al., *Nature*, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli*, *Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli*

W3110 strain 27C7 (ATCC 55,244), which has the complete genotype tonA ptr3 phoA E15 (argF-lac) 169 degP ompT kan'; *E. coli* W3110 strain 37D6, which has the complete genotype tonA ptr3 phoA E15 (argF-lac) 169 degP ompT rbs7 ilvG kan'; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for PRO-encoding vectors. *Saccharomyces cerevisiae* is a commonly used lower eukaryotic host microorganism. Others include *Schizosaccharomyces pombe* (Beach and Nurse, *Nature*, 290: 140 [1981]; EP 139,383 published 2 May 1985); *Kluyveromyces* hosts (U.S. Pat. No. 4,943,529; Fleer et al., *Bio/Technology*, 9:968-975 (1991)) such as, e.g., *K. lactis* (MW98-8C, CBS683, CBS4574; Louvencourt et al., *J. Bacteriol.*, 154(2):737-742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology*, 8:135 (1990)), *K. thermotolerans*, and *K. marxianus; yarrowia* (EP 402,226); *Pichia pastoris* (EP 183,070; Sreekrishna et al., *J. Basic Microbiol.*, 28:265-278 [1988]); *Candida; Trichoderma reesia* (EP 244,234); *Neurospora crassa* (Case et al., *Proc. Natl. Acad. Sci. USA*, 76:5259-5263 [1979]); *Schwanniomyces* such as *Schwanniomyces occidenialis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.*, 112: 284-289 [1983]; Tilburn et al., *Gene*, 26:205-221 [1983]; Yelton et al., *Proc. Natl. Acad. Sci. USA*, 81: 1470-1474 [1984]) and *A. niger* (Kelly and Hynes, *EMBO J.*, 4:475-479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, *The Biochemistry of Methylotrophs*, 269 (1982).

Suitable host cells for the expression of glycosylated PRO are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells/– DHFR (CHO, Urlaub and Chasin, *Proc. Natl. Acad. Sci. USA*, 77:4216 (1980)); mouse sertoli cells (TM4, Mather, *Biol. Reprod.*, 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding PRO may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The PRO may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the PRO-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2µ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

An example of suitable selectable markers for mammalian cells are those that enable the identification of cells competent to take up the PRO-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 [Stinchcomb et al., *Nature*, 282:39 (1979); Kingsman et al., *Gene*, 7:141 (1979); Tschemper et al., *Gene*, 10:157 (1980)]. The trp1 gene provides a selection marker for a mutant strain of yeast lacking the ability to grow in tryptophan, for example, ATCC No. 44076 or PEP4-1 [Jones, *Genetics*, 85:12 (1977)].

Expression and cloning vectors usually contain a promoter operably linked to the PRO-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature*, 275:615 (1978); Goeddel et al., *Nature*, 281:544 (1979)], alkaline phosphatase, a tryptophan (trp) promoter system [Goeddel, *Nucleic Acids Res.*, 8:4057 (1980); EP 36,776], and hybrid promoters such as the tac promoter [deBoer et al., *Proc. Natl. Acad. Sci. USA*, 80:21-25 (1983)]. Promoters for use in bacterial systems also will contain a Shine-Dalgarno (S.D.) sequence operably linked to the DNA encoding PRO.

Examples of suitable promoting sequences for use with yeast hosts include the promoters for 3-phosphoglycerate kinase [Hitzeman et al., *J. Biol. Chem.*, 255:2073 (1980)] or other glycolytic enzymes [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphateisomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

PRO transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the PRO by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the PRO coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding PRO.

Still other methods, vectors, and host cells suitable for adaptation to the synthesis of PRO in recombinant vertebrate cell culture are described in Gething et al., *Nature*, 293:620-625 (1981); Mantei et al., *Nature*, 281:40-46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA*, 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence PRO polypeptide or against a synthetic peptide based on the DNA sequences provided herein or against exogenous sequence fused to PRO DNA and encoding a specific antibody epitope.

5. Purification of Polypeptide

Forms of PRO may be recovered from culture medium or from host cell lysates. If membrane-bound, it can be released from the membrane using a suitable detergent solution (e.g. Triton-X 100) or by enzymatic cleavage. Cells employed in expression of PRO can be disrupted by various physical or chemical means, such as freeze-thaw cycling, sonication, mechanical disruption, or cell lysing agents.

It may be desired to purify PRO from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the PRO. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular PRO produced.

E. Uses for PRO

Nucleotide sequences (or their complement) encoding PRO have various applications in the art of molecular biology, including uses as hybridization probes, in chromosome and gene mapping and in the generation of anti-sense RNA and DNA. PRO nucleic acid will also be useful for the preparation of PRO polypeptides by the recombinant techniques described herein.

The full-length native sequence PRO gene, or portions thereof, may be used as hybridization probes for a cDNA library to isolate the full-length PRO cDNA or to isolate still other cDNAs (for instance, those encoding naturally-occurring variants of PRO or PRO from other species) which have a desired sequence identity to the native PRO sequence disclosed herein. Optionally, the length of the probes will be about 20 to about 50 bases. The hybridization probes may be derived from at least partially novel regions of the full length native nucleotide sequence wherein those regions may be determined without undue experimentation or from genomic sequences including promoters, enhancer elements and introns of native sequence PRO. By way of example, a screening method will comprise isolating the coding region of the PRO gene using the known DNA sequence to synthesize a selected probe of about 40 bases. Hybridization probes may be labeled by a variety of labels, including radionucleotides such as $^{32}$P or $^{35}$S, or enzymatic labels such as alkaline phosphatase coupled to the probe via avidin/biotin coupling systems. Labeled probes having a sequence complementary to that of the PRO gene of the present invention can be used to screen libraries of human cDNA, genomic DNA or mRNA to determine which members of such libraries the probe hybridizes to. Hybridization techniques are described in further detail in the Examples below.

Any EST sequences disclosed in the present application may similarly be employed as probes, using the methods disclosed herein.

Other useful fragments of the PRO nucleic acids include antisense or sense oligonucleotides comprising a singe-stranded nucleic acid sequence (either RNA or DNA) capable of binding to target PRO mRNA (sense) or PRO DNA (antisense) sequences. Antisense or sense oligonucleotides, according to the present invention, comprise a fragment of the coding region of PRO DNA. Such a fragment generally comprises at least about 14 nucleotides, preferably from about 14 to 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. The antisense oligonucleotides thus may be used to block expression of PRO proteins. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10048, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, CaPO$_4$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Antisense or sense RNA or DNA molecules are generally at least about 5 bases in length, about 10 bases in length, about 15 bases in length, about 20 bases in length, about 25 bases in length, about 30 bases in length, about 35 bases in length, about 40 bases in length, about 45 bases in length, about 50 bases in length, about 55 bases in length, about 60 bases in length, about 65 bases in length, about 70 bases in length, about 75 bases in length, about 80 bases in length, about 85 bases in length, about 90 bases in length, about 95 bases in length, about 100 bases in length, or more.

The probes may also be employed in PCR techniques to generate a pool of sequences for identification of closely related PRO coding sequences.

Nucleotide sequences encoding a PRO can also be used to construct hybridization probes for mapping the gene which encodes that PRO and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

When the coding sequences for PRO encode a protein which binds to another protein (example, where the PRO is a receptor), the PRO can be used in assays to identify the other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Also, the receptor PRO can be used to isolate correlative ligand(s). Screening assays can be designed to find lead compounds that mimic the biological activity of a native PRO or a receptor for PRO. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode PRO or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding PRO can be used to clone genomic DNA encoding PRO in accordance with established techniques and the genomic sequences used to generate transgenic animals that contain cells which express DNA encoding PRO. Methods for generating transgenic animals, particularly animals such as mice or rats, have become conventional in the art and are described, for example, in U.S. Pat. Nos. 4,736,866 and 4,870,009. Typically, particular cells would be targeted for PRO transgene incorporation with tissue-specific enhancers. Transgenic animals that include a copy of a transgene encoding PRO introduced into the germ line of the animal at an embryonic stage can be used to examine the effect of increased expression of DNA encoding PRO. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of PRO can be used to construct a PRO "knock out" animal which has a defective or altered gene encoding PRO as a result of homologous recombination between the endogenous gene encoding PRO and altered genomic DNA encoding PRO introduced into an embryonic stem cell of the animal. For example, cDNA encoding PRO can be used to clone genomic DNA encoding PRO in accordance with established techniques. A portion of the genomic DNA encoding PRO can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, Cell, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., Cell, 69:915 (1992)]. The selected cells are then injected into a blastocyst of an animal (e.g., a mouse or rat) to form aggregation chimeras [see e.g., Bradley, in Teratocarcinomas and Embryonic Stem Cells: A Practical Approach, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the PRO polypeptide.

Nucleic acid encoding the PRO polypeptides may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., Proc. Natl. Acad. Sci. USA 83:4143-4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., Trends in Biotechnology 11, 205-210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262, 4429-4432 (1987); and Wagner et al., Proc. Natl. Acad. Sci. USA 87, 3410-3414 (1990). For review of gene marking and gene therapy protocols see Anderson et al., Science 256, 808-813 (1992).

The PRO polypeptides described herein may also be employed as molecular weight markers for protein electrophoresis purposes and the isolated nucleic acid sequences may be used for recombinantly expressing those markers.

The nucleic acid molecules encoding the PRO polypeptides or fragments thereof described herein are useful for chromosome identification. In this regard, there exists an ongoing need to identify new chromosome markers, since relatively few chromosome marking reagents, based upon actual sequence data are presently available. Each PRO nucleic acid molecule of the present invention can be used as a chromosome marker.

The PRO polypeptides and nucleic acid molecules of the present invention may also be used for tissue typing, wherein the PRO polypeptides of the present invention may be differentially expressed in one tissue as compared to another. PRO nucleic acid molecules will find use for generating probes for PCR, Northern analysis, Southern analysis and Western analysis.

The PRO polypeptides described herein may also be employed as therapeutic agents. The PRO polypeptides of the present invention can be formulated according to known methods to prepare pharmaceutically useful compositions, whereby the PRO product hereof is combined in admixture with a pharmaceutically acceptable carrier vehicle. Therapeutic formulations are prepared for storage by mixing the active ingredient having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™ or PEG.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

When in vivo administration of a PRO polypeptide or agonist or antagonist thereof is employed, normal dosage amounts may vary from about 10 ng/kg to up to 100 mg/kg of mammal body weight or more per day, preferably about 1 µg/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue.

Where sustained-release administration of a PRO polypeptide is desired in a formulation with release characteristics suitable for the treatment of any disease or disorder requiring administration of the PRO polypeptide, microencapsulation of the PRO polypeptide is contemplated. Microencapsulation of recombinant proteins for sustained release has been successfully performed with human growth hormone (rhGH), interferon-(rhIFN-), interleukin-2, and MN rgp120. Johnson et al., *Nat. Med.*, 2:795-799 (1996); Yasuda, *Biomed. Ther.*, 27:1221-1223 (1993); Hora et al., *Bio/Technology*, 8:755-758 (1990); Cleland, "Design and Production of Single Immunization Vaccines Using Polylactide Polyglycolide Microsphere Systems," in *Vaccine Design: The Subunit and Adjuvant Approach*, Powell and Newman, eds, (Plenum Press: New York, 1995), pp. 439-462; WO 97/03692, WO 96/40072, WO 96/07399; and U.S. Pat. No. 5,654,010.

The sustained-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.), *Biodegradable Polymers as Drug Delivery Systems* (Marcel Dekker: New York, 1990), pp. 1-41.

This invention encompasses methods of screening compounds to identify those that mimic the PRO polypeptide (agonists) or prevent the effect of the PRO polypeptide (antagonists). Screening assays for antagonist drug candidates are designed to identify compounds that bind or complex with the PRO polypeptides encoded by the genes identified herein, or otherwise interfere with the interaction of the encoded polypeptides with other cellular proteins. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the drug candidate with a PRO polypeptide encoded by a nucleic acid identified herein under conditions and for a time sufficient to allow these two components to interact.

In binding assays, the interaction is binding and the complex formed can be isolated or detected in the reaction mixture. In a particular embodiment, the PRO polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the PRO polypeptide and drying. Alternatively, an immobilized antibody, e.g., a monoclonal antibody, specific for the PRO polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular PRO polypeptide encoded by a gene identified herein, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, *Nature (London)*, 340:245-246 (1989); Chien et al., *Proc. Natl. Acad. Sci. USA*, 88:9578-9582 (1991)) as disclosed by Chevray and Nathans, *Proc. Natl.*

*Acad. Sci. USA,* 89: 5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding a PRO polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the PRO polypeptide may be added to a cell along with the compound to be screened for a particular activity and the ability of the compound to inhibit the activity of interest in the presence of the PRO polypeptide indicates that the compound is an antagonist to the PRO polypeptide. Alternatively, antagonists may be detected by combining the PRO polypeptide and a potential antagonist with membrane-bound PRO polypeptide receptors or recombinant receptors under appropriate conditions for a competitive inhibition assay. The PRO polypeptide can be labeled, such as by radioactivity, such that the number of PRO polypeptide molecules bound to the receptor can be used to determine the effectiveness of the potential antagonist. The gene encoding the receptor can be identified by numerous methods known to those of skill in the art, for example, ligand panning and FACS sorting. Coligan et al., *Current Protocols in Immun.,* 1(2): Chapter 5 (1991). Preferably, expression cloning is employed wherein polyadenylated RNA is prepared from a cell responsive to the PRO polypeptide and a cDNA library created from this RNA is divided into pools and used to transfect COS cells or other cells that are not responsive to the PRO polypeptide. Transfected cells that are grown on glass slides are exposed to labeled PRO polypeptide. The PRO polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, labeled PRO polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro-sequencing would be used to design a set of degenerate oligonucleotide probes to screen a cDNA library to identify the gene encoding the putative receptor.

In another assay for antagonists, mammalian cells or a membrane preparation expressing the receptor would be incubated with labeled PRO polypeptide in the presence of the candidate compound. The ability of the compound to enhance or block this interaction could then be measured.

More specific examples of potential antagonists include an oligonucleotide that binds to the fusions of immunoglobulin with PRO polypeptide, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the PRO polypeptide that recognizes the receptor but imparts no effect, thereby competitively inhibiting the action of the PRO polypeptide.

Another potential PRO polypeptide antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5, coding portion of the polynucleotide sequence, which encodes the mature PRO polypeptides herein, is used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.,* 6:3073 (1979); Cooney et al., *Science,* 241: 456 (1988); Dervan et al., *Science,* 251:1360 (1991)), thereby preventing transcription and the production of the PRO polypeptide. The antisense RNA oligonucleotide hybridizes to the mRNA in vivo and blocks translation of the mRNA molecule into the PRO polypeptide (antisense—Okano, *Neurochem.,* 56:560 (1991); *Oligodeoxynucleotides as Antisense Inhibitors of Gene Expression* (CRC Press: Boca Raton, Fla., 1988). The oligonucleotides described above can also be delivered to cells such that the antisense RNA or DNA may be expressed in vivo to inhibit production of the PRO polypeptide. When antisense DNA is used, oligodeoxyribonucleotides derived from the translation-initiation site, e.g., between about −10 and +10 positions of the target gene nucleotide sequence, are preferred.

Potential antagonists include small molecules that bind to the active site, the receptor binding site, or growth factor or other relevant binding site of the PRO polypeptide, thereby blocking the normal biological activity of the PRO polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology* 4:469-471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known for those skilled in the art.

PRO241 polypeptides of the present invention which possess biological activity related to that of the endogenous biglycan protein may be employed both in vivo for therapeutic purposes and in vitro. Those of ordinary skill in the art will well know how to employ the PRO241 polypeptides of the present invention for such purposes.

Chordin is a candidate gene for a dysmorphia syndrome known as Cornelia de Lange Syndrome (CDL) which is characterized by distinctive facial features (low anterior hairline, synophrys, antenerted nares, maxillary prognathism, long philtrum, 'carp' mouth), prenatal and postnatal growth retardation, mental retardation and, often but not always, upper limb abnormalities. There are also rare cases where CDL is present in association with thrombocytopenia. The gene for CDL has been mapped by linkage to 3q26.3 (OMIM #122470). Xchd involvement in early *Xenopus* patterning and nervous system development makes CHD in intriguing candidate gene. CHD maps to the appropriate region on chromosome 3. It is very close to THPO, and deletions encompassing both THPO and CHD could result in rare cases of thrombocytopenia and developmental abnormalities. In situ analysis of CD revealed that almost all adult tissues are negative for CHD expression, the only positive signal was observed in the cleavage line of the developing synovial joint forming between the femoral head and acetabulum (hip joint) implicating CHD in the development and presumably growth of long bones. Such a function, if disrupted, could result in growth retardation.

The human CHD amino acid sequence predicted from the cDNA is 50% identical (and 66% conserved) to Xchd. All 40 cysteines in the 4 cysteine-rich domains are conserved. These cysteine rich domains are similar to those observed in thrombospondin, procollagen and von Willebrand factor. Bornstein, P. *FASEB J* 6: 3290-3299 (1992); Hunt, L. & Barker, W. *Biochem. Biophys. Res. Commun.* 144: 876-882 (1987).

The human CHD locus (genomic PRO243) comprises 23 exons in 9.6 kb of genomic DNA. The initiating methionine is in exon 1 and the stop codon in exon 23. A CpG island is located at the 5' and of the gene, beginning approximately 100 bp 5' of exon 1 and extends through the first exon and ends within the first intron. The THPO and CHD loci are organized in a head-to-head fashion with approximately 2.2 kb separating their transcription start sites. At the protein level, PRO243 is 51% identical to *Xenopus* chordin (Xchd). All forty cysteines in the one amino terminal and three carboxy terminal cysteine-rich clusters are conserved.

PRO243 is a 954 amino acid polypeptide having a signal sequence at residues 1 to about 23. There are 4 cysteine clusters: (1) residues about 51 to about 125; (2) residues about 705 to about 761; (3) residues about 784 to about 849; and (4) residues about 897 to about 931. There are potential leucine zippers at residues about 315 to about 396, and N-glycosylation sites at residues 217, 351, 365 and 434.

PRO299 polypeptides and portions thereof which have homology to the notch protein may be useful for in vivo therapeutic purposes, as well as for various other applications. The identification of novel notch proteins and related molecules may be relevant to a number of human disorders such as those effecting development. Thus, the identification of new notch proteins and notch-like molecules is of special importance in that such proteins may serve as potential therapeutics for a variety of different human disorders. Such polypeptides may also play important roles in biotechnological and medical research as well as various industrial applications. As a result, there is particular scientific and medical interest in new molecules, such as PRO299.

PRO323 polypeptides of the present invention which possess biological activity related to that of one or more endogenous dipeptidase proteins may be employed both in vivo for therapeutic purposes and in vitro. Those of ordinary skill in the art will well know how to employ the PRO323 polypeptides of the present invention for such purposes.

PRO327 polypeptides of the present invention which possess biological activity related to that of the endogenous prolactin receptor protein may be employed both in vivo for therapeutic purposes and in vitro. Those of ordinary skill in the art will well know how to employ the PRO327 polypeptides of the present invention for such purposes. PRO327 polypeptides which possess the ability to bind to prolactin may function both in vitro and in vivo as prolactin antagonists.

PRO233 polypeptides and portions thereof which have homology to reductase may also be useful for in vivo therapeutic purposes, as well as for various other applications. The identification of novel reductase proteins and related molecules may be relevant to a number of human disorders such as inflammatory disease, organ failure, atherosclerosis, cardiac injury, infertility, birth defects, premature aging, AIDS, cancer, diabetic complications and mutations in general. Given that oxygen free radicals and antioxidants appear to play important roles in a number of disease processes, the identification of new reductase proteins and reductase-like molecules is of special importance in that such proteins may serve as potential therapeutics for a variety of different human disorders. Such polypeptides may also play important roles in biotechnological and medical research, as well as various industrial applications. As a result, there is particular scientific and medical interest in new molecules, such as PRO233.

PRO344 polypeptides and portions thereof which have homology to complement proteins may also be useful for in vivo therapeutic purposes, as well as for various other applications. The identification of novel complement proteins and related molecules may be relevant to a number of human disorders such as effecting the inflammatory response of cells of the immune system. Thus, the identification of new complement proteins and complement-like molecules is of special importance in that such proteins may serve as potential therapeutics for a variety of different human disorders. Such polypeptides may also play important roles in biotechnological and medical research as well as various industrial applications. As a result, there is particular scientific and medical interest in new molecules, such as PRO344.

PRO347 polypeptides of the present invention which possess biological activity related to that of cysteine-rich secretory proteins may be employed both in vivo for therapeutic purposes and in vitro. Those of ordinary skill in the art will well know how to employ the PRO347 polypeptides of the present invention for such purposes.

PRO354 polypeptides of the present invention which possess biological activity related to that of the heavy chain of the inter-alpha-trypsin inhibitor protein may be employed both in vivo for therapeutic purposes and in vitro. Those of ordinary skill in the art will well know how to employ the PRO354 polypeptides of the present invention for such purposes.

PRO355 polypeptides and portions thereof which have homology to CRTAM may also be useful for in vivo therapeutic purposes, as well as for various other applications. The identification of novel molecules associated with T cells may be relevant to a number of human disorders such as conditions involving the immune system in general. Given that the CRTAM protein binds antibodies which play important roles in a number of disease processes, the identification of new CRTAM proteins and CRTAM-like molecules is of special importance in that such proteins may serve as potential therapeutics for a variety of different human disorders. Such polypeptides may also play important roles in biotechnological and medical research, as well as various industrial applications. As a result, there is particular scientific and medical interest in new molecules, such as PRO355.

PRO357 can be used in competitive binding assays with ALS to determine its activity with respect to ALS. Moreover, PRO357 can be used in assays to determine if it prolongs polypeptides which it may complex with to have longer half-lives in vivo. PRO357 can be used similarly in assays with carboxypeptidase, to which it also has homology. The results can be applied accordingly.

PRO715 polypeptides of the present invention which possess biological activity related to that of the tumor necrosis factor family of proteins may be employed both in vivo for therapeutic purposes and in vitro. Those of ordinary skill in the art will well know how to employ the PRO715 polypeptides of the present invention for such purposes. PRO715 polypeptides will be expected to bind to their specific receptors, thereby activating such receptors. Variants of the PRO715 polypeptides of the present invention may function as agonists or antagonists of their specific receptor activity.

PRO353 polypeptides and portions thereof which have homology to the complement protein may also be useful for in vivo therapeutic purposes, as well as for various other applications. The identification of novel complement proteins and related molecules may be relevant to a number of human disorders such as effecting the inflammatory response of cells of the immune system. Thus, the identification of new complement proteins complement-like molecules is of special importance in that such proteins may serve as potential therapeutics for a variety of different human disorders. Such polypeptides may also play important roles in biotechnological and medical research as well as various industrial applications. As a result, there is particular scientific and medical interest in new molecules, such as PRO353.

PRO361 polypeptides and portions thereof which have homology to mucin and/or chitinase proteins may also be useful for in vivo therapeutic purposes, as well as for various other applications. The identification of novel mucin and/or chitinase proteins and related molecules may be relevant to a number of human disorders such as cancer or those involving cell surface molecules or receptors. Thus, the identification of new mucin and/or chitinase proteins is of special importance in that such proteins may serve as potential therapeutics for a variety of different human disorders. Such polypeptides may also play important roles in biotechnological and medical research as well as various industrial applications. As a result, there is particular scientific and medical interest in new molecules, such as PRO361.

PRO365 polypeptides and portions thereof which have homology to the human 2-19 protein may also be useful for in vivo therapeutic purposes, as well as for various other applications. The identification of novel human 2-19 proteins and related molecules may be relevant to a number of human disorders such as modulating the binding or activity of cells of the immune system. Thus, the identification of new human 2-19 proteins and human 2-19 protein-like molecules is of special importance in that such proteins may serve as potential therapeutics for a variety of different human disorders. Such polypeptides may also play important roles in biotechnological and medical research as well as various industrial applications. As a result, there is particular scientific and medical interest in new molecules, such as PRO365.

F. Anti-PRO Antibodies

The present invention further provides anti-PRO antibodies. Exemplary antibodies include polyclonal, monoclonal, humanized, bispecific, and heteroconjugate antibodies.

1. Polyclonal Antibodies

The anti-PRO antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the PRO polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-PRO antibodies may, alternatively, be monoclonal antibodies. Monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the PRO polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51-63].

The culture medium in which the hybridoma cells are cultured can then be assayed for the presence of monoclonal antibodies directed against PRO. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Human and Humanized Antibodies

The anti-PRO antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522-525 (1986); Riechmann et al., *Nature*, 332:323-329 (1988); and Presta, *Curr. Op. Struct. Biol.*, 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522-525 (1986); Riechmann et al., *Nature*, 332:323-327 (1988); Verhoeyen et al., *Science*, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991);

Marks et al., *J. Mol. Biol.*, 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86-95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10, 779-783 (1992); Lonberg et al., *Nature* 368 856-859 (1994); Morrison, *Nature* 368, 812-13 (1994); Fishwild et al., *Nature Biotechnology* 14, 845-51 (1996); Neuberger, *Nature Biotechnology* 14, 826 (1996); Lonberg and Huszar, *Intern. Rev. Immunol.* 13 65-93 (1995).

4. Bispecific Antibodies

Bispecific antibodies are monoclonal, preferably human or humanized, antibodies that have binding specificities for at least two different antigens. In the present case, one of the binding specificities is for the PRO, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, *Nature*, 305:537-539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., *EMBO J.*, 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

According to another approach described in WO 96/27011, the interface between a pair of antibody molecules can be engineered to maximize the percentage of heterodimers which are recovered from recombinant cell culture. The preferred interface comprises at least a par of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al., *J. Exp. Med.* 175:217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various technique for making and isolating bispecific antibody fragments directly from recombinant cell culture have also been described. For example, bispecific antibodies have been produced using leucine zippers. Kostelny et al., *J. Immunol.* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., *J. Immunol.* 152:5368 (1994).

Antibodies with more than two valencies are contemplated. For example, trispecific antibodies can be prepared. Tutt et al., *J. Immunol.* 147:60 (1991).

Exemplary bispecific antibodies may bind to two different epitopes on a given PRO polypeptide herein. Alternatively, an anti-PRO polypeptide arm may be combined with an arm which binds to a triggering molecule on a leukocyte such as a T-cell receptor molecule (e.g. CD2, CD3, CD28, or B7), or Fe receptors for IgG (FcγR), such as FcγRI (CD64), FcγRII (CD32) and FcγRIII (CD16) so as to focus cellular defense mechanisms to the cell expressing the particular PRO polypeptide. Bispecific antibodies may also be used to localize cytotoxic agents to cells which express a particular PRO polypeptide. These antibodies possess a PRO-binding arm and an arm which binds a cytotoxic agent or a radionuclide chelator, such as EOTUBE, DPTA, DOTA, or TETA. Another bispecific antibody of interest binds the PRO polypeptide and further binds (issue factor (TF).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

6. Effector Function Engineering

It may be desirable to modify the antibody of the invention with respect to effector function, so as to enhance, e.g., the effectiveness of the antibody in treating cancer. For example, cysteine residue(s) may be introduced into the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.,* 176: 1191-1195 (1992) and Shopes, *J. Immunol.,* 148: 2918-2922 (1992). Homodimeric antibodies with enhanced anti-tumor activity may also be prepared using heterobifunctional cross-linkers as described in Wolff et al. *Cancer Research,* 53:2560-2565 (1993). Alternatively, an antibody can be engineered that has dual Fc regions and may thereby have enhanced complement lysis and ADCC capabilities. See Stevenson et al., *Anti-Cancer Drug Design,* 3: 219-230 (1989).

7. Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol)propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science,* 238: 1098 (1987). Carbon-14-labeled 1-isothiocyanatobenzyl-3-methyidiethylene triaminepentaacetic acid (MX-DTPA) is an exemplary chelating agent for conjugation of radionucleotide to the antibody. See WO94/11026.

In another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

8. Immunoliposomes

The antibodies disclosed herein may also be formulated as immunoliposomes. Liposomes containing the antibody are prepared by methods known in the art, such as described in Epstein et al., *Proc. Natl. Acad. Sci. USA,* 82: 3688 (1985); Hwang et al., *Proc. Natl Acad. Sci. USA,* 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.,* 257: 286-288 (1982) via a disulfide-interchange reaction. A chemotherapeutic agent (such as Doxorubicin) is optionally contained within the liposome. See Gabizon et al., *J. National Cancer Inst.,* 81(19): 1484 (1989).

9. Pharmaceutical Compositions of Antibodies

Antibodies specifically binding a PRO polypeptide identified herein, as well as other molecules identified by the screening assays disclosed hereinbefore, can be administered for the treatment of various disorders in the form of pharmaceutical compositions.

If the PRO polypeptide is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA,* 90: 7889-7893 (1993). The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate)microcapsules, respectively, in colloidal drug delivery systems (for example, liposomes, albumin microspheres, microemulsions, nano-particles, and nanocapsules) or in macroemulsions. Such techniques are disclosed in Remington's *Pharmaceutical Sciences*, supra.

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

G. Uses for Anti-PRO Antibodies

The anti-PRO antibodies of the invention have various utilities. For example, anti-PRO antibodies may be used in diagnostic assays for PRO, e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147-158]. The antibodies used in the diagnostic assays can be labeled with a detectable moiety. The detectable moiety should be capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982).

Anti-PRO antibodies also are useful for the affinity purification of PRO from recombinant cell culture or natural sources. In this process, the antibodies against PRO are immobilized on a suitable support, such a Sephadex resin or filter paper, using methods well known in the art. The immobilized antibody then is contacted with a sample containing the PRO to be purified, and thereafter the support is washed with a suitable solvent that will remove substantially all the material in the sample except the PRO, which is bound to the immobilized antibody. Finally, the support is washed with another suitable solvent that will release the PRO from the antibody.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Extracellular Domain Homology Screening to Identify Novel Polypeptides and cDNA Encoding Therefor The extracellular domain (ECD) sequences (including the secretion signal sequence, if any) from about 950 known secreted proteins from the Swiss-Prot public database were used to search EST databases. The EST databases included public databases (e.g., Dayhoff, GenBank), and proprietary databases (e.g. LIFESEQ™, Incyte Pharmaceuticals, Palo Alto, Calif.). The search was performed using the computer program BLAST or BLAST-2 (Altschul et al., *Methods in Enzymology* 266:460-480 (1996)) as a comparison of the ECD protein sequences to a 6 frame translation of the EST sequences. Those comparisons with a BLAST score of 70 (or in some cases 90) or greater that did not encode known proteins were clustered and assembled into consensus DNA sequences with the program "phrap" (Phil Green, University of Washington, Seattle, Wash.).

Using this extracellular domain homology screen, consensus DNA sequences were assembled relative to the other identified EST sequences using phrap. In addition, the consensus DNA sequences obtained were often (but not always) extended using repeated cycles of BLAST or BLAST-2 and phrap to extend the consensus sequence as far as possible using the sources of EST sequences discussed above.

Based upon the consensus sequences obtained as described above, oligonucleotides were then synthesized and used to identify by PCR a cDNA library that contained the sequence of interest and for use as probes to isolate a clone of the full-length coding sequence for a PRO polypeptide. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., *Current Protocols in Molecular Biology*, with the PCR primer pair. A positive library was then used to isolate clones encoding the gene of interest using the probe oligonucleotide and one of the primer pairs.

The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science,* 253: 1278-1280 (1991)) in the unique XhoI and NotI sites.

Example 2

Isolation of cDNA Clones by Amylase Screening

1. Preparation of Oligo dT Primed cDNA Library mRNA was isolated from a human tissue of interest using reagents and protocols from Invitrogen, San Diego, Calif. (Fast Track 2). This RNA was used to generate an oligo dT primed cDNA library in the vector pRK5D using reagents and protocols from Life Technologies, Gaithersburg, Md. (Super Script Plasmid System). In this procedure, the double stranded cDNA was sized to greater than 1000 bp and the SalI/NotI Tinkered cDNA was cloned into XhoI/NotI cleaved vector. pRK5D is a cloning vector that has an sp6 transcription initiation site followed by an SfiI restriction enzyme site preceding the XhoI/NotI cDNA cloning sites.

2. Preparation of Random Primed cDNA Library

A secondary cDNA library was generated in order to preferentially represent the 5' ends of the primary cDNA clones. Sp6 RNA was generated from the primary library (described above), and this RNA was used to generate a random primed cDNA library in the vector pSST-AMY.0 using reagents and protocols from Life Technologies (Super Script Plasmid System, referenced above). In this procedure the double stranded cDNA was sized to 500-1000 bp, linkered with blunt to NotI adaptors, cleaved with SfiI, and cloned into SfiI/NotI cleaved vector. pSST-AMY.0 is a cloning vector that has a yeast alcohol dehydrogenase promoter preceding the cDNA cloning sites and the mouse amylase sequence (the mature sequence without the secretion signal) followed by the yeast alcohol dehydrogenase terminator, after the cloning sites. Thus, cDNAs cloned into this vector that are fused in frame with amylase sequence will lead to the secretion of amylase from appropriately transfected yeast colonies.

3. Transformation and Detection

DNA from the library described in paragraph 2 above was chilled on ice to which was added electrocompetent DH10B bacteria (Life Technologies, 20 ml). The bacteria and vector mixture was then electroporated as recommended by the manufacturer. Subsequently, SOC media (Life Technologies, 1 ml) was added and the mixture was incubated at 37° C. for 30 minutes. The transformants were then plated onto 20 standard 150 mm LB plates containing ampicillin and incubated for 16 hours (37° C.). Positive colonies were scraped off the plates and the DNA was isolated from the bacterial pellet using standard protocols, e.g. CsCl-gradient. The purified DNA was then carried on to the yeast protocols below.

The yeast methods were divided into three categories: (1) Transformation of yeast with the plasmid/cDNA combined vector; (2) Detection and isolation of yeast clones secreting amylase; and (3) PCR amplification of the insert directly from the yeast colony and purification of the DNA for sequencing and further analysis.

The yeast strain used was HD56-5A (ATCC-90785). This strain has the following genotype: MAT alpha, ura3-52, leu2-3, leu2-112, his3-11, his3-15, MAL$^+$, SUC$^+$, GAL$^+$. Preferably, yeast mutants can be employed that have deficient post-translational pathways. Such mutants may have translocation deficient alleles in sec71, sec72, sec62, with truncated sec71 being most preferred. Alternatively, antagonists (including antisense nucleotides and/or ligands) which interfere with the normal operation of these genes, other proteins implicated in this post translation pathway (e.g., SEC61p, SEC72p, SEC62p, SEC63p, TDJ1p or SSA1p-4p) or the complex formation of these proteins may also be preferably employed in combination with the amylase-expressing yeast.

Transformation was performed based on the protocol outlined by Gietz et al., *Nucl. Acid. Res.,* 20:1425 (1992). Transformed cells were then inoculated from agar into YEPD complex media broth (100 ml) and grown overnight at 30° C. The YEPD broth was prepared as described in Kaiser et al., *Methods in Yeast Genetics,* Cold Spring Harbor Press, Cold Spring Harbor, N.Y., p. 207 (1994). The overnight culture was then diluted to about $2\times10^6$ cells/ml (approx. OD$_{600}$=0.1) into fresh YEPD broth (500 ml) and regrown to $1\times10^7$ cells/ml (approx. OD$_{600}$=0.4-0.5).

The cells were then harvested and prepared for transformation by transfer into GS3 rotor bottles in a Sorval GS3 rotor at 5,000 rpm for 5 minutes, the supernatant discarded, and then resuspended into sterile water, and centrifuged again in 50 ml falcon tubes at 3,500 rpm in a Beckman GS-6KR centrifuge. The supernatant was discarded and the cells were subsequently washed with LiAc/TE (10 ml, 10 mM Tris-HCl, 1 mM EDTA pH 7.5, 100 mM Li$_2$OOCCH$_3$), and resuspended into LiAc/TE (2.5 ml).

Transformation took place by mixing the prepared cells (100 µl) with freshly denatured single stranded salmon testes DNA (Lofstrand Labs, Gaithersburg, Md.) and transforming DNA (1 µg, vol. <10 µl) in microfuge tubes. The mixture was mixed briefly by vortexing, then 40% PEG/TE (600 µl, 40% polyethylene glycol-4000, 10 mM Tris-HCl, 1 mM EDTA, 100 mM Li$_2$OOCCH$_3$, pH 7.5) was added. This mixture was gently mixed and incubated at 30° C. while agitating for 30 minutes. The cells were then heat shocked at 42° C. for 15 minutes, and the reaction vessel centrifuged in a microfuge at 12,000 rpm for 5-10 seconds, decanted and resuspended into TE (500 µl, 10 mM Tris-HCl, 1 mM EDTA pH 7.5) followed by recentrifugation. The cells were then diluted into TE (1 ml) and aliquots (200 µl) were spread onto the selective media previously prepared in 150 mm growth plates (VWR).

Alternatively, instead of multiple small reactions, the transformation was performed using a single, large scale reaction, wherein reagent amounts were scaled up accordingly.

The selective media used was a synthetic complete dextrose agar lacking uracil (SCD-Ura) prepared as described in Kaiser et al., *Methods in Yeast Genetics,* Cold Spring Harbor Press, Cold Spring Harbor, N.Y., p. 208-210 (1994). Transformants were grown at 30° C. for 2-3 days.

The detection of colonies secreting amylase was performed by including red starch in the selective growth media. Starch was coupled to the red dye (Reactive Red-120, Sigma) as per the procedure described by Biely et al., *Anal. Biochem.,* 172:176-179 (1988). The coupled starch was incorporated into the SCD-Ura agar plates at a final concentration of 0.15% (w/v), and was buffered with potassium phosphate to a pH of 7.0 (50-100 mM final concentration).

The positive colonies were picked and streaked across fresh selective media (onto 150 mm plates) in order to obtain well isolated and identifiable single colonies. Well isolated single colonies positive for amylase secretion were detected by direct incorporation of red starch into buffered SCD-Ura agar. Positive colonies were determined by their ability to break down starch resulting in a clear halo around the positive colony visualized directly.

4. Isolation of DNA by PCR Amplification

When a positive colony was isolated, a portion of it was picked by a toothpick and diluted into sterile water (30 μl) in a 96 well plate. At this time, the positive colonies were either frozen and stored for subsequent analysis or immediately amplified. An aliquot of cells (5 μl) was used as a template for the PCR reaction in a 25 μl volume containing: 0.5 μl Klentaq (Clontech, Palo Alto, Calif.); 4.0 μl 10 mM dNTP's (Perkin Elmer-Cetus); 2.5 μl Kentaq buffer (Clontech); 0.25 μl forward oligo 1; 0.25 μl reverse oligo 2; 12.5 μl distilled water.

The sequence of the forward oligonucleotide 1 was:

5-TGTAAAACGACGGCCAGT<u>TAAATAGACCTGCAATTATTAATCT</u>-3' (SEQ ID NO:16)

The sequence of reverse oligonucleotide 2 was:

5'-CAGGAAACAGCTATGACC<u>ACCTGCACACCTGCAAATCCATT</u>-3' (SEQ ID NO:17)

PCR was then performed as follows:

| a. |  | Denature | 92° C., | 5 minutes |
|---|---|---|---|---|
| b. | 3 cycles of: | Denature | 92° C., | 30 seconds |
|  |  | Anneal | 59° C., | 30 seconds |
|  |  | Extend | 72° C., | 60 seconds |
| c. | 3 cycles of: | Denature | 92° C., | 30 seconds |
|  |  | Anneal | 57° C., | 30 seconds |
|  |  | Extend | 72° C., | 60 seconds |
| d. | 25 cycles of: | Denature | 92° C., | 30 seconds |
|  |  | Anneal | 55° C., | 30 seconds |
|  |  | Extend | 72° C., | 60 seconds |
| e. |  | Hold | 4° C. |  |

The underlined regions of the oligonucleotides annealed to the ADH promoter region and the amylase region, respectively, and amplified a 307 bp region from vector pSST-AMY.0 when no insert was present. Typically, the first 18 nucleotides of the 5' end of these oligonucleotides contained annealing sites for the sequencing primers. Thus, the total product of the PCR reaction from an empty vector was 343 bp. However, signal sequence-fused cDNA resulted in considerably longer nucleotide sequences.

Following the PCR, an aliquot of the reaction (5 μl) was examined by agarose gel electrophoresis in a 1% agarose gel using a Tris-Borate-EDTA (TBE) buffering system as described by Sambrook et al., supra. Clones resulting in a single strong PCR product larger than 400 bp were further analyzed by DNA sequencing after purification with a 96 Qiaquick PCR clean-up column (Qiagen Inc., Chatsworth, Calif.).

Example 3

Isolation of cDNA Clones Encoding Human PRO241

A consensus DNA sequence was assembled relative to other EST sequences as described in Example 1 above. This consensus sequence is herein designated DNA30876. Based on the DNA30876 consensus sequence, oligonucleotides were synthesized: 1) to identify by PCR a cDNA library that contained the sequence of interest, and 2) for use as probes to isolate a clone of the full-length coding sequence for PRO241.

PCR primers (forward and reverse) were synthesized:

```
forward PCR primer
5'-GGAAATGAGTGCAAACCCTC-3'        (SEQ ID NO: 3)

reverse PCR primer
5-TCCCAAGCTGAACACTCATTCTGC-3'    (SEQ ID NO: 4)
```

Additionally, a synthetic oligonucleotide hybridization probe was constructed from the consensus DNA30876 sequence which had the following nucleotide sequence
Hybridization Probe

5'-GGGTGACGGTGTTCCATATCAGAATTG-CAGAAGCAAAACTGACCTCAGTT-3' (SEQ ID NO:5)

In order to screen several libraries for a source of a full-length clone, DNA from the libraries was screened by PCR amplification with the PCR primer pair identified above. A positive library was then used to isolate clones encoding the PRO241 gene using the probe oligonucleotide and one of the PCR primers. RNA for construction of the cDNA libraries was isolated from human fetal kidney tissue (LIB29).

DNA sequencing of the clones isolated as described above gave the full-length DNA sequence for PRO241 [herein designated as DNA34392-1170](SEQ ID NO:1) and the derived protein sequence for PRO241.

The entire nucleotide sequence of DNA34392-1170 is shown in FIG. 1 (SEQ ID NO:1). Clone DNA34392-1170 contains a single open reading frame with an apparent translational initiation site at nucleotide positions 234-236 and ending at the stop codon at nucleotide positions 1371-1373 (FIG. 1). The predicted polypeptide precursor is 379 amino acids long (FIG. 2). The full-length PRO241 protein shown in FIG. 2 has an estimated molecular weight of about 43,302 daltons and a pI of about 7.30. Clone DNA34392-1170 has been deposited with ATCC and is assigned ATCC deposit no. ATCC 209526.

Analysis of the amino acid sequence of the full-length PRO241 polypeptide suggests that it possess significant homology to the various biglycan proteoglycan proteins, thereby indicating that PRO241 is a novel biglycan homolog polypeptide.

Example 4

Isolation of cDNA Clones Encoding Human PRO243 by Genomic Walking

Introduction: Human thrombopoietin (THPO) is a glycosylated hormone of 352 amino acids consisting of two domains. The N-terminal domain, sharing 50% similarity to erythropoietin, is responsible for the biological activity. The C-terminal region is required for secretion. The gene for thrombopoietin (THPO) maps to human chromosome 3q27-q28 where the six exons of this gene span 7 kilobase base pairs of genomic DNA (Gurney et al., *Blood* 85: 981-988 (1995). In order to determine whether there were any genes encoding THPO homologues located in close proximity to THPO, genomic DNA fragments from this region were identified and sequenced. Three P1 clones and one PAC clones (Genome Systems Inc., St. Louis, Mo.; cat. Nos. P1-2535 and PAC-6539) encompassing the THPO locus were isolated and a 140 kb region was sequenced using the ordered shotgun strategy (Chen et al., *Genomics* 17: 651-656 (1993)), coupled with a PCR-based gap filling approach. Analysis reveals that the region is gene-rich with four additional genes located very close to THPO: tumor necrosis factor-receptor type 1 associated protein 2 (TRAP2) and elongation initiation factor gamma (e1F4g), chloride channel 2 (CLCN2) and RNA polymerase II subunit hRPB17. While no THPO homolog was found in the region, four novel genes have been predicted by computer-assisted gene detection (GRAIL) (Xu et al., *Gen. Engin.* 16: 241-253 (1994), the presence of CpG islands (Cross, S. and Bird, A., *Curr. Opin. Genet. & Devel.* 5: 109-314 (1995), and homology to known genes (as detected by WU-BLAST2.0) (Altschul and Gish, *Methods Enzymol.* 266: 460-480 (1996) (http://blast.wustl.edu/blast/READ-ME.html).

P1 and PAC clones: The initial human P1 clone was isolated from a genomic P1 library (Genome Systems Inc., St. Louis, Mo.; cat. no.: P1-2535) screened with PCR primers designed from the THPO genomic sequence (A. L. Gurney, et al., *Blood* 85: 981-88 (1995). PCR primers were designed from the end sequences derived from this P1 clone were then used to screen P1 and PAC libraries (Genome Systems, Cat. Nos.: P1-2535 & PAC-6539) to identify overlapping clones.

Ordered Shotgun Strategy: The Ordered Shotgun Strategy (OSS) (Chen et al., *Genomics* 17: 651-656 (1993)) involves the mapping and sequencing of large genomic DNA clones with a hierarchical approach. The P1 or PAC clone was sonicated and the fragments subcloned into lambda vector (λBluestar) (Novagen, Inc., Madison, Wis.; cat. no. 69242-3). The lambda subclone inserts were isolated by long-range PCR (Barnes, W. *Proc. Natl. Acad. Sci. USA* 91: 2216-2220 (1994) and the ends sequenced. The lambda-end sequences were overlapped to create a partial map of the original clone. Those lambda clones with overlapping end-sequences were identified, the insets subcloned into a plasmid vector (pUC9 or pUC18) and the ends of the plasmid subclones were sequenced and assembled to generate a contiguous sequence. This directed sequencing strategy minimizes the redundancy required while allowing one to scan for and concentrate on interesting regions.

In order to define better the THPO locus and to search for other genes related to the hematopoietin family, four genomic clones were isolated from this region by PCR screening of human P1 and PAC libraries (Genome System, Inc., Cat. Nos.: P1-2535 and PAC-6539). The sizes of the genomic fragments are as follows: P1.t is 40 kb; P1.g is 70 kb; P1.u is 70 kb; and PAC.z is 200 kb. Approximately 80% of the 200 kb genomic DNA region was sequenced by the Ordered Shotgun Strategy (OSS) (Chen et al., *Genomics* 17: 651-56 (1993), and assembled into contigs using AutoAssembler™ (Applied Biosystems, Perkin Elmer, Foster City, Calif., cat. no. 903227). The preliminary order of these contigs was determined by manual analysis. There were 46 contigs and filling in the gaps was employed. Table 7 summarized the number and sizes of the gaps.

TABLE 7

Summary of the gaps in the 140 kb region

| Size of gap | | number |
|---|---|---|
| <50 | bp | 13 |
| 50-150 | bp | 7 |
| 150-300 | bp | 7 |
| 300-1000 | bp | 10 |

TABLE 7-continued

Summary of the gaps in the 140 kb region

| Size of gap | | number |
|---|---|---|
| 1000-5000 | bp | 7 |
| >5000 | bp | 2 |
| | | (15,000 bp) |

DNA sequencing: ABI DYE-primer™ chemistry (PE Applied Biosystems, Foster City, Calif.; Cat. No.: 402112) was used to end-sequence the lambda and plasmid subclones. ABI DYE-terminater™ chemistry (PE Applied Biosystems, Foster City, Calif., Cat. No: 403044) was used to sequence the PCR products with their respective PCR primers. The sequences were collected with an ABI377 instrument. For PCR products larger than 1 kb, walking primers were used. The sequences of contigs generated by the OSS strategy in AutoAssembler™ a (PE Applied Biosystems, Foster City, Calif.; Cat. No: 903227) and the gap-filling sequencing trace files were imported into Sequencher™ (Gene Codes Corp., Ann Arbor, Mich.) for overlapping and editing.

PCR-Based gap filling Strategy: Primers were designed based on the 5'- and 3'-end sequenced of each contig, avoiding repetitive and low quality sequence regions. All primers were designed to be 19-24-mers with 50-70% G/C content. Oligos were synthesized and gel-purified by standard methods.

Since the orientation and order of the contigs were unknown, permutations of the primers were used in the amplification reactions. Two PCR kits were used: first, XL PCR kit (Perkin Elmer, Norwalk, Conn.; Cat. No.: N8080205), with extension times of approximately 10 minutes; and second, the Taq polymerase PCR kit (Qiagen Inc., Valencia, Calif.; Cat. No.: 201223) was used under high stringency conditions if smeared or multiple products were observed with the XL PCR kit. The main PCR product from each successful reactions was extracted from a 0.9% low melting agarose gel and purified with the Geneclean DNA Purification kit prior to sequencing.

Analysis: The identification and characterization of coding regions was carried out as follows: First, repetitive sequences were masked using RepeatMasker (A. F. A. Smit & P. Green, http://ftp.genome.washington.edu/RM/RM_details.html) which screens DNA sequences in FastA format against a library of repetitive elements and returns a masked query sequence. Repeats not masked were identified by comparing the sequence to the GenBank database using WUBLAST (Altschul, S & Gish, W., *Methods Enzymol.* 266: 460-480 (1996) and were masked manually.

Next, known genes were revealed by comparing the genomic regions against Genentech's protein database using the WUBLAST2.0 algorithm and then annotated by aligning the genomic and cDNA sequences for each gene, respectively, using a Needleman-Wunch (Needleman and Wunsch, *J. Mol. Biol.* 48: 443-453 (1970) algorithm to find regions of local identity between sequences which are otherwise largely dissimilar. The strategy results in detection of all exons of the five known genes in the region, THPO, TRAP2, e1F4g, CLCN2 and hRPB17 (Table 8).

TABLE 8

Summary of known genes located in the 140 kb region analyzed

| Known genes | Map position |
|---|---|
| eukaryotic translation initiation factor 4 gamma | 3q27-qter |
| thrombopoietin | 3q26-q27 |
| chloride channel 2 | 3q26-qter |
| TNF receptor associated protein 2 | not previously mapped |
| RNA polymerase II subunit hRPB17 | not previously mapped |

Finally, novel transcription units were predicted using a number of approaches. CpG islands (S. Cross & Bird, A., *Curr. Opin. Genet. Dev.* 5: 109-314 (1995) islands were used to define promoter regions and were identified as clusters of sites cleaved by enzymes recognizing GC-rich, 6 or 8-mer palidromic sequences. CpG islands are usually associated with promoter regions of genes. WUBLAST2.0 analysis of short genomic regions (10-20 kb) versus GenBank revealed matches to ESTs. The individual EST sequences (or where possible, their sequence chromatogram files) were retrieved and assembled with Sequencher to provide a theoretical cDNA sequence (designated herein as DNA34415). GRAIL2 (ApoCom Inc., Knoxville, Tenn., command line version for the DEC alpha) was used to predict a novel exon. The five known genes in the region served as internal controls for the success of the GRAIL algorithm.

Isolation: Chordin cDNA clones were isolated from an oligo-dT-primed human fetal lung library. Human fetal lung polyA+ RNA was purchased from Clontech (cat #6528-1, lot #43777) and 5 mg used to construct a cDNA library in pKR5B (Genentech, LIB26). The 3'-primer (pGACTAGT-TCTAGATCGCGAGCGGCCGC-CCTTTTTTTTTTTTTT) (SEQ ID NO:8) and the 5'-linker (pCGGACGCGTGGGGCCTGCGCAC-CCAGCT) (SEQ ID NO:9) were designed to introduce SalI and NotI restriction sites Clones were screened with oligonucleotide probes designed from the putative human chordin cDNA sequence (DNA34415) deduced by manually "splicing" together the proposed genomic exons of the gene. PCR primers flanking the probes were used to confirm the identity of the cDNA clones prior to sequencing. The screening oligonucleotides probes were the following:

OLI5640 34415.p1 5'-GCCGCTC-CCCGAACGGGCAGCGGCTCCTTCTCAGAA-3' (SEQ ID NO:10) and

OLI5642 34415.p2 5'-GGCGCACAGCACGCAGCGCAT-CACCCCGAATGGCTC-3' (SEQ ID NO:11); and
the flanking probes used were the following:

```
OLI5639  34415.f1
5'-GTGCTGCCCATCCGTTCTGAGAAGGA-3'    (SEQ ID NO: 12)

and

OLI5643  34415.r
5'-GCAGGGTGCTCAAACAGGACAC-3'.        (SEQ ID NO: 13)
```

Example 5

Northern Blot and In Situ RNA Hybridization Analysis of PRO243

Expression of PRO243 mRNA in human tissues was examined by Northern blot analysis. Human polyA+RNA blots derived from human fetal and adult tissues (Clontech, Palo Alto, Calif.; Cat. Nos. 7760-1 and 7756-1) were hybridized to a $^{32}$P-labelled cDNA fragments probe based on the full length PRO243 cDNA. Blots were incubated with the probes in hybridization buffer (5×SSPE; 2× Denhardt's solution; 100 mg/mL denatured sheared salmon sperm DNA; 50% formamide; 2% SDS) for 60 hours at 42° C. The blots were washed several times in 2×SSC; 0.05% SDS for 1 hour at room temperature, followed by a high stringency wash 30 minute wash in 0.1×SSC; 0.1% SDS at 50° C. and autoradiographed. The blots were developed after overnight exposure by phosphorimager analysis (Fuji).

PRO243 mRNA transcripts were detected. Analysis of the expression pattern showed the strongest signal of the expected 4.0 kb transcript in adult and fetal liver and a very faint signal in the adult kidney. Fetal brain, lung and kidney were negative, as were adult heart, brain, lung and pancreas. Smaller transcripts were observed in placenta (2.0 kb), adult skeletal muscle (1.8 kb) and fetal liver (2.0 kb).

In situ hybridization of adult human tissue of PRO243 gave a positive signal in the cleavage line of the developing synovial joint forming between the femoral head and acetabulum. All other tissues were negative. Additional sections of human fetal face, head, limbs and mouse embryos were examined. Expression in human fetal tissues was observed adjacent to developing limb and facial bones in the perosteal msenchyme. The expression was highly specific and was often adjacent to areas undergoing vascularization. Expression was also observed in the developing temporal and occipital lobes of the fetal brain, but was not observed elsewhere in the brain. In addition, expression was seen in the ganglia of the developing inner ear. No expression was seen in any of the mouse tissues with the human probes.

In situ hybridization was performed using an optimized protocol, using PCR-generating $^{33}$P-labeled riboprobes. (Lu and Gillett, *Cell Vision* 1: 169-176 (1994)). Formalin-fixed, paraffin-embedded human fetal and adult tissues were sectioned, deparaffinized, deproteinated in proteinase K (20 g/ml) for 15 minutes at 37° C., and further processed for in situ hybridization as described by Lu and Gillett (1994). A [$^{33}$P]-UTP-labeled antisense riboprobe was generated from a PCR product and hybridized at 55° C. overnight. The slides were dipped in Kodak NTB2 nuclear track emulsion and exposed for 4 weeks.

Example 6

Isolation of cDNA Clones Encoding Human PRO299

A cDNA sequence designated herein as DNA28847 (FIG. 7; SEQ ID NO:18) was isolated as described in Example 2 above. After further analysis, a 3' truncated version of DNA28847 was found and is herein designated DNA35877 (FIG. 8; SEQ ID NO:19). Based on the DNA35877 sequence, oligonucleotides were synthesized: 1) to identify by PCR a cDNA library that contained the sequence of interest, and 2) for use as probes to isolate a clone of the full-length coding sequence for PRO299. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., *Current Protocols in Molecular Biology*, with the PCR primer pair. A positive library was then used to isolate clones encoding the gene of interest using the probe oligonucleotide and one of the primer pairs.

Forward and reverse PCR primers were synthesized:

```
forward PCR primer
5'-CTCTGGAAGGTCACGGCCACAGG-3'      (SEQ ID NO: 20)

reverse PCR primer
5'-CTCAGTTCGGTTGGCAAAGCTCTC-3'     (SEQ ID NO: 21)
```

Additionally, a synthetic oligonucleotide hybridization probe was constructed from the DNA35877 sequence which had the following nucleotide sequence
Hybridization Probe

```
5'-CAGTGCTCCCTCATAGATGGACGAAAGTGTG (SEQ ID NO: 22)
ACCCCCCTTTCAGGCGAGAGCTTTGCCAACCGAA
CTGA-3'
```

In order to screen several libraries for a source of a full-length clone, DNA from the libraries was screened by PCR amplification with one of the PCR primer pairs identified above. A positive library was then used to isolate clones encoding the PRO299 sequence using the probe oligonucleotide.

RNA for construction of the cDNA libraries was isolated from human fetal brain tissue. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science*, 253:1278-1280 (1991)) in the unique XhoI and NotI sites.

DNA sequencing of the clones isolated as described above gave the full-length DNA sequence for PRO299 [herein designated as DNA39976-1215] (SEQ ID NO:14) and the derived protein sequence for PRO299.

The entire nucleotide sequence of DNA39976-1215 is shown in FIG. 5 (SEQ ID NO:14). Clone DNA39976-1215 contains a single open reading frame with an apparent translational initiation site at nucleotide positions 111-113 and ending at the stop codon at nucleotide positions 2322-2324 (FIG. 5). The predicted polypeptide precursor is 737 amino acids long (FIG. 6). Important regions of the polypeptide sequence encoded by clone DNA39976-1215 have been identified and include the following: a signal peptide corresponding to amino acids 1-28, a putative transmembrane region corresponding to amino acids 638-662, 10 EGF repeats, corresponding to amino acids 80-106, 121-203, 336-360, 378-415, 416-441, 454-490, 491-528, 529-548, 567-604, and 605-622, respectively, and 10 potential N-glycosylation sites, corresponding to amino acids 107-120, 204-207, 208-222, 223-285, 286-304, 361-374, 375-377, 442-453, 549-563, and 564-566, respectively. Clone DNA39976-1215 has been deposited with ATCC and is assigned ATCC deposit no. ATCC 209524.

Analysis of the amino acid sequence of the full-length PRO299 polypeptide suggests that portions of it possess significant homology to the notch protein, thereby indicating that PRO299 may be a novel notch protein homolog and have activity typical of the notch protein.

Example 7

Isolation of cDNA Clones Encoding Human PRO323

A consensus DNA sequence was assembled relative to other EST sequences as described in Example 1 above. This consensus sequence is herein designated DNA30875. Based on the DNA30875 consensus sequence, oligonucleotides were synthesized: 1) to identify by PCR a cDNA library that contained the sequence of interest, and 2) for use as probes to isolate a clone of the full-length coding sequence for PRO323.

PCR primers (two forward and one reverse) were synthesized:

```
forward PCR primer 1
5'-AGTTCTGGTCAGCCTATGTGCC-3'       (SEQ ID NO: 25)

forward PCR primer 2
5'-CGTGATGGTGTCTTTGTCCATGGG-3'     (SEQ ID NO: 26)

reverse PCR primer
5'-CTCCACCAATCCCGATGAACTTGG-3'     (SEQ ID NO: 27)
```

Additionally, a synthetic oligonucleotide hybridization probe was constructed from the consensus DNA30875 sequence which had the following nucleotide sequence
Hybridization Probe

5'-GAGCAGATTGACCTCATACGCCGCATGT-GTGCCTCCTATTCTGAGCTGGA-3' (SEQ ID NO:28)

In order to screen several libraries for a source of a full-length clone, DNA from the libraries was screened by PCR amplification with the PCR primer pairs identified above. A positive library was then used to isolate clones encoding the PRO323 gene using the probe oligonucleotide and one of the PCR primers. RNA for construction of the cDNA libraries was isolated from human fetal liver (issue (LIB6).

DNA sequencing of the clones isolated as described above gave the full-length DNA sequence for PRO323 [herein designated as DNA35595-1228] (SEQ ID NO:23) and the derived protein sequence for PRO323.

The entire nucleotide sequence of DNA35595-1228 is shown in FIG. 9 (SEQ ID NO:23). Clone DNA35595-1228 contains a single open reading frame with an apparent translational initiation site at nucleotide positions 110-112 and ending at the stop codon at nucleotide positions 1409-1411 (FIG. 9). The predicted polypeptide precursor is 433 amino acids long (FIG. 10). The full-length PRO323 protein shown in FIG. 10 has an estimated molecular weight of about 47,787 daltons and a pI of about 6.11. Clone DNA35595-1228 has been deposited with ATCC and is assigned ATCC deposit no. 209528.

Analysis of the amino acid sequence of the full-length PRO323 polypeptide suggests that portions of it possess significant homology to various dipeptidase proteins, thereby indicating that PRO323 may be a novel dipeptidase protein.

Example 8

Isolation of cDNA Clones Encoding Human PRO327

An expressed sequence tag (EST) DNA database (LIFESEQ™, Incyte Pharmaceuticals, Palo Alto, Calif.) was searched and various EST sequences were identified which showed certain degrees of homology to human prolactin receptor protein. Those EST sequences were aligned using phrap and a consensus sequence was obtained. This consensus DNA sequence was then extended using repeated cycles of BLAST and phrap to extend the consensus sequence as far as possible using the sources of EST sequences discussed above. The extended assembly sequence is herein designated DNA38110. The above searches were performed using the computer program BLAST or BLAST2 (Altshul et al., *Methods in Enzymology* 266:460-480 (1996)). Those comparisons resulting in a BLAST score of 70 (or in some cases 90) or greater that did not encode known proteins were clustered and assembled into consensus DNA sequences with the program "phrap" (Phil Green, University of Washington, Seattle, Wash.).

Based upon the DNA38110 consensus sequence obtained as described above, oligonucleotides were synthesized: 1) to identify by PCR a cDNA library that contained the sequence of interest, and 2) for use as probes to isolate a clone of the full-length coding sequence for PRO327.

PCR primers (forward and reverse) were synthesized as follows:

```
forward PCR primer
5'-CCCGCCCGACGTGCACGTGAGCC-3'    (SEQ ID NO: 33)

reverse PCR primer
5'-TGAGCCAGCCCAGGAACTGCTTG-3'    (SEQ ID NO: 34)
```

Additionally, a synthetic oligonucleotide hybridization probe was constructed from the consensus DNA38110 consensus sequence which had the following nucleotide sequence
Hybridization Probe

5'-CAAGTGCGCTGCAACCCCTTTGGCATC-TATGGCTCCAAGAAAGCCGGGAT-3' (SEQ ID NO:35)

In order to screen several libraries for a source of a full-length clone, DNA from the libraries was screened by PCR amplification with the PCR primer pair identified above. A positive library was then used to isolate clones encoding the PRO327 gene using the probe oligonucleotide and one of the PCR primers. RNA for construction of the cDNA libraries was isolated from human fetal lung tissue (LIB26).

DNA sequencing of the clones isolated as described above gave the full-length DNA sequence for PRO327 [herein designated as DNA38113-1230] (SEQ ID NO:16) and the derived protein sequence for PRO327.

The entire nucleotide sequence of DNA38113-1230 is shown in FIG. 13 (SEQ ID NO:31). Clone DNA38113-1230 contains a single open reading frame with an apparent translational initiation site at nucleotide positions 119-121 and ending at the stop codon at nucleotide positions 1385-1387 (FIG. 13). The predicted polypeptide precursor is 422 amino acids long (FIG. 14). The full-length PRO327 protein shown in FIG. 14 has an estimated molecular weight of about 46,302 daltons and a pI of about 9.42. Clone DNA38113-1230 has been deposited with ATCC and is assigned ATCC deposit no. ATCC 209530.

Analysis of the amino acid sequence of the full-length PRO327 polypeptide suggests that it possess significant homology to the human prolactin receptor protein, thereby indicating that PRO327 may be a novel prolactin binding protein.

Example 9

Isolation of cDNA Clones Encoding Human PRO233

A consensus DNA sequence was assembled relative to other EST sequences as described in Example 1 above. This consensus sequence is herein designated DNA30945. Based on the DNA30945 consensus sequence, oligonucleotides were synthesized: 1) to identify by PCR a cDNA library that contained the sequence of interest, and 2) for use as probes to isolate a clone of the full-length coding sequence for PRO233.

PCR primers were synthesized as followed:

```
forward PCR primer
5'-GGTGAAGGCAGAAATTGGAGATG-3'    (SEQ ID NO: 38)

reverse PCR primer
5'-ATCCCATGCATCAGCCTGTTTACC-3'   (SEQ ID NO: 39)
```

Additionally, a synthetic oligonucleotide hybridization probe was constructed from the consensus DNA30945 sequence which had the following nucleotide sequence
Hybridization Probe

5'-GCTGGTGTAGTCTATACATCA-GATTTGTTTGCTACACAAGATCCTCAG-3' (SEQ ID NO:40)

In order to screen several libraries for a source of a full-length clone, DNA from the libraries was screened by PCR amplification with the PCR primer pair identified above. A positive library was then used to isolate clones encoding the PRO233 gene using the probe oligonucleotide. RNA for construction of the cDNA libraries was isolated from human fetal brain tissue.

DNA sequencing of the clones isolated as described above gave the full-length DNA sequence for PRO233 [herein designated as DNA34436-1238] (SEQ ID NO:36) and the derived protein sequence for PRO233.

The entire nucleotide sequence of DNA34436-1238 is shown in FIG. 15 (SEQ ID NO:36). Clone DNA34436-1238 contains a single open reading frame with an apparent translational initiation site at nucleotide positions 101-103 and ending at the stop codon at nucleotide positions 1001-1003 (FIG. 15). The predicted polypeptide precursor is 300 amino acids long (FIG. 16). The full-length PRO233 protein shown in FIG. 16 has an estimated molecular weight of about 32,964 daltons and a pI of about 9.52. In addition, regions of interest including the signal peptide and a putative oxidoreductase active site, are designated in FIG. 16. Clone DNA34436-1238 has been deposited with ATCC and is assigned ATCC deposit no. ATCC 209523

Analysis of the amino acid sequence of the full-length PRO233 polypeptide suggests that portions of it possess significant homology to various reductase proteins, thereby indicating that PRO233 may be a novel reductase.

Example 10

Isolation of cDNA Clones Encoding Human PRO344

A consensus DNA sequence was assembled relative to other EST sequences as described in Example 1 above. This consensus sequence is herein designated DNA34398. Based on the DNA34398 consensus sequencs, oligonucleotides were synthesized: 1) to identify by PCR a cDNA library that contained the sequence of interest, and 2) for use as probes to isolate a clone of the full-length coding sequence for PRO344.

Based on the DNA34398 consensus sequence, forward and reverse PCR primers were synthesized as follows:

```
forward PCR primer (34398.f1)  5'-TACAGGCCCAGTCAGGACCAGGGG-3'  (SEQ ID NO: 43)
forward PCR primer (34398.f2)  5'-AGCCAGCCTCGCTCTCGG-3'         (SEQ ID NO: 44)
forward PCR primer (34398.f3)  5'-GTCTGCGATCAGGTCTGG-3'         (SEQ ID NO: 45)
reverse PCR primer (34398.r1)  5'-GAAAGAGGCAATGGATTCGC-3'       (SEQ ID NO: 46)
reverse PCR primer (34398.r2)  5'-GACTTACACTTGCCAGCACAGCAC-3'   (SEQ ID NO: 47)
```

Additionally, a synthetic oligonucleotide hybridization probe was constructed from the DNA34398 consensus sequence which had the following nucleotide sequence Hybridization Probe (34398.p1)

5'-GGAGCACCACCAACTGGAGGGTCCGGAG-TAGCGAGCGCCCCGAAG-3' (SEQ ID NO:48)

In order to screen several libraries for a source of a full-length clone, DNA from the libraries was screened by PCR amplification with one of the PCR primer pairs identified above. A positive library was then used to isolate clones encoding the PRO344 genes using the probe oligonucleotide and one of the PCR primers. RNA for construction of the cDNA libraries was isolated from human fetal kidney tissue.

DNA sequencing of the clones isolated as described above gave the full-length DNA sequence for PRO344 [herein designated as DNA40592-1242] (SEQ ID NO:41) and the derived protein sequence for PRO344.

The entire nucleotide sequence of DNA40592-1242 is shown in FIG. 17 (SEQ ID NO:41). Clone DNA40592-1242 contains a single open reading frame with an apparent translational initiation site at nucleotide positions 227-229 and ending at the stop codon at nucleotide positions 956-958 (FIG. 17). The predicted polypeptide precursor is 243 amino acids long (FIG. 18). Important regions of the native PRO344 amino acid sequence include the signal peptide, the start of the mature protein, and two potential N-myristoylation sites as shown in FIG. 18. Clone DNA40592-1242 has been deposited with the ATCC and is assigned ATCC deposit no. ATCC 209492

Analysis of the amino acid sequence of the full-length PRO344 polypeptides suggests that portions of them possess significant homology to various human and murine complement proteins, thereby indicating that PRO344 may be a novel complement protein.

Example 11

Isolation of cDNA Clones Encoding Human PRO347

A consensus DNA sequence was assembled relative to other EST sequences as described in Example 1 above. This consensus sequence is herein designated DNA39499. Based on the DNA39499 consensus sequence, oligonucleotides were synthesized: 1) to identify by PCR a cDNA library that contained the sequence of interest, and 2) for use as probes to isolate a clone of the full-length coding sequence for PRO347.

PCR primers (forward and reverse) were synthesized as follows:

```
forward PCR primer
5'-AGGAACTTCTGGATCGGGCTCACC-3'   (SEQ ID NO: 51)

reverse PCR primer
5'-GGGTCTGGGCCAGGTGGAAGAGAG-3'   (SEQ ID NO: 52)
```

Additionally, a synthetic oligonucleotide hybridization probe was constructed from the consensus DNA39499 sequence which had the following nucleotide sequence
Hybridization Probe

5'-GCCAAGGACTCCTTCCGCTGGGCCA-CAGGGGAGCACCAGGCCTTC-3' (SEQ ID NO:53)

In order to screen several libraries for a source of a full-length clone, DNA from the libraries was screened by PCR amplification with the PCR primer pair identified above. A positive library was then used to isolate clones encoding the PRO347 gene using the probe oligonucleotide and one of the PCR primers. RNA for construction of the cDNA libraries was isolated from human fetal kidney tissue (LIB228).

DNA sequencing of the clones isolated as described above gave the full-length DNA sequence for PRO347 [herein designated as DNA44176-1244] (SEQ ID NO:49) and the derived protein sequence for PRO347.

The entire nucleotide sequence of DNA44176-1244 is shown in FIG. 19 (SEQ ID NO:49). Clone DNA44176-1244 contains a single open reading frame with an apparent translational initiation site at nucleotide positions 123-125 and ending at the stop codon at nucleotide positions 1488-1490 (FIG. 19). The predicted polypeptide precursor is 455 amino acids long (FIG. 20). The full-length PRO347 protein shown in FIG. 20 has an estimated molecular weight of about 50,478 daltons and a pI of about 8.44. Clone DNA44176-1244 has been deposited with ATCC and is assigned ATCC deposit no. ATCC 209532

Analysis of the amino acid sequence of the full-length PRO347 polypeptide suggests that portions of it possess significant homology to various cysteine-rich secretory proteins, thereby indicating that PRO347 may be a novel cysteine-rich secretory protein.

Example 12

Isolation of cDNA Clones Encoding Human PRO354

An expressed sequence tag (EST) DNA database (LIFESEQ™, Incyte Pharmaceuticals, Palo Alto, Calif.) was searched and various EST sequences were identified which possessed certain degress of homology with the inter-alpha-trypsin inhibitor heavy chain and with one another. Those homologous EST sequences were then aligned and a consensus sequence was obtained. The obtained consensus DNA sequence was then extended using repeated cycles of BLAST and phrap to extend the consensus sequence as far as possible using homologous EST sequences derived from both public EST databases (e.g., GenBank) and a proprietary EST DNA database (LIFESEQ™, Incyte Pharmaceuticals, Palo Alto, Calif.). The extended assembly sequence is herein designated DNA39633. The above searches were performed using the computer program BLAST or BLAST2 (Altshul et al., *Methods in Enzymology* 266:460-480 (1996)). Those comparisons resulting in a BLAST score of 70 (or in some cases 90) or greater that did not encode known proteins were clustered and assembled into consensus DNA sequences with the program "phrap" (Phil Green, University of Washington, Seattle, Wash.).

Based on the DNA39633 consensus sequence, oligonucleotides were synthesized: 1) to identify by PCR a cDNA library that contained the sequence of interest, and 2) for use as probes to isolate a clone of the full-length coding sequence for PRO354. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., *Current Protocols in Molecular Biology*, with the PCR primer pair. A positive library was then used to isolate clones encoding the gene of interest using the probe oligonucleotide and one of the primer pairs.

PCR primers were synthesized as follows:

```
forward PCR primer 1 (39633.f1)
5'-GTGGGAACCAAACTCCGGCAGACC-3'    (SEQ ID NO: 56)

forward PCR primer 2 (39633.f2)
5'-CACATCGAGCGTCTCTGG-3'           (SEQ ID NO: 57)

reverse PCR primer (39633.r1)
5'-AGCCGCTCCTTCTCCGGTTCATCG-3'     (SEQ ID NO: 58)
```

Additionally, a synthetic oligonucleotide hybridization probe was constructed from the consensus DNA39633 sequence which had the following nucleotide sequence Hybridization Probe
5'-TGGAAGGACCACTTGATATCAGTCACTC-CAGACAGCATCAGGGATGGG-3' (SEQ ID NO:59)

In order to screen several libraries for a source of a full-length clone, DNA from the libraries was screened by PCR amplification with the PCR primer pairs identified above. A positive library was then used to isolate clones encoding the PRO354 gene using the probe oligonucleotide and one of the PCR primers.

RNA for construction of the cDNA libraries was isolated from human fetal kidney (issue (LIB227). The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science*, 253:1278-1280 (1991)) in the unique XhoI and NotI sites.

DNA sequencing of the clones isolated as described above gave the full-length DNA sequence for PRO354 [herein designated as DNA44192-1246] (SEQ ID NO:54) and the derived protein sequence for PRO354.

The entire nucleotide sequence of DNA44192-1246 is shown in FIG. 21 (SEQ ID NO:54). Clone DNA44192-1246 contains a single open reading frame with an apparent translational initiation site at nucleotide positions 72-74 and ending at the stop codon at nucleotide positions 2154-2156 (FIG. 21). The predicted polypeptide precursor is 694 amino acids long (FIG. 22). The full-length PRO354 protein shown in FIG. 22 has an estimated molecular weight of about 77,400 daltons and a pI of about 954. Clone DNA44192-1246 has been deposited with ATCC and is assigned ATCC deposit no. ATCC 209531.

Analysis of the amino acid sequence of the full-length PRO354 polypeptide suggests that it possess significant homology to the inter-alpha-trypsin inhibitor heavy chain protein, thereby indicating that PRO354 may be a novel inter-alpha-trypsin inhibitor heavy chain protein homolog.

Example 13

Isolation of cDNA Clones Encoding Human PRO355

A consensus DNA sequence was assembled relative to other EST sequences using BLAST and phrap as described in Example 1 above. This consensus sequence is herein designated DNA35702. Based on the DNA35702 consensus sequence, oligonucleotides were synthesized: 1) to identify by PCR a cDNA library that contained the sequence of interest, and 2) for use as probes to isolate a clone of the full-length coding sequence for PRO355.

Forward and reverse PCR primers were synthesized as follows:

```
forward PCR primer 5'-GGCTTCTGCTGTTGCTCTTCTCCG-3'   (SEQ ID NO:62)

forward PCR primer 5'-GTACACTGTGACCAGTCAGC-3'       (SEQ ID NO:63)

forward PCR primer 5'-ATCATCACAGATTCCCGAGC-3'       (SEQ ID NO:64)
```

-continued reverse PCR primer 5'-TTCAATCTCCTCACCTTCCACCGC-3'    (SEQ ID NO:65)

reverse PCR primer 5'-ATAGCTGTGTCTGCGTCTGCTGCG-3'    (SEQ ID NO:66)

Additionally, a synthetic oligonucleotide hybridization probe was constructed from the consensus DNA35702 sequence which had the following nucleotide sequence:
Hybridization Probe
5'-CGCGGCACTGATCCCCACAGGT-GATGGGCAGAATCTGTTTACGAAAGACG-3' (SEQ ID NO:67)

In order to screen several libraries for a source of a full-length clone, DNA from the libraries was screened by PCR amplification with one of the PCR primer pairs identified above. A positive library was then used to isolate clones encoding the PRO355 gene using the probe oligonucleotide. RNA for construction of the cDNA libraries was isolated from human fetal liver tissue.

DNA sequencing of the clones isolated as described above gave the full-length DNA sequence for PRO355 [herein designated as DNA39518-1247] (SEQ ID NO:60) and the derived protein sequence for PRO355.

The entire nucleotide sequence of DNA39518-1247 is shown in FIG. 23 (SEQ ID NO:60). Clone DNA39518-1247 contains a single open reading frame with an apparent translational initiation site at nucleotide positions 22-24 and ending at the stop codon at nucleotide positions 1342-1344 (FIG. 23). The predicted polypeptide precursor is 440 amino acids long (FIG. 24). The full-length PRO355 protein shown in FIG. 24 has an estimated molecular weight of about -48,240 daltons and a pI of about 4.93. In addition, regions of interest including the signal peptide, Ig repeats in the extracellular domain, potential N-glycosylation sites, and the potential transmembrane domain, are designated in FIG. 24. Clone DNA39518-1247 has been deposited with ATCC and is assigned ATCC deposit no. ATCC 209529.

Analysis of the amino acid sequence of the full-length PRO355 polypeptide suggests that portions of it possess significant homology to the CRTAM protein, thereby indicating that PRO355 may be CRTAM protein.

Example 14

Isolation of cDNA Clones Encoding Human PRO357

The sequence expression tag clone no. "2452972" by Incyte Pharmaceuticals, Palo Alto, Calif. was used to begin a data base search. The extracellular domain (ECD) sequences (including the secretion signal, if any) of from about 950 known secreted proteins from the Swiss-Prot public protein database were used to search expressed sequence tag (EST) databases which overlapped with a portion of Incyte EST clone no. "2452972". The EST databases included public EST databases (e.g., GenBank) and a proprietary EST DNA database (LIFESEQ™, Incyte Pharmaceuticals, Palo Alto, Calif.). The search was performed using the computer program BLAST or BLAST2 (Altshul et al., *Methods in Enzymology* 266:460-480 (1996)) as a comparison of the ECD protein sequences to a 6 frame translation of the EST sequence. Those comparisons resulting in a BLAST score of 70 (or in some cases 90) or greater that did not encode known proteins were clustered and assembled into consensus DNA sequences with the program "phrap" (Phil Green, University of Washington, Seattle, Wash.).

A consensus DNA sequence was then assembled relative to other EST sequences using phrap. This consensus sequence is herein designated DNA37162. In this case, the consensus DNA sequence was extended using repeated cycles of BLAST and phrap to extend the consensus sequence as far as possible using the sources of EST sequences discussed above.

Based on the DNA37162 consensus sequence, oligonucleotides were synthesized: 1) to identify by PCR a cDNA library that contained the sequence of interest, and 2) for use as probes to isolate a clone of the full-length coding sequence for PRO357. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as ber Ausubel et al., *Current Protocols in Molecular Biology*, with the PCR primer pair. A positive library was then used to isolate clones encoding the gene of interest using the probe oligonucleotide and one of the primer pairs.

PCR primers were synthesized as follows:

forward primer 1:  5'-CCCTCCACTGCCCCACCGACTG-3';    (SEQ ID NO:70)

reverse primer 1:  5'-CGGTTCTGGGGACGTTAGGGCTCG-3';   (SEQ ID NO:71)
and forward primer 2:  5'-CTGCCCACCGTCCACCTGCCTCAAT-3'.  (SEQ ID NO:72)

Additionally, two synthetic oligonucleotide hybridization probes were constructed from the consensus DNA37162 sequence which had the following nucleotide sequences:

hybridization probe 1:
5'-AGGACTGCCCACCGTCCACCTGCCTCAATGGGGGCACATGCCACC-3';   (SEQ ID NO:73)
and hybridization probe 2:
5'-ACGCAAAGCCCTACATCTAAGCCAGAGAGAGACAGGGCAGCTGGG-3'.   (SEQ ID NO:74)

In order to screen several libraries for a source of a full-length clone, DNA from the libraries was screened by PCR amplification with a PCR primer pair identified above. A positive library was then used to isolate clones encoding the PRO357 gene using the probe oligonucleotide and one of the PCR primers.

RNA for construction of the cDNA libraries was isolated from human fetal liver tissue. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science,* 253:1278-1280 (1991)) in the unique XhoI and NotI sites.

DNA sequencing of the clones isolated as described above gave the full-length DNA sequence for PRO357 [herein designated as DNA44804-1248] (SEQ ID NO:68) and the derived protein sequence for PRO357.

The entire nucleotide sequence of DNA44804-1248 is shown in FIG. 25 (SEQ ID NO:68). Clone DNA44804-1248 contains a single open reading frame with an apparent translational initiation site at nucleotide positions 137-139 and ending at the stop codon at nucleotide positions 1931-1933 (FIG. 25). The predicted polypeptide precursor is 598 amino acids long (FIG. 26). Clone DNA44804-1248 has been deposited with ATCC and is assigned ATCC deposit no. ATCC 209527.

Analysis of the amino acid sequence of the full-length PRO357 polypeptide therefore suggests that portions of it possess significant homology to ALS, thereby indicating that PRO357 may be a novel leucine rich repeat protein related to ALS.

Example 15

Isolation of cDNA Clones Encoding Human PRO715

A proprietary EST DNA database (LIFESEQ™, Incyte Pharmaceuticals, Palo Alto, Calif.) was searched for EST sequences encoding polypeptides having homology to human TNF-α. This search resulted in the identification of Incyte Expressed Sequence Tag No. 2099855.

A consensus DNA sequence was then assembled relative to other EST sequences using seqext and "phrap" (Phil Green, University of Washington, Seattle, Wash.). This consensus sequence is herein designated DNA52092. Based upon the alignment of the various EST clones identified in this assembly, a single EST clone from the Merck/Washington University EST set (EST clone no. 725887, Accession No. AA292358) was obtained and its insert sequenced. The full-length DNA52722-1229 sequence was then obtained from sequencing the insert DNA from EST clone no. 725887.

The entire nucleotide sequence of DNA52722-1229 is shown in FIG. 27 (SEQ ID NO:75). Clone DNA52722-1229 contains a single open reading frame with an apparent translational initiation site at nucleotide positions 114-116 and ending at the stop codon at nucleotide positions 864-866 (FIG. 27). The predicted polypeptide is 250 amino acids long (FIG. 28). The full-length PRO715 protein shown in FIG. 28 has an estimated molecular weight of about 27,433 daltons and a pI of about 9.85.

Analysis of the amino acid sequence of the full-length PRO715 polypeptide suggests that it possesses significant homology to members of the tumor necrosis factor family of proteins, thereby indicating that PRO715 is a novel tumor necrosis factor protein.

Example 16

Isolation of cDNA Clones Encoding Human PRO353

A consensus DNA sequence was assembled relative to other EST sequences using phrap as described in Example 1 above. This consensus sequences is herein designated DNA36363. The consensus DNA sequence was extended using repeated cycles of BLAST and phrap to extend the consensus sequence as far as possible using the sources of EST sequences discussed above. Based on the DNA36363 consensus sequence, oligonucleotides were synthesized: 1) to identify by PCR a cDNA library that contained the sequence of interest, and 2) for use as probes to isolate a clone of the full-length coding sequence for PRO353.

Based on the DNA36363 consensus sequence, forward and reverse PCR primers were synthesized as follows:

```
forward PCR primer 5'-TACAGGCCCAGTCAGGACCAGGGG-3'  (SEQ ID NO:79)

reverse PCR primer 5'-CTGAAGAAGTAGAGGCCGGGCACG-3'. (SEQ ID NO:80)
```

Additionally, a synthetic oligonucleotide hybridization probe was constructed from the DNA36363 consensus sequence which had the following nucleotide sequence:
Hybridization Probe

5'-CCCGGTGCTTGCGCTGCTGTGACCCCGG-TACCTCCATGTACCCGG-3' (SEQ ID NO:81)

In order to screen several libraries for a source of a full-length clone, DNA from the libraries was screened by PCR amplification with one of the PCR primer pairs identified above. A positive library was then used to isolate clones encoding the PRO353 gene using the probe oligonucleotide and one of the PCR primers. RNA for construction of the cDNA libraries was isolated from human fetal kidney tissue.

DNA sequencing of the clones isolated as described above gave the full-length DNA sequence for PRO353 [herein designated as DNA41234-1242] (SEQ ID NO:77) and the derived protein sequence for PRO353.

The entire nucleotide sequence of DNA41234-1242 is shown in FIG. 29 (SEQ ID NO:77). Clone DNA41234-1242 contains a single open reading frame with an apparent translational initiation site at nucleotide positions 305-307 and ending at the stop codon at nucleotide positions 1148-1150 (FIG. 29). The predicted polypeptide precursor is 281 amino acids long (FIG. 30). Important regions of the amino acid sequence encoded by PRO353 include the signal peptide, corresponding to amino acids 1-26, the start of the mature protein at amino acid position 27, a potential N-glycosylation site, corresponding to amino acids 93-98 and a region which has homology to a 30 kd adipocyte complement-related protein precursor, corresponding to amino acids 99-281. Clone DNA41234-1242 has been deposited with the ATCC and is assigned ATCC deposit no. ATCC 209618.

Analysis of the amino acid sequence of the full-length PRO353 polypeptides suggests that portions of them possess significant homology to portions of human and murine complement proteins, thereby indicating that PRO353 may be a novel complement protein.

Example 17

Isolation of cDNA Clones Encoding Human PRO361

A consensus DNA sequence was assembled relative to other EST sequences using phrap as described in Example 1 above. This consensus sequence is herein designated DNA40654. Based on the DNA40654 consensus sequence, oligonucleotides were synthesized: 1) to identify by PCR a cDNA library that contained the sequence of interest, and 2) for use as probes to isolate a clone of the full-length coding sequence for PRO361.

Forward and reverse PCR primers were synthesized as follows:

```
forward PCR primer 5'-AGGGAGGATTATCCTTGACCTTTGAAGACC-3'   (SEQ ID NO:84)

forward PCR primer 5'-GAAGCAAGTGCCCAGCTC-3'              (SEQ ID NO:85)

forward PCR primer 5'-CGGGTCCCTGCTCTTTGG-3'              (SEQ ID NO:86)

reverse PCR primer 5'-CACCGTAGCTGGGAGCGCACTCAC-3'        (SEQ ID NO:87)

reverse PCR primer 5'-AGTGTAAGTCAAGCTCCC-3'              (SEQ ID NO:88)
```

Additionally, a synthetic oligonucleotide hybridization probe was constructed from the consensus DNA40654 sequence which had the following nucleotide sequence Hybridization Probe
5'-GCTTCCTGACACTAAGGCTGTCT-GCTAGTCAGAATTGCCTCAAAAAGAG-3' (SEQ ID NO:89)

In order to screen several libraries for a source of a full-length clone, DNA from the libraries was screened by PCR amplification with one of the PCR primer pairs identified above. A positive library was then used to isolate clones encoding the PRO361 gene using the probe oligonucleotide. RNA for construction of the cDNA libraries was isolated from human fetal kidney tissue.

DNA sequencing of the clones isolated as described above gave the full-length DNA sequence for PRO361 [herein designated as DNA45410-1250] (SEQ ID NO:82) and the derived protein sequence for PRO361.

The entire nucleotide sequence of DNA45410-1250 is shown in FIG. 31 (SEQ ID NO:82). Clone DNA45410-1250 contains a single open reading frame with an apparent translational initiation site at nucleotide positions 226-228 and ending at the stop codon at nucleotide positions 1519-1521 (FIG. 31). The predicted polypeptide precursor is 431 amino acids long (FIG. 32). The full-length PRO361 protein shown in FIG. 32 has an estimated molecular weight of about 46,810 daltons and a pI of about 6.45. In addition, regions of interest including the transmembrane domain (amino acids 380-409) and sequences typical of the arginase family of proteins (amino acids 3-14 and 39-57) are designated in FIG. 32. Clone DNA45410-1250 has been deposited with ATCC and is assigned ATCC deposit no. ATCC 209621.

Analysis of the amino acid sequence of the full-length PRO361 polypeptide suggests that portions of it possess significant homology to the mucin and/or chitinase proteins, thereby indicating that PRO361 may be a novel mucin and/or chitinase protein.

Example 18

Isolation of cDNA Clones Encoding Human PRO365

A consensus DNA sequence was assembled relative to other EST sequences using phrap as described in Example 1 above. This consensus sequence is herein designated DNA35613. Based on the DNA35613 consensus sequence, oligonucleotides were synthesized: 1) to identify by PCR a cDNA library that contained the sequence of interest, and 2) for use as probes to isolate a clone of the full-length coding sequence for PRO365.

Forward and reverse PCR primers were synthesized as follows:

```
forward PCR primer 5'-AATGTGACCACTGGACTCCC-3'      (SEQ ID NO:92)

forward PCR primer 5'-AGGCTTGGAACTCCCTTC-3'        (SEQ ID NO:93)

reverse PCR primer 5'-AAGATTCTTGAGCGATTCCAGCTG-3'  (SEQ ID NO:94)
```

Additionally, a synthetic oligonucleotide hybridization probe was constructed from the consensus DNA35613 sequence which had the following nucleotide sequence Hybridization Probe
5'-AATCCCTGCTCTTCATGGTGACCTAT-GACGACGGAAGCACAAGACTG-3' (SEQ ID NO:95)

In order to screen several libraries for a source of a full-length clone, DNA from the libraries was screened by PCR amplification with one of the PCR primer pairs identified above. A positive library was then used to isolate clones encoding the PRO365 gene using the probe oligonucleotide and one of the PCR primers. RNA for construction of the cDNA libraries was isolated from human fetal kidney tissue.

DNA sequencing of the clones isolated as described above gave the full-length DNA sequence for PRO365 [herein designated as DNA46777-1253] (SEQ ID NO:90) and the derived protein sequence for PRO365.

The entire nucleotide sequence of DNA46777-1253 is shown in FIG. 33 (SEQ ID NO:90). Clone DNA46777-1253 contains a single open reading frame with an apparent translational initiation site at nucleotide positions 15-17 and ending at the stop codon at nucleotide positions 720-722 (FIG. 33). The predicted polypeptide precursor is 235 amino acids long (FIG. 34). Important regions of the polypeptide sequence encoded by clone DNA46777-1253 have been identified and include the following: a signal peptide corresponding to amino acids 1-20, the start of the mature protein corresponding to amino acid 21, and multiple potential N-glycosylation sites as shown in FIG. 34. Clone DNA46777-1253 has been deposited with ATCC and is assigned ATCC deposit no. ATCC 209619.

Analysis of the amino acid sequence of the full-length PRO365 polypeptide suggests that portions of it possess significant homology to the human 2-19 protein, thereby indicating that PRO365 may be a novel human 2-19 protein homolog.

Example 19

Use of PRO Polypeptide-Encoding Nucleic Acid as Hybridization Probes

The following method describes use of a nucleotide sequence encoding PRO as a hybridization probe.

DNA comprising the coding sequence of full-length or mature PRO as disclosed herein is employed as a probe to screen for homologous DNAs (such as those encoding naturally-occurring variants of PRO) in human tissue cDNA libraries or human tissue genomic libraries.

Hybridization and washing of filters containing either library DNAs is performed under the following high stringency conditions. Hybridization of radiolabeled PRO-derived probe to the filters is performed in a solution of 50% formamide, 5×SSC, 0.1% SDS, 0.1% sodium pyrophosphate, 50 mM sodium phosphate, pH 6.8, 2× Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence PRO can then be identified using standard techniques known in the art.

Example 20

Expression of PRO Polypeptides in *E. coli*

This example illustrates preparation of an unglycosylated form of PRO by recombinant expression in *E. coli*.

The DNA sequence encoding PRO is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*; see Bolivar et al., *Gene*, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the PRO coding region, lambda transcriptional terminator, and an argU gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized PRO protein can then be purified using a metal chelating column under conditions that allow tight binding of the protein.

PRO may be expressed in *E. coli* in a poly-His tagged form, using the following procedure. The DNA encoding PRO is initially amplified using selected PCR primers. The primers will contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an *E. coli* host based on strain 52 (W3110 fuhA (tonA) lon galE rpoHts (htpRts) clpP (lacIq). Transformants are first grown in LB containing 50 mg/ml carbenicillin at 30° C. with shaking until an O.D. 600 of 3-5 is reached. Cultures are then diluted 50-100 fold into CRAP media (prepared by mixing 3.57 g $(NH_4)_2SO_4$, 0.71 g sodium citrate•$2H_2O$, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20-30 hours at 30° C. with shaking. Samples are removed to verify expression by SDS-PAGE analysis, and the bulk culture is centrifuged to pellet the cells. Cell pellets are frozen until purification and refolding.

*E. coli* paste from 0.5 to 1 L fermentations (6-10 g pellets) is resuspended in 10 volumes (w/v) in 7 M guanidine, 20 mM Tris, pH 8 buffer. Solid sodium sulfite and sodium tetrathionate is added to make final concentrations of 0.1M and 0.02 M, respectively, and the solution is stirred overnight at 4° C. This step results in a denatured protein with all cysteine residues blocked by sulfitolization. The solution is centrifuged at 40,000 rpm in a Beckman Ultracentrifuge for 30 min. The supernatant is diluted with 3-5 volumes of metal chelate column buffer (6 M guanidine, 20 mM Tris, pH 7.4) and filtered through 0.22 micron filters to clarify. The clarified extract is loaded onto a 5 ml Qiagen Ni—NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein are pooled and stored at 4° C. Protein concentration is estimated by its absorbance at 280 nm using the calculated extinction coefficient based on its amino acid sequence.

The proteins are refolded by diluting the sample slowly into freshly prepared refolding buffer consisting of: 20 mM Tris, pH 8.6, 0.3 M NaCl, 2.5 M urea, 5 mM cysteine, 20 mM glycine and 1 mM EDTA Refolding volumes are chosen so that the final protein concentration is between 50 to 100 micrograms/ml. The refolding solution is stirred gently at 4°

C. for 12-36 hours. The refolding reaction is quenched by the addition of TFA to a final concentration of 0.4% (pH of approximately 3). Before further purification of the protein, the solution is filtered through a 0.22 micron filter and acetonitrile is added to 2-10% final concentration. The refolded protein is chromatographed on a Poros R1/H reversed phase column using a mobile buffer of 0.1% TFA with elution with a gradient of acetonitrile from 10 to 80%. Aliquots of fractions with A280 absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded PRO polypeptide are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

Many of the PRO polypeptides disclosed herein were successfully expressed as described above.

Example 21

Expression of PRO Polypeptides in Mammalian Cells

This example illustrates preparation of a potentially glycosylated form of PRO by recombinant expression in mammalian cells.

The vector, pRK5 (see EP 307,247, published Mar. 15, 1989), is employed as the expression vector. Optionally, the PRO DNA is ligated into pRK5 with selected restriction enzymes to allow insertion of the PRO DNA using ligation methods such as described in Sambrook et al., supra. The resulting vector is called pRK5-PRO.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 µg pRK5-PRO DNA is mixed with about 1 µg DNA encoding the VA RNA gene [Thimmappaya et al., *Cell,* 31:543 (1982)] and dissolved in 500 µl of 1 mM Tris-HCl, 0.1 mM EDTA, 0.227 M $CaCl_2$. To this mixture is added, dropwise, 500 µl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 µCi/ml $^{35}S$-cysteine and 200 µCi/ml $^{35}S$-methionine. After a 12 hour incubation, the conditioned medium is collected, concentrated on a spin filter, and loaded onto a 15% SDS gel. The processed gel may be dried and exposed to film for a selected period of time to reveal the presence of PRO polypeptide. The cultures containing transfected cells may undergo further incubation (in serum free medium) and the medium is tested in selected bioassays.

In an alternative technique, PRO may be introduced into 293 cells transiently using the dextran sulfate method described by Somparyrac et al., *Proc. Natl. Acad. Sci.,* 12:7575 (1981). 293 cells are grown to maximal density in a spinner flask and 700 µg pRK5-PRO DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 µg/ml bovine insulin and 0.1 µg/ml bovine transferrin. After about four days, the conditioned media is centrifuged and filtered to remove cells and debris. The sample containing expressed PRO can then be concentrated and purified by any selected method, such as dialysis and/or column chromatography.

In another embodiment, PRO can be expressed in CHO cells. The pRK5-PRO can be transfected into CHO cells using known reagents such as $CaPO_4$ or DEAE-dextran. As described above, the cell cultures can be incubated, and the medium replaced with culture medium (alone) or medium containing a radiolabel such as $^{35}S$-methionine. After determining the presence of PRO polypeptide, the culture medium may be replaced with serum free medium. Preferably, the cultures are incubated for about 6 days, and then the conditioned medium is harvested. The medium containing the expressed PRO can then be concentrated and purified by any selected method.

Epitope-tagged PRO may also be expressed in host CHO cells. The PRO may be subcloned out of the pRK5 vector. The subclone insert can undergo PCR to fuse in frame with a selected epitope tag such as a poly-his tag into a Baculovirus expression vector. The poly-his tagged PRO insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged PRO can then be concentrated and purified by any selected method, such as by $Ni^{2+}$-chelate affinity chromatography.

PRO may also be expressed in CHO and/or COS cells by a transient expression procedure or in CHO cells by another stable expression procedure.

Stable expression in CHO cells is performed using the following procedure. The proteins are expressed as an IgG construct (immunoadhesin), in which the coding sequences for the soluble forms (e.g. extracellular domains) of the respective proteins are fused to an IgG1 constant region sequence containing the hinge, CH2 and CH2 domains and/or is a poly-His tagged form.

Following PCR amplification, the respective DNAs are subcloned in a CHO expression vector using standard techniques as described in Ausubel et al., *Current Protocols of Molecular Biology*, Unit 3.16, John Wiley and Sons (1997). CHO expression vectors are constructed to have compatible restriction sites 5' and 3' of the DNA of interest to allow the convenient shuttling of cDNA's. The vector used expression in CHO cells is as described in Lucas et al., *Nucl. Acids Res.* 24:9 (1774-1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents Superfect* (Quiagen), Dosper* or Fugene* (Boehringer Mannheim). The cells are grown as described in Lucas et al., supra. Approximately $3 \times 10^{-7}$ cells are frozen in an ampule for further growth and production as described below.

The ampules containing the plasmid DNA are thawed by placement into water bath and mixed by vortexing. The contents are pipetted into a centrifuge tube containing 10 mLs of media and centrifuged at 1000 rpm for 5 minutes. The supernatant is aspirated and the cells are resuspended in 10 mL of selective media (0.2 μm filtered PS20 with 5% 0.2 μm diafiltered fetal bovine serum). The cells are then aliquoted into a 100 mL spinner containing 90 mL of selective media. After 1-2 days, the cells are transferred into a 250 mL spinner filled with 150 mL selective growth medium and incubated at 37° C. After another 2-3 days, 250 mL, 500 mL and 2000 mL spinners are seeded with $3 \times 10^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3 L production spinner is seeded at $1.2 \times 10^6$ cells/mL. On day 0, the cell number pH ie determined. On day 1, the spinner is sampled and sparging with filtered air is commenced. On day 2, the spinner is sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion) taken. Throughout the production, the pH is adjusted as necessary to keep it at around 7.2. After 10 days, or until the viability dropped below 70%, the cell culture is harvested by centrifugation and filtering through a 0.22 μm filter. The filtrate was either stored at 4° C. or immediately loaded onto columns for purification.

For the poly-His tagged constructs, the proteins are purified using a Ni—NTA column (Qiagen). Before purification, imidazole is added to the conditioned media to a concentration of 5 mM. The conditioned media is pumped onto a 6 ml Ni—NTA column equilibrated in 20 mM Hepes, pH 7.4, buffer containing 0.3 M NaCl and 5 mM imidazole at a flow rate of 4-5 ml/min at 4° C. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc-containing) constructs are purified from the conditioned media as follows. The conditioned medium is pumped onto a 5 ml Protein A column (Pharmacia) which had been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 μL of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Many of the PRO polypeptides disclosed herein were successfully expressed as described above.

Example 22

Expression of PRO in Yeast

The following method describes recombinant expression of PRO in yeast.

First, yeast expression vectors are constructed for intracellular production or secretion of PRO from the ADH2/GAPDH promoter. DNA encoding PRO and the promoter is inserted into suitable restriction enzyme sites in the selected plasmid to direct intracellular expression of PRO. For secretion, DNA encoding PRO can be cloned into the selected plasmid, together with DNA encoding the ADH2/GAPDH promoter, a native PRO signal peptide or other mammalian signal peptide, or, for example, a yeast alpha-factor or invertase secretory signal/leader sequence, and linker sequences (if needed) for expression of PRO.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant PRO can subsequently be isolated and purified by removing the yeast cells from the fermentation medium by centrifugation and then concentrating the medium using selected cartridge filters. The concentrate containing PRO may further be purified using selected column chromatography resins.

Many of the PRO polypeptides disclosed herein were successfully expressed as described above.

Example 23

Expression of PRO in Baculovirus-Infected Insect Cells

The following method describes recombinant expression of PRO in Baculovirus-infected insect cells.

The sequence coding for PRO is fused upstream of an epitope tag contained within a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the sequence encoding PRO or the desired portion of the coding sequence of PRO such as the sequence encoding the extracellular domain of a transmembrane protein or the sequence encoding the mature protein if the protein is extracellular is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4-5 days of incubation at 28° C., the released viruses are harvested and used for further amplifications. Viral infection and protein expression are performed as described by O'Reilley et al., *Baculovirus expression vectors: A Laboratory Manual*, Oxford: Oxford University Press (1994).

Expressed poly-his tagged PRO can then be purified, for example, by $Ni^{2+}$-chelate affinity chromatography as follows. Extracts are prepared from recombinant virus-infected Sf9 cells as described by Rupert et al., *Nature,* 362:175-179 (1993). Briefly, Sf9 cells are washed, resuspended in sonication buffer (25 mL Hepes, pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 µm filter. A $Ni^{2+}$—NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or Western blot with $Ni^{2+}$—NTA-conjugated to alkaline phosphatase (Qiagen). Fractions containing the eluted $His_{10}$-tagged PRO are pooled and dialyzed against loading buffer.

Alternatively, purification of the IgG tagged (or Fc tagged) PRO can be performed using known chromatography techniques, including for instance, Protein A or protein G column chromatography.

Many of the PRO polypeptides disclosed herein were successfully expressed as described above.

Example 24

Preparation of Antibodies that Bind PRO

This example illustrates preparation of monoclonal antibodies which can specifically bind PRO.

Techniques for producing the monoclonal antibodies are known in the art and are described, for instance, in Goding, supra. Immunogens that may be employed include purified PRO, fusion proteins containing PRO, and cells expressing recombinant PRO on the cell surface. Selection of the immunogen can be made by the skilled artisan without undue experimentation.

Mice, such as Balb/c, are immunized with the PRO immunogen emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retroorbital bleeding for testing in ELISA assays to detect anti-PRO antibodies.

After a suitable antibody titer has been detected, the animals "positive" for antibodies can be injected with a final intravenous injection of PRO. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against PRO. Determination of "positive" hybridoma cells secreting the desired monoclonal antibodies against PRO is within the skill in the art.

The positive hybridoma cells can be injected intraperitoneally into syngeneic Balb/c mice to produce ascites containing the anti-PRO monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 25

Purification of PRO Polypeptides Using Specific Antibodies

Native or recombinant PRO polypeptides may be purified by a variety of standard techniques in the art of protein purification. For example, pro-PRO polypeptide, mature PRO polypeptide, or pre-PRO polypeptide is purified by immunoaffinity chromatography using antibodies specific for the PRO polypeptide of interest. In general, an immunoaffinity column is constructed by covalently coupling the anti-PRO polypeptide antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE™ (Pharmacia LKB Biotechnology). The antibody is coupled to the resin, the resin is blocked, and the derivative resin is washed according to the manufacturer's instructions.

Such an immunoaffinity column is utilized in the purification of PRO polypeptide by preparing a fraction from cells containing PRO polypeptide in a soluble form. This preparation is derived by solubilization of the whole cell or of a subcellular fraction obtained via differential centrifugation by the addition of detergent or by other methods well known in the art. Alternatively, soluble PRO polypeptide containing a signal sequence may be secreted in useful quantity into the medium in which the cells are grown.

A soluble PRO polypeptide-containing preparation is passed over the immunoaffinity column, and the column is washed under conditions that allow the preferential absorbance of PRO polypeptide (e.g., high ionic strength buffers in the presence of detergent). Then, the column is eluted under conditions that disrupt antibody/PRO polypeptide binding (e.g., a low pH buffer such as approximately pH 2-3, or a high concentration of a chaotrope such as urea or thiocyanale ion), and PRO polypeptide is collected.

Example 26

Drug Screening

This invention is particularly useful for screening compounds by using PRO polypeptides or binding fragment thereof in any of a variety of drug screening techniques. The PRO polypeptide or fragment employed in such a test may either be free in solution, affixed to a solid support, borne on a cell surface, or located intracellularly. One method of drug screening utilizes eukaryotic or prokaryotic host cells which are stably transformed with recombinant nucleic acids expressing the PRO polypeptide or fragment. Drugs are screened against such transformed cells in competitive binding assays. Such cells, either in viable or fixed form, can be used for standard binding assays. One may measure, for example, the formation of complexes between PRO polypeptide or a fragment and the agent being tested. Alternatively, one can examine the diminution in complex formation between the PRO polypeptide and its target cell or target receptors caused by the agent being tested.

Thus, the present invention provides methods of screening for drugs or any other agents which can affect a PRO polypeptide-associated disease or disorder. These methods comprise contacting such an agent with an PRO polypeptide or fragment thereof and assaying (I) for the presence of a complex between the agent and the PRO polypeptide or fragment, or (ii) for the presence of a complex between the PRO polypeptide or fragment and the cell, by methods well known in the art. In such competitive binding assays, the PRO polypeptide or fragment is typically labeled. After suitable incubation, free PRO polypeptide or fragment is separated from that present in bound form, and the amount of free or uncomplexed label is a measure of the ability of the particular agent to bind to PRO polypeptide or to interfere with the PRO polypeptide/cell complex.

Another technique for drug screening provides high throughput screening for compounds having suitable binding affinity to a polypeptide and is described in detail in WO 84/03564, published on Sep. 13, 1984. Briefly stated, large numbers of different small peptide test compounds are synthesized on a solid substrate, such as plastic pins or some other surface. As applied to a PRO polypeptide, the peptide test compounds are reacted with PRO polypeptide and washed. Bound PRO polypeptide is detected by methods well known in the art. Purified PRO polypeptide can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding PRO polypeptide specifically compete with a test compound for binding to PRO polypeptide or fragments thereof. In this manner, the antibodies can be used to detect the presence of any peptide which shares one or more antigenic determinants with PRO polypeptide.

Example 27

Rational Drug Design

The goal of rational drug design is to produce structural analogs of biologically active polypeptide of interest (i.e., a PRO polypeptide) or of small molecules with which they interact, e.g., agonists, antagonists, or inhibitors. Any of these examples can be used to fashion drugs which are more active or stable forms of the PRO polypeptide or which enhance or interfere with the function of the PRO polypeptide in vivo (c.f., Hodgson, *Bio/Technology*, 9: 19-21 (1991)).

In one approach, the three-dimensional structure of the PRO polypeptide, or of an PRO polypeptide-inhibitor complex, is determined by x-ray crystallography, by computer modeling or, most typically, by a combination of the two approaches. Both the shape and charges of the PRO polypeptide must be ascertained to elucidate the structure and to determine active site(s) of the molecule. Less often, useful information regarding the structure of the PRO polypeptide may be gained by modeling based on the structure of homologous proteins. In both cases, relevant structural information is used to design analogous PRO polypeptide-like molecules or to identify efficient inhibitors. Useful examples of rational drug design may include molecules which have improved activity or stability as shown by Braxton and Wells, *Biochemistry*, 31:7796-7801 (1992) or which act as inhibitors, agonists, or antagonists of native peptides as shown by Athauda et al., *J. Biochem.*, 113:742-746 (1993).

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amounts of the PRO polypeptide may be made available to perform such analytical studies as X-ray crystallography. In addition, knowledge of the PRO polypeptide amino acid sequence provided herein will provide guidance to those employing computer modeling techniques in place of or in addition to x-ray crystallography.

Example 28

Gene Amplification

This example shows that the PRO327-, PRO344-, PRO347-, PRO357- and PRO715-encoding genes are amplified in the genome of certain human lung, colon and/or breast cancers and/or cell lines. Amplification is associated with overexpression of the gene product, indicating that the polypeptides are useful targets for therapeutic intervention in certain cancers such as colon, lung, breast and other cancers. Therapeutic agents may take the form of antagonists of PRO327, PRO344, PRO347, PRO357 aor PRO715 polypeptide, for example, murine-human chimeric, humanized or human antibodies against a PRO327, PRO344, PRO347, PRO357 or PRO715 polypeptide. These amplifications also are useful as diagnostic markers for the presence of a specific type of tumor type.

The starting material for the screen was genomic DNA isolated from a variety cancers. The DNA is quantitated precisely, e.g., fluorometrically. As a negative control, DNA was isolated from the cells of ten normal healthy individuals which was pooled and used as assay controls for the gene copy in healthy individuals (not shown). The 5' nuclease assay (for example, TaqMan™) and real-time quantitative PCR (for example, ABI Prizm 7700 Sequence Detection System™ (Perkin Elmer, Applied Biosystems Division, Foster City, Calif.)), were used to find genes potentially amplified in certain cancers. The results were used to determine whether the DNA encoding PRO327, PRO344, PRO347, PRO357 or PRO715 is over-represented in any of the primary lung or colon cancers or cancer cell lines or breast cancer cell lines that were screened. The primary lung cancers were obtained from individuals with tumors of the type and stage as indicated in Table 9. An explanation of the abbreviations used for the designation of the primary tumors listed in Table 9 and the primary tumors and cell lines referred to throughout this example are given below.

The results of the TaqMan™ are reported in delta (Δ) Ct units. One unit corresponds to 1 PCR cycle or approximately a 2-fold amplification relative to normal, two units corresponds to 4-fold, 3 units to 8-fold amplification and so on Quantitation was obtained using primers and a TaqMan™ fluorescent probe derived from the PRO327-, PRO344-, PRO347-, PRO357- or PRO715-encoding gene. Regions of PRO327, PRO344, PRO347, PRO357 or PRO715 which are most likely to contain unique nucleic acid sequences and which are least likely to have spliced out introns are preferred for the primer and probe derivation, e.g., 3'-untranslated regions. The sequences for the primers and probes (forward, reverse and probe) used for the PRO327, PRO344, PRO347, PRO357 or PRO715 gene amplification analysis were as follows:

dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

The 5' nuclease procedure is run on a real-time quantitative PCR device such as the ABI Prism 7700TM Sequence Detection. The system consists of a thermocycler, laser, charge-coupled device (CCD) camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

5' Nuclease assay data are initially expressed as Ct, or the threshold cycle. This is defined as the cycle at which the

```
PRO327 (DNA38113-1230)
forward  5'-CTCAAGAAGCACGCGTACTGC-3'        (SEQ ID NO:96)

probe    5'-CCAACCTCAGCTTCCGCCTCTACGA-3'    (SEQ ID NO:97)

reverse  5'-CATCCAGGCTCGCCACTG-3'           (SEQ ID NO:98)

PRO344 (DNA40592-1242)
forward  5'-TGGCAAGGAATGGGAACAGT-3'         (SEQ ID NO:99)

probe    5'-ATGCTGCCAGACCTGATCGCAGACA-3'    (SEQ ID NO:100)

reverse  5'-GGGCAGAAATCCAGCCACT-3'          (SEQ ID NO:101)

PRO347 (DNA44176-1244)
forward  5'-CCCTTCGCCTGCTTTTGA-3'           (SEQ ID NO:102)

probe    5'-GCCATCTAATTGAAGCCCATCTTCCCA-3' (SEQ ID NO:103)

reverse  5'-CTGGCGGTGTCCTCTCCTT-3'          (SEQ ID NO:104)

PRO357 (DNA44804-1248)
forward  5'-CCTCGGTCTCCTCATCTGTGA-3'        (SEQ ID NO:105)

probe    5'-TGGCCCAGCTGACGAGCCCT-3'         (SEQ ID NO:106)

reverse  5'-CTCATAGGCACTCGGTTCTGG-3'        (SEQ ID NO:107)

PRO715 (DNA52722-1229)
forward  5'-TGGCTCCCAGCTTGGAAGA-3'          (SEQ ID NO:108)

probe    5'-CAGCTCTTGGCTGTCTCCAGTATGTACCCA-3' (SEQ ID NO:109)

reverse  5'-GATGCCTCTGTTCCTGCACAT-3'        (SEQ ID NO:110)
```

The 5' nuclease assay reaction is a fluorescent PCR-based technique which makes use of the 5' exonuclease activity of Taq DNA polymerase enzyme to monitor amplification in real time. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent reporter signal accumulates above the background level of fluorescence. The ΔCt values are used as quantitative measurement of the relative number of starting copies of a particular target sequence in a nucleic acid sample when comparing cancer DNA results to normal human DNA results.

Table 9 describes the stage, T stage and N stage of various primary tumors which were used to screen the PRO327, PRO344, PRO347, PRO357 and PRO715 compounds of the invention.

TABLE 9

Primary Lung and Colon Tumor Profiles

| Primary Tumor Stage | Stage | Other Stage | Dukes Stage | T Stage | N Stage |
|---|---|---|---|---|---|
| Human lung tumor AdenoCa (SRCC724) [LT1] | IIA | | | T1 | N1 |
| Human lung rumor SqCCa (SRCC725) [LT1a] | IIB | | | T3 | N0 |
| Human lung tumor AdenoCa (SRCC726) [LT2] | IB | | | T2 | N0 |
| Human lung tumor AdenoCa (SRCC727) [LT3] | IIIA | | | T1 | N2 |
| Human lung tumor AdenoCa (SRCC728) [LT4] | IB | | | T2 | N0 |
| Human lung tumor SqCCa (SRCC729) [LT6] | IB | | | T2 | N0 |
| Human lung tumor Aden/SqCCa (SRCC730) [LT7] | IA | | | T1 | N0 |
| Human lung tumor AdenoCa (SRCC731) [LT9] | IB | | | T2 | N0 |
| Human lung tumor SqCCa (SRCC732) [LT10] | IIB | | | T2 | N1 |
| Human lung tumor SqCCa (SRCC733) [LT11] | IIA | | | T1 | N1 |
| Human lung tumor AdenoCa (SRCC734) [LT12] | IV | | | T2 | N0 |
| Human lung tumor AdenoSqCCa (SRCC735)[LT13] | IB | | | T2 | N0 |
| Human lung tumor SqCCa (SRCC736) [LT15] | IB | | | T2 | N0 |
| Human lung tumor SqCCa (SRCC737) [LT16] | IB | | | T2 | N0 |
| Human lung tumor SqCCa (SRCC738) [LT17] | IIB | | | T2 | N1 |
| Human lung tumor SqCCa (SRCC739) [LT18] | IB | | | T2 | N0 |
| Human lung tumor SqCCa (SRCC740) [LT19] | IB | | | T2 | N0 |
| Human lung tumor LCCa (SRCC741) [LT21] | IIB | | | T3 | N1 |
| Human lung AdenoCa (SRCC811) [LT22] | IA | | | T1 | N0 |
| Human colon AdenoCa (SRCC742) [CT2] | | M1 | D | pT4 | N0 |
| Human colon AdenoCa (SRCC743) [CT3] | | | B | pT3 | N0 |
| Human colon AdenoCa (SRCC744) [CT8] | | | B | T3 | N0 |
| Human colon AdenoCa (SRCC745) [CT10] | | | A | pT2 | N0 |
| Human colon AdenoCa (SRCC746) [CT12] | | M0, R1 | B | T3 | N0 |
| Human colon AdenoCa (SRCC747) [CT14] | | pM0, R0 | B | pT3 | pN0 |
| Human colon AdenoCa (SRCC748) [CT15] | | M1, R2 | D | T4 | N2 |
| Human colon AdenoCa (SRCC749) [CT16] | | pM0 | B | pT3 | pN0 |
| Human colon AdenoCa (SRCC750) [CT17] | | | C1 | pT3 | pN1 |
| Human colon AdenoCa (SRCC751) [CT1] | | M0, R1 | B | pT3 | N0 |
| Human colon AdenoCa (SRCC752) [CT4] | | | B | pT3 | M0 |
| Human colon AdenoCa (SRCC753) [CT5] | | G2 | C1 | pT3 | pN0 |
| Human colon AdenoCa (SRCC754) [CT6] | | pM0, R0 | B | pT3 | pN0 |
| Human colon AdenoCa (SRCC755) [CT7] | | G1 | A | pT2 | pN0 |
| Human colon AdenoCa (SRCC756) [CT9] | | G3 | D | pT4 | pN2 |
| Human colon AdenoCa (SRCC757) [CT11] | | | B | T3 | N0 |
| Human colon AdenoCa (SRCC758) [CT18] | | M0, R0 | B | pT3 | pN0 |

DNA Preparation:

DNA was prepared from cultured cell lines, primary tumors, normal human blood. The isolation was performed using purification kit, buffer set and protease and all from Quiagen, according to the manufacturer's instructions and the description below.

Cell Culture Lysis:

Cells were washed and trypsinized at a concentration of $7.5 \times 10^8$ per tip and pelleted by centrifuging at 1000 rpm for 5 minutes at 4° C., followed by washing again with ½ volume of PBS recentrifugation. The pellets were washed a third time, the suspended cells collected and washed 2× with PBS. The cells were then suspended into 10 ml PBS Buffer C1 was equilibrated at 4° C. Qiagen protease #19155 was diluted into 6.25 ml cold ddH$_2$O to a final concentration of 20 mg/ml and equilibrated at 4° C. 10 ml of G2 Buffer was prepared by diluting Qiagen RNAse A stock (100 mg/ml) to a final concentration of 200 μg/ml.

Buffer C1 (10 ml, 4° C.) and ddH2O (40 ml, 4° C.) were then added to the 10 ml of cell suspension, mixed by inverting and incubated on ice for 10 minutes. The cell nuclei were pelleted by centrifuging in a Beckman swinging bucket rotor at 2500 rpm at 4° C. for 15 minutes. The supernatant was discarded and the nuclei were suspended with a vortex into 2 ml Buffer C1 (at 4° C.) and 6 ml ddH$_2$O, followed by a second 4° C. centrifugation at 2500 rpm for 15 minutes. The nuclei were then resuspended into the residual buffer using 200 μl per tip. G2 buffer (10 ml) was added to the suspended nuclei while gentle vortexing was applied. Upon completion of buffer addition, vigorous vortexing was applied for 30 seconds. Quiagen protease (200 μl, prepared as indicated above) was added and incubated at 50° C. for 60 minutes. The incubation and centrifugation was repeated until the lysates were clear (e.g., incubating additional 30-60 minutes, pelleting at 3000×g for 10 min., 4° C.).

Solid Human Tumor Sample Preparation and Lysis:

Tumor samples were weighed and placed into 50 ml conical tubes and held on ice. Processing was limited to no more than 250 mg tissue per preparation (1 tip/preparation). The protease solution was freshly prepared by diluting into 6.25 ml cold ddH$_2$O to a final concentration of 20 mg/ml and stored at 4° C. G2 buffer (20 ml) was prepared by diluting DNAse A to a final concentration of 200 mg/ml (from 100 mg/ml stock). The tumor tissue was homogenated in 19 ml G2 buffer for 60 seconds using the large tip of the polytron in a laminar-flow TC hood in order to avoid inhalation of aerosols, and held at room temperature. Between samples, the polytron was cleaned by spinning at 2×30 seconds each in 2 L ddH$_2$O, followed by G2 buffer (50 ml). If tissue was still present on the generator tip, the apparatus was disassembled and cleaned.

Quiagen protease (prepared as indicated above, 1.0 ml) was added, followed by vortexing and incubation at 50° C. for 3 hours. The incubation and centrifugation was repeated until the lysates were clear (e.g., incubating additional 30-60 minutes, pelleting at 3000×g for 10 min., 4° C.).

Human Blood Preparation and Lysis:

Blood was drawn from healthy volunteers using standard infectious agent protocols and citrated into 10 ml samples per tip. Quiagen protease was freshly prepared by dilution into 6.25 ml cold ddH$_2$O to a final concentration of 20 mg/ml and stored at 4° C. G2 buffer was prepared by diluting RNAse A to a final concentration of 200 µg/ml from 100 mg/ml stock. The blood (10 ml) was placed into a 50 ml conical tube and 10 ml C1 buffer and 30 ml ddH$_2$O (both previously equilibrated to 4° C.) were added, and the components mixed by inverting and held on ice for 10 minutes. The nuclei were pelleted with a Beckman swinging bucket rotor at 2500 rpm, 4° C. for 15 minutes and the supernatant discarded. With a vortex, the nuclei were suspended into 2 ml C1 buffer (4° C.) and 6 ml ddH$_2$O (4° C.). Vortexing was repeated until the pellet was white. The nuclei were then suspended into the residual buffer using a 200 µl tip. G2 buffer (10 ml) were added to the suspended nuclei while gently vortexing, followed by vigorous vortexing for 30 seconds. Quiagen protease was added (200 µl) and incubated at 50° C. for 60 minutes. The incubation and centrifugation was repeated until the lysates were clear (e.g., incubating additional 30-60 minutes, pelleting at 3000×g for 10 min., 4° C.).

Purification of Cleared Lysates:

(1) Isolation of Genomic DNA:

Genomic DNA was equilibrated (1 sample per maxi tip preparation) with 10 ml QBT buffer. QF elution buffer was equilibrated at 50° C. The samples were vortexed for 30 seconds, then loaded onto equilibrated tips and drained by gravity. The tips were washed with 2×15 ml QC buffer. The DNA was eluted into 30 ml silanized, autoclaved 30 ml Corex tubes with 15 ml QF buffer (50° C.). Isopropanol (10.5 ml) was added to each sample, the tubes covered with parafin and mixed by repeated inversion until the DNA precipitated. Samples were pelleted by centrifugation in the SS-34 rotor at 15,000 rpm for 10 minutes at 4° C. The pellet location was marked, the supernatant discarded, and 10 ml 70% ethanol (4° C.) was added. Samples were pelleted again by centrifugation on the SS-34 rotor at 10,000 rpm for 10 minutes at 4° C. The pellet location was marked and the supernatant discarded. The tubes were then placed on their side in a drying rack and dried 10 minutes at 37° C., taking care not to overdry the samples.

After drying, the pellets were dissolved into 1.0 ml TE (pH 8.5) and placed at 50° C. for 1-2 hours. Samples were held overnight at 4° C. as dissolution continued. The DNA solution was then transferred to 1.5 ml tubes with a 26 gauge needle on a tuberculin syringe. The transfer was repeated 5× in order to shear the DNA. Samples were then placed at 50° C. for 1-2 hours.

(2) Quantitation of Genomic DNA and Preparation for Gene Amplification Assay:

The DNA levels in each tube were quantified by standard A$_{260}$, A$_{280}$ spectrophotometry on a 1:20 dilution (5 µl DNA+ 95 µl ddH$_2$O) using the 0.1 ml quartz cuvetts in the Beckman DU640 spectrophotometer. A$_{260}$/A$_{280}$ ratios were in the range of 1.8-1.9. Each DNA samples was then diluted further to approximately 200 ng/ml in TE (pH 8.5). If the original material was highly concentrated (about 700 ng/µl), the material was placed at 50° C. for several hours until resuspended.

Fluorometric DNA quantitation was then performed on the diluted material (20-600 ng/ml) using the manufacturer's guidelines as modified below. This was accomplished by allowing a Hoeffer DyNA Quant 200 fluorometer to warm-up for about 15 minutes. The Hoechst dye working solution (#H33258, 10 µl, prepared within 12 hours of use) was diluted into 100 ml 1×TNE buffer. A 2 ml cuvette was filled with the fluorometer solution, placed into the machine, and the machine was zeroed. pGEM 3Zf(+) (2 µl, lot #360851026) was added to 2 ml of fluorometer solution and calibrated at 200 units. An additional 2 µl of pGEM 3Zf(+) DNA was then tested and the reading confirmed at 400+/−10 units. Each sample was then read at least in triplicate. When 3 samples were found to be within 10% of each other, their average was taken and this value was used as the quantification value.

The fluorometricly determined concentration was then used to dilute each sample to 10 ng/µl in ddH$_2$O. This was done simultaneously on all template samples for a single TaqMan plate assay, and with enough material to run 500-1000 assays. The samples were tested in triplicate with Taqman™ primers and probe both B-actin and GAPDH on a single plate with normal human DNA and no-template controls. The diluted samples were used provided that the CT value of normal human DNA subtracted from test DNA was +/−1 Ct. The diluted, lot-qualified genomic DNA was stored in 1.0 ml aliquots at −80° C. Aliquots which were subsequently to be used in the gene amplification assay were stored at 4° C. Each 1 ml aliquot is enough for 8-9 plates or 64 tests.

Gene Amplification Assay:

The PRO327, PRO344, PRO347, PRO357 and PRO715 compounds of the invention were screened in the following primary tumors and the resulting ΔCt values greater than or equal to 1.0 are reported in Table 10.

TABLE 10

ΔCt values in primary tumor and cell lines models

| Primary Tumors or Cell Lines | PRO327 | PRO344 | PRO347 | PRO357 | PRO715 |
| --- | --- | --- | --- | --- | --- |
| LT1 | — | — | 1.035 | — | 1.625 |
| LT1a | 1.045 | — | 1.865 1.0 1.93 | 1.18 2.47 | 1.045 |
| LT3 | 1.135 | — | 1.325 | 2.93 1.2 | — |
| LT6 | 1.395 | — | 1.945 1.42 | 2.6 3.18 | — |
| LT9 | — | — | 2.645 | 3.47 2.91 | 1.005 |
| LT10 | 1.305 | — | 1.845 1.13 | 3.42 3.51 | 1.125 |
| LT11 | 1.53 | 1.52 | 1.395 1.35 | 1.185 2.875 | 1.75 1.12 |
| LT12 | 2.99 2.15 | 1.2 | 1.425 1.73 | 1.225 2.225 | 1.63 1.11 1.14 |
| LT13 | 2.48 1.69 | 1.81 1.175 1.05 | 2.035 2.28 1.15 | 1.585 1.665 1.31 | 2.29 1.83 |
| LT15 | 3.99 2.89 | 1.62 1.33 | 1.615 2.73 1.27 1.44 | 2.205 2.445 1.89 | 2.33 1.89 |
| LT16 | 1.16 2.65 | 1.13 1.09 | — | 2.605 | 1.2 1.1 |
| LT17 | 1.76 1.09 | 1.46 | 1.24 | 1.275 2.855 1.01 | 1.95 1.33 |
| LT18 | — | — | — | 2.455 | 1.14 |
| LT19 | 3.58 | 2.47 | 1.835 1.35 | 2.295 2.645 | 2.38 |
| LT21 | — | 1.09 | 1.14 | 2.675 | — |
| CT2 | 3.645 | 1.84 | 2.1 1.605 | 2.01 | 1.675 1.605 |
| CT3 | 1.125 | — | 1.01 | — | 1.135 1.105 |
| CT8 | 1.645 | — | 1.3 | 1.1 | 1.285 1.345 |

TABLE 10-continued

ΔCt values in primary tumor and cell lines models

| Primary Tumors or Cell Lines | PRO327 | PRO344 | PRO347 | PRO357 | PRO715 |
|---|---|---|---|---|---|
| CT10 | 2.535 | — | — | 1.42 | 2.155 |
|  |  |  |  |  | 1.785 |
| CT12 | 1.885 | — | — | — | — |
| CT14 | 2.515 | 1.16 | 1.39 | 1.5 | 1.265 |
|  |  |  | 1.45 |  | 1.575 |
| CT15 | 1.305 | 1.17 | 1.3 | 1.25 | 1.585 |
|  |  |  |  |  | 1.475 |
| CT16 | 1.475 | — | 1.33 | 1.05 | 1.095 |
|  |  |  | 1.055 |  | 1.475 |
| CT17 | 1.715 | — | — | — | 1.245 |
|  |  |  |  |  | 1.375 |
| CT1 | 1.375 | 1.245 | 1.045 | 1.045 | 1.285 |
|  |  |  |  |  | 1.6 |
|  |  |  |  |  | 1.085 |
| CT4 | 2.225 | 1.465 | — | 1.275 | 1.375 |
|  |  |  |  |  | 2.23 |
|  |  |  |  |  | 1.165 |
| CT5 | 2.505 | 1.515 | 1.625 | 1.695 | 1.975 |
|  |  |  | 1.985 |  | 2.07 |
|  |  |  |  |  | 1.715 |
| CT6 | 2.285 | — | — | 1.085 | 1.305 |
|  |  |  |  |  | 1.73 |
|  |  |  |  |  | 1.245 |
| CT7 | — | — | — | 1.735 | 1.005 |
|  |  |  |  |  | 1.65 |
|  |  |  |  |  | 1.025 |
| CT9 | 1.585 | — | — | — | 1.0 |
| CT11 | 3.335 | 1.355 | 1.315 | 1.835 | 2.185 |
|  |  |  | 1.525 |  | 2.54 |
| CT18 | 1.075 | — | — | — | 1.69 |
| SRCC771 (H157) | 1.65 | — | — | — | — |
| SRCC772 (H441) | 2.23 | — | — | — | — |
| SRCC773 (H460) | 1.12 | — | — | — | — |
| SRCC774 (SKMES-1) | 1.18 | — | — | — | — |
| SRCC777 (SW620) | 2.24 | — | — | — | — |
| SRCC778 (Colo320) | 1.01 | — | — | — | — |
| SRCC830 (HCC2998) | 1.23 | — | — | — | — |
| SRCC831 (KM12) | 1.61 | — | — | — | — |
| SRCC832 (H522) | 1.02 | — | — | — | — |
| SRCC833 (H810) | 1.11 | — | — | — | — |

PRO327:

PRO327 (DNA38113-1230) was reexamined along with selected tumors from the above initial screen with framework mapping. Table 11 describes the framework markers that were employed in association with PRO327 (DNA38113-1230). The framework markers are located approximately every 20 megabases along Chromosome 19, and are used to control aneuploidy. The ΔCt values for the described framework markers along Chromosome 19 relative to PRO327 (DNA38113-1230) are indicated for selected tumors in Table 13.

PRO327 (DNA38113-1230) was also reexamined along with selected tumors from the above initial screen with epicenter mapping. Table 12 describes the epicenter markers that were employed in association with PRO327 (DNA38113-1230). These markers are located in close proximity to DNA38113-1230 and are used to assess the amplification status of the region of Chromosome 19 in which DNA38113-1230 is located. The distance between markers is measured in centirays (cR), which is a radiation breakage unit approximately equal to a 1% chance of a breakage between two markers. One cR is very roughly equivalent to 20 kilobases.

Table 14 indicates the ΔCt values for results of epicenter mapping relative to DNA38113-1230, indicating the relative amplification in the region more immediate to the actual location of DNA38113-1230 along Chromosome 19.

TABLE 11

Framework Markers Along Chromosome 19

| Map Position on Chromosome 19 | Stanford Human Genome Center Marker Name |
|---|---|
| S12 | AFMa107xc9 |
| S50 | SHGC-31335 |
| S105 | SHGC-34102 |
| S155 | SHGC-16175 |

TABLE 12

Epicenter Markers Along Chromosome 19 used for DNA38113-1230

| Map Position on Chromosome 19 | Stanford Human Genome Center Marker Name | Distance to next Marker (cR[1]) |
|---|---|---|
| S42 | WI-7289 | 5 |
| S43 | SHGC-32638 | 28 |
| S44 | SHGC-11753[2] | 7 |
| DNA38113-1230 | — | — |
| S45 | SHGC-14810 | 37 |
| S46 | AFM214YF6 | 15 |
| S48 | SHGC-36583 | — |

TABLE 13

Amplification of framework markers relative to DNA38113-1230 (ΔCt)

| | Framework Markers | | | |
|---|---|---|---|---|
| Tumor | S12 | DNA38113-1230 | S50 | S105 | S155 |
|---|---|---|---|---|---|
| LT1 | 0.16 | −0.15 | 0.06 | −0.42 | 0.11 |
| LT1a | 0.05 | 0.57 | −0.27 | 0.17 | 0.40 |
| LT2 | 0.48 | 0.57 | 0.41 | 0.52 | 0.13 |
| LT3 | 0.27 | 0.77 | 0.83 | 0.11 | 0.50 |
| LT4 | 0.48 | 0.08 | 0.67 | 0.20 | 0.56 |
| LT6 | 0.72 | 0.33 | 0.74 | 0.32 | 0.35 |
| LT7 | 0.82 | 0.29 | 0.85 | 0.95 | 0.95 |
| LT9 | 0.72 | −0.19 | 0.61 | 0.19 | 0.64 |
| LT10 | 0.82 | 1.45 | 0.98 | 0.62 | 0.53 |
| CT2 | 0.25 | 2.94 | 0.29 | 0.37 | −0.02 |
| CT3 | −0.17 | 1.23 | −0.10 | 0.34 | −0.28 |
| CT8 | 0.13 | 1.45 | 0.57 | 0.18 | −0.16 |
| CT10 | 0.15 | 1.72 | 0.51 | −0.01 | −0.81 |
| CT12 | 0.13 | 1.60 | 0.57 | 0.41 | 0.20 |
| CT14 | 0.40 | 2.03 | 0.39 | 0.45 | 0.36 |
| CT15 | −0.23 | 0.68 | −0.30 | −0.06 | 0.56 |
| CT16 | 0.38 | 1.07 | 0.31 | 0.24 | 0.04 |
| CT17 | 0.25 | 0.50 | 0.71 | 0.32 | 0.09 |

TABLE 14

Amplification of epicenter markers relative to DNA38113-1230 (ΔCt)

| Tumor | S41 | S42 | S43 | S44 | DNA38113-1230 | S45 | S46 | S48 |
|---|---|---|---|---|---|---|---|---|
| LT1 | −1.03 | −0.25 | −0.18 | −0.11 | −0.31 | 0.13 | 0.26 | 0.29 |
| LT1a | 0.14 | −0.30 | −0.11 | −0.01 | 0.21 | −0.44 | 0.45 | −0.30 |
| LT2 | 0.03 | 0.06 | 0.06 | 0.12 | 0.14 | 0.16 | 0.11 | 0.65 |
| LT3 | −1.08 | −0.08 | −0.01 | 0.11 | 0.43 | −0.37 | 0.33 | 0.56 |
| LT4 | 0.66 | −0.14 | −0.48 | −0.79 | −0.28 | −0.31 | 0.04 | 0.09 |
| LT6 | −0.88 | −0.08 | −0.12 | −1.00 | 0.20 | −0.43 | 0.48 | 0.63 |
| LT7 | 0.65 | −0.19 | −0.19 | −0.04 | 0.04 | −0.42 | 0.43 | 0.57 |
| LT9 | 0.66 | −0.26 | −0.01 | −0.14 | −0.06 | −0.31 | −16.48 | 0.16 |
| LT10 | 1.16 | −0.30 | −0.11 | −0.31 | 0.13 | −0.33 | 0.34 | 0.50 |
| LT11 | 0.46 | 0.01 | −0.04 | −0.86 | 0.67 | 0.23 | 0.24 | −0.57 |
| LT12 | 1.39 | −0.01 | −0.22 | −1.33 | 1.57 | −0.25 | 0.26 | 0.07 |
| LT13 | 1.62 | −0.03 | 0.00 | −0.08 | 1.22 | −0.08 | 0.48 | 0.14 |
| LT15 | 1.09 | 0.20 | 0.47 | 0.62 | 2.47 | 0.38 | 0.01 | 0.44 |
| LT16 | 1.51 | 0.04 | −0.04 | 0.29 | 2.23 | 0.51 | 0.50 | 0.90 |
| LT17 | 2.12 | 0.23 | 0.11 | 0.20 | 1.02 | 0.45 | 0.46 | −0.41 |
| LT18 | 1.80 | −0.11 | 0.07 | −0.70 | 0.9 | 0.10 | 0.00 | −0.02 |
| LT22 | −0.12 | 0.06 | 0.41 | −0.11 | −0.06 | 0.34 | 0.03 | 0.52 |
| CT1 | −0.09 | 0.33 | 0.11 | 0.22 | 1.38 | 0.09 | −0.25 | −0.10 |
| CT2 | 1.76 | 0.04 | 0.30 | 0.65 | 2.94 | 0.18 | −0.04 | 0.01 |
| CT3 | 1.10 | −0.31 | −0.24 | 0.16 | 1.23 | −0.64 | 0.78 | −0.17 |
| CT4 | 1.63 | 0.22 | 0.32 | −0.72 | 2.23 | −0.04 | 0.44 | 0.72 |
| CT5 | 2.22 | 0.02 | 0.21 | 0.10 | 2.51 | 0.02 | 0.18 | 0.24 |
| CT6 | 0.48 | 0.20 | 0.22 | 0.63 | 2.29 | 0.03 | 0.14 | 0.97 |
| CT7 | 0.93 | 0.20 | 0.32 | 0.14 | 0.95 | −0.01 | 0.20 | 0.54 |
| CT8 | 1.15 | −0.50 | −0.14 | 0.15 | 1.45 | −0.31 | 0.54 | 0.07 |
| CT9 | 0.82 | 0.38 | 0.64 | −0.71 | 1.59 | 1.04 | 0.26 | 0.93 |
| CT10 | 1.57 | −0.41 | −0.03 | −0.14 | 1.72 | −0.27 | 0.04 | 0.10 |
| C11 | 1.49 | −0.05 | 0.07 | 0.01 | 3.34 | 0.54 | 0.28 | 0.88 |
| CT12 | 0.89 | −0.09 | −0.01 | −0.62 | 1.6 | −0.07 | 1.16 | 0.92 |
| CT14 | 2.16 | 0.32 | 0.37 | 0.47 | 2.03 | −0.07 | 1.21 | 0.44 |
| CT15 | 0.64 | −0.52 | −0.21 | −0.12 | 0.68 | −0.61 | 1.01 | 0.32 |
| CT16 | 1.75 | −0.31 | 0.28 | 0.47 | 1.07 | 0.04 | 1.01 | −0.29 |
| CT17 | 0.77 | −0.18 | 0.13 | −0.04 | 0.5 | −0.27 | 0.93 | 0.31 |
| CT18 | 0.91 | 0.05 | 0.14 | 0.60 | 1.08 | 0.22 | −0.59 | 0.61 |

PRO715 (DNA52722-1229):

PRO715 was also reexamined with both framework and epicenter mapping. Table 15 indicates the chromosomal localizations of the framework markers that were used for the procedure. The framework markers are located approximately every 20 megabases and were used to control aneuploidy. Table 16 indicates the epicenter mapping markers that were used in the procedure. The epicenter markers were located in close proximity to DNA52722-1229 and are used to determine the relative DNA amplification in the immediate vicinity of DNA52722-1229. The distance between individual markers is measured in centirays, which is a radiation breakage unit approximately equal to a 1% chance of a breakage between two markers. One cR is very roughly equivalent to about 20 kilobases. In Table 16, "BAC" means bacterial artificial chromosome. The ends of a BAC clone which contained the gene of interest were sequenced. TaqMan primers and probes were made from this sequence, which are indicated in the table. BAC clones are typically 100 to 150 Kb, so these primers and probes can be used as nearby markers to probe DNA from tumors. In Table 16, the marker SHGC-31370 is the marker found to be the closest to the location on chromosome 17 where DNA52722-1229 maps.

TABLE 15

Framework Markers Used Along Chromosome 17 for DNA52722-1229

| Map Position on Chromosome 17 | Stanford Human Genome Center Marker Name |
|---|---|
| Q4 | SHGC-31242 |
| Q52 | SHGC-35988 |
| Q110 | AFM200zf4 |
| Q169 | SHGC-32689 |
| Q206 | SHGC-11717 |
| Q232 | SHGC-32338 |

TABLE 16

Epicenter Markers Used on Chromosome 17 in Vicinity of DNA52722-1229

| Map Position on Chromosome 17 | Stanford Human Genome Marker Name | Distance to next Marker (cR) |
|---|---|---|
| Q33 | SHGC-35547 | 18 cR to Q34 |
| 120F17FOR1 | Marker from forward end of BAC sequence | |
| 120F17FOR2 | Marker from forward end of BAC sequence | |
| DNA52722-1229 | — | |
| 120F17REV1 | Marker from reverse end of BAC sequence | |
| 120F17REV2 | Marker from reverse end of BAC sequence | |
| Q34 | SHGC-31370 | |

Table 17 indicates the ΔCt values of the above described framework markers along chromosome 17 relative to DNA52722-1229 for selected tumors.

TABLE 17

Amplification of Framework Markers Relative to DNA52722-1229

| Tumor | Q4 | Q52 | DNA52722-1229 | Q110 | Q169 | Q206 | Q232 |
|---|---|---|---|---|---|---|---|
| LT1 | 0.02 | −0.50 | −0.04 | 0.05 | −0.32 | −0.21 | −0.34 |
| LT1a | −0.01 | −0.34 | 0.64 | 0.23 | −0.20 | −0.25 | −0.15 |
| LT2 | 0.25 | 0.15 | 0.19 | 0.05 | −0.16 | −0.14 | −0.09 |
| LT3 | −0.08 | −0.20 | 0.54 | 0.56 | −0.06 | 0.32 | 0.05 |
| LT4 | −0.32 | −0.45 | 0.31 | 0.19 | −0.06 | −0.12 | 0.04 |
| LT6 | −0.21 | −0.38 | 0.31 | 0.13 | −0.08 | −0.30 | 0.01 |
| LT7 | −0.66 | −1.02 | 0.02 | 0.62 | −0.20 | 0.06 | 0.16 |
| LT9 | −0.03 | −0.29 | 0.46 | 1.20 | −1.75 | −0.22 | −0.13 |
| LT10 | −0.16 | −0.09 | 0.58 | 0.11 | 0.01 | −0.33 | −0.45 |
| LT11 | −0.14 | 0.29 | 1.03 | 0.04 | 0.30 | 0.52 | 0.17 |
| LT12 | −0.25 | −0.68 | 0.72 | 0.65 | 0.86 | 0.97 | 0.58 |
| LT13 | 0.20 | 0.00 | 1.37 | −0.15 | −0.04 | 0.25 | −0.01 |
| LT15 | 0.11 | −0.39 | 1.75 | 0.00 | −0.02 | 0.43 | −0.19 |
| LT16 | −0.07 | −0.56 | 1.11 | 0.22 | 0.19 | 0.68 | −0.55 |

TABLE 17-continued

Amplification of Framework Markers Relative to DNA52722-1229

| Tumor | Q4 | Q52 | DNA52722-1229 | Q110 | Q169 | Q206 | Q232 |
|---|---|---|---|---|---|---|---|
| LT17 | 0.41 | −0.09 | 1.14 | 0.27 | 0.22 | 0.73 | 0.07 |
| LT18 | 0.14 | −0.22 | 1.04 | 0.27 | 0.35 | 0.48 | −0.03 |
| LT22 | −0.07 | −0.73 | 0.00 | 0.13 | −0.02 | 0.41 | 0.05 |
| CT2 | 0.12 | −0.47 | 1.29 | −0.19 | 0.32 | — | 0.18 |
| CT3 | 0.05 | 0.17 | 1.06 | −0.41 | 0.05 | — | −0.06 |
| CT8 | 0.44 | 0.14 | 1.08 | 0.02 | −0.04 | — | −0.11 |
| CT10 | 0.35 | 0.26 | 1.60 | −0.05 | 0.00 | — | −0.02 |
| CT12 | −0.15 | −0.46 | 0.52 | −0.13 | 0.02 | — | −0.20 |
| CT14 | 0.26 | −0.59 | 1.05 | −0.01 | 0.68 | — | 0.48 |
| CT15 | 0.55 | −0.51 | 1.36 | −0.69 | 0.11 | — | −0.16 |
| CT16 | 0.09 | −0.14 | 1.06 | 0.00 | 0.00 | — | −0.15 |
| CT17 | 0.40 | −0.16 | 1.00 | −0.47 | 0.04 | — | −0.29 |

Table 18 indicates the ΔCt values for the indicated epicenter markers, indicating the relative amplification along chromosome 17 in the immediate vicinity of DNA52722-1229.

TABLE 18

Amplification of Epicenter Markers Relative to DNA52722-1229

| Tumor | Q33 | 120F17FOR1 | 120F17FOR2 | DNA52722-1229 | 120F17REV1 | 120F17REV2 | Q34 |
|---|---|---|---|---|---|---|---|
| LT1 | −0.18 | 0.11 | 0.00 | 0.20 | −0.08 | 0.07 | −0.36 |
| LT1a | 0.32 | −0.06 | 0.00 | 0.68 | −0.09 | −0.20 | 0.32 |
| LT2 | 0.06 | 0.14 | 0.00 | 0.27 | −0.29 | 0.16 | −0.16 |
| LT3 | 0.08 | −2.06 | 0.00 | 0.16 | −0.84 | −0.38 | −0.16 |
| LT4 | — | — | — | — | — | — | — |
| LT6 | — | — | — | — | — | — | — |
| LT7 | −0.20 | −0.51 | 0.00 | 0.23 | −0.63 | −0.37 | −0.41 |
| LT9 | 0.08 | −0.17 | 0.00 | 0.59 | 0.02 | −0.66 | −0.01 |
| LT10 | 0.09 | 0.05 | 0.00 | 0.59 | −0.22 | −0.12 | 0.36 |
| LT11 | 0.75 | 0.09 | 0.00 | 1.07 | 0.43 | −0.01 | 0.63 |
| LT12 | 0.00 | −0.45 | 0.00 | 0.63 | −0.49 | −0.82 | 0.18 |
| LT13 | 0.72 | −0.02 | 0.00 | 1.29 | 0.04 | 0.02 | 0.66 |
| LT15 | 0.75 | 0.11 | 0.00 | 1.33 | 0.15 | −0.19 | 0.90 |
| LT16 | 0.34 | −0.41 | 0.00 | 1.11 | −0.39 | −0.89 | 0.15 |
| LT17 | 1.06 | 0.29 | 0.00 | 1.13 | −0.26 | −0.12 | 0.90 |
| LT18 | 0.66 | 0.11 | 0.00 | 1.21 | −0.28 | 0.11 | 0.47 |
| LT19 | −0.09 | −0.37 | 0.00 | 0.12 | −0.53 | −0.48 | −0.53 |
| CT1 | 0.50 | 0.14 | 0.00 | 1.22 | 0.27 | 0.43 | 0.72 |
| CT2 | 0.69 | −0.47 | 0.00 | 0.95 | −0.72 | −0.17 | 0.77 |
| CT3 | 0.87 | 0.08 | 0 | 1.19 | −0.06 | 0.74 | 0.97 |
| CT4 | 0.45 | −0.11 | 0 | 1.26 | 0.43 | 0.38 | 0.79 |
| CT5 | 0.36 | −0.39 | 0 | 1.79 | −0.48 | 0.09 | 0.95 |
| CT6 | 0.41 | 0.08 | 0 | 1.71 | −0.21 | 0.57 | 0.47 |
| CT7 | 0.40 | 0.18 | 0 | 1.19 | 0.31 | 0.40 | 0.54 |
| CT8 | 0.48 | 0.17 | 0 | 0.93 | 0.23 | 0.47 | 0.72 |
| CT10 | 0.72 | 0.15 | 0 | 1.86 | 0.81 | 0.67 | 0.97 |
| CT11 | 0.80 | −0.09 | 0 | 2.29 | 0.20 | 0.25 | 0.85 |
| CT12 | 0.01 | −0.55 | 0 | 0.49 | −0.43 | −0.09 | 0.11 |
| CT14 | 0.22 | −0.36 | 0 | 1.05 | 0.63 | 0.41 | 0.40 |
| CT15 | 1.06 | −0.04 | 0 | 1.27 | 0.74 | 0.98 | 1.13 |
| CT16 | 0.84 | 0.06 | 0 | 1.03 | 0.26 | 0.40 | 0.91 |

TABLE 18-continued

Amplification of Epicenter Markers Relative to DNA52722-1229

| Tumor | Q33 | 120F17FOR1 | 120F17FOR2 | Epicenter marker<br>DNA52722-1229 | 120F17REV1 | 120F17REV2 | Q34 |
|---|---|---|---|---|---|---|---|
| CT17 | 0.80 | 0.04 | 0 | 0.95 | 0.78 | 1.29 | 0.90 |
| CT18 | 0.34 | 0.13 | 0 | 1.06 | 0.06 | 0.34 | 0.50 |

PRO357 (DNA44804-1248):

PRO357 was reexamined with selected tumors from the above initial screen with framework mapping. Table 19 indicate the chromosomal mapping of the framework markers that were used in the present example. The framework markers are located approximately every 20 megabases and were used to control aneuploidy.

PRO357 was also examined with epicenter mapping. The markers indicated in Table 20 are located in close proximity (in the genome) to DNA44804-1248 and are used to assess the relative amplification in the immediate vicinity of chromosome 16 wherein DNA44804-1248 is located. The distance between individual markers is measured in centirays (cR), which is a radiation breakage unit approximately equal to a 1% chance of a breakage between the two markers. One cR is very roughly equivalent to 20 kilobases. The marker SHGC-6154 is the marker found to be the closest to the location on chromosome 16 where DNA44804-1248 maps.

TABLE 19

Framework markers for DNA44804-1248

| Map position on<br>chromosome 16 | Stanford Human Genome<br>Center Marker Name |
|---|---|
| P7 | SHGC-2835 |
| P55 | SHGC-9643 |
| P99 | GATA7B02 |
| P154 | SHGC-33727 |
| P208 | SHGC-13577 |

TABLE 20

Epicenter markers for DNA44804-1248 along chromosome 16

| Map position on<br>chromosome 16 | Stanford Human Genome<br>Center Marker Name | Distance to next<br>Marker (cR) |
|---|---|---|
| P1 | AFMA139WG1 | 6 |
| P3 | SHGC-32420 | 170<br>(gap) |
| P4 | SHGC-14817 | 40 |
| P5 | SHGC-12265 | 4 |
| P6 | SHGC-6154 | 33 |
| DNA44804-1248 | — | — |
| P7 | SHGC-2835 | 10 |
| P8 | SHGC-2850 | 9 |
| P9 | AFM297yg5 | 67 |
| P15 | CHLC.GATA70B04 | — |

The ΔCt values of the above described framework markers along chromosome 16 relative to DNA44804-1248 is described in Table 21.

TABLE 21

Amplification of Framework Markers relative to DNA44804-1248 (ΔCt)

| Tumor | DNA44804-1248 | P7 | Framework marker<br>P55 | P99 | P154 | 208 |
|---|---|---|---|---|---|---|
| LT1 | 0.25 | 0.22 | −0.17 | 0.42 | 0.04 | 0.43 |
| LT1a | 0.90 | 0.09 | −0.10 | −0.38 | 0.29 | 0.93 |
| LT2 | −0.16 | 0.03 | 0.19 | −0.18 | 0.18 | 0.54 |
| LT3 | 1.15 | 0.68 | 0.57 | −0.34 | −0.03 | 0.86 |
| LT4 | 0.19 | 0.58 | 0.36 | −0.31 | 0.08 | 1.14 |
| LT6 | 0.28 | 0.27 | −0.11 | −0.74 | −0.13 | 0.22 |
| LT7 | 0.58 | 0.63 | 0.14 | 0.82 | 0.09 | −0.21 |
| LT9 | 0.68 | 0.63 | 0.14 | 0.82 | 0.09 | −0.21 |
| LT10 | 1.21 | 0.52 | 0.40 | −0.39 | −0.15 | 0.77 |
| LT11 | 1.71 | −0.79 | 1.31 | 0.73 | −0.08 | 0.90 |
| LT12 | 1.96 | −0.95 | 0.94 | 0.00 | −0.63 | 0.18 |
| LT13 | 2.32 | −0.97 | 0.94 | 0.88 | −0.04 | 0.70 |
| LT15 | 3.01 | −0.54 | 0.60 | 0.12 | 0.14 | 1.15 |
| LT16 | 0.67 | −0.27 | 0.57 | −0.39 | 0.08 | 1.04 |
| LT17 | 1.64 | 0.25 | 1.10 | 0.28 | 0.10 | 0.23 |
| LT18 | 0.34 | 0.09 | 0.51 | 0.33 | −0.20 | −0.09 |
| LT19 | 3.03 | −0.82 | 0.63 | 0.06 | 0.09 | 0.55 |
| LT21 | 1.33 | −1.19 | 1.01 | 0.11 | 0.34 | 0.07 |

Table 22 indicates the ΔCt values for the results of epicenter mapping relative to DNA44804-1248, indicating the relative amplification in the region more immediate to the actual location of DNA44804-1248 along chromosome 16.

TABLE 22

Amplification of epicenter markers relative to DNA44804-1248

| Tumor | P1 | P3 | P4 | P5 | P6 | DNA44804-1248 | P7 | P8 | P9 | P15 |
|---|---|---|---|---|---|---|---|---|---|---|
| LT1   |  0.31 |  -0.30 |  0.65 |  0.05 | -0.33 |  0.16 | -0.41 |  0.20 |  0.1  |  0.17 |
| LT1a  | -0.23 | -17.67 |  0.97 | -0.65 | -1.83 |  0.56 | -0.65 | -0.28 | -0.27 | -0.07 |
| LT2   |  0.18 |  -0.06 |  0.33 | -0.11 | -0.38 | -0.32 | -1.08 | -0.31 | -0.53 | -0.05 |
| LT3   |  0.00 |   0.25 |  1.07 | -0.23 | -0.11 |  0.70 | -0.71 | -0.12 | -0.17 | -0.01 |
| LT4   |  0.07 |  -0.25 |  0.55 | -1.15 | -1.78 | -0.09 | -0.82 | -0.07 | -0.34 | -0.07 |
| LT6   |  0.24 |   0.07 |  0.48 | -0.55 | -0.34 | -0.07 | -1.33 | -0.41 | -0.7  | -0.27 |
| LT7   |  0.07 |  -0.07 |  0.61 | -0.19 | -0.36 |  0.29 | -0.96 | -0.09 | -0.26 | -0.08 |
| LT9   |  0.16 |  -0.16 |  0.64 | -0.33 | -0.14 |  0.43 | -1.01 | -0.19 | -0.36 | -0.21 |
| LT10  |  0.47 |   0.76 | -0.30 |  0.80 | -0.09 |  0.00 | -0.85 | -0.17 | -0.28 | -0.07 |
| LT11  |  0.14 |   0.14 |  0.96 | -0.02 |  0.37 |  1.27 | -0.23 |  0.09 | -0.33 | -0.07 |
| LT12  | -0.12 |  -0.04 |  0.84 | -1.52 | -0.28 |  1.42 | -0.39 | -0.38 | -1.21 | -0.25 |
| LT13  |  0.41 |  -0.02 |  1.19 | -0.34 |  0.14 |  1.67 | -0.87 | -0.22 | -0.72 | -0.33 |
| LT15  |  0.01 |   0.21 |  1.30 | -0.48 | -0.35 |  2.36 | -0.96 | -0.36 | -0.54 | -0.22 |
| LT16  | -0.38 |  -0.07 |  0.41 | -0.32 | -1.22 | -0.08 | -0.45 | -0.25 | -0.52 | -0.31 |
| LT17  |  0.36 |   0.23 |  1.39 | -1.39 | 01.37 |  1.17 | -0.39 | -0.13 |  0.52 |  0.01 |
| LT18  |  0.17 |  -0.27 |  0.04 | -0.04 |  0.18 | -0.39 | -0.59 | -0.25 | -0.21 | -0.22 |
| LT19  |  0.11 |  -0.02 |  1.27 | -0.12 |  1.27 |  2.49 | -0.30 | -0.36 | -0.82 | -0.40 |
| LT21  |  0.28 |  -0.18 |  0.85 |  0.09 |  0.66 |  0.85 | -0.49 | -0.35 | -0.27 | -0.16 |

Conclusion:

The ΔCt values for the above DNAs in a variety of tumors are reported. A ΔCt of >1 was typically used as the threshold value for amplification scoring, as this represents a doubling of gene copy. The above data indicates that significant amplification of the tested nucleic acids occurred in primary lung tumors and/or primary colon tumors: Amplification has been confirmed by framework mapping. The framework markers analysis reports the relative amplification of particular chromosomal regions in the indicated tumors, while the epicenter markers analysis gives a more precise reading of the relative amplification in the region immediately in the vicinity of the gene of interest.

Amplification has been confirmed by epicenter mapping and the data evidenced significant amplification in primary colon tumors and/or primary lung tumors: Amplification of the closest known epicenter markers does not occur to a greater extent than that of the DNAs tested. This strongly suggests that the DNAs tested are responsible for the amplification of the particular region on the respective chromosome.

Because amplification of the DNAs tested occurs in various lung and colon tumors, it is highly probable that these DNAs play a significant role in tumor formation or growth. As a result, antagonists (e.g., antibodies) directed against the proteins encoded by the DNAs tested would be expected to have utility in cancer therapy and as useful diagnostic reagents. The polypeptides encoded by the DNAs tested have utility as diagnostic markers for determining the presence of tumor cells in lung and/or colon tissue samples. The nucleic acid sequences encoding these polypeptides have utility as sources of nucleic acid probes for carrying out the above diagnostic procedures.

Example 29

Ability of PRO241 to Stimulate the Release of Proteotlycans from Cartilage (Assay 97)

The ability of PRO241 to stimulate the release of proteoglycans from cartilage tissue was tested as follows. A positive result in this assay evidences that the polypeptide is expected to be useful in the therapeutic treatment of various cartilage and/or bone injuries or disorders including, for example, arthritis.

The metacarphophalangeal joint of 4-6 month old pigs was aseptically dissected, and articular cartilage was removed by free hand slicing being careful to avoid the underlying bone. The cartilage was minced and cultured in bulk for 24 hours in a humidified atmosphere of 95% air, 5% $CO_2$ in serum free (SF) media (DME/F12 1:1) woth 0.1% BSA and 100 U/ml penicillin and 100 µg/ml streptomycin. After washing three times, approximately 100 mg of articular cartilage was aliquoted into micronics tubes and incubated for an additional 24 hours in the above SF media. PRO241 polypeptides were then added at 1% either alone or in combination with 18 ng/ml interleukin-1α, a known stimulator of proteoglycan release from cartilage tissue. The supernatant was then harvested and assayed for the amount of proteoglycans using the 1,9-dimethyl-methylene blue (DMB) calorimetric assay (Farndale and Buttle, Biochem. Biophys. Acta 883:173-177 (1985)). A positive result in this assay indicates that the test polypeptide will find use, for example, in the treatment of sports-related joint problems, articular cartilage defects, osteoarthritis or rheumatoid arthritis.

When PRO241 polypeptides were tested in the above assay, the polypeptides demonstrated a marked ability to stimulate release of proteoglycans from cartilage tissue both basally and after stimulation with interleukin-1α and at 24 and 72 hours after treatment, thereby indicating that PRO241 polypeptides are useful for stimulating proteoglycan release from cartilage tissue. As such, PRO241 polypeptides are useful for the treatment of sports-related joint problems, articular cartilage defects, osteoarthritis or rheumatoid arthritis.

Example 30

In Vitro Antitumor Assay with PRO344 (Assay 161)

The antiproliferative activity of the PRO344 polypeptide was determined in the investigational, disease-oriented in vitro anti-cancer drug discovery assay of the National Cancer Institute (NCI), using a sulforhodamine B (SRB) dye binding assay essentially as described by Skehan et al., J. Natl. Cancer Inst. 82:1107-1112 (1990). The 60 tumor cell lines employed in this study ("the NCI panel"), as well as conditions for their maintenance and culture in vitro have been described by Monks et al., *J. Natl. Cancer Inst.* 83:757-766 (1991). The purpose of this screen is to initially evaluate the cytotoxic and/or cytostatic activity of the test compounds against different types of tumors (Monks et al., supra; Boyd, *Cancer: Princ. Pract. Oncol. Update* 3(10):1-12 [1989]).

Cells from approximately 60 human tumor cell lines were harvested with trypsin/EDTA (Gibco), washed once, resuspended in IMEM and their viability was determined. The cell suspensions were added by pipet (100 μL volume) into separate 96-well microtiter plates. The cell density for the 6-day incubation was less than for the 2 day incubation to prevent overgrowth. Inoculates were allowed a preincubation period of 24 hours at 37° C. for stabilization. Dilutions at twice the intended test concentration were added at time zero in 100 μL aliquots to the microtiter plate wells (1:2 dilution). Test compounds were evaluated at five half-log dilutions (1000 to 100,000-fold). Incubations took place for two days and six days in a 5% $CO_2$ atmosphere and 100% humidity.

After incubation, the medium was removed and the cells were fixed in 0.1 ml of 10% trichloroacetic acid at 40° C. The plates were rinsed five times with deionized water, dried, stained for 30 minutes with 0.1 ml of 0.4% sulforhodamine B dye (Sigma) dissolved in 1% acetic acid, rinsed four times with 1% acetic acid to remove unbound dye, dried, and the stain was extracted for five minutes with 0.1 ml of 10 mM Tris base [tris(hydroxymethyl)aminomethane], pH 10.5. The absorbance (OD) of sulforhodamine B at 492 nm was measured using a computer-interfaced, 96-well microtiter plate reader.

A test sample is considered positive if it shows at least 50% growth inhibitory effect at one or more concentrations. The results are shown in the following Table 23, where the abbreviations are as follows:

NSCL=non-small cell lung carcinoma
CNS=central nervous system

TABLE 23

| Test compound | Concentration | Days | Tumor Cell Line Type | Cell Line Designation |
|---|---|---|---|---|
| PRO344 | 1.2 nM | 2 | Leukemia | HL-60 (TB) |
| PRO344 | 1.2 nM | 6 | Renal | UO-31 and CAKI-1 |
| PRO344 | 14.9 nM | 2 | Colon | KM-12 |
| PRO344 | 14.9 nM | 2 | CNS | SF-268 |
| PRO344 | 14.9 nM | 2 | Ovarian | OVCAR-4 |
| PRO344 | 14.9 nM | 2 | Renal | CAKI-1 |
| PRO344 | 14.9 nM | 2 | Breast | MDA-MB-435 |
| PRO344 | 14.9 nM | 6 | Leukemia | HL-60 (TB) |
| PRO344 | 14.9 nM | 6 | Colon | KM-12 |
| PRO344 | 14.9 nM | 6 | CNS | SF-295 |
| PRO344 | 14.9 nM | 6 | NSCL | HOP62 |

The results of these assays demonstrate that PRO344 polypeptides are useful for inhibiting neoplastic growth in a number of different tumor cell types and may be used therapeutically therefor. Antibodies against PRO344 are useful for affinity purification of this useful polypeptide. Nucleic acids encoding PRO344 polypeptides are useful for the recombinant preparation of these polypeptides.

Example 31

Inhibition of Vascular Endothelial Growth Factor (VEGF) Stimulated Proliferation of Endothelial Cell Growth (Assay 9)

The ability of various PRO polypeptides to inhibit VEGF stimulated proliferation of endothelial cells was tested. Polypeptides testing positive in this assay are useful for inhibiting endothelial cell growth in mammals where such an effect would be beneficial, e.g., for inhibiting tumor growth.

Specifically, bovine adrenal cortical capillary endothelial cells (ACE) (from primary culture, maximum of 12-14 passages) were plated in 96-well plates at 500 cells/well per 100 microliter. Assay media included low glucose DMEM, 10% calf serum, 2 mM glutamine, and 1× penicillin/streptomycin/fungizone. Control wells included the following: (1) no ACE cells added; (2) ACE cells alone; (3) ACE cells plus 5 ng/ml FGF; (4) ACE cells plus 3 ng/ml VEGF; (5) ACE cells plus 3 ng/ml VEGF plus 1 ng/ml TGF-beta; and (6) ACE cells plus 3 ng/ml VEGF plus 5 ng/ml LIF. The test samples, poly-his tagged PRO polypeptides (in 100 microliter volumes), were then added to the wells (at dilutions of 1%, 0.1% and 0.01%, respectively). The cell cultures were incubated for 6-7 days at 37° C./5% $CO_2$. After the incubation, the media in the wells was aspirated, and the cells were washed 1× with PBS. An acid phosphatase reaction mixture (100 microliter; 0.1M sodium acetate, pH 5.5, 0.1% Triton X-100, 10 mM p-nitrophenyl phosphate) was then added to each well. After a 2 hour incubation at 37° C., the reaction was stopped by addition of 10 microliters 1N NaOH. Optical density (OD) was measured on a microplate reader at 405 nm.

The activity of PRO polypeptides was calculated as the percent inhibition of VEGF (3 ng/ml) stimulated proliferation (as determined by measuring acid phosphatase activity at OD 405 nm) relative to the cells without stimulation. TGF-beta was employed as an activity reference at 1 ng/ml, since TGF-beta blocks 70-90% of VEGF-stimulated ACE cell proliferation. The results are indicative of the utility of the PRO polypeptides in cancer therapy and specifically in inhibiting tumor angiogenesis. Numerical values (relative inhibition) are determined by calculating the percent inhibition of VEGF stimulated proliferation by the PRO polypeptides relative to cells without stimulation and then dividing that percentage into the percent inhibition obtained by TGF-β at 1 ng/ml which is known to block 70-90% of VEGF stimulated cell proliferation. The results are considered positive if the PRO polypeptide exhibits 30% or greater inhibition of VEGF stimulation of endothelial cell growth (relative inhibition 30% or greater).

The following polypeptide tested positive in this assay: PRO323.

Example 32

Rod Photoreceptor Cell Survival (Assay 56)

This assay shows that certain polypeptides of the invention act to enhance the survival/proliferation of rod photoreceptor cells and, therefore, are useful for the therapeutic treatment of retinal disorders or injuries including, for example, treating sight loss in mammals due to retinitis pigmentosum, AMD, etc. Sprague Dawley rat pups at 7 day postnatal (mixed population: glia and retinal neuronal cell types) are killed by decapitation following $CO_2$ anesthesia and the eyes are removed under sterile conditions. The neural retina is dissected away form the pigment epithelium and other ocular tissue and then dissociated into a single cell suspension using 0.25% trypsin in $Ca^{2+}$, $Mg^{2+}$-free PBS. The retinas are incubated at 37° C. for 7-10 minutes after which the trypsin is inactivated by adding 1 ml soybean trypsin inhibitor. The cells are plated at 100,000 cells per well in 96 well plates in DMEM/F12 supplemented with $N_2$. Cells for all experiments are grown at 37° C. in a water saturated atmosphere of 5% $CO_2$. After 2-3 days in culture, cells are fixed using 4% paraformaldehyde, and then stained using CellTracker Green CMFDA. Rho 4D2 (ascites or IgG 1:100), a monoclonal antibody directed towards the visual pigment rhodopsin is used to detect rod photoreceptor cells by indirect immunofluorescence. The results are calculated as % survival: total number of calcein–rhodopsin positive cells at 2-3 days in culture, divided by the total number of rhodopsin positive cells at time 2-3 days in culture. The total cells (fluorescent) are quantified at 20× objective magnification using a CCD camera and NIH image software for Macintosh. Fields in the well are chosen at random.

The following polypeptides tested positive in this assay: PRO243.

Example 33

Pericyte c-Fos Induction (Assay 93)

This assay shows that certain polypeptides of the invention act to induce the expression of c-fos in pericyte cells and, therefore, are useful not only as diagnostic markers for particular types of pericyte-associated tumors but also for giving rise to antagonists which would be expected to be useful for the therapeutic treatment of pericyte-associated tumors. Specifically, on day 1, pericytes are received from VEC Technologies and all but 5 ml of media is removed from flask. On day 2, the pericytes are trypsinized, washed, spun and then plated onto 96 well plates. On day 7, the media is removed and the pericytes are treated with 100 µl of PRO polypeptide test samples and controls (positive control=DME+5% serum+/− PDGF at 500 ng/ml; negative control=protein 32). Replicates are averaged and SD/CV are determined. Fold increase over Protein 32 (buffer control) value indicated by chemiluminescence units (RLU) luminometer reading verses frequency is plotted on a histogram Twofold above Protein 32 value is considered positive for the assay ASY Matrix: Growth media=low glucose DMEM=20% FBS+1×pen strep+1×fungizone. Assay Media=low glucose DMEM+5% FBS.

The following polypeptides tested positive in this assay: PRO241.

Example 34

Inhibitory Activity in Mixed Lymphocyte Reaction (MLR) Assay (Assay 67)

This example shows that one or more of the polypeptides of the invention are active as inhibitors of the proliferation of stimulated T-lymphocytes. Compounds which inhibit proliferation of lymphocytes are useful therapeutically where suppression of an immune response is beneficial.

The basic protocol for this assay is described in Current Protocols in Immunology, unit 3.12; edited by J E Coligan, A M Kruisbeek, D H Marglies, E M Shevach, W Strober, National Insitutes of Health, Published by John Wiley & Sons, Inc.

More specifically, in one assay variant, peripheral blood mononuclear cells (PBMC) are isolated from mammalian individuals, for example a human volunteer, by leukopheresis (one donor will supply stimulator PBMCs, the other donor will supply responder PBMCs). If desired, the cells are frozen in fetal bovine serum and DMSO after isolation. Frozen cells may be thawed overnight in assay media (37° C., 5% $CO_2$) and then washed and resuspended to $3 \times 10^6$ cells/ml of assay media (RPMI; 10% fetal bovine serum, 1% penicillin/streptomycin, 1% glutamine, 1% HEPES, 1% non-essential amino acids, 1% pyruvate). The stimulator PBMCs are prepared by irradiating the cells (about 3000 Rads).

The assay is prepared by plating in triplicate wells a mixture of:

100:1 of test sample diluted to 1% or to 0.1%,

50:1 of irradiated stimulator cells, and

50:1 of responder PBMC cells.

100 microliters of cell culture media or 100 microliter of CD4-IgG is used as the control. The wells are then incubated at 37° C., 5% $CO_2$ for 4 days. On day 5, each well is pulsed with tritiated thymidine (1.0 mC/well; Amersham). After 6 hours the cells are washed 3 times and then the uptake of the label is evaluated.

In another variant of this assay, PBMCs are isolated from the spleens of Balb/c mice and C57B6 mice. The cells are teased from freshly harvested spleens in assay media (RPMI; 10% fetal bovine serum, 1% penicillin/streptomycin, 1% glutamine, 1% HEPES, 1% non-essential amino acids, 1% pyruvate) and the PBMCs are isolated by overlaying these cells over Lympholyte M (Organon Teknika), centrifuging at 2000 rpm for 20 minutes, collecting and washing the mononuclear cell layer in assay media and resuspending the cells to $1 \times 10^7$ cells/ml of assay media. The assay is then conducted as described above.

Any decreases below control is considered to be a positive result for an inhibitory compound, with decreases of less than or equal to 80% being preferred. However, any value less than control indicates an inhibitory effect for the test protein.

The following polypeptide tested positive in this assay: PRO361.

Example 35

Tissue Expression Distribution

Oligonucleotide probes were constructed from the PRO polypeptide-encoding nucleotide sequences shown in the accompanying figures for use in quantitative PCR amplification reactions. The oligonucleotide probes were chosen so as to give an approximately 200-600 base pair amplified fragment from the 3' end of its associated template in a standard PCR reaction. The oligonucleotide probes were employed in standard quantitative PCR amplification reactions with cDNA libraries isolated from different human adult and/or fetal tissue sources and analyzed by agarose gel electrophoresis so as to obtain a quantitative determination of the level of expression of the PRO polypeptide-encoding nucleic acid in the various tissues tested. Knowledge of the expression pattern or the differential expression of the PRO polypeptide-encoding nucleic acid in various different human tissue types provides a diagnostic marker useful for tissue typing, with or without other tissue-specific markers, for determining the primary tissue source of a metastatic tumor, and the like. The results of these assays are shown in Table 24 below.

TABLE 24

| Nucleic Acid | Significantly Expressed In | Not Significantly Expressed In |
|---|---|---|
| DNA34392-1170 | liver, kidney, brain, lung | placenta |
| DNA39976-1215 | brain | lung |
| DNA35595-1228 | | pancreas, brain, kidney, liver |
| DNA34436-1238 | lung, placenta, brain | testis |
| DNA44176-1244 | liver | brain, lung |
| DNA44192-1246 | kidney | liver |
| DNA44804-1248 | | lung, brain |
| DNA41234-1242 | lung, liver, kidney | brain |
| DNA45410-1250 | lung, brain, kidney, liver | |
| DNA46777-1253 | | liver, placenta, brain |

Example 36

Fetal Hemoglobin Induction in an Erythroblastic Cell Line (Assay 107)

This assay is useful for screening PRO polypeptides for the ability to induce the switch from adult hemoglobin to fetal hemoglobin in an erythroblastic cell line. Molecules testing positive in this assay are expected to be useful for therapeutically treating various mammalian hemoglobin-associated disorders such as the various thalassemias. The assay is performed as follows. Erythlroblastic cells are plated in standard growth medium at 1000 cells/well in a 96 well format. PRO polypeptides are added to the growth medium at a concentration of 0.2% or 2% and the cells are incubated for 5 days at 37° C. As a positive control, cells are treated with 100 µM hemin and as a negative control, the cells are untreated. After 5 days, cell lysates are prepared and analyzed for the expression of gamma globin (a fetal marker). A positive in the assay is a gamma globin level at least 2-fold above the negative control.

The following polypeptide tested positive in this assay: PRO243.

Example 37

In Situ Hybridization

In situ hybridization is a powerful and versatile technique for the detection and localization of nucleic acid sequences within cell or tissue preparations. It may be useful, for example, to identify sites of gene expression, analyze the tissue distribution of transcription, identify and localize viral infection, follow changes in specific mRNA synthesis and aid in chromosome mapping.

In situ hybridization was performed following an optimized version of the protocol by Lu and Gillett, *Cell Vision* 1:169-176 (1994), using PCR-generated $^{33}$P-labeled riboprobes. Briefly, formalin-fixed, paraffin-embedded human tissues were sectioned, deparaffinized, deproteinated in proteinase K (20 g/ml) for 15 minutes at 37° C., and further processed for in situ hybridization as described by Lu and Gillett, supra. A [$^{33}$-P] UTP-labeled antisense riboprobe was generated from a PCR product and hybridized at 55° C. overnight. The slides were dipped in Kodak NTB2 nuclear track emulsion and exposed for 4 weeks.

$^{33}$P-Riboprobe Synthesis 6.0 µl (125 mCi) of $^{33}$P-UTP (Amersham BF 1002, SA<2000 Ci/mmol) were speed vac dried. To each tube containing dried $^{33}$P-UTP, the following ingredients were added:

2.0 µl 5× transcription buffer
1.0 µl DTT (100 mM)
2.0 µl NTP mix (2.5 mM: 10µ; each of 10 mM GTP, CTP & ATP+10 µl H$_2$O)
1.0 µl UTP (50 µM)
1.0 µl Rnasin
1.0 µl DNA template (1 µg)
1.0 µl H$_2$O
1.0 µl RNA polymerase (for PCR products T3=AS, T7=S, usually)

The tubes were incubated at 37° C. for one hour. 1.0 µl RQ1 DNase were added, followed by incubation at 37° C. for 15 minutes. 90 µl TE (10 mM Tris pH 76/1 mM EDTA pH 8.0) were added, and the mixture was pipetted onto DE81 paper. The remaining solution was loaded in a Microcon-50 ultrafiltration unit, and spun using program 10 (6 minutes). The filtration unit was inverted over a second tube and spun using program 2 (3 minutes). After the final recovery spin, 100 µl TE were added. 1 µl of the final product was pipetted on DE81 paper and counted in 6 ml of Biofluor II.

The probe was run on a TBE/urea gel. 1-3 µl of the probe or 5 µl of RNA Mrk III were added to 3 µl of loading buffer. After heating on a 95° C. heat block for three minutes, the gel was immediately placed on ice. The wells of gel were flushed, the sample loaded, and run at 180-250 volts for 45 minutes. The gel was wrapped in saran wrap and exposed to XAR film with an intensifying screen in –70° C. freezer one hour to overnight.

$^{33}$P-Hybridization

A. Pretreatment of Frozen Sections

The slides were removed from the freezer, placed on aluminum trays and thawed at room temperature for 5 minutes. The trays were placed in 55° C. incubator for five minutes to reduce condensation. The slides were fixed for 10 minutes in 4% paraformaldehyde on ice in the fume hood, and washed in 0.5×SSC for 5 minutes, at room temperature (25 ml 20×SSC+ 975 ml SQ H$_2$O). After deproteination in 0.5 µg/ml proteinase K for 10 minutes at 37° C. (125 µl of 10 mg/ml stock in 250 ml prewarmed RNase-free RNAse buffer), the sections were washed in 05×SSC for 10 minutes at room temperature. The sections were dehydrated in 70%, 95%, 100% ethanol, 2 minutes each.

B. Pretreatment of Paraffin-embedded Sections

The slides were deparaffinized, placed in SQ H$_2$O, and rinsed twice in 2×SSC at room temperature, for 5 minutes each time. The sections were deproteinated in 20 µg/ml proteinase K (500 µl of 10 mg/ml in 250 ml RNase-free RNase buffer; 37° C., 15 minutes)—human embryo, or 8× proteinase K (100 µl in 250 ml Rnase buffer, 37° C., 30 minutes)— formalin tissues. Subsequent rinsing in 0.5×SSC and dehydration were performed as described above.

C. Prehybridization

The slides were laid out in a plastic box lined with Box buffer (4×SSC, 50% formamide)—saturated filter paper. The tissue was covered with 50 µl of hybridization buffer (3.75 g Dextran Sulfate+6 ml SQ H$_2$O), vortexed and heated in the microwave for 2 minutes with the cap loosened. After cooling on ice, 18.75 ml formamide, 3.75 ml 20×SSC and 9 ml SQ H$_2$O were added, the tissue was vortexed well, and incubated at 42° C. for 1-4 hours.

D. Hybridization 1.0×10$^6$ cpm probe and 1.0 µl tRNA (50 mg/ml stock) per slide were heated at 95° C. for 3 minutes. The slides were cooled on ice, and 48 µl hybridization buffer were added per slide. After vortexing, 50 µl $^{33}$P mix were added to 50 µl prehybridization on slide. The slides were incubated overnight at 55° C.

E. Washes

Washing was done 2×10 minutes with 2×SSC, EDTA at room temperature (400 ml 20×SSC+16 ml 0.25M EDTA, $V_f$=4 L), followed by RNaseA treatment at 37° C. for 30 minutes (500 µl of 10 mg/ml in 250 ml Rnase buffer=20 µg/ml), The slides were washed 2×10 minutes with 2×SSC, EDTA at room temperature. The stringency wash conditions were as follows: 2 hours at 55° C., 0.1×SSC, EDTA (20 ml 20×SSC+16 ml EDTA, $V_f$=4 L).

F. Oligonucleotides

In situ analysis was performed on a variety of DNA sequences disclosed herein. The oligonucleotides employed for these analyses are as follows.

```
(1) DNA44804-1248 (PRO357)
p1 5'-GGATTCTAATACGACTCACTATAGGGCTGCCCGCAACCCCTTCAACTG-3'  (SEQ ID NO:111)

p2 5'-CTATGAAATTAACCCTCACTAAAGGGACCGCAGCTGGGTGACCGTGTA-3'  (SEQ ID NO:112)

(2) DNA52722-1229 (PRO715)
p1 5'-GGATTCTAATACGACTCACTATAGGGCCGCCCCGCCACCTCCT-3'       (SEQ ID NO:113)

p2 5'-CTATGAAATTAACCCTCACTAAAGGGACTCGAGACACCACCTGACCCA-3'  (SEQ ID NO:114)

p3 5'-GGATTCTAATACGACTCACTATAGGGCCCAAGGAAGGCAGGAGACTCT-3'  (SEQ ID NO:115)

p4 5'-CTATGAAATTAACCCTCACTAAAGGGACTAGGGGGTGGGAATGAAAAG-3'  (SEQ ID NO:116)

(3) DNA38113-1230 (PRO327)
p1 5'-GGATTCTAATACGACTCACTATAGGGCCCCCCTGAGCTCTCCCGTGTA-3'  (SEQ ID NO:117)

p2 5'-CTATGAAATTAACCCTCACTAAAGGGAAGGCTCGCCACTGGTCGTAGA-3'  (SEQ ID NO:118)

(4) DNA35917-1207 (PRO243)
p1 5'-GGATTCTAATACGACTCACTATAGGGCAAGGAGCCGGGACCCAGGAGA-3'  (SEQ ID NO:119)

p2 5'-CTATGAAATTAACCCTCACTAAAGGGAGGGGCCCTTGGTGCTGAGT-3'    (SEQ ID NO:120)
```

G. Results

In situ analysis was performed on a variety of DNA sequences disclosed herein. The results from these analyses are as follows.

(1) DNA44804-1248 (PRO357)

Low to moderate level expression at sites of bone formation in fetal tissues and in the malignant cells of an osteosarcoma. Possible signal in placenta and cord. All other tissues negative.

Fetal tissues examined (E12-E16 weeks) include: liver, kidney, adrenals, lungs, heart, great vessels, oesophagus, stomach, spleen, gonad, brain, spinal cord and body wall.

Adult human tissues examined: liver, kidney, stomach, spleen, adrenal, pancreas, lung, colonic carcinoma, renal cell carcinoma and osteosarcoma. Acetominophen induced liver injury and hepatic cirrhosis.

Chimp Tissues examined: thyroid, parathyroid, lymph node, nerve, tongue, thymus, adrenal, gastric mucosa and salivary gland.

Rhesus Monkey: cerebrum and cerebellum.

(2) DNA52722-1229 (PRO715)

Generalized high signal seen over many tissues—highest signal seen over placenta, osteoblasts, injured renal tubules, injured liver, colorectal liver metastasis and gall bladder.

Fetal tissues examined (E12-E16 weeks) include: placenta, umbilical cord, liver, kidney, adrenals, thyroid, lungs, heart, great vessels, oesophagus, stomach, small intestine, spleen, thymus, pancreas, brain, eye, spinal cord, body wall, pelvis and lower limb.

Adult human tissues examined: liver, kidney, adrenal, myocardium, aorta, spleen, lung, skin, chondrosarcoma, eye, stomach, colon, colonic carcinoma, prostate, bladder mucosa and gall bladder. Acetominophen induced liver injury and hepatic cirrhosis.

Rhesus Tissues examined: cerebral cortex (rm), hippocampus (rm)

Chimp Tissues examined: thyroid, parathyroid, lymph node, nerve, tongue, thymus, adrenal, gastric mucosa and salivary gland.

(3) DNA38113-1230 (PRO327)

High level of expression observed in developing mouse and human fetal lung. Normal human adult lung, including bronchial epithelium, was negative. Expression in submucosa of human fetal trachea, possibly in smooth muscle cells. Expression also observed in non-trophoblastic cells of uncertain histogenesis in the human placenta. In the mouse expression was observed in the developing snout and in the developing tongue. All other tissues were negative. Speculated function: Probable role in bronchial development.

Fetal tissues examined (E12-E16 weeks) include: placenta, umbilical cord, liver, kidney, adrenals, thyroid, lungs, heart, great vessels, oesophagus, stomach, small intestine, spleen, thymus, pancreas, brain, eye, spinal cord, body wall, pelvis and lower limb.

Adult tissues examined: liver, kidney, adrenal, myocardium, aorta, spleen, lymph node, pancreas, lung, skin, cerebral cortex (rm), hippocampus (rm), cerebellum (rm), penis, eye, bladder, stomach, gastric carcinoma, colon, colonic carcinoma, thyroid (chimp), parathyroid (chimp) ovary (chimp) and chondrosarcoma.

(4) DNA35917-1207 (PRO243)

Cornelia de Lange syndrome (CdLS) is a congenital syndrome. That means it is present from birth. CdLS is a disorder that causes a delay in physical, intellectual, and langauge development. The vast majority of children with CdLS are mentally retarded, with the degree of mental retardation ranging from mild to severe. Reported IQ's from 30 to 85. The average IQ is 53. The head and facial features include small head size, thin eyebrows which often meet at the midline, long eyelashes, short upturned nose, thin downturned lips, lowset ears and high arched palate or cleft palate. Other characteristics may include language delay, even in the most mildly affected, delayed growth and small stature, low pitched cry, small hands and feet, incurved fifth fingers, simian creases, and excessive body hair. Diagnosis depends on the presence of a combination of these characteristics. Many of these characteristics appear in varying degrees. In some cases these characteristics may not be present or be so mild that they will be recognized only when observed by a trained geneticist or other person familar with the syndrome. Although much is known about CdLS, recent reports suggest that there is much more to be learned.

In this study additional sections of human fetal face, head, limbs and mouse embryos were examined. No expression was seen in any of the mouse tissues. Expression was only seen with the antisense probe.

Expression was observed adjacent to developing limb and facial bones in the perosteal mesenchyme. The expression was highly specific and was often adjacent to areas undergoing vascularization. The distribution is consistent with the observed skeletal abnormalities in the Cornelia de Lange syndrome. Expression was also observed in the developing temporal and occipital lobes of the fetal brain, but was not observed elsewhere. In addition, expression was seen in the ganglia of the developing inner ear; the significance of this finding is unclear.

Though these data do not provide functional information, the distribution is consistent with the sites that are known to be affected most severely in this syndrome.

Additionally, faint expression was observed at the cleavage line in the developing synovial joint forming between the femoral head and acetabulum (hip joint). If this pattern of expression were observed at sites of joint formation elsewhere, it might explain the facial and limb abnormalities observed in the Cornelia de Lange syndrome.

Example 38

Activity of PRO243 mRNA in *Xenopus* Oocytes

In order to demonstrate that the human chordin clone (DNA35917-1207) encoding PRO243 is functional and acts in a manner predicted by the *Xenopus* chordin and *Drosophila* sog genes, supercoiled plasmid DNA from DNA35917-1207 was prepared by Qiagen and used for injection into *Xenopus laevis* embryos. Microinjection of *Xenopus* chordin mRNA into ventrovegetal blastomeres induces secondary (twinned) axes (Sasai et al., Cell 79:779-790 (1994)) and *Drosophila* sog also induces a secondary axis when ectopically expresed on the ventral side of the *Xenopus* embryo (Holley et al., Nature 376:249-253 (1995) and Schmidt et al., Development 121:4319-4328 (1995)). The ability of sog to function in *Xenopus* ooctyes suggests that the processes involved in dorsoventral patterning have been conserved during evolution.

Methods

Manipulation of *Xenopus* Embryos:

Adult female frogs were boosted with 200 I.U. pregnant mare serum 3 days before use and with 800 I.U. of human chorionic gonadotropin the night before injection. Fresh oocytes were squeezed out from female frogs the next morning and in vitro fertilization of oocytes was performed by mixing oocytes with minced testis from sacrificed male frogs. Developing embryos were maintained and staged according to Nieuwkoop and Faber, Normal Table of *Xenopus laevis*, N.-H. P. Co, ed. (Amsterdam, 1967).

Fertilized eggs were dejellied with 2% cysteine (pH 7.8) for 10 minutes, washed once with distilled water and transferred to 0.1×MBS with 5% Ficoll. Fertilized eggs were lined on injection trays in 0.1×MBS with 5% Ficoll. Two-cell stage developing *Xenopus* embryos were injected with 200 pg of pRK5 containing wild type chordin (DNA35917-1207) or 200 pg of pRK5 without an insert as a control. Injected embryos were kept on trays for another 6 hours, after which they were transferred to 0.1×MBS with 50 mg/ml gentamycin until reaching Nieukwkoop stage 37-38.

Results:

Injection of human chordin cDNA into single blastomeres resulted in the ventralization of the tadpole. The ventralization of the tadpole is visible in the shortening and kinking of the tail and the expansion of the cement gland. The ability of human chordin to function as a ventralizing agent in *Xenopus* shows that the protein encoded by DNA35917-1207 is functional and influences dorsal-ventral patterning in frogs and suggests that the processes involved in dorsoventral patterning have been conserved during evolution, with mechanisms in common between humans, flies and frogs.

DEPOSIT OF MATERIAL

The following materials have been deposited with the American Type Culture Collection, 10801 University Blvd., Manassas, Va. 20110-2209, USA (ATCC):

| Material | ATCC Dep. No. | Deposit Date |
| --- | --- | --- |
| DNA34392-1170 | ATCC 209526 | Dec. 10, 1997 |
| DNA35917-1207 | ATCC 209508 | Dec. 3, 1997 |
| DNA39976-1215 | ATCC 209524 | Dec. 10, 1997 |
| DNA35595-1228 | ATCC 209528 | Dec. 10, 1997 |
| DNA38113-1230 | ATCC 209530 | Dec. 10, 1997 |
| DNA34436-1238 | ATCC 209523 | Dec. 10, 1997 |
| DNA40592-1242 | ATCC 209492 | Nov. 21, 1997 |
| DNA44176-1244 | ATCC 209532 | Dec. 10, 1997 |
| DNA44192-1246 | ATCC 209531 | Dec. 10, 1997 |
| DNA39518-1247 | ATCC 209529 | Dec. 10, 1997 |
| DNA44804-1248 | ATCC 209527 | Dec. 10, 1997 |
| DNA52722-1229 | ATCC 209570 | Jan. 7, 1998 |
| DNA41234-1242 | ATCC 209618 | Feb. 5, 1998 |
| DNA45410-1250 | ATCC 209621 | Feb. 5, 1998 |
| DNA46777-1253 | ATCC 209619 | Feb. 5, 1998 |

These deposits were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit The deposits will be made available by ATCC under the terms of the Budapest Treaty, and subject to an agreement between Genentech, Inc. and ATCC, which assures that all restrictions imposed by the depositor on the availability to the public of the deposited material will be irrevocably removed upon the ciranting of the pertinent U.S. patent, assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35

USC § 122 and the Commissioner's rules pursuant thereto (including 37 CFR § 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. An isolated antibody that binds to the polypeptide shown in FIG. 32 (SEQ ID NO:83).

2. The antibody or a fragment thereof, of claim 1 which is a monoclonal antibody.

3. The antibody of claim 1 which is a humanized antibody.

4. The antibody of claim 1 which is labeled.

* * * * *